(12) United States Patent
Reed et al.

(10) Patent No.: US 8,455,628 B2
(45) Date of Patent: Jun. 4, 2013

(54) PP1 LIGANDS

(75) Inventors: Thomas Reed, Blacksburg, VA (US);
Amy Atzel, Minneapolis, MN (US);
David Bachinsky, Charlotte, NC (US);
Anna Tretiakova, Royersford, PA (US)

(73) Assignee: Intrexon Corporation, Blacksburg, VA (US)

( * ) Notice: Subject to any disclaimer, the term of this patent is extended or adjusted under 35 U.S.C. 154(b) by 468 days.

(21) Appl. No.: 12/598,137

(22) PCT Filed: May 2, 2008

(86) PCT No.: PCT/US2008/062425
§ 371 (c)(1),
(2), (4) Date: May 26, 2010

(87) PCT Pub. No.: WO2008/137681
PCT Pub. Date: Nov. 13, 2008

(65) Prior Publication Data
US 2010/0273212 A1 Oct. 28, 2010

Related U.S. Application Data

(60) Provisional application No. 60/915,611, filed on May 2, 2007, provisional application No. 60/915,622, filed on May 2, 2007, provisional application No. 60/915,618, filed on May 2, 2007, provisional application No. 60/988,021, filed on Nov. 14, 2007.

(51) Int. Cl.
*C07H 21/02* (2006.01)
*C12P 21/04* (2006.01)
*C12N 7/00* (2006.01)
*C12N 1/12* (2006.01)
*C12N 15/00* (2006.01)
*C12N 5/00* (2006.01)

(52) U.S. Cl.
USPC .... 536/23.1; 435/320.1; 435/325; 435/252.1; 435/235.1; 435/70.1

(58) Field of Classification Search
None
See application file for complete search history.

(56) References Cited

U.S. PATENT DOCUMENTS

| | | |
|---|---|---|
| 7,071,295 B2 | 7/2006 | Reed |
| 7,091,038 B2 | 8/2006 | Palli et al. |
| 2002/0032167 A1 | 3/2002 | Chien et al. |
| 2004/0018556 A1 | 1/2004 | Cantor |
| 2004/0033600 A1 | 2/2004 | Palli et al. |
| 2004/0203027 A1 | 10/2004 | Reed |
| 2006/0172377 A1 | 8/2006 | Padidam |
| 2006/0200416 A1 | 9/2006 | White et al. |
| 2008/0032947 A1 | 2/2008 | Reed |
| 2008/0050808 A1 | 2/2008 | Reed et al. |
| 2008/0051360 A1 | 2/2008 | Reed et al. |
| 2008/0213834 A1 | 9/2008 | Reed et al. |
| 2008/0220475 A1 | 9/2008 | Reed et al. |
| 2009/0186379 A1 | 7/2009 | Reed |
| 2009/0215173 A1 | 8/2009 | Reed |
| 2009/0215866 A1 | 8/2009 | Reed |

FOREIGN PATENT DOCUMENTS

| | | |
|---|---|---|
| WO | WO 00/25804 A2 | 5/2000 |
| WO | WO 2005/040336 A3 | 5/2005 |
| WO | WO 2005/116231 A1 | 12/2005 |
| WO | WO 2007/028969 A2 | 3/2007 |
| WO | WO 2007/048103 A9 | 4/2007 |
| WO | WO 2007/076166 A3 | 7/2007 |
| WO | WO 2008/119058 A3 | 10/2008 |

OTHER PUBLICATIONS

Genbank Accession No. NP_003591 (Aurora Kinase A revision history, Retrieved from Internet <URL:http://www.ncbi.nlm.nih.gov/protein/NP_003591.2?report=girevhist>, Retrieved on Jun. 22, 2012).*
Ammosova, T., et al., "Dephosphorylation of CDK9 by protein phosphatase 2A and protein phosphatase-I in Tat-activated HIV-I transcription," *Retrovirology* 2:47 (15 pages), BioMed Central Ltd., UK (2005).
Ayllón, V., et al., "Protein phosphatase 1α is a Ras-activated Bad phosphatase that regulates interleukin-2 deprivation-induced apoptosis," *EMBO J.* 19(10): 2237-2246, European Molecular Biology Organization, UK (2000).
Beullens, M., et al., "The C-terminus of NIPP1 (nuclear inhibitor of protein phosphatase-1) contains a novel binding site for protein phosphatase-1 that is controlled by tyrosine phosphorylation and RNA binding," *Biochem. J.* 352: 651-658, Biochemical Society, GB (2000).
Bibb, J., et al., "Phosphorylation of DARPP-32 by Cdk5 modulates dopamine signaling in neurons," *Nature* 402: 669-671, Macmillan Magazines Ltd., UK (1999).
Carr, A., et al., "Type 1 Phosphatase, a Negative Regulator of Cardiac Function," *Mol. Cell. Bio.* 22(12):4124-4135, American Society for Microbiology, US (2002).
Ceulemans, H. and Bollen, M., "Functional Diversity of Protein Phosphatase-1, a Cellular Economizer and Reset Button," *Physiol. Rev.* 84: 1-39, American Physiological Society, US (2003).
Champion, H., "Targeting Protein Phosphatase 1 in Heart Failure," *Circ. Res.* 96: 708-710, American Heart Association, Inc., US (2005).
Cohen, P., "Protein phosphatase 1—targeted in many directions," *J. Cell Sci.* 115: 241-256, The Company of Biologists Ltd, UK (2002).
Den Hertog, J., "Regulation of protein phosphatases in disease and behaviour," *EMBO Reports* 4(11): 1027-1032, European Molecular Biology Organization, UK (2003).
Deng, J., et al., "Phosphorylation of the myosin phosphatase inhibitors, CPI-17 and PHI-1, by integrin-linked kinase," *Biochem. J.* 367: 517-524, Biochemical Society, GB (2002).

(Continued)

*Primary Examiner* — Suzanne M Noakes
*Assistant Examiner* — Jae W Lee
(74) *Attorney, Agent, or Firm* — Sterne, Kessler, Goldstein & Fox P.L.L.C.

(57) ABSTRACT

The invention relates to phosphatase ligands and polyligands. In particular, the invention relates to ligands, homopolyligands, and heteropolyligands that modulate PP1 activity. The ligands and polyligands are utilized as research tools or as therapeutics. The invention includes linkage of the ligands, homopolyligands, and heteropolyligands to a cellular localization signal, epitope tag and/or a reporter. The invention also includes polynucleotides encoding the ligands and polyligands.

18 Claims, 35 Drawing Sheets

OTHER PUBLICATIONS

Egloff, M., et al., "Structural basis for the recognition of regulatory subunits by the catalytic subunit of protein phosphatase 1," *EMBO J.* 16(8): 1876-1887, Oxford University Press, UK (1997).

El-Armouche, A., et al., "Decreased protein and phosphorylation level of the protein phosphatase inhibitor-1 in failing human hearts," *Cardiov. Res.* 61: 87-93, Elsevier B.V., UK (2003).

Endo, S., et al., "Multiple Structural Elements Define the Specificity of Recombinant Human Inhibitor-1 as a Protein Phosphatase-1 Inhibitor," *Biochem.* 35: 5220-5228, American Chemical Society, US (1996).

Eto, M., et al., "Phosphoprotein inhibitor CPI-17 specificity depends on allosteric regulation of protein phosphatase-1 by regulatory subunits," *Proc. Natl. Acad. Sci. USA* 101(24): 8888-8893, National Academy of Sciences, US (2004).

Garcia, A., "Introduction," PP1signature.pasteur.fr, accessed at http://web.archive.org/web/20061123035849/http://pp1signature.pasteur.fr/index.html, accessed on Jul. 16, 2010, 1 page.

Garcia, A., "General Information," PP1signature.pasteur.fr, accessed at http://web.archive.org/web/20061123035819/http://pp1signature.pasteur.fr/in dex.html, accessed on Jul. 16, 2010, 4 pages.

Garcia, A., "Protein Phosphatase 1 interacting proteins," PP1signature.pasteur.fr, accessed at http://web.archive.org/web/20061123035757/http://pp1signature.pasteur.fr/index.html, accessed on Jul. 16, 2010, 6 pages.

Guergnon, J., et al., "Use of Penetrating Peptides Interacting with PP1/PP2A Proteins as a General Approach for a Drug Phosphatase Technology," *Mol. Pharmacol.* 69: 1115-1124, American Society for Pharmacology and Experimental Therapeutics, US (2006).

Haghighi, K, et al., "Superinhibition of Sarcoplasmic Reticulum Function by Phospholamban Induces Cardiac Contractile Failure," *J. Biol. Chem.* 276(26): 24145-24152, American Society for Biochemistry and Molecular Biology, Inc., US (2001).

Hagiwara, M., et al., "Transcriptional Attenuation Following cAMP Induction Requires PP-1-Mediated Dephosphorylation of CREB," *Cell* 70: 105-113, Cell Press, US (1992).

Huang, H., et al., "Characterization of the Inhibition of Protein Phosphatase-1 by DARPP-32 and Inhibitor-2," *J. Biol. Chem.* 274(12): 7870-7878, American Society for Biochemistry and Molecular Biology, Inc., US (1999).

Ji, Y., et al., "Targeted Inhibition of $Ca^{2+}$/Calmodulin-dependent Protein Kinase II in Cardiac Longitudinal Sarcoplasmic Reticulum Results in Decreased Phosphorylation at Threonine 17," *J. Biol. Chem.* 278(27): 25063-25071, American Society for Biochemistry and Molecular Biology, Inc., US (2003).

Jideama, N., et al., "Dephosphorylation specificities of protein phosphatase for cardiac troponin I, troponin T, and sites within troponin T," *Int. J. Biol. Sci.* 2: 1-9, Ivyspring International Publisher, AU (2006).

Jin, Q., et al., "The Protein Phosphatase-1 (PP1) Regulator, Nuclear Inhibitor of PP1, (NIPP1), Interacts with the Polycomb Group Protein, Embryonic Ectoderm Development (EED), and Functions as a Transcriptional Repressor," *J. Biol. Chem.* 278(33): 30677-30685, American Society for Biochemistry and Molecular Biology, Inc., US (2003).

Kim, Y., et al., "PNUTS, a Protein Phosphatase 1 (PP1) Nuclear Targeting Subunit," *J. Biol. Chem.* 278(16): 13819-13828, American Society for Biochemistry and Molecular Biology, Inc., US (2003).

Kimura., Y., et al., "Phospholamban domain I/cytochrome $b_5$ transmembrane sequence chimeras do not inhibit SERCA2a," *FEBS Let.* 425: 509-512, Federation of European Biochemical Societies, ES (1998).

Kimura, Y., et al., "Phospholamban Inhibitory Function Is Activated by Depolymerization," *J. Biol. Chem.* 272(24): 15061-15064, American Society for Biochemistry and Molecular Biology, Inc., US (1997).

Kimura, Y., et al., "Phospholamban Regulates the $Ca^{2+}$-ATPase through Intramembrane Interactions," *J. Biol. Chem.* 271(36): 21726-21731, American Society for Biochemistry and Molecular Biology, Inc., US (1996).

Kirchhefer, U., et al., "Enhanced cardiac function in mice overexpressing protein phosphatase Inhibitor-2," *Cardiovasc. Res.* 68: 98-108, Elsevier B.V., UK (2005).

Landsverk, H., et al., "PNUTS enhances in vitro chromosome decondensation in a PP1-dependent manner," *Biochem. J.* 390: 709-717, Biochemical Society, GB (2005).

Lees-Miller, S., et al., "Human DNA-Activated Protein Kinase Phosphorylates Serines 15 and 37 in the Amino-Terminal Transactivation Domain of Human p53," *Mol. Cell. Biol.* 12(11): 5041-5049, American Society for Microbiology, US (1992).

Li, D., et al., "Protein serine/threonine phosphatase-1 dephosphorylates p53 at Ser-15 and Ser-37 to modulate its transcriptional and apoptotic activities," *Oncogene* 25: 3006-3022, Nature Publishing Group, UK (May 18, 2006).

Liu, F., et al., "Contributions of protein phosphatases PP1, PP2A, PP2B and PP5 to the regulation of tau phosphorylation," *Eur. J Neruosci.* 22: 1942-1950, Wiley-Blackwell, UK (2005).

Liu, Y., et al., "Regulation of BRCA1 Phosphorylation by Interaction with Protein Phosphatase 1α," *Cancer Res.* 62: 6365-6361, American Association for Cancer Research, US (2002).

Margolis, S., et al., "PP1 control of M phase entry exerted through 14-3-3- regulated Cdc25 dephosphorylation," *EMBO J.* 22(21): 5734-5745, Nature Publishing Group, UK (2003).

NCBI Entrez, GenBank Report, Accession No. Q96A00, Yamawaki, K., et al., Entry Date Nov. 9, 2004, accessed on Jul. 16, 2010 at http://www.ncbi.nlm.nih.gov/protein/55583974.

Neumann, J., "Altered phosphatase activity in heart failure, influence on $Ca^{2+}$ movement," *Basic Res. Cardiol.* 97(Suppl. 1) I/91-I/95, Steinkopff Verlag, DE (2002).

Ohki, S., et al., "Distinctive Solution Conformation of Phosphatase Inhibitor CPI-17 Substituted with Aspartate at the Phosphorylation-site Threonine Residue," *J. Mol. Biol.* 326: 1539-1547, Elsevier Science Ltd., UK (2003).

Oliver, C., et al., "Targeting Protein Phosphatase 1 (PP1) to the Actin Cytoskeleton: the Neurabin I/PP1 Complex Regulates Cell Morphology," *Mol. Cell. Bio.* 22(13): 4690-4701, American Society for Microbiology, US (2002).

Park, I., et al., "Molecular Mechanism of the Synergistic Phosphorylation of Phosphatase Inhibitor-2," *J. Biol. Chem.* 269(2): 944-954, American Society for Biochemistry and Molecular Biology, Inc., US (1994).

Pathak, A., et al., "Enhancement of Cardiac Function and Suppression of Heart Failure Progression by Inhibition of Protein Phosphatase 1," *Circ. Res.* 96: 756-766, American Heart Association, Inc., US (2005).

Quevedo, C., et al., "Initiation Factor 2B Activity Is Regulated by Protein Phosphatase 1, Which Is Activated by the Mitogen-activated Protein Kinase-dependent Pathway in Insulin-like Growth Factor 1-stimulated Neuronal Cells," *J. Biol. Chem.* 278(19): 16579-16586, American Society for Biochemistry and Molecular Biology, Inc., US (2003).

Rameau, G., et al., "Bidirectional Regulation of Neuronal Nitric-oxide Synthase Phosphorylation at Serine 847 by the *N*-Methyl-D-aspartate Receptor," *J. Biol. Chem.* 279(14): 14307-14314, American Society for Biochemistry and Molecular Biology, Inc., US (2004).

Rubin, E., et al., "Site-specific and temporally-regulated retinoblastoma protein dephosphorylation by protein phosphatase type 1," *Oncogene* 20: 3776-3785, Nature Publishing Group, UK (2001).

Sagara, J., et al., "Scapinin, a Putative Protein Phosphatase-1 Regulatory Subunit Associated with the Nuclear Nonchromatin Structure," *J. Biol. Chem.* 278(46): 45611-45619, American Society for Biochemistry and Molecular Biology, Inc., US (2003).

Santoro, M., et al., "Protein phosphatase 1 binds to phospho-Ser-1394 of the macrophage-stimulating protein receptor," *Biochem. J.* 376: 587-594, Biochemical Society, GB (2003).

Shmueli, A., et al., "Site-specific dephosphorylation of *doublecortin* (DCX) by protein phosphatase 1 (PP1)," *Mol. Cell. Neurosci.* 32: 15-26, Elsevier Inc., UK (May-Jun. 2006).

Siino, J., et al., "Photobleaching of GFP-labeled H2AX in chromatin: H2AX has low diffusional mobility in the nucleus," *Biochem. Biophys. Res. Comm.* 297: 1318-1323, Academic Press, US (2002).

Strack, S., et al., "Differential Inactivation of Postsynaptic Density-Associated and Soluble $Ca^{2+}$/Calmodulin-Dependent Protein Kinase II by Protein Phosphates 1 and 2A," *J. Neurochem.* 68: 2119-2128, Lippincott-Raven Publishers, US (1997).

Szatmari, E., et al., "A Positive Feedback Loop between Glycogen Synthase Kinase 3β and Protein Phosphatase 1 after Stimulation of NR2B NMDA Receptors in Forebrain Neurons," *J. Biol. Chem.* 280(45): 37526-37535, American Society for Biochemistry and Molecular Biology, US (2005).

Tang, T., et al., "Modulation of Type 1 Inositol (1,4,5)-Trisphosphate Receptor Function by Protein Kinase A and Protein Phosphatase 1α," *J. Neurosci.* 23(2): 403-415, Society for Neuroscience, US (2003).

Terrak, M., et al., "Structural basis of protein phosphatase 1 regulation," *Nature 429*: 780-784, Nature Publishing Group, UK (2004).

Toyofuku, T., et al., "Amino Acids Lys-Asp-Asp-Lys-Pro-Val$^{402}$ in the Ca$^{2+}$-ATPase of Cardiac Sarcoplasmic Reticulum Are Critical for Functional Association with Phospholamban," *J. Biol. Chem.* 269(37): 22929-22932, American Society for Biochemistry and Molecular Biology, Inc., US (1994).

Toyoshima, C., et al., "Modeling of the inhibitory interaction of phospholamban with the Ca$^{2+}$ ATPase," *Proc. Natl. Acad. Sci.*, USA 100(2): 467-472, National Academy of Sciences, US (2003).

Tsukada, M., et al., "Neurabin II mediates doublecortin-dephosphorylation on actin filaments," *Biochem. Biophys. Res. Comm. 343*: 839-847, Elsevier Inc., UK (May 12, 2006).

Uematsu, K., et al., "Regulation of spinophilin Ser94 phosphorylation in neostriatal neurons involves both DARPP-32-dependent and independent pathways," *J. Neurochem.* 95: 1642-1652, Wiley-Blackwell, US (2005).

Walter, A., et al., "The mitotic serine/threonine kinase Aurora2/AIK is regulated by phosphorylation and degradation," *Oncogene 19*: 4906-4916, Macmillan Publishers, Ltd., UK (2000).

Washington, K., et al., "Protein Phosphatase-1 Dephosphorylates the C-terminal Domain of RNA Polymerase-II," *J. Biol. Chem. 277*(43): 40442-40448, American Society for Biochemistry and Molecular Biology, Inc., US (2002).

Weiser, D., et al., "The Inhibitor-1 C Terminus Facilitates Hormonal Regulation of Cellular Protein Phosphatase-1," *J. Biol. Chem. 279*(47): 48904-48914, American Society for Biochemistry and Molecular Biology, Inc., US (2004).

Welsh, G., et al., "Peptide Substrates Suitable for Assaying Glycogen Synthase Kinase-3 in Crude Cell Extracts," *Analyt. Biochem. 244*: 16-21, Academic Press, Inc., US (1997).

Yamada, M., et al., "Inhibition of protein phosphatase 1 by inhibitor-2 gene delivery ameliorates heart failure progression in genetic cardiomyopathy," *FASEB J. 20*: 1197-1199, FASEB, US (Jun. 2006).

Yamawaki, K., et al., "Identification of Human CPI-17, an Inhibitory Phosphoprotein for Myosin Phosphatase," *Biochem. Biophys. Res. Comm. 285*: 1040-1045, Academic Press, US (2001).

Zhan, Q., et al., "p21-Activated Kinase 2 in Neutrophils Can Be Regulated by Phosphorylation at Multiple Sites and by a Variety of Protein Phosphatases," *J. Immunol. 171*: 3785-3793, American Association of Immunologists, Inc., US (2003).

U.S. Appl. No. 12/532,912, inventors Bachinsky et al., U.S. national phase of International Application No. PCT/US08/058531, filed Mar. 27, 2008.

Katayama, H. et al., "Interaction and Feedback Regulation between STK15/BTAK/Aurora-A Kinase and Protein Phosphatase 1 through Mitotic Cell Division Cycle," *J. Biol. Chem. 276*: 46219-46224, American Society of Biochemistry and Molecular Biology, Rockville, MD (2001).

Oxenoid, K. and J.J. Chou, "The structure of phospholamban pentamer reveals a channel-like architecture in membranes," *Proceedings of the National Academy of Sciences USA 102*: 10870-10875, National Academy of Sciences, Washington, DC (2005).

Pinksy, B. et al., "Glc7/Protein Phosphatase 1 Regulatory Subunits can Oppose the Ip11/Aurora Protein Kinase by Redistributing Glc7," *Molecular and Cellular Biology 26*; : 2648-2660, American Society for Microbiology, Washiturton, DC (2006).

Swain, J. et al., "Specific Inhibition of Mouse Oocyte Nuclear Protein Phosphataste-1 Stimulates Germinal Vesical Breakdown," *Molecular Reproduction and Development 65*: 96-103, Wiley-Liss, Inc., Wilmington, Delaware (2003).

Satinover, D.L. et al., "Activation of Aurora-A kinase by protein phosphatase inhibitor-2, a bifunctional signaling protein," *Proceedings of the National Academy of Sciences USA 101*: 8625-8630, National Academy of Sciences, Washington, DC (2004).

Berrebi-Bertrand, I. et al., "Biophysical interaction between phospholamban and protein phosphatase 1 regulatory subunit GM," *FEBS Letters 439*: 224-230, Federation of European Biochemical Societies (1998).

MacLennan, D.H. and E.G. Kranias, "Phospholamban: A Crucial Regulatory of Cardiac Contractility," *Nature Reviews Molecular Cell Biology 4*: 566-577, Nature Publishing Group, New York, NY (2003).

Jaillon, O, et al., "Full=Chromosome 3 SCAF14978, whole genome shotgun sequence," Accession No. Q4RY65, XP-002689420 (2005).

Shiina, S. el at., amino acid sequence for "FB19 [*Homo sapiens*]," GenBank Accession No. BAB63324.1 (2001), downloaded from ncbi.nlm.nih.gov/protein/15277231 on Mar. 7, 2013.

\* cited by examiner

| SEQ ID | name(aa range)_plus_name(aa range) [not all mutations are indicated – see specification and sequence listing] |
|---|---|
| SEQ ID NO:1 | NIPP1(144-221)_plus_spacer_plus_AuroraBetaKinase(258-299)_plus_spacer_plus_CPI17(2-147) |
| SEQ ID NO:5 | ScapininI(439-515)_plus_spacer_plus_TP53(2-59)_plus_spacer_plus_PPPIR1A(2-99) |
| SEQ ID NO:9 | NeurabinII(1-27)_plus_spacer_plus_MYPTI(2-59)_plus_spacer_plus_DARPP32(2-36) |
| SEQ ID NO:13 | PNUTS(383-449)_plus_spacer_plus_RNAPII(1741-1796)_plus_spacer_plus_PP1R3C(2-107) |
| SEQ ID NO:17 | CPI17(2-147)_plus_spacer_plus_Rb(784-867)_plus_spacer_plus_NIPP1(144-221) |
| SEQ ID NO:21 | MST1R(1328-1400)_plus_spacer_plus_ScapininI(439-518)_plus_spacer_plus_DARPP32(2-90) |
| SEQ ID NO:25 | PNUTS(383-449)_plus_spacer_plus_PPPIR3C(2-107)_plus_spacer_plus_PPPIR1A(2-99) |
| SEQ ID NO:29 | PPPIR1A(2-99)_plus_spacer_plus_TP53(2-59)_plus_spacer_plus_ScapaninI(435-518) |
| SEQ ID NO:33 | PLN(2-24)_plus_spacer_plus_PPPIR1A(2-65)_plus_spacer_plus_PPPIR2(2-end) |
| SEQ ID NO:37 | PLN(2-24)_plus_spacer_plus_PPPIR1A(2-65)_plus_spacer_plus_PPPIR2(2-end) |
| SEQ ID NO:41 | NIPPI(144-221)_plus_spacer_plus_AuroraBetaKinase(285-299)_plus_spacer_plus_CPI17(2-147) |
| SEQ ID NO:45 | CPI17(2-147)_plus_spacer_plus_RNAPII(1615-1730)_plus_spacer_plus_NIPPI(131-230) |
| SEQ ID NO:49 | PPPIR2(2-150)_plus_spacer_plus_CDC25(2-237)_plus_spacer_plus_NeurabinI(393-483) |
| SEQ ID NO:53 | PPPIR1A(2-99)_plus_spacer_plus_EF2(2-94)_plus_spacer_plus_DARPP32(2-36) |
| SEQ ID NO:165 | PLN(1-30-EDmut)_plus_spacer_plus_PLN(1-52-DEmut-tailmut) |
| SEQ ID NO:169 | PLN(1-19-DEmut)_plus_spacer_plus_PLN(1-52-DEmut-tailmut) |
| SEQ ID NO:173 | PLN(1-20-DEmut)_plus_spacer_plus_PLN(10-30-DEmut)_plus_spacer_plus_PLN(11-29-DEmut)_plus_spacer_plus_PLN(11-29-DEmut) |
| SEQ ID NO:177 | BRCA(964-1006)-histoneH2AX(114-143) |
| SEQ ID NO:181 | BAD(66-109)-histoneH2AX(114-143) |
| SEQ ID NO:185 | EF2rat(523-554)-IP3receptor(1570-1608) |
| SEQ ID NO:189 | AuroraBetaKinase(270-310)-MYPT1(6-39) |
| SEQ ID NO:193 | PPPIR1A(10-60)-NeurabinI(423-479) |
| SEQ ID NO:197 | PNUTS(383-449)-ScapininI(450-507) |

FIG. 1A

| | |
|---|---|
| SEQ ID NO:224 | PROTEIN PHOSPHATASE 1, SUBUNIT 12A [GALLUS GALLUS] (174-273)_plus_SPACER 1_plus_PROTEIN PHOSPHATASE 1,SUBUNIT 14A [HOMO SAPIENS] (30-36, 38-47)_plus_PROTEIN PHOSPHATASE 1,SUBUNIT 14A [HOMO SAPIENS] (48-67 G66E, M67A) |
| SEQ ID NO:227 | PROTEIN PHOSPHATASE 1, SUBUNIT 12A [GALLUS GALLUS] (4-83)_plus_SPACER 1_plus_PROTEIN PHOSPHATASE 1,SUBUNIT 14A [HOMO SAPIENS] (30-36, 38-47)_plus_PROTEIN PHOSPHATASE 1,SUBUNIT 14A [HOMO SAPIENS] (48-67 G66E, M67A) |
| SEQ ID NO:230 | PROTEIN PHOSPHATASE 1,SUBUNIT 14A [HOMO SAPIENS] (35-47)_plus_PROTEIN PHOSPHATASE 1,SUBUNIT 14A [HOMO SAPIENS] (48-67 G66E, M67A)_plus_PROTEIN PHOSPHATASE 1, SUBUNIT 12A [GALLUS GALLUS] (3-59) |
| SEQ ID NO:233 | PROTEIN PHOSPHATASE 1,SUBUNIT 14A [HOMO SAPIENS] (35-47)_plus_PROTEIN PHOSPHATASE 1,SUBUNIT 14A [HOMO SAPIENS] (48-67 G66E, M67A)_plus_PROTEIN PHOSPHATASE 1, SUBUNIT 12A [GALLUS GALLUS] (3-51) |
| SEQ ID NO:236 | PROTEIN PHOSPHATASE 1, SUBUNIT 12A [GALLUS GALLUS] (4-83)_plus_SPACER 3_plus_PHOSPHATASE INHIBITOR 1-LIKE PROTEIN [XENOPUS LAEVIS] (22-39)_plus_SPACER 5 |
| SEQ ID NO:239 | PROTEIN PHOSPHATASE 1, SUBUNIT 12A [GALLUS GALLUS] (4-48) (76-83)_plus_SPACER 3_plus_PHOSPHATASE INHIBITOR 1-LIKE PROTEIN [XENOPUS LAEVIS] (22-39)_plus_SPACER 5 |
| SEQ ID NO:242 | PROTEIN PHOSPHATASE 1, SUBUNIT 12A [GALLUS GALLUS] (4-48) (76-83)_plus_SPACER 3_plus_ PROTEIN PHOSPHATASE 1,SUBUNIT 14A [HOMO SAPIENS] (30-36, 38-47, T38D)_plus_SPACER 5 |
| SEQ ID NO:245 | PROTEIN PHOSPHATASE 1,SUBUNIT 14A [HOMO SAPIENS] (35-47, T38D)_plus_PROTEIN PHOSPHATASE 1,SUBUNIT 14A [HOMO SAPIENS] (48-67 G66E, M67A)_plus_PROTEIN PHOSPHATASE 1, SUBUNIT 12A [GALLUS GALLUS] (3-51) |
| SEQ ID NO:248 | PROTEIN PHOSPHATASE 1, SUBUNIT 12A [GALLUS GALLUS] (4-48) (76-83)_plus_SPACER 3_plus_PHOSPHATASE INHIBITOR 1-LIKE PROTEIN [XENOPUS LAEVIS] (22-39, T35D, T38D)_plus_SPACER 5 |

FIG. 1B

| LIGAND B | SPACER | LIGAND A |

FIGURE 4A

| LIGAND A | SPACER | LIGAND C | SPACER |

FIGURE 4B

| SPACER | LIGAND Y | SPACER | LIGAND Z |

FIGURE 4C

| LIGAND A | SPACER | LIGAND B | SPACER | LIGAND C | SPACER | LIGAND D |

FIGURE 4D

| LIGAND A | SPACER | LIGAND B | LIGAND C |

FIGURE 4E

| LIGAND A | LIGAND A | SPACER | LIGAND B | LIGAND C |

FIGURE 4F

| LIGAND A | SPACER | LIGAND B | SPACER | LIGAND C |

FIGURE 4G

| LIGAND X | LIGAND Y | SPACER | LIGAND Y | LIGAND X |

FIGURE 4H

| LIGAND X | SPACER | LIGAND Y | SPACER | LIGAND Z | SPACER | LIGAND Y |

FIGURE 4I

| LIGAND X | LIGAND X | LOCALIZATION SIGNAL |

FIGURE 7A

| LOCALIZATION SIGNAL | LIGAND X | LIGAND Y |

FIGURE 7B

| LIGAND B | LIGAND A | LOCALIZATION SIGNAL |

FIGURE 7C

| LOCALIZATION SIGNAL | LIGAND X | SPACER | LIGAND Y |

FIGURE 7D

| LIGAND X | SPACER | LIGAND Y | LIGAND B | LOCALIZATION SIGNAL |

FIGURE 7E

| LOCALIZATION SIGNAL | LIGAND A | LIGAND B | LIGAND C | LIGAND D |

FIGURE 7F

| LOCALIZATION SIGNAL | LIGAND Z |

FIGURE 7G

| LIGAND X | SPACER | LIGAND X | LOCALIZATION SIGNAL |

FIGURE 7H

| LOCALIZATION SIGNAL | LIGAND X | SPACER | LIGAND Y |

FIGURE 7I

| LIGAND A | LIGAND B | LIGAND C | LIGAND D | EPITOPE | LOCALIZATION SIGNAL |

FIGURE 8A

| LOCALIZATION SIGNAL | LIGAND X | LIGAND Y | EPITOPE |

FIGURE 8B

| LIGAND X | SPACER | LIGAND B | EPITOPE | LOCALIZATION SIGNAL |

FIGURE 8C

| LOCALIZATION SIGNAL | LIGAND X | SPACER | LIGAND Y | EPITOPE |

FIGURE 8D

| EPITOPE | LIGAND X | LIGAND Y | LIGAND B | LOCALIZATION SIGNAL |

FIGURE 8E

| LOCALIZATION SIGNAL | EPITOPE | LIGAND A | SPACER | LIGAND B |

FIGURE 8F

| EPITOPE | LIGAND B | LOCALIZATION SIGNAL |

FIGURE 8G

| LOCALIZATION SIGNAL | EPITOPE | SPACER | LIGAND A | SPACER | LIGAND B |

FIGURE 8H

| LIGAND X | SPACER | LIGAND Z | SPACER | EPITOPE | LOCALIZATION SIGNAL |

FIGURE 8I

| EPITOPE | LIGAND X | SPACER | LIGAND X | LOCALIZATION SIGNAL |

FIGURE 8J

| LOCALIZATION SIGNAL | LIGAND Z | SPACER | LIGAND Y | LIGAND B | EPITOPE |

FIGURE 8K

| PROMOTER | LIGAND or POLYLIGAND | EPITOPE | LOCALIZATION SIGNAL | STOP | POLY-A |

FIGURE 9A

| PROMOTER | OPTIONAL REPORTER | OPTIONAL EPITOPE | LIGAND or POLYLIGAND | OPTIONAL LOCALIZATION SIGNAL | STOP | POLY-A |

FIGURE 9B

| PROMOTER | LIGAND or POLYLIGAND | REPORTER | LOCALIZATION SIGNAL | STOP | POLY-A |

FIGURE 9C

| PROMOTER | LIGAND or POLYLIGAND | OPTIONAL EPITOPE | OPTIONAL REPORTER | OPTIONAL LOCALIZATION SIGNAL | STOP | POLY-A |

FIGURE 9D

| PROMOTER | LIGAND or POLYLIGAND | LOCALIZATION SIGNAL | STOP | POLY-A |

FIGURE 9E

| PROMOTER | LOCALIZATION SIGNAL | LIGAND or POLYLIGAND | STOP | POLY-A |

FIGURE 9F

| PROMOTER | LIGAND or POLYLIGAND | STOP | POLY-A |

| SEQ ID NO | VVN # | OD405 | % Inhibition | Inhibitor Concentration (nM) |
|---|---|---|---|---|
| 224 | 8387 | 0.299 | 25.7 % | 46 |
| 233 | 8390 | 0.181 | 55.0 % | 55 |
| 239 | 8392 | 0.299 | 25.7 % | 76 |
| 230 | 8389 | 0.27 | 33.0 % | 97 |
| 242 | 8393 | 0.298 | 26.1 % | 71 |
| 245 | 8394 | 0.248 | 38.4 % | 90 |
| 248 | 8395 | 0.246 | 38.9 % | 59 |
| 236 | 8391 | 0.512 | 0 % | 78 |
| Control (no inhibitor) | | 0.4025 | 0 % | |
| I-2 | | 0.169 | 58 % | 1000 |

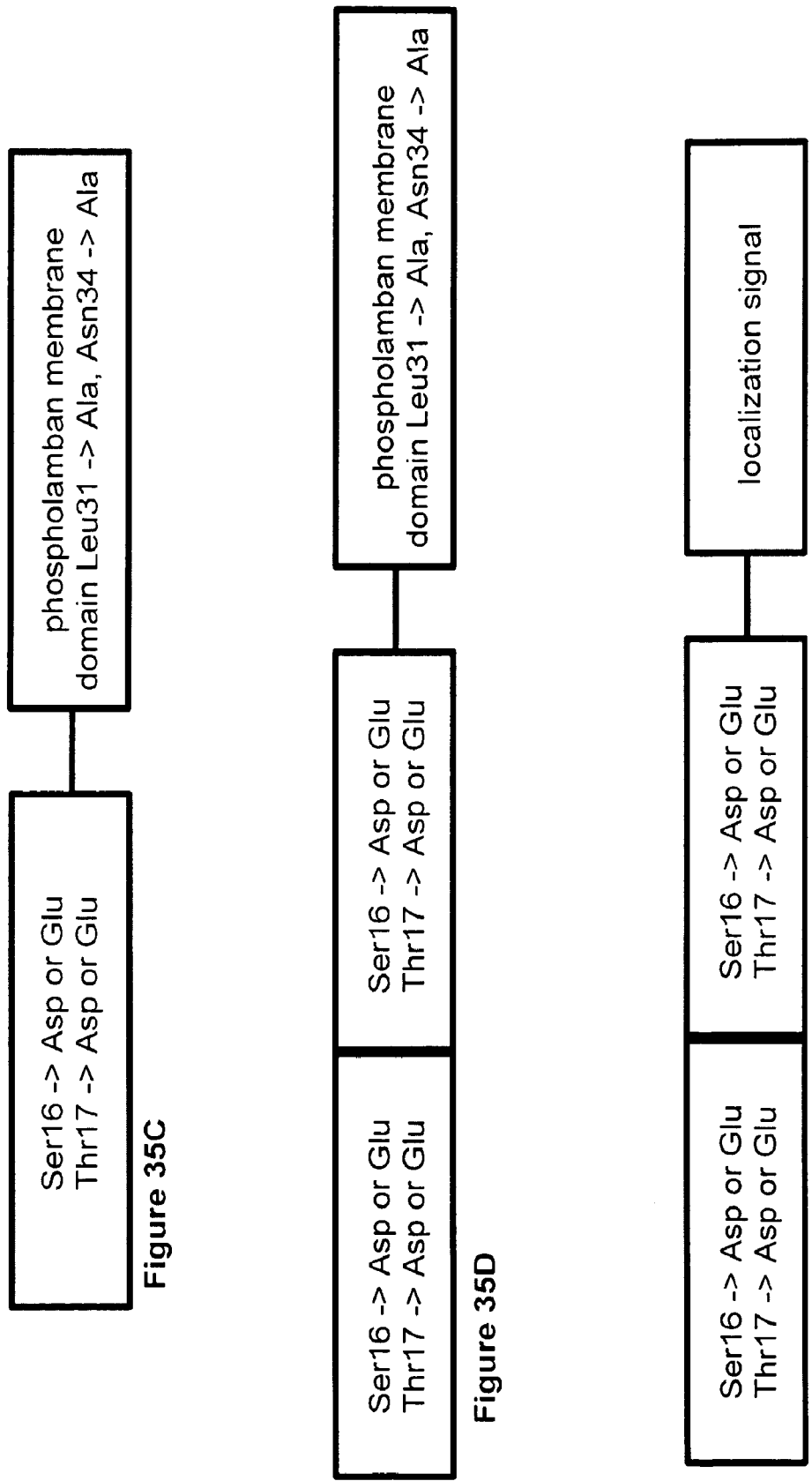

PHOSPHOLAMBAN (SEQ ID NO:112)
mekvqyltrs airrastiem pqqarqklqn lfinfclili cllliciivmll    WT PP1 INHIBITORS (SEQ ID NOS:114-136)
mekvqyltrs airraXXiem pqqarqklqn lfinfclili cllliciivmlX
mekvqyltrs airraXXiem pqqarqklqn lfinfclili cllliciivmXl
mekvqyltrs airraXXiem pqqarqklqn lfinfclili cllliciivXll
mekvqyltrs airraXXiem pqqarqklqn lfinfclili cllliciiXmll
mekvqyltrs airraXXiem pqqarqklqn lfinfclili clliciXvmll
mekvqyltrs airraXXiem pqqarqklqn lfinfclili cllicXivmll
mekvqyltrs airraXXiem pqqarqklqn lfinfclili clliXiivmll
mekvqyltrs airraXXiem pqqarqklqn lfinfclili clllXciivmll
mekvqyltrs airraXXiem pqqarqklqn lfinfclili cllXiciivmll
mekvqyltrs airraXXiem pqqarqklqn lfinfclili clXliciivmll
mekvqyltrs airraXXiem pqqarqklqn lfinfclili cXlliciivmll
mekvqyltrs airraXXiem pqqarqklqn lfinfclili Xllliciivmll
mekvqyltrs airraXXiem pqqarqklqn lfinfclilX cllliciivmll
mekvqyltrs airraXXiem pqqarqklqn lfinfcliXi cllliciivmll
mekvqyltrs airraXXiem pqqarqklqn lfinfclXli cllliciivmll
mekvqyltrs airraXXiem pqqarqklqn lfinfcXili cllliciivmll
mekvqyltrs airraXXiem pqqarqklqn lfinfXlili cllliciivmll
mekvqyltrs airraXXiem pqqarqklqn lfinXclili cllliciivmll
mekvqyltrs airraXXiem pqqarqklqn lfiXfclili cllliciivmll
mekvqyltrs airraXXiem pqqarqklqn lfXnfclili cllliciivmll
mekvqyltrs airraXXiem pqqarqklqn lXinfclili cllliciivmll
mekvqyltrs airraXXiem pqqarqklqn Xfinfclili cllliciivmll mekvqyltrs airraXXiem pqqarqklqn XfiXfclili cllliciivmll

Figure 36 mekvqyltrs airrastiem pqqarqklqn lfinfclili clllicii vmll (SEQ ID NO:112)

mekvqyltrs airraXtiem pqqarqklqn (SEQ ID NO:137)
mekvqyltrs airrasXiem pqqarqklqn (SEQ ID NO:138)
mekvqyltrs airraXXiem pqqarqklqn (SEQ ID NO:139)
mDkvqyltrs airraXXiem pqqarqklqn (SEQ ID NO:140)
mekvqyItrs airraXXiem pqqarqklqn (SEQ ID NO:141)
mekvqyltrs aLrraXXiem pqqarqklqn (SEQ ID NO:142)
mekvqyltrs airraXtiem (SEQ ID NO:143)
mekvqyltrs airrasXiem (SEQ ID NO:144)
mekvqyltrs airraXXiem (SEQ ID NO:145)
mDkvqyltrs airraXXiem (SEQ ID NO:146)
mekvqyItrs airraXXiem (SEQ ID NO:147)
mekvqyltrs aLrraXXiem (SEQ ID NO:148)
mekvqyltrs airraXXie (SEQ ID NO:152)
mDkvqyltrs airraXXie (SEQ ID NO:153)
mekvqyItrs airraXXie (SEQ ID NO:154)
mekvqyltrs aLrraXXie (SEQ ID NO:155)
mekvqyltrs GirraXXie (SEQ ID NO:156)
mekvqyltrs GirraXXiem (SEQ ID NO:149)
mDkvqyltrs GirraXXiem (SEQ ID NO:150)
mekvqyItrs GirraXXiem (SEQ ID NO:151)
s airraXXiem pqqarqklqn (SEQ ID NO:157)
s GirraXXiem pqqarqklqn (SEQ ID NO:158)
s airraXXiem pqqGrqklqn (SEQ ID NO:159)
s airraXXiem pqqarqkIqn (SEQ ID NO:160)
airraXXiem pqqarqklq (SEQ ID NO:161)
GirraXXiem pqqarqklq (SEQ ID NO:162)
airraXXiem pqqGrqklq (SEQ ID NO:163)
airraXXiem pqqarqkIq (SEQ ID NO:164)

Figure 37

PP1 INHIBITOR = (MONOMER X)1-n where n is an integer

FIGURE 38A

PP1 INHIBITOR = (mekvqyltrsairraXXiem)1-n where n is an integer and X is either Asp or Glu

| SEQ ID NO | VVN # | OD405 | % Inhibition | Inhibitor Concentration (nM) |
|---|---|---|---|---|
| 1 | 8319 | 0.460 | 0 | |
| 5 | 8320 | 0.489 | 0 | |
| 9 | 8321 | 0.484 | 0 | |
| 17 | 8323 | 0.503 | 0 | |
| 25 | 8325 | 0.456 | 0 | |
| 29 | 8326 | 0.489 | 0 | |
| 33 | 8327 | 0.478 | 0 | |
| 37 | 8328 | 0.482 | 0 | |
| Positive Control | | 0.414 | | |
| I-2 | | 0.077 | 82 % | 1000 |
| I-2 | | 0.222 | 46 % | 10 |

SEQUENCE LISTING

```
<160> NUMBER OF SEQ ID NOS: 273

<210> SEQ ID NO 1
<211> LENGTH: 249
<212> TYPE: PRT
<213> ORGANISM: artificial sequence
<220> FEATURE:
<223> OTHER INFORMATION: synthetic

<400> SEQUENCE: 1

Glu Asp Asp Glu Leu Lys Gly Leu Leu Gly Leu Pro Glu Glu Glu Ala
1               5                   10                  15

Glu Leu Asp Asn Leu Thr Glu Phe Asn Thr Ala His Asn Lys Arg Ile
            20                  25                  30

Ala Thr Leu Thr Ile Glu Glu Gly Asn Leu Asp Ile Gln Arg Pro Lys
        35                  40                  45

Arg Lys Arg Lys Asn Ala Arg Val Thr Phe Ala Glu Asp Asp Glu Ile
    50                  55                  60

Ile Asn Pro Glu Asp Val Asp Pro Ser Val Gly Arg Phe Arg Pro Gly
65                  70                  75                  80
```

```
Ala Gly Gly Arg Arg Thr Glu Leu Cys Gly Thr Leu Asp Tyr Leu Pro
                85                  90                  95

Pro Glu Pro Gly Ala Ala Gly Ala Ala Gln Arg Leu Gly Lys Arg Val
            100                 105                 110

Leu Ser Lys Leu Gln Ser Pro Ser Arg Ala Arg Gly Pro Gly Gly Ser
        115                 120                 125

Pro Gly Gly Leu Gln Lys Arg His Ala Arg Val Glu Val Lys Tyr Asp
    130                 135                 140

Arg Arg Glu Leu Gln Arg Arg Leu Asp Val Glu Lys Trp Ile Asp Gly
145                 150                 155                 160

Arg Leu Glu Glu Leu Tyr Arg Gly Met Glu Ala Asp Met Pro Asp Glu
                165                 170                 175

Ile Asn Ile Asp Glu Leu Leu Glu Leu Glu Ser Glu Glu Glu Arg Ser
            180                 185                 190

Arg Lys Ile Gln Gly Leu Leu Lys Ser Cys Gly Lys Pro Val Glu Asp
        195                 200                 205

Phe Ile Gln Glu Leu Leu Ala Lys Leu Gln Gly Leu His Arg Gln Pro
    210                 215                 220

Gly Leu Arg Gln Pro Ser Pro Ser His Asp Gly Ser Leu Ser Pro Leu
225                 230                 235                 240

Gln Asp Arg Ala Arg Thr Ala His Pro
                245
```

<210> SEQ ID NO 2
<211> LENGTH: 747
<212> TYPE: DNA
<213> ORGANISM: artificial sequence
<220> FEATURE:
<223> OTHER INFORMATION: synthetic

<400> SEQUENCE: 2

```
gaggacgacg agctgaaggg cctgctggga ctgcccgagg aggaggccga gctggacaac      60
ctgaccgagt caacaccgc ccacaacaag aggatcgcca ccctgaccat cgaggagggc     120
aacctggaca tccagaggcc aagaggaaa aggaagaacg ccagggtgac cttcgccgag     180
gacgacgaga tcatcaaccc cgaggacgtg accccagcg tgggcagatt caggcccggc     240
gccggaggca ggaggaccga gctgtgcggc accctggact acctcccccc cgagcccggc     300
gccgccggag ccgcccagag gctgggcaag agggtgctga gcaagctgca gagccccagc     360
agggccaggg gccccggcgg aagcccccgg ggactgcaga aaaggcacgc cagggtggag     420
gtgaagtacg acaggaggga gctgcagagg aggctggacg tggagaagtg gatcgacggc     480
aggctggagg agctgtacag gggcatggag gccgacatgc ccgacgagat caacatcgac     540
gagctgctgg agctggagag cgaggaggag aggagcagga gatccaggg cctgctgaaa     600
agctgcggca agcccgtgga ggacttcatc caggagctgc tggccaagct gcagggcctc     660
cacaggcagc ccggcctgag gcagcccagc cccagccacg acggaagcct gagcccctg     720
caagacaggg ccaggaccgc ccacccc                                         747
```

<210> SEQ ID NO 3
<211> LENGTH: 781
<212> TYPE: DNA
<213> ORGANISM: artificial sequence
<220> FEATURE:
<223> OTHER INFORMATION: synthetic

<400> SEQUENCE: 3

```
gctagcgccg gcgaggacga cgagctgaag ggcctgctgg gactgcccga ggaggaggcc      60
```

```
gagctggaca acctgaccga gttcaacacc gcccacaaca agaggatcgc caccctgacc    120
atcgaggagg gcaacctgga catccagagg cccaagagga aaaggaagaa cgccagggtg    180
accttcgccg aggacgacga gatcatcaac cccgaggacg tggacccag cgtgggcaga     240 ttcaggcccg gcgccggagg caggaggacc gagctgtgcg gcaccctgga ctacctcccc    300
cccgagcccg gcgccgccgg agccgcccag aggctgggca gagggtgct gagcaagctg    360 cagagcccca gcagggccag ggcccccggc ggaagcccg gcggactgca gaaaaggcac     420
gccagggtgg aggtgaagta cgacaggagg gagctgcaga ggaggctgga cgtggagaag    480
tggatcgacg gcaggctgga ggagctgtac aggggcatgg aggccgacat gcccgacgag    540
atcaacatcg acgagctgct ggagctggag agcgaggagg agaggagcag aagatccag    600 ggcctgctga aaagctgcgg caagcccgtg gaggacttca tccaggagct gctggccaag    660
ctgcagggcc tccacaggca gcccggcctg aggcagccca gccccagcca cgacggaagc    720
ctgagccccc tgcaagacag ggccaggacc gccaccccc cgggggagg cggaatcgat     780 t                                                                    781

<210> SEQ ID NO 4
<211> LENGTH: 790
<212> TYPE: DNA
<213> ORGANISM: artificial sequence
<220> FEATURE:
<223> OTHER INFORMATION: synthetic

<400> SEQUENCE: 4
gctagcgcca ccatggccgg cgaggacgac gagctgaagg gcctgctggg actgcccgag     60
gaggaggccg agctggacaa cctgaccgag ttcaacaccg cccacaacaa gaggatcgcc    120
accctgacca tcgaggaggg caacctggac atccagaggc ccaagaggaa aaggaagaac    180
gccagggtga ccttcgccga ggacgacgag atcatcaacc ccgaggacgt ggaccccagc    240
gtgggcagat tcaggcccgg cgccggaggc aggaggaccg agctgtgcgg caccctggac    300
tacctccccc ccgagcccgg cgccgccgga gccgcccaga ggctgggcaa gagggtgctg    360
agcaagctgc agagccccag cagggccagg gcccccggcg aagcccggc ggactgcag     420 aaaaggcacg ccagggtgga ggtgaagtac gacaggaggg agctgcagag gaggctggac    480
gtggagaagt ggatcgacgg caggctggag gagctgtaca ggggcatgga ggccgacatg    540
cccgacgaga tcaacatcga cgagctgctg gagctggaga gcgaggagga gaggagcagg    600
aagatccagg gcctgctgaa aagctgcggc aagcccgtgg aggacttcat ccaggagctg    660
ctggccaagc tgcagggcct ccacaggcag cccggcctga ggcagcccag ccccagccac    720
gacggaagcc tgagccccct gcaagacagg gccaggaccg ccaccccc cggggggagg    780 ggaatcgatt                                                          790

<210> SEQ ID NO 5
<211> LENGTH: 247
<212> TYPE: PRT
<213> ORGANISM: artificial sequence
<220> FEATURE:
<223> OTHER INFORMATION: synthetic

<400> SEQUENCE: 5

Arg Lys Leu Asn Gln Arg Pro Thr Val Asp Glu Leu Arg Asp Arg Lys
1               5                   10                  15

Ile Leu Ile Arg Phe Ser Asp Tyr Val Glu Val Ala Lys Ala Gln Asp
            20                  25                  30
```

```
Tyr Asp Arg Arg Ala Asp Lys Pro Trp Thr Arg Leu Ser Ala Ala Asp
         35                  40                  45

Lys Ala Ala Ile Arg Lys Glu Leu Asn Glu Tyr Lys Ser Asn Glu Met
 50                  55                  60

Glu Val His Ala Ser Ser Lys His Leu Thr Arg Phe His Arg Pro Pro
 65                  70                  75                  80

Gly Ala Gly Gly Glu Glu Pro Gln Ser Asp Pro Ser Val Glu Pro Pro
                 85                  90                  95

Leu Ser Gln Glu Thr Phe Ser Asp Leu Trp Lys Leu Leu Pro Glu Asn
                100                 105                 110

Asn Val Leu Ser Pro Leu Pro Ser Gln Ala Met Asp Asp Leu Met Leu
            115                 120                 125

Ser Pro Asp Asp Ile Glu Gln Trp Phe Thr Glu Asp Pro Gly Pro Pro
            130                 135                 140

Gly Ala Ala Gly Glu Gln Asp Asn Ser Pro Gln Lys Ile Gln Phe Thr
145                 150                 155                 160

Val Pro Leu Leu Glu Pro His Leu Asp Pro Glu Ala Ala Glu Gln Ile
                165                 170                 175

Arg Arg Arg Arg Pro Thr Pro Ala Thr Leu Val Leu Thr Ser Asp Gln
                180                 185                 190

Ser Ser Pro Glu Ile Asp Glu Asp Arg Ile Pro Asn Pro His Leu Lys
            195                 200                 205

Ser Thr Leu Ala Met Ser Pro Arg Gln Arg Lys Lys Met Thr Arg Ile
    210                 215                 220

Thr Pro Thr Met Lys Glu Leu Gln Met Met Val Glu His His Leu Gly
225                 230                 235                 240

Gln Gln Gln Gln Gly Glu Glu
                245

<210> SEQ ID NO 6
<211> LENGTH: 741
<212> TYPE: DNA
<213> ORGANISM: artificial sequence
<220> FEATURE:
<223> OTHER INFORMATION: synthetic

<400> SEQUENCE: 6
aggaagctga accagaggcc caccgtggac gagctgaggg acaggaagat cctgatcagg      60
ttcagcgact acgtggaggt ggccaaggcc caggactacg acaggagggc cgacaagccc     120
tggaccaggc tgagcgccgc cgacaaagcc gccatcagga aggagctgaa cgagtacaag     180
agcaacgaga tggaggtcca cgccagcagc aagcacctga ccaggttcca caggcccccc     240
ggcgccggag gcgaggagcc ccagagcgac cccagcgtgg agccccccct gagccaggag     300
accttcagcg acctgtggaa gctgctgccc gagaacaacg tgctgagccc cctgcccagc     360
caggccatgg acgacctgat gctgagcccc gacgacatcg agcagtggtt caccgaggac     420
cccggccccc ccggagccgc cggagagcag gacaacagcc cccagaagat ccagttcacc     480
gtgcccctgc tggagcccca cctggacccc gaggccgccg agcagatcag gaggaggagg     540
cccacccccg ccaccctggt gctgaccagc gaccagagca gccccgagat cgacgaggac     600
aggattccca accccacct gaaaagcacc ctggccatga gccccaggca gaggaagaag     660
atgaccagga tcacccccac catgaaggag ctgcagatga tggtggagca ccacctgggc     720
cagcagcagc agggcgagga g                                               741
```

<210> SEQ ID NO 7
<211> LENGTH: 775
<212> TYPE: DNA
<213> ORGANISM: artificial sequence
<220> FEATURE:
<223> OTHER INFORMATION: synthetic

<400> SEQUENCE: 7

```
gctagcgccg gcaggaagct gaaccagagg cccaccgtgg acgagctgag ggacaggaag      60
atcctgatca ggttcagcga ctacgtggag gtggccaagg cccaggacta cgacaggagg     120
gccgacaagc cctggaccag gctgagcgcc gccgacaaag ccgccatcag gaaggagctg     180
aacgagtaca gagcaacga gatggaggtc cacgccagca gcaagcacct gaccaggttc      240
cacaggcccc ccggcgccgg aggcgaggag ccccagagcg accccagcgt ggagcccccc     300
ctgagccagg agaccttcag cgacctgtgg aagctgctgc ccgagaacaa cgtgctgagc     360
cccctgccca gccaggccat ggacgacctg atgctgagcc ccgacgacat cgagcagtgg     420
ttcaccgagg accccggccc ccccggagcc gccggagagc aggacaacag cccccagaag     480
atccagttca ccgtgcccct gctggagccc cacctggacc ccgaggccgc cgagcagatc     540
aggaggagga ggcccacccc cgccaccctg gtgctgacca cgaccagag cagccccgag      600
atcgacgagg acaggattcc caaccccac ctgaaaagca ccctggccat gagccccagg      660
cagaggaaga agatgaccag gatcaccccc ccatgaagg agctgcagat gatggtggag      720
caccacctgg ccagcagca gcagggcgag gagcccgggg gaggcggaat cgatt            775
```

<210> SEQ ID NO 8
<211> LENGTH: 784
<212> TYPE: DNA
<213> ORGANISM: artificial sequence
<220> FEATURE:
<223> OTHER INFORMATION: synthetic

<400> SEQUENCE: 8

```
gctagcgcca ccatggccgg caggaagctg aaccagaggc ccaccgtgga cgagctgagg      60
gacaggaaga tcctgatcag gttcagcgac tacgtggagg tggccaaggc ccaggactac     120
gacaggaggg ccgacaagcc ctggaccagg ctgagcgccg ccgacaaagc cgccatcagg     180
aaggagctga cgagtacaa gagcaacgag atggaggtcc acgccagcag caagcacctg      240
accaggttcc acaggccccc cggcgccgga ggcgaggagc cccagagcga ccccagcgtg     300
gagcccccc tgagccagga gaccttcagc gacctgtgga agctgctgcc cgagaacaac      360
gtgctgagcc cctgcccag ccaggccatg gacgacctga tgctgagccc cgacgacatc      420
gagcagtggt tcaccgagga ccccggcccc ccggagccg ccggagagca ggacaacagc      480
ccccagaaga tccagttcac cgtgcccctg ctggagcccc acctggaccc cgaggccgcc     540
gagcagatca ggaggaggag gcccaccccc gccaccctgg tgctgaccag cgaccagagc     600
agccccgaga tcgacgagga caggattccc aaccccacc tgaaaagcac cctggccatg      660
agccccaggc agaggaagaa gatgaccagg atcaccccca ccatgaagga gctgcagatg     720
atggtggagc accacctggg ccagcagcag cagggcgagg agcccggggg aggcggaatc     780
gatt                                                                  784
```

<210> SEQ ID NO 9
<211> LENGTH: 229
<212> TYPE: PRT
<213> ORGANISM: artificial sequence
<220> FEATURE:
<223> OTHER INFORMATION: synthetic

<400> SEQUENCE: 9

Lys Thr Glu Pro Arg Gly Pro Gly Gly Pro Leu Arg Ser Ala Ser Pro
1               5                   10                  15

His Arg Ser Ala Tyr Glu Ala Gly Ile Gln Ala Leu Lys Pro Pro Asp
            20                  25                  30

Ala Pro Gly Pro Asp Glu Ala Pro Lys Gly Ala His His Lys Lys Tyr
        35                  40                  45

Gly Ser Asn Val His Arg Ile Lys Ser Met Phe Leu Gln Met Gly Thr
    50                  55                  60

Thr Ala Gly Pro Ser Gly Glu Ala Gly Gly Ala Gly Leu Ala Glu
65                  70                  75                  80

Ala Pro Arg Ala Ser Glu Arg Gly Val Arg Leu Ser Leu Pro Arg Ala
                85                  90                  95

Ser Ser Leu Asn Glu Asn Val Asp His Ser Ala Leu Leu Lys Leu Gly
            100                 105                 110

Thr Ser Val Ser Glu Arg Val Ser Arg Phe Asp Ser Lys Pro Gly Gly
        115                 120                 125

Ala Gly Lys Met Ala Asp Ala Lys Gln Lys Arg Asn Glu Gln Leu Lys
    130                 135                 140

Arg Trp Ile Gly Asp Glu Thr Asp Leu Glu Pro Pro Val Val Lys Arg
145                 150                 155                 160

Gln Lys Thr Lys Val Lys Phe Asp Asp Gly Ala Val Phe Leu Ala Ala
                165                 170                 175

Cys Ser Ser Gly Asp Thr Asp Glu Val Leu Lys Leu Leu Pro Gly Ala
            180                 185                 190

Ala Gly Asp Pro Lys Asp Arg Lys Lys Ile Gln Phe Ser Val Pro Ala
        195                 200                 205

Pro Pro Ser Gln Leu Asp Pro Arg Gln Val Glu Met Ile Arg Arg Arg
    210                 215                 220

Arg Pro Thr Pro Ala
225

<210> SEQ ID NO 10
<211> LENGTH: 687
<212> TYPE: DNA
<213> ORGANISM: artificial sequence
<220> FEATURE:
<223> OTHER INFORMATION: synthetic

<400> SEQUENCE: 10

```
aagaccgagc ccaggggccc cggcggaccc ctgaggagcg ccagccccca caggagcgcc      60
tacgaagccg gaatccaggc cctgaagccc ccgacgccc ccggcccga cgaggccccc       120
aagggcgccc accacaagaa gtacggcagc aacgtgcata ggatcaagag catgttcctg     180
cagatgggca ccaccgccgg acccagcggc gaggccggag cggcgccgg actcgccgag      240
gcccccagag ccagcgagag gggcgtgagg ctgagcctgc caggggccag cagcctgaac     300
gagaacgtgg accacagcgc cctgctgaag ctgggcacca gcgtgagcga gagggtgtcc     360
aggttcgaca gcaagcccgg cggcgccgga aagatggccg acgccaagca gaaaaggaac     420
gagcagctga aaaggtggat cggcgacgag accgacctgg agccccccgt ggtgaaaagg     480
cagaagacca aggtgaagtt cgacgacggc gccgtgttcc tggccgcctg cagcagcggc     540
gacaccgacg aggtgctgaa gctgctgccc ggcgccgccg agacccccaa ggacaggaag     600
aagatccagt tcagcgtgcc cgccccccc agccagctcg accccaggca agtcgagatg       660
```

```
atcaggagga ggaggcccac ccccgcc                                         687
```

<210> SEQ ID NO 11
<211> LENGTH: 721
<212> TYPE: DNA
<213> ORGANISM: artificial sequence
<220> FEATURE:
<223> OTHER INFORMATION: synthetic

<400> SEQUENCE: 11

```
gctagcgccg gcaagaccga gcccaggggc cccggcggac ccctgaggag cgccagcccc    60
cacaggagcg cctacgaagc cggaatccag gccctgaagc ccccgacgc ccccggcccc    120
gacgaggccc ccaagggcgc ccaccacaag aagtacggca gcaacgtgca taggatcaag    180
agcatgttcc tgcagatggg caccaccgcc ggacccagcg cgaggccgg aggcggcgcc     240
ggactcgccg aggcccccag agccagcgag aggggcgtga ggctgagcct gcccagggcc    300
agcagcctga cgagaacgt ggaccacagc gccctgctga gctgggcac cagcgtgagc     360
gagagggtgt ccaggttcga cagcaagccc ggcggcgccg aaagatggc cgacgccaag     420
cagaaaagga cgagcagct gaaaaggtgg atcggcgacg agaccgacct ggagcccccc    480
gtggtgaaaa ggcagaagac caaggtgaag ttcgacgacg cgccgtgtt cctggccgcc    540
tgcagcagcg cgacaccga cgaggtgctg aagctgctgc ccggcgccgc cggagacccc    600
aaggacagga agaagatcca gttcagcgtg cccgccccc ccagccagct cgaccccagg     660
caagtcgaga tgatcaggag gaggaggccc accccgccc cggggagg cggaatcgat      720
t                                                                  721
```

<210> SEQ ID NO 12
<211> LENGTH: 730
<212> TYPE: DNA
<213> ORGANISM: artificial sequence
<220> FEATURE:
<223> OTHER INFORMATION: synthetic

<400> SEQUENCE: 12

```
gctagcgcca ccatggccgg caagaccgag cccaggggcc ccggcggacc cctgaggagc    60
gccagccccc acaggagcgc ctacgaagcc ggaatccagg ccctgaagcc ccccgacgcc   120
cccggccccc acgaggcccc caagggcgcc caccacaaga agtacggcag caacgtgcat   180
aggatcaaga gcatgttcct gcagatgggc accaccgccg gacccagcgg cgaggccgga   240
ggcggcgccg gactcgccga ggcccccaga gccagcgaga gggggcgtgag gctgagcctg   300
cccagggcca gcagcctgaa cgagaacgtg gaccacagcg ccctgctgaa gctgggcacc   360
agcgtgagcg agagggtgtc caggttcgac agcaagcccg gcggcgccgg aaagatggcc   420
gacgccaagc agaaaaggaa cgagcagctg aaaaggtgga tcggcgacga gaccgacctg   480
gagcccccg tggtgaaaag gcagaagacc aaggtgaagt tcgacgacgg cgccgtgttc    540
ctggccgcct gcagcagcgg cgacaccgac gaggtgctga agctgctgcc cggcgccgcc   600
ggagacccca aggacaggaa gaagatccag ttcagcgtgc ccgccccccc cagccagctc   660
gaccccaggc aagtcgagat gatcaggagg aggaggccca ccccgcccc cggggaggc    720
ggaatcgatt                                                         730
```

<210> SEQ ID NO 13
<211> LENGTH: 238
<212> TYPE: PRT
<213> ORGANISM: artificial sequence
<220> FEATURE:

<223> OTHER INFORMATION: synthetic

<400> SEQUENCE: 13

```
Gly Asp Pro Asn Gln Leu Thr Arg Lys Gly Arg Lys Arg Lys Ser Val
1               5                   10                  15

Thr Trp Pro Glu Glu Gly Lys Leu Arg Glu Tyr Phe Tyr Phe Glu Leu
            20                  25                  30

Asp Glu Thr Glu Arg Val Asn Val Asn Lys Ile Lys Asp Phe Gly Glu
        35                  40                  45

Ala Ala Lys Arg Glu Ile Leu Ser Asp Arg His Ala Phe Glu Thr Ala
50                  55                  60

Arg Arg Pro Gly Gly Ala Gly Tyr Asp Pro Thr Ser Pro Asn Tyr Asp
65                  70                  75                  80

Pro Thr Ser Pro Asn Tyr Thr Pro Thr Ser Pro Ser Tyr Asp Pro Thr
                85                  90                  95

Ser Pro Ser Tyr Asp Pro Thr Ser Pro Asn Tyr Thr Pro Thr Ser Pro
            100                 105                 110

Asn Tyr Asp Pro Thr Ser Pro Ser Tyr Asp Pro Thr Ser Pro Ser Pro
        115                 120                 125

Gly Ala Ala Gly Ser Cys Thr Arg Met Ile Gln Val Leu Asp Pro Arg
130                 135                 140

Pro Leu Thr Ser Ser Val Met Pro Val Asp Val Ala Met Arg Leu Cys
145                 150                 155                 160

Leu Ala His Ser Pro Pro Val Lys Ser Phe Leu Gly Pro Tyr Asp Glu
                165                 170                 175

Phe Gln Arg Arg His Phe Val Asn Lys Leu Lys Pro Leu Lys Ser Cys
            180                 185                 190

Leu Asn Ile Lys His Lys Ala Lys Ser Gln Asn Asp Trp Lys Cys Ser
        195                 200                 205

His Asn Gln Ala Lys Lys Arg Val Val Phe Ala Asp Ser Lys Gly Leu
210                 215                 220

Ser Leu Thr Ala Ile His Val Phe Ser Asp Leu Pro Glu Glu
225                 230                 235
```

<210> SEQ ID NO 14
<211> LENGTH: 714
<212> TYPE: DNA
<213> ORGANISM: artificial sequence
<220> FEATURE:
<223> OTHER INFORMATION: synthetic

<400> SEQUENCE: 14

```
ggcgacccca accagctgac caggaagggc aggaaaagga aaagcgtgac ctggcccgag    60
gagggcaagc tgagggagta cttctacttc gagctggacg agaccgagag ggtgaacgtg   120
aacaagatca aggacttcgg cgaggccgcc aagagggaga tcctgagcga caggcacgcc   180
ttcgagaccg ccaggaggcc cggcggcgcc ggatacgacc ccaccagccc caactacgac   240
cccaccagcc caactacac cccaccagc cccagctacg accccaccag cccagctac    300
gaccccacca gccccaacta cacccccacc agccccaact acgaccccac cagcccagc   360
tacgaccccca ccagcccag ccccggcgcc gccggaagct gcaccaggat gatccaggtg   420
ctggacccca ggccctgac cagcagcgtg atgcccgtgg acgtggccat gaggctgtgc   480
ctggcccaca gcccccccgt gaaaagcttc ctgggcccct acgacgagtt ccagaggagg   540
cacttcgtca acaagctgaa gcccctgaaa agctgcctga acatcaagca caaggccaag   600
agccagaacg actggaagtg cagccacaac caggccaaga aagggtggt gttcgccgac   660
```

```
agcaagggcc tgagcctgac cgccatccac gtcttcagcg acctccccga ggag      714
```

<210> SEQ ID NO 15
<211> LENGTH: 748
<212> TYPE: DNA
<213> ORGANISM: artificial sequence
<220> FEATURE:
<223> OTHER INFORMATION: synthetic

<400> SEQUENCE: 15

```
gctagcgccg gcggcgaccc caaccagctg accaggaagg gcaggaaaag gaaaagcgtg    60
acctggcccg aggagggcaa gctgagggag tacttctact tcgagctgga cgagaccgag   120
agggtgaacg tgaacaagat caaggacttc ggcgaggccg ccaagaggga gatcctgagc   180
gacaggcacg ccttcgagac cgccaggagg cccggcggcg ccggatacga ccccaccagc   240
cccaactacg accccaccag ccccaactac accccccacca gcccagcta cgaccccacc   300
agccccagct acgaccccac cagccccaac tacacccccca ccagcccaa ctacgacccc   360
accagcccca gctacgaccc caccagcccc agccccggcg ccgccggaag ctgcaccagg   420
atgatccagg tgctggaccc caggccctg accagcagcg tgatgcccgt ggacgtggcc   480
atgaggctgt gcctggccca gccccccccg tgaaaagct tcctgggccc ctacgacgag   540
ttccagagga ggcacttcgt caacaagctg aagccctga aaagctgcct gaacatcaag   600
cacaaggcca gagccagaa cgactggaag tgcagccaca ccaggccaa gaaaagggtg   660
gtgttcgccg acagcaaggg cctgagcctg accgccatcc acgtcttcag cgacctcccc   720
gaggagcccg ggggaggcgg aatcgatt                                     748
```

<210> SEQ ID NO 16
<211> LENGTH: 757
<212> TYPE: DNA
<213> ORGANISM: artificial sequence
<220> FEATURE:
<223> OTHER INFORMATION: synthetic

<400> SEQUENCE: 16

```
gctagcgcca ccatggccgg cggcgacccc aaccagctga ccaggaaggg caggaaaagg    60
aaaagcgtga cctggcccga ggagggcaag ctgagggagt acttctactt cgagctggac   120
gagaccgaga gggtgaacgt gaacaagatc aaggacttcg gcgaggccgc caagagggag   180
atcctgagcg acaggcacgc cttcgagacc gccaggaggc ccggcggcgc cggatacgac   240
cccaccagcc ccaactacga ccccaccagc cccaactaca ccccccaccag ccccagctac   300
gaccccacca gccccagcta cgaccccacc agccccaact acaccccccac cagccccaac   360
tacgaccccca ccagccccag ctacgacccc accagcccca gccccggcgc cgccggaagc   420
tgcaccagga tgatccaggt gctggacccc aggcccctga ccagcagcgt gatgcccgtg   480
gacgtggcca tgaggctgtg cctggcccac agccccccccg tgaaaagctt cctgggcccc   540
tacgacgagt tccagaggag gcacttcgtc aacaagctga agcccctgaa aagctgcctg   600
aacatcaagc acaaggccaa gagccagaac gactggaagt gcagccacaa ccaggccaag   660
aaaagggtgg tgttcgccga cagcaagggc ctgagcctga ccgccatcca cgtcttcagc   720
gacctccccg aggagcccgg gggaggcgga atcgatt                            757
```

<210> SEQ ID NO 17
<211> LENGTH: 316
<212> TYPE: PRT
<213> ORGANISM: artificial sequence
<220> FEATURE:
<223> OTHER INFORMATION: synthetic

<400> SEQUENCE: 17

Ala Ala Gln Arg Leu Gly Lys Arg Val Leu Ser Lys Leu Gln Ser Pro
1               5                   10                  15

Ser Arg Ala Arg Gly Pro Gly Ser Pro Gly Gly Leu Gln Lys Arg
            20                  25                  30

His Ala Arg Val Glu Val Lys Tyr Asp Arg Arg Glu Leu Gln Arg Arg
            35                  40                  45

Leu Asp Val Glu Lys Trp Ile Asp Gly Arg Glu Leu Tyr Arg Gly
    50                  55                  60

Met Glu Ala Asp Met Pro Asp Glu Ile Asn Ile Asp Glu Leu Leu Glu
65                  70                  75                  80

Leu Glu Ser Glu Glu Glu Arg Ser Arg Lys Ile Gln Gly Leu Leu Lys
                85                  90                  95

Ser Cys Gly Lys Pro Val Glu Asp Phe Ile Gln Glu Leu Leu Ala Lys
            100                 105                 110

Leu Gln Gly Leu His Arg Gln Pro Gly Leu Arg Gln Pro Ser Pro Ser
        115                 120                 125

His Asp Gly Ser Leu Ser Pro Leu Gln Asp Arg Ala Arg Thr Ala His
    130                 135                 140

Pro Pro Gly Ala Gly His Ile Pro Arg Ser Pro Tyr Lys Phe Pro Ser
145                 150                 155                 160

Ser Pro Leu Arg Ile Pro Gly Gly Asn Ile Tyr Ile Ser Pro Leu Lys
                165                 170                 175

Ser Pro Tyr Lys Ile Ser Glu Gly Leu Pro Asp Pro Thr Lys Met Asp
            180                 185                 190

Pro Arg Ser Arg Ile Leu Val Ser Ile Gly Glu Ser Phe Gly Thr Ser
        195                 200                 205

Glu Lys Phe Gln Lys Ile Asn Gln Met Val Cys Asn Ser Asp Arg Val
210                 215                 220

Leu Lys Arg Ser Ala Glu Gly Ser Asn Pro Gly Ala Ala Gly Glu Asp
225                 230                 235                 240

Asp Glu Leu Lys Gly Leu Leu Gly Leu Pro Glu Glu Ala Glu Leu
                245                 250                 255

Asp Asn Leu Thr Glu Phe Asn Thr Ala His Asn Lys Arg Ile Ala Thr
            260                 265                 270

Leu Thr Ile Glu Glu Gly Asn Leu Asp Ile Gln Arg Pro Lys Arg Lys
        275                 280                 285

Arg Lys Asn Ala Arg Val Thr Phe Ala Glu Asp Glu Ile Ile Asn
    290                 295                 300

Pro Glu Asp Val Asp Pro Ser Val Gly Arg Phe Arg
305                 310                 315

<210> SEQ ID NO 18
<211> LENGTH: 948
<212> TYPE: DNA
<213> ORGANISM: artificial sequence
<220> FEATURE:
<223> OTHER INFORMATION: synthetic

<400> SEQUENCE: 18
gccgcccaga ggctgggcaa gagggtgctg agcaagctgc agagcccag cagggccagg      60 ggccccggcg gaagccccgg cggactgcag aaaaggcacg ccagggtgga ggtgaagtac    120
gacaggaggg agctgcagag gaggctggac gtggagaagt ggatcgacgg cagggaggag    180

```
ctgtacaggg gcatggaggc cgacatgccc gacgagatca acatcgacga gctgctggag    240
ctggagagcg aggaggagag gagcaggaag atccagggcc tgctgaaaag ctgcggcaag    300
cccgtggagg acttcatcca ggagctgctg gccaagctgc agggcctcca caggcagccc    360
ggcctgaggc agcccagccc cagccacgac ggaagcctga gcccctgca agacagggcc    420 aggaccgccc accccccgg cgccggacac atccccagga gccctacaa gttcccagc      480 agcccctga ggattcccgg cggcaacatc tacatcagcc cctgaaaag cccctacaag     540 atcagcgagg gcctgcccga ccctaccaag atggacccca ggagcaggat tctggtgagc    600
atcggcgaga gcttcggcac cagcgagaag ttccagaaga tcaaccagat ggtgtgcaac    660
agcgacaggg tgctgaaaag gagcgccgag ggcagcaacc ccggcgccgc cggagaggac    720
gacgagctga agggcctgct gggactgccc gaggaggagg ccgagctgga caacctgacc    780
gagttcaaca ccgcccacaa caagaggatc gccaccctga ccatcgagga gggcaacctg    840
gacatccaga ggcccaagag gaaaaggaag aacgccaggt gaccttcgc cgaggacgac    900 gagatcatca ccccgagga cgtggacccc agcgtgggca gattcagg              948

<210> SEQ ID NO 19
<211> LENGTH: 982
<212> TYPE: DNA
<213> ORGANISM: artificial sequence
<220> FEATURE:
<223> OTHER INFORMATION: synthetic

<400> SEQUENCE: 19
gctagcgccg gcgccgccca gaggctgggc aagagggtgc tgagcaagct gcagagcccc    60
agcagggcca gggcccccgg cggaagcccc ggcggactgc agaaaaggca cgccagggtg   120
gaggtgaagt acgacaggag ggagctgcag aggaggctgg acgtggagaa gtggatcgac   180
ggcagggagg agctgtacag gggcatggag gccgacatgc ccgacgagat caacatcgac   240
gagctgctgg agctggagag cgaggaggag aggagcagga agatccagggg cctgctgaaa   300 agctgcggca gcccgtgga ggacttcatc caggagctgc tggccaagct gcagggcctc   360
cacaggcagc ccggcctgag gcagcccagc cccagccacg acggaagcct gagcccctg    420 caagacaggg ccaggaccgc ccacccccc ggcgccggac atccccag gagccctac    480 aagttcccca gcagcccct gaggattccc ggcggcaaca tctacatcag ccccctgaaa    540 agccctaca agatcagcga gggcctgccc gaccctacca agatggaccc caggagcagg   600
attctggtga gcatcggcga gagcttcggc accagcgaga gttccagaa gatcaaccag    660 atggtgtgca acagcgacag ggtgctgaaa ggagcgccg agggcagcaa ccccggcgcc    720
gccggagagg acgacgagct gaagggcctg ctgggactgc cgaggagga ggccgagctg   780 gacaacctga ccgagttcaa caccgcccac aacaagagga tcgccaccct gaccatcgag    840
gagggcaacc tggacatcca gaggcccaag aggaaaagga gaacgccag ggtgaccttc   900 gccgaggacg acgagatcat caccccgag gacgtggacc ccagcgtggg cagattcagg    960
cccgggggag gcggaatcga tt                                         982

<210> SEQ ID NO 20
<211> LENGTH: 991
<212> TYPE: DNA
<213> ORGANISM: artificial sequence
<220> FEATURE:
<223> OTHER INFORMATION: synthetic

<400> SEQUENCE: 20
```

```
gctagcgcca ccatggccgg cgccgcccag aggctgggca agagggtgct gagcaagctg      60
cagagcccca gcagggccag ggcccccggc ggaagcccg gcggactgca gaaaaggcac      120 gccaggtgg aggtgaagta cgacaggagg gagctgcaga ggaggctgga cgtggagaag      180
tggatcgacg gcagggagga gctgtacagg ggcatggagg ccgacatgcc cgacgagatc      240
aacatcgacg agctgctgga gctggagagc gaggaggaga ggagcaggaa gatccagggc      300
ctgctgaaaa gctgcggcaa gcccgtggag gacttcatcc aggagctgct ggccaagctg      360
cagggcctcc acaggcagcc cggcctgagg cagcccagcc ccagccacga cggaagcctg      420
agccccctgc aagacagggc caggaccgcc caccccccg gcgccggaca catccccagg      480 agccccctaca gttccccag cagccccctg aggattcccg gcggcaacat ctacatcagc      540
cccctgaaaa gccctacaa gatcagcgag ggcctgcccg accctaccaa gatggacccc      600
aggagcagga ttctggtgag catcggcgag agcttcggca ccagcgagaa gttccagaag      660
atcaaccaga tggtgtgcaa cagcgacagg gtgctgaaaa ggagcgccga gggcagcaac      720
cccggcgccg ccggagagga cgacgagctg aagggcctgc tgggactgcc cgaggaggag      780
gccgagctgg acaacctgac cgagttcaac accgcccaca caagaggat cgccaccctg      840 accatcgagg agggcaacct ggacatccag aggcccaaga ggaaaaggaa gaacgccagg      900
gtgaccttcg ccgaggacga cgagatcatc aaccccgagg acgtggaccc cagcgtgggc      960
agattcaggc ccgggggagg cggaatcgat t                                    991
```

<210> SEQ ID NO 21
<211> LENGTH: 251
<212> TYPE: PRT
<213> ORGANISM: artificial sequence
<220> FEATURE:
<223> OTHER INFORMATION: synthetic

<400> SEQUENCE: 21

```
Pro Ala Val Arg Pro Thr Phe Arg Val Leu Val Gly Glu Val Glu Gln
1               5                   10                  15

Ile Val Ser Ala Leu Leu Gly Asp His Tyr Val Gln Leu Pro Ala Thr
            20                  25                  30

Tyr Met Asn Leu Gly Pro Ser Thr Ser His Glu Met Asn Val Arg Pro
        35                  40                  45

Glu Gln Pro Gln Phe Ser Pro Met Pro Gly Asn Val Arg Arg Pro Arg
    50                  55                  60

Pro Leu Asp Glu Pro Pro Arg Pro Thr Pro Gly Gly Ala Gly Arg Lys
65                  70                  75                  80

Leu Asn Gln Arg Pro Thr Val Asp Glu Leu Arg Asp Arg Lys Ile Leu
                85                  90                  95

Ile Arg Phe Ser Asp Tyr Val Glu Val Ala Lys Ala Gln Asp Tyr Asp
            100                 105                 110

Arg Arg Ala Asp Lys Pro Trp Thr Arg Leu Ser Ala Ala Asp Lys Ala
        115                 120                 125

Ala Ile Arg Lys Glu Leu Asn Glu Tyr Lys Ser Asn Glu Met Glu Val
    130                 135                 140

His Ala Ser Ser Lys His Leu Thr Arg Phe His Arg Pro Pro Gly Ala
145                 150                 155                 160

Ala Gly Asp Pro Lys Asp Arg Lys Lys Ile Gln Phe Ser Val Pro Ala
                165                 170                 175

Pro Pro Ser Gln Leu Asp Pro Arg Gln Val Glu Met Ile Arg Arg Arg
            180                 185                 190
```

```
Arg Pro Glu Pro Ala Met Leu Phe Arg Leu Ser Glu His Ser Ser Pro
        195                 200                 205
Glu Glu Glu Ala Ser Pro His Gln Arg Ala Ser Gly Glu Gly His His
    210                 215                 220
Leu Lys Ser Lys Arg Pro Asn Pro Cys Ala Tyr Thr Pro Pro Ser Leu
225                 230                 235                 240
Lys Ala Val Gln Arg Ile Ala Glu Ser His Leu
                245                 250

<210> SEQ ID NO 22
<211> LENGTH: 753
<212> TYPE: DNA
<213> ORGANISM: artificial sequence
<220> FEATURE:
<223> OTHER INFORMATION: synthetic

<400> SEQUENCE: 22
cccgccgtga ggcccacctt cagggtgctg gtgggcgagg tggagcagat cgtgagcgcc      60
ctgctgggcg accactacgt ccagctgccc gccacctaca tgaacctggg ccccagcacc     120
agccacgaga tgaacgtgag gcccgagcag ccccagttca gccccatgcc cggcaacgtg     180
aggaggccca ggcccctcga cgagccccca gacccacccc cggcggcgc cggaaggaag      240
ctgaaccaga ggcccaccgt ggacgagctg agggacagga agatcctgat caggttcagc     300
gactacgtgg aggtggccaa ggcccaggac tacgacagga gggccgacaa gccctggacc     360
aggctgagcg ccgccgacaa agccgccatc aggaaggagc tgaacgagta caagagcaac     420
gagatggagg tccacgccag cagcaagcac ctgaccaggt tccacaggcc cccggcgcc      480
gccggagacc ccaaggacag gaagaagatc cagttcagcg tgcccgcccc ccccagccag     540
ctcgacccca ggcaagtcga gatgatcagg aggaggaggc ccgagcccgc catgctgttc     600
aggctgagcg agcacagcag ccccgaggag gaggccagcc ccaccagag gccagcggc      660
gagggccacc acctgaaaag caagaggccc aaccctgcg cctacacccc ccccagcctg     720
aaggccgtgc agaggatcgc cgagagccac ctg                                   753

<210> SEQ ID NO 23
<211> LENGTH: 787
<212> TYPE: DNA
<213> ORGANISM: artificial sequence
<220> FEATURE:
<223> OTHER INFORMATION: synthetic

<400> SEQUENCE: 23
gctagcgccg ccccgccgt gaggcccacc ttcagggtgc tggtgggcga ggtggagcag      60
atcgtgagcg ccctgctggg cgaccactac gtccagctgc cgccaccta catgaacctg     120
ggccccagca ccagccacga gatgaacgtg aggcccgagc agccccagtt cagccccatg     180
cccggcaacg tgaggaggcc caggcccctc gacgagcccc cagacccac ccccggcggc     240
gccggaagga agctgaacca gaggcccacc gtggacgagc tgagggacag gaagatcctg     300
atcaggttca gcgactacgt ggaggtggcc aaggcccagg actacgacag gagggccgac     360
aagccctgga ccaggctgag cgccgccgac aaagccgcca tcaggaagga gctgaacgag     420
tacaagagca acgagatgga ggtccacgcc agcagcaagc acctgaccag gttccacagg     480
cccccggcg ccgccggaga ccccaaggac aggaagaaga tccagttcag cgtgcccgcc     540
cccccagcc agctcgaccc caggcaagtc gagatgatca ggaggaggag gcccgagccc     600
gccatgctgt tcaggctgag cgagcacagc agccccgagg aggaggccag ccccaccag     660
```

```
agggccagcg gcgagggcca ccacctgaaa agcaagaggc ccaaccccctg cgcctacacc    720 ccccccagcc tgaaggccgt gcagaggatc gccgagagcc acctgcccgg gggaggcgga    780
atcgatt                                                              787
```

<210> SEQ ID NO 24
<211> LENGTH: 799
<212> TYPE: DNA
<213> ORGANISM: artificial sequence
<220> FEATURE:
<223> OTHER INFORMATION: synthetic

<400> SEQUENCE: 24

```
gctagcgcca ccatggccgg cggacccgcc gtgaggccca ccttcagggt gctggtgggc     60
gaggtggagc agatcgtgag cgccctgctg ggcgaccact acgtccagct gcccgccacc    120
tacatgaacc tgggccccag caccagccac gagatgaacg tgaggcccga gcagccccag    180
ttcagcccca tgcccggcaa cgtgaggagg cccaggcccc tcgacgagcc cccagaccc     240 accccccggcg cgccggaag gaagctgaac cagaggccca ccgtggacga gctgagggac    300
aggaagatcc tgatcaggtt cagcgactac gtggaggtgg ccaaggccca ggactacgac    360
aggagggccg acaagccctg gaccaggctg agcgccgccg acaaagccgc catcaggaag    420
gagctgaacg agtacaagag caacgagatg gaggtccacg ccagcagcaa gcacctgacc    480
aggttccaca ggccccccgg cgccgccgga ccccaagg acaggaagaa gatccagttc    540
agcgtgcccg ccccccccag ccagctcgac cccaggcaag tcgagatgat caggaggagg    600
aggcccgagc cgccatgct gttcaggctg agcgagcaca gcagccccga ggaggaggcc    660
agcccccacc agagggccag cggcgagggc caccacctga aaagcaagag gcccaacccc    720
tgcgcctaca ccccccccag cctgaaggcc gtgcaggaga tcgccgagag ccacctgccc    780
gggggaggcg gaatcgatt                                                 799
```

<210> SEQ ID NO 25
<211> LENGTH: 281
<212> TYPE: PRT
<213> ORGANISM: artificial sequence
<220> FEATURE:
<223> OTHER INFORMATION: synthetic

<400> SEQUENCE: 25

```
Gly Asp Pro Asn Gln Leu Thr Arg Lys Gly Arg Lys Arg Ser Val
1               5                  10                  15

Thr Trp Pro Glu Glu Gly Lys Leu Arg Glu Tyr Phe Tyr Phe Glu Leu
            20                  25                  30

Asp Glu Thr Glu Arg Val Asn Val Asn Lys Ile Lys Asp Phe Gly Glu
        35                  40                  45

Ala Ala Lys Arg Glu Ile Leu Ser Asp Arg His Ala Phe Glu Thr Ala
    50                  55                  60

Arg Arg Pro Gly Gly Ala Gly Ser Cys Thr Arg Met Ile Gln Val Leu
65                  70                  75                  80

Asp Pro Arg Pro Leu Thr Ser Ser Val Met Pro Val Asp Val Ala Met
                85                  90                  95

Arg Leu Cys Leu Ala His Ser Pro Pro Val Ser Phe Leu Gly Pro
            100                 105                 110

Tyr Asp Glu Phe Gln Arg Arg His Phe Val Asn Lys Leu Lys Pro Leu
        115                 120                 125

Lys Ser Cys Leu Asn Ile Lys His Lys Ala Lys Ser Gln Asn Asp Trp
```

```
                130                 135                 140
Lys Cys Ser His Asn Gln Ala Lys Lys Arg Val Val Phe Ala Asp Ser
145                 150                 155                 160

Lys Gly Leu Ser Leu Thr Ala Ile His Val Phe Ser Asp Leu Pro Glu
                165                 170                 175

Glu Pro Gly Ala Ala Gly Glu Gln Asp Asn Ser Pro Gln Lys Ile Gln
                180                 185                 190

Phe Thr Val Pro Leu Leu Glu Pro His Leu Asp Pro Glu Ala Ala Glu
                195                 200                 205

Gln Ile Arg Arg Arg Pro Glu Pro Ala Thr Leu Val Leu Thr Ser
210                 215                 220

Asp Gln Ser Ser Pro Glu Ile Asp Glu Asp Arg Ile Pro Asn Pro His
225                 230                 235                 240

Leu Lys Ser Thr Leu Ala Met Asp Pro Arg Gln Arg Lys Lys Met Glu
                245                 250                 255

Arg Ile Thr Pro Thr Met Lys Glu Leu Gln Met Met Val Glu His His
                260                 265                 270

Leu Gly Gln Gln Gln Gln Gly Glu Glu
        275                 280

<210> SEQ ID NO 26
<211> LENGTH: 843
<212> TYPE: DNA
<213> ORGANISM: artificial sequence
<220> FEATURE:
<223> OTHER INFORMATION: synthetic

<400> SEQUENCE: 26
ggcgacccca accagctgac caggaagggc aggaaaagga aaagcgtgac ctggcccgag      60
gagggcaagc tgagggagta cttctacttc gagctggacg agaccgagag ggtgaacgtg     120
aacaagatca aggacttcgg cgaggccgcc aagagggaga tcctgagcga caggcacgcc     180
ttcgagaccg ccaggaggcc cggcggcgcc ggaagctgca ccaggatgat ccaggtgctg     240
gaccccaggc ccctgaccag cagcgtgatg cccgtggacg tggccatgag gctgtgcctg     300
gcccacagcc cccccgtgaa aagcttcctg ggcccctacg acgagttcca gaggaggcac     360
ttcgtcaaca gcctgaagcc cctgaaaagc tgcctgaaca tcaagcacaa ggccaagagc     420
cagaacgact ggaagtgcag ccacaaccag gccaagaaaa gggtggtgtt cgccgacagc     480
aagggcctga gcctgaccgc catccacgtc ttcagcgacc tccccgagga gcccggcgcc     540
gccggagagc aggacaacag ccccccagaag atccagttca ccgtgcccct gctggagccc     600
cacctggacc ccgaggccgc cgagcagatc aggaggagga ggcccgagcc cgccacccta     660
gtgctgacca gcgaccagag cagccccgag atcgacgagg acaggattcc caacccccac     720
ctgaaaagca ccctggccat ggaccccagg cagaggaaga gatggagag gatcacccc      780 accatgaagg agctgcagat gatggtggag caccacctgg gccagcagca gcagggcgag     840
gag                                                                    843

<210> SEQ ID NO 27
<211> LENGTH: 877
<212> TYPE: DNA
<213> ORGANISM: artificial sequence
<220> FEATURE:
<223> OTHER INFORMATION: synthetic

<400> SEQUENCE: 27
gctagcgccg gcggcgaccc caaccagctg accaggaagg gcaggaaaag gaaaagcgtg      60
```

```
acctggcccg aggagggcaa gctgagggag tacttctact tcgagctgga cgagaccgag    120
agggtgaacg tgaacaagat caaggacttc ggcgaggccg ccaagaggga gatcctgagc    180
gacaggcacg ccttcgagac cgccaggagg cccggcggcg ccggaagctg caccaggatg    240
atccaggtgc tggaccccag gcccctgacc agcagcgtga tgcccgtgga cgtggccatg    300
aggctgtgcc tggcccacag cccccccgtg aaaagcttcc tgggccccta cgacgagttc    360
cagaggaggc acttcgtcaa caagctgaag cccctgaaaa gctgcctgaa catcaagcac    420
aaggccaaga gccagaacga ctggaagtgc agccacaacc aggccaagaa agggtggtg     480 ttcgccgaca gcaagggcct gagcctgacc gccatccacg tcttcagcga cctccccgag    540
gagcccggcg ccgccggaga gcaggacaac agcccccaga gatccagtt caccgtgccc     600 ctgctggagc cccacctgga ccccgaggcc gccgagcaga tcaggaggag gagcccgag     660 cccgccaccc tggtgctgac cagcgaccag agcagccccg agatcgacga ggacaggatt    720
cccaaccccc acctgaaaag caccctggcc atggacccca ggcagaggaa gaagatggag    780
aggatcaccc ccaccatgaa ggagctgcag atgatggtgg agcaccacct gggccagcag    840
cagcagggcg aggagcccgg gggaggcgga atcgatt                             877

<210> SEQ ID NO 28
<211> LENGTH: 886
<212> TYPE: DNA
<213> ORGANISM: artificial sequence
<220> FEATURE:
<223> OTHER INFORMATION: synthetic

<400> SEQUENCE: 28
gctagcgcca ccatggccgg cggcgacccc aaccagctga ccaggaaggg caggaaaagg     60
aaaagcgtga cctggcccga ggagggcaag ctgagggagt acttctactt cgagctggac    120
gagaccgaga gggtgaacgt gaacaagatc aaggacttcg gcgaggccgc caagagggag    180
atcctgagcg acaggcacgc cttcgagacc gccaggaggc ccggcggcgc cggaagctgc    240
accaggatga tccaggtgct ggaccccagg cccctgacca gcagcgtgat gcccgtggac    300
gtggccatga ggctgtgcct ggcccacagc cccccgtga aaagcttcct gggcccctac     360
gacgagttcc agaggaggca cttcgtcaac aagctgaagc ccctgaaaag ctgcctgaac    420
atcaagcaca aggccaagag ccagaacgac tggaagtgca gccacaacca ggccaagaaa    480
agggtggtgt tcgccgacag caagggcctg agcctgaccg ccatccacgt cttcagcgac    540
ctccccgagg agcccggcgc cgccggagag caggacaaca gcccccagaa gatccagttc    600
accgtgcccc tgctggagcc ccacctggac cccgaggccg ccgagcagat caggaggagg    660
aggcccgagc ccgccaccct ggtgctgacc agcgaccaga gcagcccga gatcgacgag     720 gacaggattc ccaaccccca cctgaaaagc accctggcca tggaccccag gcagaggaag    780
aagatggaga ggatcacccc caccatgaag gagctgcaga tgatggtgga gcaccacctg    840
ggccagcagc agcagggcga ggagcccggg ggaggcggaa tcgatt                   886

<210> SEQ ID NO 29
<211> LENGTH: 246
<212> TYPE: PRT
<213> ORGANISM: artificial sequence
<220> FEATURE:
<223> OTHER INFORMATION: synthetic

<400> SEQUENCE: 29

Glu Gln Asp Asn Ser Pro Gln Lys Ile Gln Phe Thr Val Pro Leu Leu
```

```
            1               5               10              15
Glu Pro His Leu Asp Pro Glu Ala Ala Glu Gln Ile Arg Arg Arg
                    20                  25                  30

Pro Thr Pro Ala Thr Leu Val Leu Thr Ser Asp Gln Ser Ser Pro Glu
            35                  40                  45

Ile Asp Glu Asp Arg Ile Pro Asn Pro His Leu Lys Ser Thr Leu Ala
    50                  55                  60

Met Ser Pro Arg Gln Arg Lys Lys Met Thr Arg Ile Thr Pro Thr Met
65                  70                  75                  80

Lys Glu Leu Gln Met Met Val Glu His His Leu Gly Gln Gln Gln
                85                  90                  95

Gly Glu Glu Pro Gly Gly Ala Gly Glu Glu Pro Gln Ser Asp Pro Ser
                    100                 105                 110

Val Glu Pro Pro Leu Ser Gln Glu Thr Phe Ser Asp Leu Trp Lys Leu
            115                 120                 125

Leu Pro Glu Asn Asn Val Leu Ser Pro Leu Pro Ser Gln Ala Met Asp
        130                 135                 140

Asp Leu Met Leu Ser Pro Asp Asp Ile Glu Gln Trp Phe Thr Glu Asp
145                 150                 155                 160

Pro Gly Pro Pro Gly Ala Ala Gly Arg Lys Leu Asn Gln Arg Pro Val
                    165                 170                 175

Asp Glu Leu Arg Asp Arg Lys Ile Leu Ile Arg Phe Ser Asp Tyr Val
                180                 185                 190

Glu Val Ala Lys Ala Gln Asp Tyr Asp Arg Arg Ala Asp Lys Pro Trp
            195                 200                 205

Thr Arg Leu Ser Ala Ala Asp Lys Ala Ala Ile Arg Lys Glu Leu Asn
        210                 215                 220

Glu Tyr Lys Ser Asn Glu Met Glu Val His Ala Ser Ser Lys His Leu
225                 230                 235                 240

Thr Arg Phe His Arg Pro
            245

<210> SEQ ID NO 30
<211> LENGTH: 738
<212> TYPE: DNA
<213> ORGANISM: artificial sequence
<220> FEATURE:
<223> OTHER INFORMATION: synthetic

<400> SEQUENCE: 30
gagcaggaca acagccccca gaagatccag ttcaccgtgc ccctgctgga gccccacctg      60
gaccccgagg ccgccgagca gatcaggagg aggaggccca ccccgccac cctggtgctg     120 accagcgacc agagcagccc cgagatcgac gaggacagga ttcccaaccc ccacctgaaa     180
agcaccctgg ccatgagccc caggcagagg aagaagatga ccaggatcac ccccaccatg     240
aaggagctgc agatgatggt ggagcaccac ctgggccagc agcagcaggg cgaggagccc     300
ggcggcgccg gagaggagcc ccagagcgac cccagcgtgg agcccccct gagccaggag     360 accttcagcg acctgtggaa gctgctgccc gagaacaacg tgctgagccc cctgcccagc     420
caggccatgg acgacctgat gctgagcccc gacgacatcg agcagtggtt caccgaggac     480
cccggccccc ccggagccgc cggaaggaag ctgaaccaga ggcccgtgga cgagctgagg     540
gacaggaaga tcctgatcag gttcagcgac tacgtggagg tggccaaggc ccaggactac     600
gacaggaggg ccgacaagcc ctggaccagg ctgagcgccg ccgacaaagc cgccatcagg     660
aaggagctga acgagtacaa gagcaacgag atggaggtcc acgccagcag caagcacctg     720
```

```
accaggttcc acaggccc                                              738

<210> SEQ ID NO 31
<211> LENGTH: 772
<212> TYPE: DNA
<213> ORGANISM: artificial sequence
<220> FEATURE:
<223> OTHER INFORMATION: synthetic

<400> SEQUENCE: 31
gctagcgccg gcgagcagga caacagcccc cagaagatcc agttcaccgt gcccctgctg     60 gagcccacc tggaccccga ggccgccgag cagatcagga ggaggaggcc cacccccgcc    120
accctggtgc tgaccagcga ccagagcagc ccgagatcg acgaggacag gattcccaac    180
ccccacctga aaagcaccct ggccatgagc cccaggcaga ggaagaagat gaccaggatc    240 accccccacca tgaaggagct gcagatgatg gtggagcacc acctgggcca gcagcagcag    300
ggcgaggagc ccggcggcgc cggagaggag ccccagagcg accccagcgt ggagccccc    360 ctgagccagg agaccttcag cgacctgtgg aagctgctgc ccgagaacaa cgtgctgagc    420
cccctgccca gcaggccat ggacgacctg atgctgagcc ccgacgacat cgagcagtgg    480
ttcaccgagg accccggccc cccggagcc gccggaagga agctgaacca gaggcccgtg    540
gacgagctga gggacaggaa gatcctgatc aggttcagcg actacgtgga ggtggccaag    600
gcccaggact acgacaggag ggccgacaag ccctggacca ggctgagcgc cgccgacaaa    660
gccgccatca ggaaggagct gaacgagtac aagagcaacg atgaggt ccacgccagc    720 agcaagcacc tgaccaggtt ccacaggccc ccgggggag gcggaatcga tt           772

<210> SEQ ID NO 32
<211> LENGTH: 781
<212> TYPE: DNA
<213> ORGANISM: artificial sequence
<220> FEATURE:
<223> OTHER INFORMATION: synthetic

<400> SEQUENCE: 32
gctagcgcca ccatggccgg cgagcaggac aacagcccc agaagatcca gttcaccgtg     60
cccctgctgg agccccacct ggaccccgag gccgccgagc agatcaggag gaggaggccc    120 accccgcca ccctggtgct gaccagcgac cagagcagcc ccgagatcga cgaggacagg    180
attcccaacc cccacctgaa aagcaccctg gccatgagcc ccaggcagag gaagaagatg    240
accaggatca ccccaccat gaaggagctg cagatgatgg tggagcacca cctgggccag    300
cagcagcagg gcgaggagcc cggcggcgcc ggagaggagc cccagagcga ccccagcgtg    360 gagccccc tgagccagga gaccttcagc gacctgtgga agctgctgcc cgagaacaac    420
gtgctgagcc cctgcccag ccaggccatg gacgacctga tgctgagccc cgacgacatc    480
gagcagtggt tcaccgagga ccccggcccc ccggagccg ccggaaggaa gctgaaccag    540
aggcccgtgg acgagctgag ggacaggaag atcctgatca ggttcagcga ctacgtggag    600
gtggccaagg cccaggacta cgacaggagg gccgacaagc cctggaccag gctgagcgcc    660
gccgacaaag ccgccatcag gaaggagctg aacgagtaca agagcaacga tgaggtc    720 cacgccagca gcaagcacct gaccaggttc acaggcccc ccgggggagg cggaatcgat    780
t                                                                   781

<210> SEQ ID NO 33
<211> LENGTH: 300
```

<212> TYPE: PRT
<213> ORGANISM: artificial sequence
<220> FEATURE:
<223> OTHER INFORMATION: synthetic

<400> SEQUENCE: 33

```
Glu Lys Val Gln Tyr Leu Thr Arg Ser Ala Ile Arg Arg Ala Asp Thr
1               5                   10                  15
Ile Glu Met Pro Gln Gln Ala Pro Gly Gly Ala Gly Glu Gln Asp Asn
            20                  25                  30
Ser Pro Gln Lys Ile Gln Phe Thr Val Pro Leu Leu Glu Pro His Leu
        35                  40                  45
Asp Pro Glu Ala Ala Glu Gln Ile Arg Arg Arg Arg Pro Glu Pro Ala
    50                  55                  60
Thr Leu Val Leu Thr Ser Asp Gln Ser Ser Pro Glu Ile Asp Glu Asp
65                  70                  75                  80
Arg Ile Pro Asn Pro His Leu Lys Ser Thr Leu Ala Pro Gly Ala Ala
                85                  90                  95
Gly Ala Ala Ser Thr Ala Ser His Arg Pro Ile Lys Gly Ile Leu Lys
            100                 105                 110
Asn Lys Thr Ser Thr Thr Ser Ser Met Val Ala Ser Ala Glu Gln Pro
        115                 120                 125
Arg Gly Asn Val Asp Glu Glu Leu Ser Lys Lys Ser Gln Lys Trp Asp
    130                 135                 140
Glu Met Asn Ile Leu Ala Thr Tyr His Pro Ala Asp Lys Asp Tyr Leu
145                 150                 155                 160
Met Lys Ile Asp Glu Pro Ser Glu Pro Tyr His Ser Met Met Gly Asp
                165                 170                 175
Asp Glu Asp Ala Cys Ser Asp Thr Glu Ala Thr Glu Ala Met Ala Pro
            180                 185                 190
Asp Ile Leu Ala Arg Lys Leu Ala Ala Ala Glu Gly Leu Glu Pro Lys
        195                 200                 205
Tyr Arg Ile Gln Glu Gln Glu Ser Ser Gly Glu Glu Asp Ser Asp Leu
    210                 215                 220
Ser Pro Glu Glu Arg Glu Lys Lys Arg Gln Phe Glu Met Lys Arg Lys
225                 230                 235                 240
Leu His Tyr Asn Glu Gly Leu Asn Ile Lys Leu Ala Arg Gln Leu Ile
                245                 250                 255
Ser Lys Asp Leu His Asp Asp Glu Asp Glu Glu Met Leu Glu Thr
            260                 265                 270
Ala Asp Gly Glu Ser Met Asn Thr Glu Glu Ser Asn Gln Gly Ser Thr
        275                 280                 285
Pro Ser Asp Gln Gln Gln Asn Lys Leu Arg Ser Ser
    290                 295                 300
```

<210> SEQ ID NO 34
<211> LENGTH: 900
<212> TYPE: DNA
<213> ORGANISM: artificial sequence
<220> FEATURE:
<223> OTHER INFORMATION: synthetic

<400> SEQUENCE: 34

```
gagaaggtgc agtacctgac caggagcgcc atcaggaggg ccgacaccat cgagatgccc      60
cagcaggccc ccggcggcgc cggagagcag gacaacagcc cccagaagat ccagttcacc    120
gtgcccctgc tggagcccca cctggacccc gaggccgccg agcagatcag gaggaggagg    180
```

```
cccgagcccg ccaccctggt gctgaccagc gaccagagca gccccgagat cgacgaggac      240
aggattccca accccacct gaaaagcacc ctggcccccg cgccgccgg agccgccagc       300 accgccagcc acaggcccat caagggcatc ctgaagaaca agaccagcac cacctccagc     360
atggtcgcca gcgccgagca gcccaggggc aacgtggacg aggagctgag caagaaaagc     420
cagaagtggg acgagatgaa catcctggcc acctaccacc ccgccgacaa ggactacctg    480
atgaagatcg acgagcccag cgagccctac cacagcatga tgggcgacga cgaggacgcc    540
tgcagcgaca ccgaggccac cgaagccatg gccccgaca tcctggccag gaagctcgcc     600
gccgccgagg gcctggagcc caagtacagg attcaggagc aggagagcag cggcgaggag    660
gacagcgacc tgagccccga ggagagggag aagaaaggc agttcgagat gaaaggaag     720 ctgcactaca acgagggcct gaacatcaag ctggccaggc agctgatcag caaggacctc    780
cacgacgacg acgaggacga ggagatgctg gagaccgccg acggcgagag catgaacacc    840
gaggagagca accagggcag cacccccagc gaccagcagc agaacaagct gaggagcagc    900
```

<210> SEQ ID NO 35
<211> LENGTH: 934
<212> TYPE: DNA
<213> ORGANISM: artificial sequence
<220> FEATURE:
<223> OTHER INFORMATION: synthetic

<400> SEQUENCE: 35

```
gctagcgccg gcgagaaggt gcagtacctg accaggagcg ccatcaggag ggccgacacc      60
atcgagatgc cccagcaggc ccccggcggc gccggagagc aggacaacag ccccagaag    120 atccagttca ccgtgcccct gctggagccc cacctggacc ccgaggccgc cgagcagatc    180
aggaggagga ggcccgagcc cgccaccctg gtgctgacca cgaccagag cagccccgag     240 atcgacgagg acaggattcc caaccccac ctgaaaagca ccctggcccc cggcgccgcc     300
ggagccgcca gcaccgccag ccacaggccc atcaagggca tcctgaagaa caagaccagc    360
accacctcca gcatggtcgc cagcgccgag cagcccaggg gcaacgtgga cgaggagctg    420
agcaagaaaa gccagaagtg ggacgagatg aacatcctgg ccacctacca ccccgccgac    480
aaggactacc tgatgaagat cgacgagccc agcgagccct accacagcat gatgggcgac    540
gacgaggacg cctgcagcga caccgaggcc accgaagcca tggccccgga catcctggcc    600
aggaagctcg ccgccgccga gggcctggag cccaagtaca ggattcagga gcaggagagc    660
agcggcgagg aggacagcga cctgagcccc gaggagaggg agaagaaaag cagttcgag    720 atgaaaagga agctgcacta caacgagggc ctgaacatca agctggccag gcagctgatc    780
agcaaggacc tccacgacga cgacgaggac gaggagatgc tggagaccgc cgacggcgag    840
agcatgaaca ccgaggagag caaccagggc agcaccccca gcgaccagca gcagaacaag    900
ctgaggagca gccccggggg aggcggaatc gatt                                934
```

<210> SEQ ID NO 36
<211> LENGTH: 943
<212> TYPE: DNA
<213> ORGANISM: artificial sequence
<220> FEATURE:
<223> OTHER INFORMATION: synthetic

<400> SEQUENCE: 36

```
gctagcgcca ccatggccgg cgagaaggtg cagtacctga ccaggagcgc catcaggagg     60
gccgacacca tcgagatgcc ccagcaggcc cccggcggcg ccggagagca ggacaacagc    120
```

```
cccagaaga tccagttcac cgtgcccctg ctggagcccc acctggaccc cgaggccgcc    180
gagcagatca ggaggaggag gcccgagccc gccaccctgg tgctgaccag cgaccagagc    240
agccccgaga tcgacgagga caggattccc aaccccacc tgaaaagcac cctggccccc    300
ggcgccgccg gagccgccag caccgccagc acaggccca tcaagggcat cctgaagaac    360
aagaccagca ccacctccag catggtcgcc agcgccgagc agcccagggg caacgtggac    420
gaggagctga gcaagaaaag ccagaagtgg gacgagatga acatcctggc cacctaccac    480
cccgccgaca aggactacct gatgaagatc gacgagccca gcgagcccta ccacagcatg    540
atgggcgacg acgaggacgc ctgcagcgac accgaggcca ccgaagccat ggccccccga c    600 atcctggcca ggaagctcgc cgccgccgag ggcctggagc ccaagtacag gattcaggag    660
caggagagca gcggcgagga ggacagcgac ctgagcccccg aggagaggga agaaaaagg    720 cagttcgaga tgaaaaggaa gctgcactac aacgagggcc tgaacatcaa gctggccagg    780
cagctgatca gcaaggacct ccacgacgac gacgaggacg aggagatgct ggagaccgcc    840
gacggcgaga gcatgaacac cgaggagagc aaccagggca gcacccccag cgaccagcag    900
cagaacaagc tgaggagcag ccccggggga ggcggaatcg att                     943
```

<210> SEQ ID NO 37
<211> LENGTH: 300
<212> TYPE: PRT
<213> ORGANISM: artificial sequence
<220> FEATURE:
<223> OTHER INFORMATION: synthetic

<400> SEQUENCE: 37

```
Glu Lys Val Gln Tyr Leu Thr Arg Ser Ala Ile Arg Arg Ala Glu Thr
1               5                   10                  15

Ile Glu Met Pro Gln Gln Ala Pro Gly Gly Ala Gly Glu Gln Asp Asn
            20                  25                  30

Ser Pro Gln Lys Ile Gln Phe Thr Val Pro Leu Leu Glu Pro His Leu
        35                  40                  45

Asp Pro Glu Ala Ala Glu Gln Ile Arg Arg Arg Arg Pro Glu Pro Ala
    50                  55                  60

Thr Leu Val Leu Thr Ser Asp Gln Ser Ser Pro Glu Ile Asp Glu Asp
65                  70                  75                  80

Arg Ile Pro Asn Pro His Leu Lys Ser Thr Leu Ala Pro Gly Ala Ala
                85                  90                  95

Gly Ala Ala Ser Thr Ala Ser His Arg Pro Ile Lys Gly Ile Leu Lys
            100                 105                 110

Asn Lys Thr Ser Thr Thr Ser Ser Met Val Ala Ser Ala Glu Gln Pro
        115                 120                 125

Arg Gly Asn Val Asp Glu Glu Leu Ser Lys Lys Ser Gln Lys Trp Asp
    130                 135                 140

Glu Met Asn Ile Leu Ala Thr Tyr His Pro Ala Asp Lys Asp Tyr Leu
145                 150                 155                 160

Met Lys Ile Asp Glu Pro Ser Glu Pro Tyr His Ser Met Met Gly Asp
                165                 170                 175

Asp Glu Asp Ala Cys Ser Asp Thr Glu Ala Thr Glu Ala Met Ala Pro
            180                 185                 190

Asp Ile Leu Ala Arg Lys Leu Ala Ala Ala Glu Gly Leu Glu Pro Lys
        195                 200                 205

Tyr Arg Ile Gln Glu Gln Glu Ser Ser Gly Glu Glu Asp Ser Asp Leu
    210                 215                 220
```

| Ser 225 | Pro | Glu | Glu | Arg 230 | Glu | Lys | Lys | Arg | Gln 235 | Phe | Glu | Met | Lys | Arg 240 | Lys |

| Leu | His | Tyr | Asn | Glu 245 | Gly | Leu | Asn | Ile | Lys 250 | Leu | Ala | Arg | Gln | Leu 255 | Ile |

| Ser | Lys | Asp 260 | Leu | His | Asp | Asp | Asp 265 | Glu | Asp | Glu | Glu | Met 270 | Leu | Glu | Thr |

| Ala | Asp 275 | Gly | Glu | Ser | Met | Asn 280 | Thr | Glu | Glu | Ser | Asn 285 | Gln | Gly | Ser | Thr |

| Pro 290 | Ser | Asp | Gln | Gln | Gln 295 | Asn | Lys | Leu | Arg | Ser 300 | Ser |

<210> SEQ ID NO 38
<211> LENGTH: 900
<212> TYPE: DNA
<213> ORGANISM: artificial sequence
<220> FEATURE:
<223> OTHER INFORMATION: synthetic

<400> SEQUENCE: 38

```
gagaaggtgc agtacctgac caggagcgcc atcaggaggg ccgagaccat cgagatgccc    60
cagcaggccc ccggcggcgc cggagagcag gacaacagcc cccagaagat ccagttcacc   120
gtgcccctgc tggagcccca cctggacccc gaggccgccg agcagatcag gaggaggagg   180
cccgagcccg ccaccctggt gctgaccagc gaccagagca gccccgagat cgacgaggac   240
aggattccca acccccacct gaaaagcacc ctggcccccg gcgccgccgg agccgccagc   300
accgccagcc acaggcccat caagggcatc ctgaagaaca agaccagcac cacctccagc   360
atggtcgcca gcgccgagca gcccaggggc aacgtggacg aggagctgag caagaaaagc   420
cagaagtggg acgagatgaa catcctggcc acctaccacc ccgccgacaa ggactacctg   480
atgaagatcg acgagcccag cgagccctac acagcatga tgggcgacga cgaggacgcc   540
tgcagcgaca ccgaggccac cgaagccatg gcccccgaca tcctggccag gaagctcgcc   600
gccgccgagg gcctggagcc caagtacagg attcaggagc aggagagcag cggcgaggag   660
gacagcgacc tgagccccga ggagagggag aagaaaaggc agttcgagat gaaaaggaag   720
ctgcactaca cgagggcct gaacatcaag ctggccaggc agctgatcag caaggacctc   780
cacgacgacg acgaggacga ggagatgctg gagaccgccg acggcgagag catgaacacc   840
gaggagagca accagggcag caccccccagc gaccagcagc agaacaagct gaggagcagc   900
```

<210> SEQ ID NO 39
<211> LENGTH: 934
<212> TYPE: DNA
<213> ORGANISM: artificial sequence
<220> FEATURE:
<223> OTHER INFORMATION: synthetic

<400> SEQUENCE: 39

```
gctagcgccg gcgagaaggt gcagtacctg accaggagcg ccatcaggag ggccgagacc    60
atcgagatgc cccagcaggc ccccggcggc gccggagagc aggacaacag cccccagaag   120
atccagttca ccgtgcccct gctggagccc cacctggacc ccgaggccgc cgagcagatc   180
aggaggagga ggcccgagcc cgccaccctg gtgctgacca gcgaccagag cagccccgag   240
atcgacgagg acaggattcc caaccccac ctgaaaagca ccctggcccc cggcgccgcc   300
ggagccgcca gcaccgccag ccacaggccc atcaagggca tcctgaagaa caagaccagc   360
accacctcca gcatggtcgc cagcgccgag cagcccaggg gcaacgtgga cgaggagctg   420
agcaagaaaa gccagaagtg ggacgagatg aacatcctgg ccacctacca ccccgccgac   480
```

```
aaggactacc tgatgaagat cgacgagccc agcgagccct accacagcat gatgggcgac    540
gacgaggacg cctgcagcga caccgaggcc accgaagcca tggcccccga catcctggcc    600
aggaagctcg ccgccgccga gggcctggag cccaagtaca ggattcagga gcaggagagc    660
agcggcgagg aggacagcga cctgagcccc gaggagaggg agaagaaaag gcagttcgag    720
atgaaaagga agctgcacta caacgagggc ctgaacatca gctggccagg cagctgatc     780 agcaaggacc tccacgacga cgacgaggac gaggagatgc tggagaccgc cgacggcgag    840
agcatgaaca ccgaggagag caaccagggc agcaccccca gcgaccagca gcagaacaag    900
ctgaggagca gccccggggg aggcggaatc gatt                                934
```

<210> SEQ ID NO 40
<211> LENGTH: 943
<212> TYPE: DNA
<213> ORGANISM: artificial sequence
<220> FEATURE:
<223> OTHER INFORMATION: synthetic

<400> SEQUENCE: 40

```
gctagcgcca ccatggccgg cgagaaggtg cagtacctga ccaggagcgc catcaggagg     60
gccgagacca tcgagatgcc ccagcaggcc cccggcggcg ccggagagca ggacaacagc    120
ccccagaaga tccagttcac cgtgcccctg ctggagcccc acctggaccc cgaggccgcc    180
gagcagatca ggaggaggag gcccgagccc gccaccctgg tgctgaccag cgaccagagc    240
agccccgaga tcgacgagga caggattccc aaccccacc tgaaaagcac cctggccccc     300
ggcgccgccg agccgccag caccgccagc acaggcccca tcaagggcat cctgaagaac    360
aagaccagca ccacctccag catggtcgcc agcgccgagc agcccagggg caacgtggac    420
gaggagctga gcaagaaaag ccagaagtgg gacgagatga acatcctggc cacctaccac    480
cccgccgaca ggactacct gatgaagatc gacgagccca gcgagcccta ccacagcatg    540
atgggcgacg acgaggacgc ctgcagcgac accgaggcca ccgaagccat ggcccccgac    600
atcctggcca ggaagctcgc cgccgccgag ggcctggagc ccaagtacag gattcaggag    660
caggagagca gcggcgagga ggacagcgac ctgagccccg aggagaggga agaaaaagg    720 cagttcgaga tgaaaaggaa gctgcactac aacgagggcc tgaacatcaa gctggccagg    780
cagctgatca gcaaggacct ccacgacgac gacgaggacg aggagatgct ggagaccgcc    840
gacggcgaga gcatgaacac cgaggagagc aaccagggca gcaccccag cgaccagcag    900 cagaacaagc tgaggagcag ccccgggga ggcggaatcg att                      943
```

<210> SEQ ID NO 41
<211> LENGTH: 249
<212> TYPE: PRT
<213> ORGANISM: artificial sequence
<220> FEATURE:
<223> OTHER INFORMATION: synthetic

<400> SEQUENCE: 41

Glu Asp Asp Glu Leu Lys Gly Leu Leu Gly Leu Pro Glu Glu Thr
1               5                   10                  15

Glu Leu Asp Asn Leu Thr Glu Phe Asn Thr Ala His Asn Lys Arg Ile
            20                  25                  30

Ser Thr Leu Thr Ile Glu Glu Gly Asn Leu Asp Ile Gln Arg Pro Lys
        35                  40                  45

Arg Lys Arg Lys Asn Ser Arg Val Thr Phe Ser Glu Asp Asp Glu Ile
    50                  55                  60

```
Ile Asn Pro Glu Asp Val Asp Pro Ser Val Gly Arg Phe Arg Pro Gly
 65                  70                  75                  80

Ala Gly Gly Arg Arg Thr Glu Leu Cys Gly Thr Leu Asp Tyr Leu Pro
                 85                  90                  95

Pro Glu Pro Gly Ala Ala Gly Ala Ala Gln Arg Leu Gly Lys Arg Val
            100                 105                 110

Leu Ser Lys Leu Gln Ser Pro Ser Arg Ala Arg Gly Pro Gly Gly Ser
        115                 120                 125

Pro Gly Gly Leu Gln Lys Arg His Ala Arg Val Glu Val Lys Tyr Asp
    130                 135                 140

Arg Arg Glu Leu Gln Arg Arg Leu Asp Val Glu Lys Trp Ile Asp Gly
145                 150                 155                 160

Arg Leu Glu Glu Leu Tyr Arg Gly Met Glu Ala Asp Met Pro Asp Glu
                165                 170                 175

Ile Asn Ile Asp Glu Leu Leu Glu Leu Glu Ser Glu Glu Glu Arg Ser
            180                 185                 190

Arg Lys Ile Gln Gly Leu Leu Lys Ser Cys Gly Lys Pro Val Glu Asp
        195                 200                 205

Phe Ile Gln Glu Leu Leu Ala Lys Leu Gln Gly Leu His Arg Gln Pro
    210                 215                 220

Gly Leu Arg Gln Pro Ser Pro Ser His Asp Gly Ser Leu Ser Pro Leu
225                 230                 235                 240

Gln Asp Arg Ala Arg Thr Ala His Pro
                245

<210> SEQ ID NO 42
<211> LENGTH: 747
<212> TYPE: DNA
<213> ORGANISM: artificial sequence
<220> FEATURE:
<223> OTHER INFORMATION: synthetic

<400> SEQUENCE: 42
gaggacgacg agctgaaggg cctgctggga ctgcccgagg aggagaccga gctggacaac      60
ctgaccgagt tcaacaccgc ccacaacaag aggatcagca ccctgaccat cgaggagggc     120
aacctggaca tccagaggcc caagaggaaa aggaagaaca gcagggtgac cttcagcgag     180
gacgacgaga tcatcaaccc cgaggacgtg accccagcg tgggcagatt caggcccggc      240
gccggaggca ggaggaccga gctgtgcggc accctggact acctcccccc cgagcccggc     300
gccgccggag ccgcccagag gctgggcaag agggtgctga gcaagctgca gagccccagc     360
agggccaggg gccccggcgg aagcccccggc ggactgcaga aaaggcacgc cagggtggag     420
gtgaagtacg acaggaggga gctgcagagg aggctggacg tggagaagtg gatcgacggc     480
aggctggagg agctgtacag gggcatggag gccgacatgc ccgacgagat caacatcgac     540
gagctgctgg agctggagag cgaggaggag aggagcagga gatccaggg cctgctgaaa      600 agctgcggca gcccgtggag ggacttcatc caggagctgc tggccaagct gcagggcctc     660
cacaggcagc ccggcctgag gcagcccagc cccagccacg acggaagcct gagccccctg     720
caagacaggg ccaggaccgc ccaccc                                          747

<210> SEQ ID NO 43
<211> LENGTH: 781
<212> TYPE: DNA
<213> ORGANISM: artificial sequence
<220> FEATURE:
<223> OTHER INFORMATION: synthetic
```

<400> SEQUENCE: 43

```
gctagcgccg gcgaggacga cgagctgaag ggcctgctgg gactgcccga ggaggagacc    60
gagctggaca acctgaccga gttcaacacc gcccacaaca agaggatcag caccctgacc   120
atcgaggagg gcaacctgga catccagagg cccaagagga aaggaagaa cagcagggtg    180
accttcagcg aggacgacga gatcatcaac cccgaggacg tggacccag cgtgggcaga    240
ttcaggcccg gcgccggagg caggaggacc gagctgtgcg gcaccctgga ctacctcccc   300
cccgagcccg gcgccgccgg agccgcccag aggctgggca gagggtgct gagcaagctg    360
cagagcccca gcagggccag ggcccccggc ggaagccccg gcggactgca gaaaaggcac   420
gccagggtgg aggtgaagta cgacaggagg gagctgcaga ggaggctgga cgtggagaag   480
tggatcgacg gcaggctgga ggagctgtac agggggcatgg aggccgacat gcccgacgag   540
atcaacatcg acgagctgct ggagctggag agcgaggagg agaggagcag gaagatccag   600
ggcctgctga aaagctgcgg caagcccgtg gaggacttca tccaggagct gctggccaag   660
ctgcagggcc tccacaggca gcccggcctg aggcagccca gccccagcca cgacggaagc   720
ctgagccccc tgcaagacag ggccaggacc gcccaccccc cggggggagg cggaatcgat   780
t                                                                   781
```

<210> SEQ ID NO 44
<211> LENGTH: 790
<212> TYPE: DNA
<213> ORGANISM: artificial sequence
<220> FEATURE:
<223> OTHER INFORMATION: synthetic

<400> SEQUENCE: 44

```
gctagcgcca ccatggccgg cgaggacgac gagctgaagg gcctgctggg actgcccgag    60
gaggagaccg agctggacaa cctgaccgag ttcaacaccg cccacaacaa gaggatcagc   120
accctgacca tcgaggaggg caacctggac atccagaggc caagaggaa aggaagaac    180
agcagggtga ccttcagcga ggacgacgag atcatcaacc ccgaggacgt ggaccccagc   240
gtgggcagat tcaggcccgg cgccggaggc aggaggaccg agctgtgcgg caccctggac   300
tacctccccc ccgagcccgg cgccgccgga gccgcccaga ggctgggcaa gagggtgctg   360
agcaagctgc agagccccag cagggccagg ggcccccggcg gaagccccgg cggactgcag   420
aaaaggcacg ccagggtgga ggtgaagtac gacaggaggg agctgcagag gaggctggac   480
gtggagaagt ggatcgacgg caggctggag gagctgtaca gggggcatgga ggccgacatg   540
cccgacgaga tcaacatcga cgagctgctg gagctggaga gcgaggagga gaggagcagg   600
aagatccagg gcctgctgaa aagctgcggc aagcccgtgg aggacttcat ccaggagctg   660
ctggccaagc tgcagggcct ccacaggcag cccggcctga ggcagcccag ccccagccac   720
gacggaagcc tgagccccct gcaagacagg gccaggaccg cccacccccc ggggggaggc   780
ggaatcgatt                                                           790
```

<210> SEQ ID NO 45
<211> LENGTH: 372
<212> TYPE: PRT
<213> ORGANISM: artificial sequence
<220> FEATURE:
<223> OTHER INFORMATION: synthetic

<400> SEQUENCE: 45

Ala Ala Gln Arg Leu Gly Lys Arg Val Leu Ser Lys Leu Gln Ser Pro

```
                1               5                   10                  15
Ser Arg Ala Arg Gly Pro Gly Gly Ser Pro Gly Gly Leu Gln Lys Arg
                20                  25                  30

His Ala Arg Val Glu Val Lys Tyr Asp Arg Arg Glu Leu Gln Arg Arg
                35                  40                  45

Leu Asp Val Glu Lys Trp Ile Asp Gly Arg Leu Glu Glu Leu Tyr Arg
50                  55                  60

Gly Met Glu Ala Asp Met Pro Asp Glu Ile Asn Ile Asp Glu Leu Leu
65                  70                  75                  80

Glu Leu Glu Ser Glu Glu Arg Ser Arg Lys Ile Gln Gly Leu Leu
                85                  90                  95

Lys Ser Cys Gly Lys Pro Val Glu Asp Phe Ile Gln Glu Leu Leu Ala
                100                 105                 110

Lys Leu Gln Gly Leu His Arg Gln Pro Gly Leu Arg Gln Pro Ser Pro
                115                 120                 125

Ser His Asp Gly Ser Leu Ser Pro Leu Gln Asp Arg Ala Arg Thr Ala
                130                 135                 140

His Pro Pro Gly Ala Gly Gly Tyr Glu Pro Thr Ser Pro Ser Tyr Glu
145                 150                 155                 160

Pro Thr Ser Pro Ser Tyr Glu Pro Thr Ser Pro Asn Tyr Glu Pro Thr
                165                 170                 175

Ser Pro Ser Tyr Glu Pro Thr Ser Pro Ser Tyr Glu Pro Thr Ser Pro
                180                 185                 190

Ser Tyr Glu Pro Thr Ser Pro Ser Tyr Glu Pro Thr Ser Pro Ser Tyr
                195                 200                 205

Glu Pro Thr Ser Pro Ser Tyr Glu Pro Thr Ser Pro Ser Tyr Glu Pro
210                 215                 220

Thr Ser Pro Ser Tyr Glu Pro Thr Ser Pro Ser Tyr Glu Pro Thr Ser
225                 230                 235                 240

Pro Ser Tyr Glu Pro Thr Ser Pro Ser Tyr Glu Pro Thr Ser Pro Ser
                245                 250                 255

Tyr Glu Pro Thr Ser Pro Ser Tyr Glu Pro Thr Pro Gly Ala Ala Gly
                260                 265                 270

Gln Thr Leu Pro Ser Ala Val Lys Gly Asp Glu Lys Met Gly Gly Glu
                275                 280                 285

Asp Asp Glu Leu Lys Gly Leu Leu Gly Leu Pro Glu Glu Ala Glu
                290                 295                 300

Leu Asp Asn Leu Thr Glu Phe Asn Thr Ala His Asn Lys Arg Ile Ala
305                 310                 315                 320

Thr Leu Thr Ile Glu Glu Gly Asn Leu Asp Ile Gln Arg Pro Lys Arg
                325                 330                 335

Lys Arg Lys Asn Ala Arg Val Thr Phe Ala Glu Asp Asp Glu Ile Ile
                340                 345                 350

Asn Pro Glu Asp Val Asp Pro Ser Val Gly Arg Phe Arg Asn Met Val
                355                 360                 365

Gln Thr Ala Val
    370

<210> SEQ ID NO 46
<211> LENGTH: 1116
<212> TYPE: DNA
<213> ORGANISM: artificial sequence
<220> FEATURE:
<223> OTHER INFORMATION: synthetic

<400> SEQUENCE: 46
```

```
gccgcccaga ggctgggcaa gagggtgctg agcaagctgc agagcccag cagggccagg       60 ggccccggcg gaagcccggc cggactgcag aaaaggcacg ccagggtgga ggtgaagtac     120
gacaggaggg agctgcagag gaggctggac gtggagaagt ggatcgacgg caggctggag     180
gagctgtaca ggggcatgga ggccgacatg cccgacgaga tcaacatcga cgagctgctg     240
gagctggaga gcgaggagga gaggagcagg aagatccagg gcctgctgaa agctgcggc      300 aagcccgtgg aggacttcat ccaggagctg ctggccaagc tgcagggcct ccacaggcag     360
cccggcctga ggcagcccag ccccagccac gacggaagcc tgagcccct gcaagacagg      420 gccaggaccg cccaccccc cggcgccgga ggctacgagc ccaccagccc cagctacgag      480
cccaccagcc ccagctacga gcccaccagc cccaactacg agcccaccag cccagctac     540 gagcccacca gccccagcta cgagcccacc agccccagct acgagcccac cagccccagc    600
tacgagccca ccagccccag ctacgagccc accagcccca gctacgagcc caccagcccc    660
agctacgagc ccaccagccc cagctacgag cccaccagcc ccagctacga gcccaccagc    720
cccagctacg agcccaccag ccccagctac gagcccacca gccccagcta cgagcccacc    780
agccccagct acgagcccac cccggcgcc gccggacaga ccctgcccag cgccgtgaag     840
ggcgacgaga agatgggcgg cgaggacgac gagctgaagg gcctgctggg actgcccgag    900
gaggaggccg agctggacaa cctgaccgag ttcaacaccg cccacaacaa ggatcgcc       960 accctgacca tcgaggaggg caacctggac atccagaggc caagaggaa aaggaagaac    1020 gccagggtga ccttcgccga ggacgacgag atcatcaacc ccgaggacgt ggaccccagc   1080
gtgggcagat tcaggaacat ggtgcagacc gccgtg                              1116

<210> SEQ ID NO 47
<211> LENGTH: 1150
<212> TYPE: DNA
<213> ORGANISM: artificial sequence
<220> FEATURE:
<223> OTHER INFORMATION: synthetic

<400> SEQUENCE: 47
gctagcgccg gcgccgccca gaggctgggc aagagggtgc tgagcaagct gcagagcccc     60
agcagggcca ggggcccccgg cggaagcccc ggcggactgc agaaaaggca cgccagggtg    120
gaggtgaagt acgacaggag ggagctgcag aggaggctgg acgtggagaa gtggatcgac    180
ggcaggctgg aggagctgta caggggcatg gaggccgaca tgcccgacga gatcaacatc    240
gacgagctgc tggagctgga gagcgaggag gagaggagca ggaagatcca gggcctgctg    300
aaaagctgcg gcaagcccgt ggaggacttc atccaggagc tgctggccaa gctgcagggc    360
ctccacaggc agcccggcct gaggcagccc agccccagcc acgacggaag cctgagcccc    420
ctgcaagaca gggccaggac cgcccacccc ccggcgccg aggctacga gcccaccagc      480 cccagctacg agcccaccag ccccagctac gagcccacca gccccaacta cgagcccacc    540
agccccagct acgagcccac cagccccagc tacgagccca ccagccccag ctacgagccc    600
accagcccca gctacgagcc caccagcccc agctacgagc ccaccagccc cagctacgag    660
cccaccagcc ccagctacga gcccaccagc cccagctacg agcccaccag ccccagctac    720
gagcccacca gccccagcta cgagcccacc agccccagct acgagcccac cagccccagc    780
tacgagccca ccagccccag ctacgagccc accccggcgc cgccggacag accctgccc     840 agcgccgtga agggcgacga gaagatgggc ggcgaggacg acgagctgaa gggcctgctg    900
ggactgcccg aggaggaggc cgagctggac aacctgaccg agttcaacac cgcccacaac    960
```

```
aagaggatcg ccaccctgac catcgaggag ggcaacctgg acatccagag gcccaagagg    1020
aaaaggaaga acgccagggt gaccttcgcc gaggacgacg agatcatcaa ccccgaggac    1080
gtggacccca gcgtgggcag attcaggaac atggtgcaga ccgccgtgcc cggggggaggc   1140 ggaatcgatt                                                          1150
```

<210> SEQ ID NO 48
<211> LENGTH: 1159
<212> TYPE: DNA
<213> ORGANISM: artificial sequence
<220> FEATURE:
<223> OTHER INFORMATION: synthetic

<400> SEQUENCE: 48

```
gctagcgcca ccatggccgg cgccgcccag aggctgggca gagggtgct gagcaagctg      60 cagagcccca gcagggccag ggccccggc ggaagccccg cggactgca gaaaaggcac      120 gccagggtgg aggtgaagta cgacaggagg gagctgcaga ggaggctgga cgtggagaag    180
tggatcgacg gcaggctgga ggagctgtac aggggcatgg aggccgacat gcccgacgag    240
atcaacatcg acgagctgct ggagctggag agcgaggagg agaggagcag gaagatccag    300
ggcctgctga aaagctgcgg caagcccgtg gaggacttca tccaggagct gctggccaag    360
ctgcagggcc tccacaggca gcccggcctg aggcagccca gccccagcca cgacggaagc    420
ctgagccccc tgcaagacag ggccaggacc gccaccccc ccggcgccgg aggctacgag     480
cccaccagcc ccagctacga gcccaccagc cccagctacg agcccaccag ccccaactac    540
gagcccacca gccccagcta cgagcccacc agccccagct acgagcccac cagccccagc    600
tacgagccca ccagccccag ctacgagccc accagcccca gctacgagcc accagccccc   660
agctacgagc ccaccagccc cagctacgag cccaccagcc cagctacga gcccaccagc     720 cccagctacg agcccaccag ccccagctac gagcccacca gccccagcta cgagcccacc    780
agccccagct acgagcccac cagccccagc tacgagccca cccccggcgc cgccggacag    840
accctgccca gcgccgtgaa gggcgacgag aagatgggcg cgaggacga cgagctgaag    900 ggcctgctgg actgcccga ggaggaggcc gagctggaca acctgaccga gttcaacacc    960
gcccacaaca gaggatcgc caccctgacc atcgaggagg caacctgga catccagagg    1020 cccaagagga aaaggaagaa cgccagggtg accttcgccg aggacgacga gatcatcaac   1080
cccgaggacg tggaccccag cgtgggcaga ttcaggaaca tggtgcagac cgccgtgccc   1140
gggggaggcg gaatcgatt                                               1159
```

<210> SEQ ID NO 49
<211> LENGTH: 494
<212> TYPE: PRT
<213> ORGANISM: artificial sequence
<220> FEATURE:
<223> OTHER INFORMATION: synthetic

<400> SEQUENCE: 49

```
Ala Ala Ser Thr Ala Ser His Arg Pro Ile Lys Gly Ile Leu Lys Asn
1               5                   10                  15

Lys Thr Ser Thr Thr Ser Ser Met Val Ala Ser Ala Glu Gln Pro Arg
            20                  25                  30

Gly Asn Val Asp Glu Glu Leu Ser Lys Lys Ser Gln Lys Trp Asp Glu
        35                  40                  45

Met Asn Ile Leu Ala Thr Tyr His Pro Ala Asp Lys Asp Tyr Gly Leu
    50                  55                  60
```

```
Met Lys Ile Asp Glu Pro Ser Glu Pro Tyr His Ser Met Met Gly Asp
 65                  70                  75                  80

Asp Glu Asp Ala Cys Ser Asp Thr Glu Ala Thr Glu Ala Met Ala Pro
                 85                  90                  95

Asp Ile Leu Ala Arg Lys Leu Ala Ala Glu Gly Leu Glu Pro Lys
            100                 105                 110

Tyr Arg Ile Gln Glu Gln Glu Ser Ser Gly Glu Asp Ser Asp Leu
        115                 120                 125

Ser Pro Glu Glu Arg Glu Lys Lys Arg Gln Phe Glu Met Lys Arg Lys
130                 135                 140

Leu His Tyr Asn Glu Pro Gly Ala Gly Gly Ser Thr Glu Leu Phe Ser
145                 150                 155                 160

Ser Thr Arg Glu Glu Gly Ser Ser Gly Ser Gly Pro Ser Phe Arg Ser
                165                 170                 175

Asn Gln Arg Lys Met Leu Asn Leu Leu Leu Glu Arg Asp Thr Ser Phe
            180                 185                 190

Thr Val Cys Pro Asp Val Pro Arg Glu Pro Val Gly Lys Phe Leu Gly
            195                 200                 205

Asp Ser Ala Asn Leu Ser Ile Leu Ser Gly Gly Glu Pro Lys Cys Cys
            210                 215                 220

Leu Asp Leu Ser Asn Leu Ser Ser Gly Glu Ile Thr Ala Thr Gln Leu
225                 230                 235                 240

Thr Thr Ser Ala Asp Leu Asp Glu Thr Gly His Leu Asp Ser Ser Gly
                245                 250                 255

Leu Gln Glu Val His Leu Ala Gly Met Asn His Asp Gln His Leu Met
                260                 265                 270

Lys Cys Asp Pro Ala Gln Leu Leu Cys Ser Glu Pro Asn Gly Leu Asp
            275                 280                 285

Arg Gly His Arg Lys Arg Asp Ala Met Cys Ser Ser Ser Ala Asn Lys
            290                 295                 300

Glu Asn Asp Asn Gly Asn Leu Val Asp Ser Glu Met Lys Tyr Leu Gly
305                 310                 315                 320

Asp Pro Ile Thr Thr Val Pro Lys Leu Asp Lys Asn Pro Asn Leu Gly
                325                 330                 335

Glu Asp Gln Ala Glu Glu Ile Asp Asp Glu Leu Met Glu Phe Asp Leu
            340                 345                 350

Lys Asp Gln Glu Ala Lys Val Ser Arg Ser Gly Leu Tyr Arg Asp Pro
            355                 360                 365

Asp Met Pro Glu Asn Leu Asn Arg Pro Arg Leu Lys Gln Val Glu Lys
            370                 375                 380

Phe Lys Asp Asn Thr Ile Pro Gly Ala Ala Gly Glu Asp Ser Asn Asn
385                 390                 395                 400

Phe Asp Gly Ser His Val Tyr Met His Ser Asp Tyr Asn Val Tyr Arg
                405                 410                 415

Val Arg Ser Arg Tyr Asn Ser Asp Trp Gly Glu Thr Gly Thr Glu Gln
            420                 425                 430

Asp Glu Glu Glu Asp Ser Asp Glu Asn Ser Tyr Tyr Gln Pro Asp Met
            435                 440                 445

Glu Tyr Ser Glu Ile Val Gly Leu Pro Glu Glu Glu Ile Pro Ala
            450                 455                 460

Asn Arg Lys Ile Lys Phe Ser Ser Ala Pro Ile Lys Val Phe Asn Thr
465                 470                 475                 480

Tyr Ser Asn Glu Asp Tyr Asp Arg Arg Asn Asp Glu Val Asp
```

485        490

<210> SEQ ID NO 50
<211> LENGTH: 1482
<212> TYPE: DNA
<213> ORGANISM: artificial sequence
<220> FEATURE:
<223> OTHER INFORMATION: synthetic

<400> SEQUENCE: 50

| | | | | |
|---|---|---|---|---|
| gccgccagca | ccgccagcca | caggcccatc | aagggcatcc | tgaagaacaa gaccagcacc | 60 |
| acctccagca | tggtcgccag | cgccgagcag | cccaggggca | acgtggacga ggagctgagc | 120 |
| aagaaaagcc | agaagtggga | cgagatgaac | atcctggcca | cctaccaccc cgccgacaag | 180 |
| gactacggcc | tgatgaagat | cgacgagccc | agcgagccct | accacagcat gatgggcgac | 240 |
| gacgaggacg | cctgcagcga | caccgaggcc | accgaagcca | tggcccccga catcctggcc | 300 |
| aggaagctcg | ccgccgccga | gggcctggag | cccaagtaca | ggattcagga gcaggagagc | 360 |
| agcggcgagg | aggacagcga | cctgagcccc | gaggagaggg | agaagaaaag gcagttcgag | 420 |
| atgaaaagga | agctgcacta | caacgagccc | ggcgccggag | gcagcaccga gctgttcagc | 480 |
| agcaccaggg | aggagggcag | cagcggcagc | ggccccagct | tcaggagcaa ccagaggaag | 540 |
| atgctgaacc | tcctgctgga | gagggacacc | agcttcaccg | tctgccccga cgtgcccagg | 600 |
| gagcccgtgg | gcaagttcct | gggcgacagc | gccaacctga | gcatcctgag cggcggcgag | 660 |
| cccaagtgct | gcctggacct | gagcaacctg | agcagcggcg | agatcaccgc cacccagctg | 720 |
| accaccagcg | ccgacctgga | cgagaccggc | cacctggaca | gcagcggcct gcaagaggtc | 780 |
| catctggccg | gaatgaacca | cgaccagcac | ctgatgaagt | gcgaccccgc ccagctgctg | 840 |
| tgcagcgagc | ccaacggcct | cgacaggggc | cacaggaaaa | gggacgccat gtgcagcagc | 900 |
| agcgccaaca | ggagaacga | caacggcaac | ctggtggaca | gcgagatgaa gtacctgggc | 960 |
| gaccccatca | ccaccgtgcc | caagctggac | aagaaccca | acctgggcga ggaccaggcc | 1020 |
| gaggagatcg | acgacgagct | gatggagttc | gacctgaagg | accaggaggc caaggtgtcc | 1080 |
| aggagcggcc | tgtacaggga | ccccgacatg | cccgagaacc | tgaacaggcc caggctgaag | 1140 |
| caagtcgaga | agttcaagga | caacaccatc | cccggcgccg | ccggagagga cagcaacaac | 1200 |
| ttcgacggca | gccacgtcta | catgcacagc | gactacaacg | tgtacagggt gaggagcaga | 1260 |
| tacaacagcg | actggggcga | gaccggcacc | gagcaggacg | aggaggagga cagcgacgag | 1320 |
| aacagctact | accagcccga | catggagtac | agcgagatcg | tgggcctgcc cgaggaggag | 1380 |
| gagatccccg | ccaacaggaa | gatcaagttc | agcagcgccc | ccatcaaggt gttcaacacc | 1440 |
| tacagcaacg | aggactacga | caggaggaac | gacgaggtgg | ac | 1482 |

<210> SEQ ID NO 51
<211> LENGTH: 1516
<212> TYPE: DNA
<213> ORGANISM: artificial sequence
<220> FEATURE:
<223> OTHER INFORMATION: synthetic

<400> SEQUENCE: 51

| | | | | |
|---|---|---|---|---|
| gctagcgccg | cgccgccag | caccgccagc | acaggcccca | tcaagggcat cctgaagaac | 60 |
| aagaccagca | ccacctccag | catggtcgcc | agcgccgagc | agcccagggg caacgtggac | 120 |
| gaggagctga | gcaagaaaag | ccagaagtgg | gacgagatga | acatcctggc cacctaccac | 180 |
| cccgccgaca | aggactacgg | cctgatgaag | atcgacgagc | cagcgagcc ctaccacagc | 240 |

```
atgatgggcg acgacgagga cgcctgcagc gacaccgagg ccaccgaagc catggccccc     300
gacatcctgg ccaggaagct cgccgccgcc gagggcctgg agcccaagta caggattcag     360
gagcaggaga gcagcggcga ggaggacagc gacctgagcc ccgaggagag ggagaagaaa     420
aggcagttcg agatgaaaag gaagctgcac tacaacgagc ccggcgccgg aggcagcacc     480
gagctgttca gcagcaccag ggaggagggc agcagcggca gcggccccag cttcaggagc     540
aaccagagga agatgctgaa cctcctgctg gagagggaca ccagcttcac cgtctgcccc     600
gacgtgccca gggagcccgt gggcaagttc ctgggcgaca cgccaacct gagcatcctg      660
agcggcggcg agcccaagtg ctgcctggac ctgagcaacc tgagcagcgg cgagatcacc     720
gccacccagc tgaccaccag cgccgacctg gacgagaccg gccacctgga cagcagcggc     780
ctgcaagagg tccatctggc cggaatgaac acgaccagc acctgatgaa gtgcgacccc      840
gcccagctgc tgtgcagcga gcccaacggc ctcgacaggg ccacaggaa agggacgcc       900
atgtgcagca gcgcgccaa caaggagaac gacaacggca acctggtgga cagcgagatg      960
aagtacctgg gcgaccccat caccaccgtg cccaagctgg acaagaaccc caacctgggc    1020
gaggaccagg ccgaggagat cgacgacgag ctgatggagt tcgacctgaa ggaccaggag    1080
gccaaggtgt ccaggagcgg cctgtacagg gaccccgaca tgcccgagaa cctgaacagg    1140
cccaggctga gcaagtcga gaagttcaag gacaacacca tccccggcgc cgccggagag     1200
gacagcaaca acttcgacgg cagccacgtc tacatgcaca gcgactacaa cgtgtacagg    1260
gtgaggagca gatacaacag cgactgggc gagaccggca ccgagcagga cgaggaggag     1320
gacagcgacg agaacagcta ctaccagccc gacatggagt acagcgagat cgtgggcctg    1380
cccgaggagg aggagatccc cgccaacagg aagatcaagt tcagcagcgc ccccatcaag    1440
gtgttcaaca cctacagcaa cgaggactac gacaggagga cgacgaggt ggaccccggg     1500
ggaggcggaa tcgatt                                                    1516
```

<210> SEQ ID NO 52
<211> LENGTH: 1525
<212> TYPE: DNA
<213> ORGANISM: artificial sequence
<220> FEATURE:
<223> OTHER INFORMATION: synthetic

<400> SEQUENCE: 52

```
gctagcgcca ccatggccgg cgccgccagc accgccagcc acaggcccat caagggcatc      60
ctgaagaaca agaccagcac cacctccagc atggtcgcca cgccgagca gcccagggc       120
aacgtggacg aggagctgag caagaaaagc cagaagtggg acgagatgaa catcctggcc     180
acctaccacc ccgccgacaa ggactacggc ctgatgaaga tcgacgagcc cagcgagccc     240
taccacagca tgatgggcga cgacgaggac gcctgcagcg acaccgaggc caccgaagcc     300
atggccccg acatcctggc caggaagctc gccgccgccg agggcctgga gcccaagtac     360
aggattcagg agcaggagag cagcggcgag gaggacagcg acctgagccc cgaggagagg    420
gagaagaaaa ggcagttcga gatgaaaagg aagctgcact acaacgagcc cggcgccgga    480
ggcagcaccg agctgttcag cagcaccagg gaggagggca gcagcggcag cggccccagc    540
ttcaggagca accagaggaa gatgctgaac ctcctgctgg agagggacac cagcttcacc    600
gtctgcccg acgtgcccag ggagcccgtg ggcaagttcc tgggcgacag cgccaacctg     660
agcatcctga gcggcggcga gcccaagtgc tgcctggacc tgagcaacct gagcagcggc    720
gagatcaccg ccacccagct gaccaccagc gccgacctg acgagaccgg ccacctggac     780
```

-continued

```
agcagcggcc tgcaagaggt ccatctggcc ggaatgaacc acgaccagca cctgatgaag      840
tgcgaccccg cccagctgct gtgcagcgag cccaacggcc tcgacagggg ccacaggaaa      900
agggacgcca tgtgcagcag cagcgccaac aaggagaacg acaacggcaa cctggtggac      960
agcgagatga agtacctggg cgaccccatc accaccgtgc ccaagctgga caagaacccc     1020
aacctgggcg aggaccaggc cgaggagatc gacgacgagc tgatggagtt cgacctgaag     1080
gaccaggagg ccaaggtgtc caggagcggc ctgtacaggg accccgacat gcccgagaac     1140
ctgaacaggc ccaggctgaa gcaagtcgag aagttcaagg acaacaccat ccccggcgcc     1200
gccgagagaa cagcaacaa cttcgacggc agccacgtct acatgcacag cgactacaac     1260
gtgtacaggg tgaggagcag atacaacagc gactggggcg agaccggcac cgagcaggac     1320
gaggaggagg acagcgacga gaacagctac taccagcccg acatggagta cagcgagatc     1380
gtgggcctgc ccgaggagga ggagatcccc gccaacagga agatcaagtt cagcagcgcc     1440
cccatcaagg tgttcaacac ctacagcaac gaggactacg acaggaggaa cgacgaggtg     1500
gaccccgggg gaggcggaat cgatt                                            1525
```

<210> SEQ ID NO 53
<211> LENGTH: 237
<212> TYPE: PRT
<213> ORGANISM: artificial sequence
<220> FEATURE:
<223> OTHER INFORMATION: synthetic

<400> SEQUENCE: 53

```
Glu Gln Asp Asn Ser Pro Gln Lys Ile Gln Phe Thr Val Pro Leu Leu
1               5                   10                  15

Glu Pro His Leu Asp Pro Glu Ala Ala Glu Gln Ile Arg Arg Arg Arg
            20                  25                  30

Pro Glu Pro Ala Thr Leu Val Leu Thr Ser Asp Gln Ser Ser Pro Glu
        35                  40                  45

Ile Asp Glu Asp Arg Ile Pro Asn Pro His Leu Lys Ser Thr Leu Ala
    50                  55                  60

Met Asp Pro Arg Gln Arg Lys Lys Met Ala Arg Ile Thr Pro Thr Met
65                  70                  75                  80

Lys Glu Leu Gln Met Met Val Glu His His Leu Gly Gln Gln Gln Gln
                85                  90                  95

Gly Glu Glu Pro Gly Ala Gly Gly Val Asn Phe Thr Val Asp Gln Ile
            100                 105                 110

Arg Ala Ile Met Asp Lys Lys Ala Asn Ile Arg Asn Met Ser Val Ile
        115                 120                 125

Ala His Val Asp His Gly Lys Ser Thr Leu Thr Asp Ser Leu Val Cys
    130                 135                 140

Lys Ala Gly Ile Ile Ala Ser Ala Arg Ala Gly Glu Glu Arg Phe Glu
145                 150                 155                 160

Asp Glu Arg Lys Asp Glu Gln Glu Arg Cys Ile Thr Ile Lys Ser Thr
                165                 170                 175

Ala Ile Ser Leu Phe Tyr Glu Leu Ser Glu Asn Asp Leu Asn Phe Ile
            180                 185                 190

Lys Gln Ser Lys Asp Pro Gly Ala Ala Gly Asp Pro Lys Asp Arg Lys
        195                 200                 205

Lys Ile Gln Phe Ser Val Pro Ala Pro Pro Ser Gln Leu Asp Pro Arg
    210                 215                 220

Gln Val Glu Met Ile Arg Arg Arg Pro Glu Pro Ala
225                 230                 235
```

```
<210> SEQ ID NO 54
<211> LENGTH: 711
<212> TYPE: DNA
<213> ORGANISM: artificial sequence
<220> FEATURE:
<223> OTHER INFORMATION: synthetic

<400> SEQUENCE: 54
gagcaggaca acagccccca gaagatccag ttcaccgtgc ccctgctgga gccccacctg      60
gaccccgagg ccgccgagca gatcaggagg aggaggcccg agcccgccac cctggtgctg     120
accagcgacc agagcagccc cgagatcgac gaggacagga ttcccaaccc ccacctgaaa     180
agcaccctgg ccatggaccc caggcagagg aagaagatgg ccaggatcac ccccaccatg     240
aaggagctgc agatgatggt ggagcaccac ctgggccagc agcagcaggg cgaggagccc     300
ggcgccggag gcgtgaactt caccgtggac cagatcaggg ccatcatgga caagaaggcc     360
aacatcagga catgagcgt gatcgcccac gtcgatcacg gcaagagcac cctgaccgac     420
agcctggtgt gcaaggccgg aatcatcgcc agcgccaggg ccggagagga gaggttcgag     480
gacgagagga aggacgagca ggagaggtgc atcaccatca agagcaccgc catcagcctg     540
ttctacgagc tgagcgagaa cgacctgaac ttcatcaagc agagcaagga ccccggcgcc     600 gccgagacc ccaaggacag gaagaagatc cagttcagcg tgcccgcccc cccagccag     660 ctcgacccca ggcaagtcga gatgatcagg aggaggaggc ccgagcccgc c              711

<210> SEQ ID NO 55
<211> LENGTH: 745
<212> TYPE: DNA
<213> ORGANISM: artificial sequence
<220> FEATURE:
<223> OTHER INFORMATION: synthetic

<400> SEQUENCE: 55
gctagcgccg gcgagcagga caacagcccc cagaagatcc agttcaccgt gcccctgctg      60
gagccccacc tggaccccga ggccgccgag cagatcagga ggaggaggcc cgagcccgcc     120
accctggtgc tgaccagcga ccagagcagc cccgagatcg acgaggacag gattcccaac     180
ccccacctga aaagcaccct ggccatggac cccaggcaga ggaagaagat ggccaggatc     240 accccccacca tgaaggagct gcagatgatg gtggagcacc acctgggcca gcagcagcag     300
ggcgaggagc ccggcgccgg aggcgtgaac ttcaccgtgg accagatcag ggccatcatg     360
gacaagaagg ccaacatcag gaacatgagc gtgatcgccc acgtcgatca cggcaagagc     420
accctgaccg acagcctggt gtgcaaggcc ggaatcatcg ccagcgccag gccggagag     480 gagaggttcg aggacgagag gaaggacgag caggagaggt gcatcaccat caagagcacc     540
gccatcagcc tgttctacga gctgagcgag aacgacctga acttcatcaa gcagagcaag     600
gaccccggcg ccgccggaga ccccaaggac aggaagaaga tccagttcag cgtgcccgcc     660 cccccccagcc agctcgaccc caggcaagtc gagatgatca ggaggaggag gcccgagccc     720 gccccccgggg gaggcggaat cgatt                                          745

<210> SEQ ID NO 56
<211> LENGTH: 754
<212> TYPE: DNA
<213> ORGANISM: artificial sequence
<220> FEATURE:
<223> OTHER INFORMATION: synthetic

<400> SEQUENCE: 56
```

```
gctagcgcca ccatggccgg cgagcaggac aacagccccc agaagatcca gttcaccgtg      60
cccctgctgg agccccacct ggaccccgag gccgccgagc agatcaggag gaggaggccc     120
gagcccgcca ccctggtgct gaccagcgac cagagcagcc ccgagatcga cgaggacagg     180
attcccaacc cccacctgaa aagcaccctg gccatggacc ccaggcagag gaagaagatg     240
gccaggatca cccccaccat gaaggagctg cagatgatgg tggagcacca cctgggccag     300
cagcagcagg gcgaggagcc cggcgccgga ggcgtgaact tcaccgtgga ccagatcagg     360
gccatcatgg acaagaaggc caacatcagg aacatgagcg tgatcgccca cgtcgatcac     420
ggcaagagca ccctgaccga cagcctggtg tgcaaggccg aatcatcgc cagcgccagg     480 gccggagagg agaggttcga ggacgagagg aaggacgagc aggagaggtg catcaccatc     540
aagagcaccg ccatcagcct gttctacgag ctgagcgaga cgacctgaa cttcatcaag     600 cagagcaagg accccggcgc cgccggagac cccaaggaca ggaagaagat ccagttcagc     660
gtgcccgccc cccccagcca gctcgacccc aggcaagtcg agatgatcag gaggaggagg     720
cccgagcccg cccccggggg aggcggaatc gatt                                754
```

<210> SEQ ID NO 57
<211> LENGTH: 403
<212> TYPE: PRT
<213> ORGANISM: Homo sapiens
<220> FEATURE:
<221> NAME/KEY: misc_feature
<222> LOCATION: (288)..(288)
<223> OTHER INFORMATION: Xaa can be any naturally occurring amino acid

<400> SEQUENCE: 57

```
Met Asp Arg Ser Lys Glu Asn Cys Ile Ser Gly Pro Val Lys Ala Thr
1               5                   10                  15

Ala Pro Val Gly Gly Pro Lys Arg Val Leu Val Thr Gln Gln Phe Pro
                20                  25                  30

Cys Gln Asn Pro Leu Pro Val Asn Ser Gly Gln Ala Gln Arg Val Leu
            35                  40                  45

Cys Pro Ser Asn Ser Ser Gln Arg Ile Pro Leu Gln Ala Gln Lys Leu
        50                  55                  60

Val Ser Ser His Lys Pro Val Gln Asn Gln Lys Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu
                100                 105                 110

Glu Leu Ala Ser Lys Gln Lys Asn Glu Glu Ser Lys Lys Arg Gln Trp
            115                 120                 125

Ala Leu Glu Asp Phe Glu Ile Gly Arg Pro Leu Gly Lys Gly Lys Phe
        130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                165                 170                 175

Gln Leu Arg Arg Glu Val Glu Ile Gln Ser His Leu Arg His Pro Asn
            180                 185                 190

Ile Leu Arg Leu Tyr Gly Tyr Phe His Asp Ala Thr Arg Val Tyr Leu
        195                 200                 205

Ile Leu Glu Tyr Ala Pro Leu Gly Thr Val Tyr Arg Glu Leu Gln Lys
    210                 215                 220
```

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
            245                 250                 255

Ile Lys Pro Glu Asn Leu Leu Leu Gly Ser Ala Gly Glu Leu Lys Ile
        260                 265                 270

Ala Asp Phe Gly Trp Ser Val His Ala Pro Ser Ser Arg Arg Thr Xaa
    275                 280                 285

Leu Cys Gly Thr Leu Asp Tyr Leu Pro Pro Glu Met Ile Glu Gly Arg
290                 295                 300

Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu
                325                 330                 335

Thr Tyr Lys Arg Ile Ser Arg Val Glu Phe Thr Phe Pro Asp Phe Val
            340                 345                 350

Thr Glu Gly Ala Arg Asp Leu Ile Ser Arg Leu Leu Lys His Asn Pro
        355                 360                 365

Ser Gln Arg Pro Met Leu Arg Glu Val Leu Glu His Pro Trp Ile Thr
    370                 375                 380

Ala Asn Ser Ser Lys Pro Ser Asn Cys Gln Asn Lys Glu Ser Ala Ser
385                 390                 395                 400

Lys Gln Ser

<210> SEQ ID NO 58
<211> LENGTH: 393
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (371)..(371)

```
<223> OTHER INFORMATION: Xaa can be any naturally occurring amino acid
<220> FEATURE:
<221> NAME/KEY: misc_feature
<222> LOCATION: (376)..(376)
<223> OTHER INFORMATION: Xaa can be any naturally occurring amino acid
<220> FEATURE:
<221> NAME/KEY: misc_feature
<222> LOCATION: (378)..(378)
<223> OTHER INFORMATION: Xaa can be any naturally occurring amino acid
<220> FEATURE:
<221> NAME/KEY: misc_feature
<222> LOCATION: (392)..(392)
<223> OTHER INFORMATION: Xaa can be any naturally occurring amino acid

<400> SEQUENCE: 58
```

| | | | | | | | | | | | | | | | |
|---|---|---|---|---|---|---|---|---|---|---|---|---|---|---|---|
| Met | Glu | Glu | Pro | Gln | Ser | Asp | Pro | Xaa | Val | Glu | Pro | Pro | Leu | Xaa | Gln |
| 1 | | | | 5 | | | | | 10 | | | | | 15 | |
| Glu | Xaa | Phe | Xaa | Asp | Leu | Trp | Lys | Leu | Leu | Pro | Glu | Asn | Asn | Val | Leu |
| | | | 20 | | | | | 25 | | | | | 30 | | |
| Xaa | Pro | Leu | Pro | Xaa | Gln | Ala | Met | Asp | Asp | Leu | Met | Leu | Xaa | Pro | Asp |
| | | 35 | | | | | 40 | | | | | 45 | | | |
| Asp | Ile | Glu | Gln | Trp | Phe | Xaa | Glu | Asp | Pro | Gly | Pro | Asp | Glu | Ala | Pro |
| | 50 | | | | | 55 | | | | | 60 | | | | |
| Arg | Met | Pro | Glu | Ala | Ala | Pro | Pro | Val | Ala | Pro | Ala | Pro | Ala | Ala | Pro |
| 65 | | | | | 70 | | | | | 75 | | | | | 80 |
| Thr | Pro | Ala | Ala | Pro | Ala | Pro | Ala | Pro | Ser | Trp | Pro | Leu | Ser | Ser | Ser |
| | | | | 85 | | | | | 90 | | | | | 95 | |
| Val | Pro | Ser | Gln | Lys | Thr | Tyr | Gln | Gly | Ser | Tyr | Gly | Phe | Arg | Leu | Gly |
| | | | 100 | | | | | 105 | | | | | 110 | | |
| Phe | Leu | His | Ser | Gly | Thr | Ala | Lys | Ser | Val | Thr | Cys | Thr | Tyr | Ser | Pro |
| | | 115 | | | | | 120 | | | | | 125 | | | |
| Ala | Leu | Asn | Lys | Met | Phe | Cys | Gln | Leu | Ala | Lys | Thr | Cys | Pro | Val | Gln |
| | 130 | | | | | 135 | | | | | 140 | | | | |
| Leu | Trp | Val | Asp | Ser | Thr | Pro | Pro | Pro | Gly | Thr | Arg | Val | Arg | Ala | Met |
| 145 | | | | | 150 | | | | | 155 | | | | | 160 |
| Ala | Ile | Tyr | Lys | Gln | Ser | Gln | His | Met | Thr | Glu | Val | Val | Arg | Arg | Cys |
| | | | | 165 | | | | | 170 | | | | | 175 | |
| Pro | His | His | Glu | Arg | Cys | Ser | Asp | Ser | Asp | Gly | Leu | Ala | Pro | Pro | Gln |
| | | | 180 | | | | | 185 | | | | | 190 | | |
| His | Leu | Ile | Arg | Val | Glu | Gly | Asn | Leu | Arg | Val | Glu | Tyr | Leu | Asp | Asp |
| | | 195 | | | | | 200 | | | | | 205 | | | |
| Arg | Asn | Thr | Phe | Arg | His | Xaa | Val | Val | Val | Pro | Tyr | Glu | Pro | Pro | Glu |
| | 210 | | | | | 215 | | | | | 220 | | | | |
| Val | Gly | Ser | Asp | Cys | Thr | Thr | Ile | His | Tyr | Asn | Tyr | Met | Cys | Asn | Ser |
| 225 | | | | | 230 | | | | | 235 | | | | | 240 |
| Ser | Cys | Met | Gly | Gly | Met | Asn | Arg | Arg | Pro | Ile | Leu | Thr | Ile | Ile | Thr |
| | | | | 245 | | | | | 250 | | | | | 255 | |
| Leu | Glu | Asp | Ser | Ser | Gly | Asn | Leu | Leu | Gly | Arg | Asn | Ser | Phe | Glu | Val |
| | | | 260 | | | | | 265 | | | | | 270 | | |
| Arg | Val | Cys | Ala | Cys | Pro | Gly | Arg | Asp | Arg | Arg | Thr | Glu | Glu | Glu | Asn |
| | | 275 | | | | | 280 | | | | | 285 | | | |
| Leu | Arg | Lys | Lys | Gly | Glu | Pro | His | His | Glu | Leu | Pro | Pro | Gly | Ser | Thr |
| | 290 | | | | | 295 | | | | | 300 | | | | |
| Lys | Arg | Ala | Leu | Pro | Asn | Asn | Thr | Ser | Ser | Ser | Pro | Gln | Pro | Lys | Lys |
| 305 | | | | | 310 | | | | | 315 | | | | | 320 |
| Lys | Pro | Leu | Asp | Gly | Glu | Tyr | Phe | Thr | Leu | Gln | Ile | Arg | Gly | Arg | Glu |
| | | | | 325 | | | | | 330 | | | | | 335 | |
| Arg | Phe | Glu | Met | Phe | Arg | Glu | Leu | Asn | Glu | Ala | Leu | Glu | Leu | Lys | Asp |

-continued

```
                     340                 345                 350
Ala Gln Ala Gly Lys Glu Pro Gly Gly Ser Arg Ala His Ser Ser His
                355                 360                 365

Leu Lys Xaa Lys Lys Gly Gln Xaa Thr Xaa Arg His Lys Lys Leu Met
            370                 375                 380

Phe Lys Thr Glu Gly Pro Asp Xaa Asp
385                 390

<210> SEQ ID NO 59
<211> LENGTH: 1030
<212> TYPE: PRT
<213> ORGANISM: Homo sapiens
<220> FEATURE:
<221> NAME/KEY: misc_feature
<222> LOCATION: (20)..(20)
<223> OTHER INFORMATION: Xaa can be any naturally occurring amino acid

<400> SEQUENCE: 59

Met Lys Met Ala Asp Ala Lys Gln Lys Arg Asn Glu Gln Leu Lys Arg
1               5                   10                  15

Trp Ile Gly Xaa Glu Thr Asp Leu Glu Pro Val Val Lys Arg Gln
                20                  25                  30

Lys Thr Lys Val Lys Phe Asp Asp Gly Ala Val Phe Leu Ala Ala Cys
            35                  40                  45

Ser Ser Gly Asp Thr Asp Glu Val Leu Lys Leu His Arg Gly Ala
50                  55                  60

Asp Ile Asn Tyr Ala Asn Val Asp Gly Leu Thr Ala Leu His Gln Ala
65                  70                  75                  80

Cys Ile Asp Asp Asn Val Asp Met Val Lys Phe Leu Val Glu Asn Gly
                85                  90                  95

Ala Asn Ile Asn Gln Pro Asp Asn Glu Gly Trp Ile Pro Leu His Ala
            100                 105                 110

Ala Ala Ser Cys Gly Tyr Leu Asp Ile Ala Glu Phe Leu Ile Gly Gln
        115                 120                 125

Gly Ala His Val Gly Ala Val Asn Ser Glu Gly Asp Thr Pro Leu Asp
    130                 135                 140

Ile Ala Glu Glu Glu Ala Met Glu Glu Leu Leu Gln Asn Glu Val Asn
145                 150                 155                 160

Arg Gln Gly Val Asp Ile Glu Ala Ala Arg Lys Glu Glu Arg Ile
                165                 170                 175

Met Leu Arg Asp Ala Arg Gln Trp Leu Asn Ser Gly His Ile Asn Asp
            180                 185                 190

Val Arg His Ala Lys Ser Gly Gly Thr Ala Leu His Val Ala Ala Ala
        195                 200                 205

Lys Gly Tyr Thr Glu Val Leu Lys Leu Leu Ile Gln Ala Gly Tyr Asp
    210                 215                 220

Val Asn Ile Lys Asp Tyr Asp Gly Trp Thr Pro Leu His Ala Ala Ala
225                 230                 235                 240

His Trp Gly Lys Glu Glu Ala Cys Arg Ile Leu Val Asp Asn Leu Cys
                245                 250                 255

Asp Met Glu Met Val Asn Lys Val Gly Gln Thr Ala Phe Asp Val Ala
            260                 265                 270

Asp Glu Asp Ile Leu Gly Tyr Leu Glu Glu Leu Gln Lys Lys Gln Asn
        275                 280                 285

Leu Leu His Ser Glu Lys Arg Asp Lys Lys Ser Pro Leu Ile Glu Ser
    290                 295                 300
```

-continued

```
Thr Ala Asn Met Asp Asn Asn Gln Ser Gln Lys Thr Phe Lys Asn Lys
305                 310                 315                 320

Glu Thr Leu Ile Ile Glu Pro Glu Lys Asn Ala Ser Arg Ile Glu Ser
            325                 330                 335

Leu Glu Gln Glu Lys Val Asp Glu Glu Glu Gly Lys Lys Asp Glu
        340                 345                 350

Ser Ser Cys Ser Ser Glu Glu Asp Glu Asp Asp Ser Glu Ser Glu
        355                 360                 365

Ala Glu Thr Asp Lys Thr Lys Pro Leu Ala Ser Val Thr Asn Ala Asn
370                 375                 380

Thr Ser Ser Thr Gln Ala Ala Pro Val Ala Val Thr Thr Pro Thr Val
385                 390                 395                 400

Ser Ser Gly Gln Ala Thr Pro Thr Ser Pro Ile Lys Lys Phe Pro Thr
            405                 410                 415

Thr Ala Thr Lys Ile Ser Pro Lys Glu Glu Arg Lys Asp Glu Ser
            420                 425                 430

Pro Ala Thr Trp Arg Leu Gly Leu Arg Lys Thr Gly Ser Tyr Gly Ala
            435                 440                 445

Leu Ala Glu Ile Thr Ala Ser Lys Glu Gly Lys Glu Lys Asp Thr
450                 455                 460

Ala Gly Val Thr Arg Ser Ala Ser Ser Pro Arg Leu Ser Ser Ser Leu
465                 470                 475                 480

Asp Asn Lys Glu Lys Glu Lys Asp Ser Lys Gly Thr Arg Leu Ala Tyr
            485                 490                 495

Val Ala Pro Thr Ile Pro Arg Arg Leu Ala Ser Thr Ser Asp Ile Glu
            500                 505                 510

Glu Lys Glu Asn Arg Asp Ser Ser Ser Leu Arg Thr Ser Ser Ser Tyr
            515                 520                 525

Thr Arg Arg Lys Trp Glu Asp Asp Leu Lys Lys Asn Ser Ser Val Asn
            530                 535                 540

Glu Gly Ser Thr Tyr His Lys Ser Cys Ser Phe Gly Arg Arg Gln Asp
545                 550                 555                 560

Asp Leu Ile Ser Ser Ser Val Pro Ser Thr Thr Ser Thr Pro Thr Val
            565                 570                 575

Thr Ser Ala Ala Gly Leu Gln Lys Ser Leu Leu Ser Ser Thr Ser Thr
            580                 585                 590

Thr Thr Lys Ile Thr Thr Gly Ser Ser Ala Gly Thr Gln Ser Ser
            595                 600                 605

Thr Ser Asn Arg Leu Trp Ala Glu Asp Ser Thr Glu Lys Glu Lys Asp
            610                 615                 620

Ser Val Pro Thr Ala Val Thr Ile Pro Val Ala Pro Thr Val Val Asn
625                 630                 635                 640

Ala Ala Ala Ser Thr Thr Thr Leu Thr Thr Thr Thr Ala Gly Thr Val
            645                 650                 655

Ser Ser Thr Thr Glu Val Arg Glu Arg Arg Ser Tyr Leu Thr Pro
            660                 665                 670

Val Arg Asp Glu Glu Ser Glu Ser Gln Arg Lys Ala Arg Ser Arg Gln
            675                 680                 685

Ala Arg Gln Ser Arg Arg Ser Thr Gln Gly Val Thr Leu Thr Asp Leu
            690                 695                 700

Gln Glu Ala Glu Lys Thr Ile Gly Arg Ser Arg Ser Thr Arg Thr Arg
705                 710                 715                 720

Glu Gln Glu Asn Glu Glu Lys Glu Lys Glu Lys Glu Lys Gln Asp
            725                 730                 735
```

```
Lys Glu Lys Gln Glu Glu Lys Glu Ser Glu Thr Ser Arg Glu Asp
            740                 745                 750

Glu Tyr Lys Gln Lys Tyr Ser Arg Thr Tyr Asp Glu Thr Tyr Gln Arg
        755                 760                 765

Tyr Arg Pro Val Ser Thr Ser Ser Thr Thr Pro Ser Ser Ser Leu
770                 775                 780

Ser Thr Met Ser Ser Ser Leu Tyr Ala Ser Ser Gln Leu Asn Arg Pro
785                 790                 795                 800

Asn Ser Leu Val Gly Ile Thr Ser Ala Tyr Ser Arg Gly Ile Thr Lys
                805                 810                 815

Glu Asn Glu Arg Glu Gly Glu Lys Arg Glu Glu Lys Glu Gly Glu
            820                 825                 830

Asp Lys Ser Gln Pro Lys Ser Ile Arg Glu Arg Arg Pro Arg Glu
            835                 840                 845

Lys Arg Arg Ser Thr Gly Val Ser Phe Trp Thr Gln Asp Ser Asp Glu
            850                 855                 860

Asn Glu Gln Glu Gln Gln Ser Asp Thr Glu Glu Gly Ser Asn Lys Lys
865                 870                 875                 880

Glu Thr Gln Thr Asp Ser Ile Ser Arg Tyr Glu Thr Ser Ser Thr Ser
                885                 890                 895

Ala Gly Asp Arg Tyr Asp Ser Leu Leu Gly Arg Ser Gly Ser Tyr Ser
                900                 905                 910

Tyr Leu Glu Glu Arg Lys Pro Tyr Ser Ser Arg Leu Glu Lys Asp Asp
            915                 920                 925

Ser Thr Asp Phe Lys Lys Leu Tyr Glu Gln Ile Leu Ala Glu Asn Glu
930                 935                 940

Lys Leu Lys Ala Gln Leu His Asp Thr Asn Met Glu Leu Thr Asp Leu
945                 950                 955                 960

Lys Leu Gln Leu Glu Lys Ala Thr Gln Arg Gln Glu Arg Phe Ala Asp
                965                 970                 975

Arg Ser Leu Leu Glu Met Glu Lys Arg Glu Arg Ala Leu Glu Arg
            980                 985                 990

Arg Ile Ser Glu Met Glu Glu Glu  Leu Lys Met Leu Pro  Asp Leu Lys
            995                 1000                1005

Ala Asp Asn Gln Arg Leu Lys  Asp Glu Asn Gly Ala  Leu Ile Arg
           1010                1015                1020

Val Ile  Ser Lys Leu Ser Lys
1025                1030

<210> SEQ ID NO 60
<211> LENGTH: 1970
<212> TYPE: PRT
<213> ORGANISM: Homo sapiens
<220> FEATURE:
<221> NAME/KEY: misc_feature
<222> LOCATION: (1562)..(1562)
<223> OTHER INFORMATION: Xaa can be any naturally occurring amino acid
<220> FEATURE:
<221> NAME/KEY: misc_feature
<222> LOCATION: (1594)..(1594)
<223> OTHER INFORMATION: Xaa can be any naturally occurring amino acid
<220> FEATURE:
<221> NAME/KEY: misc_feature
<222> LOCATION: (1616)..(1616)
<223> OTHER INFORMATION: Xaa can be any naturally occurring amino acid
<220> FEATURE:
<221> NAME/KEY: misc_feature
<222> LOCATION: (1623)..(1623)
<223> OTHER INFORMATION: Xaa can be any naturally occurring amino acid
<220> FEATURE:
```

```
<221> NAME/KEY: misc_feature
<222> LOCATION: (1630)..(1630)
<223> OTHER INFORMATION: Xaa can be any naturally occurring amino acid
<220> FEATURE:
<221> NAME/KEY: misc_feature
<222> LOCATION: (1637)..(1637)
<223> OTHER INFORMATION: Xaa can be any naturally occurring amino acid
<220> FEATURE:
<221> NAME/KEY: misc_feature
<222> LOCATION: (1644)..(1644)
<223> OTHER INFORMATION: Xaa can be any naturally occurring amino acid
<220> FEATURE:
<221> NAME/KEY: misc_feature
<222> LOCATION: (1651)..(1651)
<223> OTHER INFORMATION: Xaa can be any naturally occurring amino acid
<220> FEATURE:
<221> NAME/KEY: misc_feature
<222> LOCATION: (1658)..(1658)
<223> OTHER INFORMATION: Xaa can be any naturally occurring amino acid
<220> FEATURE:
<221> NAME/KEY: misc_feature
<222> LOCATION: (1665)..(1665)
<223> OTHER INFORMATION: Xaa can be any naturally occurring amino acid
<220> FEATURE:
<221> NAME/KEY: misc_feature
<222> LOCATION: (1672)..(1672)
<223> OTHER INFORMATION: Xaa can be any naturally occurring amino acid
<220> FEATURE:
<221> NAME/KEY: misc_feature
<222> LOCATION: (1686)..(1686)
<223> OTHER INFORMATION: Xaa can be any naturally occurring amino acid
<220> FEATURE:
<221> NAME/KEY: misc_feature
<222> LOCATION: (1693)..(1693)
<223> OTHER INFORMATION: Xaa can be any naturally occurring amino acid
<220> FEATURE:
<221> NAME/KEY: misc_feature
<222> LOCATION: (1700)..(1700)
<223> OTHER INFORMATION: Xaa can be any naturally occurring amino acid
<220> FEATURE:
<221> NAME/KEY: misc_feature
<222> LOCATION: (1707)..(1707)
<223> OTHER INFORMATION: Xaa can be any naturally occurring amino acid
<220> FEATURE:
<221> NAME/KEY: misc_feature
<222> LOCATION: (1714)..(1714)
<223> OTHER INFORMATION: Xaa can be any naturally occurring amino acid
<220> FEATURE:
<221> NAME/KEY: misc_feature
<222> LOCATION: (1721)..(1721)
<223> OTHER INFORMATION: Xaa can be any naturally occurring amino acid
<220> FEATURE:
<221> NAME/KEY: misc_feature
<222> LOCATION: (1728)..(1728)
<223> OTHER INFORMATION: Xaa can be any naturally occurring amino acid
<220> FEATURE:
<221> NAME/KEY: misc_feature
<222> LOCATION: (1735)..(1735)
<223> OTHER INFORMATION: Xaa can be any naturally occurring amino acid
<220> FEATURE:
<221> NAME/KEY: misc_feature
<222> LOCATION: (1742)..(1742)
<223> OTHER INFORMATION: Xaa can be any naturally occurring amino acid
<220> FEATURE:
<221> NAME/KEY: misc_feature
<222> LOCATION: (1749)..(1749)
<223> OTHER INFORMATION: Xaa can be any naturally occurring amino acid
<220> FEATURE:
<221> NAME/KEY: misc_feature
<222> LOCATION: (1763)..(1763)
<223> OTHER INFORMATION: Xaa can be any naturally occurring amino acid
<220> FEATURE:
<221> NAME/KEY: misc_feature
<222> LOCATION: (1770)..(1770)
<223> OTHER INFORMATION: Xaa can be any naturally occurring amino acid
<220> FEATURE:
<221> NAME/KEY: misc_feature
<222> LOCATION: (1784)..(1784)
<223> OTHER INFORMATION: Xaa can be any naturally occurring amino acid
<220> FEATURE:
```

```
<221> NAME/KEY: misc_feature
<222> LOCATION: (1791)..(1791)
<223> OTHER INFORMATION: Xaa can be any naturally occurring amino acid
<220> FEATURE:
<221> NAME/KEY: misc_feature
<222> LOCATION: (1805)..(1805)
<223> OTHER INFORMATION: Xaa can be any naturally occurring amino acid
<220> FEATURE:
<221> NAME/KEY: misc_feature
<222> LOCATION: (1826)..(1826)
<223> OTHER INFORMATION: Xaa can be any naturally occurring amino acid
<220> FEATURE:
<221> NAME/KEY: misc_feature
<222> LOCATION: (1833)..(1833)
<223> OTHER INFORMATION: Xaa can be any naturally occurring amino acid
<220> FEATURE:
<221> NAME/KEY: misc_feature
<222> LOCATION: (1847)..(1847)
<223> OTHER INFORMATION: Xaa can be any naturally occurring amino acid
<220> FEATURE:
<221> NAME/KEY: misc_feature
<222> LOCATION: (1861)..(1861)
<223> OTHER INFORMATION: Xaa can be any naturally occurring amino acid
<220> FEATURE:
<221> NAME/KEY: misc_feature
<222> LOCATION: (1868)..(1868)
<223> OTHER INFORMATION: Xaa can be any naturally occurring amino acid
<220> FEATURE:
<221> NAME/KEY: misc_feature
<222> LOCATION: (1875)..(1875)
<223> OTHER INFORMATION: Xaa can be any naturally occurring amino acid
<220> FEATURE:
<221> NAME/KEY: misc_feature
<222> LOCATION: (1882)..(1882)
<223> OTHER INFORMATION: Xaa can be any naturally occurring amino acid
<220> FEATURE:
<221> NAME/KEY: misc_feature
<222> LOCATION: (1889)..(1889)
<223> OTHER INFORMATION: Xaa can be any naturally occurring amino acid
<220> FEATURE:
<221> NAME/KEY: misc_feature
<222> LOCATION: (1896)..(1896)
<223> OTHER INFORMATION: Xaa can be any naturally occurring amino acid
<220> FEATURE:
<221> NAME/KEY: misc_feature
<222> LOCATION: (1910)..(1910)
<223> OTHER INFORMATION: Xaa can be any naturally occurring amino acid
<220> FEATURE:
<221> NAME/KEY: misc_feature
<222> LOCATION: (1917)..(1917)
<223> OTHER INFORMATION: Xaa can be any naturally occurring amino acid
<220> FEATURE:
<221> NAME/KEY: misc_feature
<222> LOCATION: (1924)..(1924)
<223> OTHER INFORMATION: Xaa can be any naturally occurring amino acid
<220> FEATURE:
<221> NAME/KEY: misc_feature
<222> LOCATION: (1931)..(1931)
<223> OTHER INFORMATION: Xaa can be any naturally occurring amino acid
<220> FEATURE:
<221> NAME/KEY: misc_feature
<222> LOCATION: (1941)..(1941)
<223> OTHER INFORMATION: Xaa can be any naturally occurring amino acid
<220> FEATURE:
<221> NAME/KEY: misc_feature
<222> LOCATION: (1948)..(1948)
<223> OTHER INFORMATION: Xaa can be any naturally occurring amino acid
<220> FEATURE:
<221> NAME/KEY: misc_feature
<222> LOCATION: (1955)..(1955)
<223> OTHER INFORMATION: Xaa can be any naturally occurring amino acid

<400> SEQUENCE: 60

Met His Gly Gly Gly Pro Pro Ser Gly Asp Ser Ala Cys Pro Leu Arg
1               5                   10                  15

Thr Ile Lys Arg Val Gln Phe Gly Val Leu Ser Pro Asp Glu Leu Lys
            20                  25                  30
```

```
Arg Met Ser Val Thr Glu Gly Ile Lys Tyr Pro Glu Thr Thr Glu
     35                  40                  45

Gly Gly Arg Pro Lys Leu Gly Leu Met Asp Pro Arg Gln Gly Val
 50                  55                  60

Ile Glu Arg Thr Gly Arg Cys Gln Thr Cys Ala Gly Asn Met Thr Glu
 65                  70                  75                  80

Cys Pro Gly His Phe Gly His Ile Glu Leu Ala Lys Pro Val Phe His
                 85                  90                  95

Val Gly Phe Leu Val Lys Thr Met Lys Val Leu Arg Cys Val Cys Phe
                100                 105                 110

Phe Cys Ser Lys Leu Leu Val Asp Ser Asn Pro Lys Ile Lys Asp
            115                 120                 125

Ile Leu Ala Lys Ser Lys Gly Gln Pro Lys Lys Arg Leu Thr His Val
130                 135                 140

Tyr Asp Leu Cys Lys Gly Lys Asn Ile Cys Glu Gly Gly Glu Glu Met
145                 150                 155                 160

Asp Asn Lys Phe Gly Val Glu Gln Pro Glu Gly Asp Glu Asp Leu Thr
                165                 170                 175

Lys Glu Lys Gly His Gly Gly Cys Gly Arg Tyr Gln Pro Arg Ile Arg
            180                 185                 190

Arg Ser Gly Leu Glu Leu Tyr Ala Glu Trp Lys His Val Asn Glu Asp
        195                 200                 205

Ser Gln Glu Lys Lys Ile Leu Leu Ser Pro Glu Arg Val His Glu Ile
    210                 215                 220

Phe Lys Arg Ile Ser Asp Glu Glu Cys Phe Val Leu Gly Met Glu Pro
225                 230                 235                 240

Arg Tyr Ala Arg Pro Glu Trp Met Ile Val Thr Val Leu Pro Val Pro
                245                 250                 255

Pro Leu Ser Val Arg Pro Ala Val Val Met Gln Gly Ser Ala Arg Asn
            260                 265                 270

Gln Asp Asp Leu Thr His Lys Leu Ala Asp Ile Val Lys Ile Asn Asn
        275                 280                 285

Gln Leu Arg Arg Asn Glu Gln Asn Gly Ala Ala Ala His Val Ile Ala
    290                 295                 300

Glu Asp Val Lys Leu Leu Gln Phe His Val Ala Thr Met Val Asp Asn
305                 310                 315                 320

Glu Leu Pro Gly Leu Pro Arg Ala Met Gln Lys Ser Gly Arg Pro Leu
                325                 330                 335

Lys Ser Leu Lys Gln Arg Leu Lys Gly Lys Glu Gly Arg Val Arg Gly
            340                 345                 350

Asn Leu Met Gly Lys Arg Val Asp Phe Ser Ala Arg Thr Val Ile Thr
        355                 360                 365

Pro Asp Pro Asn Leu Ser Ile Asp Gln Val Gly Val Pro Arg Ser Ile
    370                 375                 380

Ala Ala Asn Met Thr Phe Ala Glu Ile Val Thr Pro Phe Asn Ile Asp
385                 390                 395                 400

Arg Leu Gln Glu Leu Val Arg Arg Gly Asn Ser Gln Tyr Pro Gly Ala
                405                 410                 415

Lys Tyr Ile Ile Arg Asp Asn Gly Asp Arg Ile Asp Leu Arg Phe His
            420                 425                 430

Pro Lys Pro Ser Asp Leu His Leu Gln Thr Gly Tyr Lys Val Glu Arg
        435                 440                 445

His Met Cys Asp Gly Asp Ile Val Ile Phe Asn Arg Gln Pro Thr Leu
450                 455                 460
```

-continued

```
His Lys Met Ser Met Met Gly His Arg Val Arg Ile Leu Pro Trp Ser
465                 470                 475                 480

Thr Phe Arg Leu Asn Leu Ser Val Thr Thr Pro Tyr Asn Ala Asp Phe
            485                 490                 495

Asp Gly Asp Glu Met Asn Leu His Leu Pro Gln Ser Leu Glu Thr Arg
                500                 505                 510

Ala Glu Ile Gln Glu Leu Ala Met Val Pro Arg Met Ile Val Thr Pro
            515                 520                 525

Gln Ser Asn Arg Pro Val Met Gly Ile Val Gln Asp Thr Leu Thr Ala
530                 535                 540

Val Arg Lys Phe Thr Lys Arg Asp Val Phe Leu Glu Arg Gly Glu Val
545                 550                 555                 560

Met Asn Leu Leu Met Phe Leu Ser Thr Trp Asp Gly Lys Val Pro Gln
                565                 570                 575

Pro Ala Ile Leu Lys Pro Arg Pro Leu Trp Thr Gly Lys Gln Ile Phe
            580                 585                 590

Ser Leu Ile Ile Pro Gly His Ile Asn Cys Ile Arg Thr His Ser Thr
            595                 600                 605

His Pro Asp Asp Glu Asp Ser Gly Pro Tyr Lys His Ile Ser Pro Gly
    610                 615                 620

Asp Thr Lys Val Val Glu Asn Gly Glu Leu Ile Met Gly Ile Leu
625                 630                 635                 640

Cys Lys Lys Ser Leu Gly Thr Ser Ala Gly Ser Leu Val His Ile Ser
                645                 650                 655

Tyr Leu Glu Met Gly His Asp Ile Thr Arg Leu Phe Tyr Ser Asn Ile
                660                 665                 670

Gln Thr Val Ile Asn Asn Trp Leu Leu Ile Gly His Thr Ile Gly
            675                 680                 685

Ile Gly Asp Ser Ile Ala Asp Ser Lys Thr Tyr Gln Asp Ile Gln Asn
            690                 695                 700

Thr Ile Lys Lys Ala Lys Gln Asp Val Ile Glu Val Ile Glu Lys Ala
705                 710                 715                 720

His Asn Asn Glu Leu Glu Pro Thr Pro Gly Asn Thr Leu Arg Gln Thr
                725                 730                 735

Phe Glu Asn Gln Val Asn Arg Ile Leu Asn Asp Ala Arg Asp Lys Thr
            740                 745                 750

Gly Ser Ser Ala Gln Lys Ser Leu Ser Glu Tyr Asn Asn Phe Lys Ser
            755                 760                 765

Met Val Val Ser Gly Ala Lys Gly Ser Lys Ile Asn Ile Ser Gln Val
770                 775                 780

Ile Ala Val Val Gly Gln Gln Asn Val Glu Gly Lys Arg Ile Pro Phe
785                 790                 795                 800

Gly Phe Lys His Arg Thr Leu Pro His Phe Ile Lys Asp Asp Tyr Gly
                805                 810                 815

Pro Glu Ser Arg Gly Phe Val Glu Asn Ser Tyr Leu Ala Gly Leu Thr
            820                 825                 830

Pro Thr Glu Phe Phe Phe His Ala Met Gly Gly Arg Glu Gly Leu Ile
            835                 840                 845

Asp Thr Ala Val Lys Thr Ala Glu Thr Gly Tyr Ile Gln Arg Arg Leu
            850                 855                 860

Ile Lys Ser Met Glu Ser Val Met Val Lys Tyr Asp Ala Thr Val Arg
865                 870                 875                 880

Asn Ser Ile Asn Gln Val Val Gln Leu Arg Tyr Gly Glu Asp Gly Leu
```

-continued

```
                885                 890                 895
Ala Gly Glu Ser Val Glu Phe Gln Asn Leu Ala Thr Leu Lys Pro Ser
                900                 905                 910

Asn Lys Ala Phe Glu Lys Lys Phe Arg Phe Asp Tyr Thr Asn Glu Arg
                915                 920                 925

Ala Leu Arg Arg Thr Leu Gln Glu Asp Leu Val Lys Asp Val Leu Ser
930                 935                 940

Asn Ala His Ile Gln Asn Glu Leu Glu Arg Glu Phe Glu Arg Met Arg
945                 950                 955                 960

Glu Asp Arg Glu Val Leu Arg Val Ile Phe Pro Thr Gly Asp Ser Lys
                965                 970                 975

Val Val Leu Pro Cys Asn Leu Leu Arg Met Ile Trp Asn Ala Gln Lys
                980                 985                 990

Ile Phe His Ile Asn Pro Arg Leu Pro Ser Asp Leu His Pro Ile Lys
                995                1000                1005

Val Val Glu Gly Val Lys Glu Leu Ser Lys Lys Leu Val Ile Val
    1010                1015                1020

Asn Gly Asp Asp Pro Leu Ser Arg Gln Ala Gln Glu Asn Ala Thr
    1025                1030                1035

Leu Leu Phe Asn Ile His Leu Arg Ser Thr Leu Cys Ser Arg Arg
    1040                1045                1050

Met Ala Glu Glu Phe Arg Leu Ser Gly Glu Ala Phe Asp Trp Leu
    1055                1060                1065

Leu Gly Glu Ile Glu Ser Lys Phe Asn Gln Ala Ile Ala His Pro
    1070                1075                1080

Gly Glu Met Val Gly Ala Leu Ala Ala Gln Ser Leu Gly Glu Pro
    1085                1090                1095

Ala Thr Gln Met Thr Leu Asn Thr Phe His Tyr Ala Gly Val Ser
    1100                1105                1110

Ala Lys Asn Val Thr Leu Gly Val Pro Arg Leu Lys Glu Leu Ile
    1115                1120                1125

Asn Ile Ser Lys Lys Pro Lys Thr Pro Ser Leu Thr Val Phe Leu
    1130                1135                1140

Leu Gly Gln Ser Ala Arg Asp Ala Glu Arg Ala Lys Asp Ile Leu
    1145                1150                1155

Cys Arg Leu Glu His Thr Thr Leu Arg Lys Val Thr Ala Asn Thr
    1160                1165                1170

Ala Ile Tyr Tyr Asp Pro Asn Pro Gln Ser Thr Val Val Ala Glu
    1175                1180                1185

Asp Gln Glu Trp Val Asn Val Tyr Tyr Glu Met Pro Asp Phe Asp
    1190                1195                1200

Val Ala Arg Ile Ser Pro Trp Leu Leu Arg Val Glu Leu Asp Arg
    1205                1210                1215

Lys His Met Thr Asp Arg Lys Leu Thr Met Glu Gln Ile Ala Glu
    1220                1225                1230

Lys Ile Asn Ala Gly Phe Gly Asp Asp Leu Asn Cys Ile Phe Asn
    1235                1240                1245

Asp Asp Asn Ala Glu Lys Leu Val Leu Arg Ile Arg Ile Met Asn
    1250                1255                1260

Ser Asp Glu Asn Lys Met Gln Glu Glu Glu Val Val Asp Lys
    1265                1270                1275

Met Asp Asp Asp Val Phe Leu Arg Cys Ile Glu Ser Asn Met Leu
    1280                1285                1290
```

-continued

```
Thr Asp Met Thr Leu Gln Gly Ile Glu Gln Ile Ser Lys Val Tyr
1295                1300                1305

Met His Leu Pro Gln Thr Asp Asn Lys Lys Ile Ile Ile Thr
1310                1315                1320

Glu Asp Gly Glu Phe Lys Ala Leu Gln Glu Trp Ile Leu Glu Thr
1325                1330                1335

Asp Gly Val Ser Leu Met Arg Val Leu Ser Glu Lys Asp Val Asp
1340                1345                1350

Pro Val Arg Thr Thr Ser Asn Asp Ile Val Glu Ile Phe Thr Val
1355                1360                1365

Leu Gly Ile Glu Ala Val Arg Lys Ala Leu Glu Arg Glu Leu Tyr
1370                1375                1380

His Val Ile Ser Phe Asp Gly Ser Tyr Val Asn Tyr Arg His Leu
1385                1390                1395

Ala Leu Leu Cys Asp Thr Met Thr Cys Arg Gly His Leu Met Ala
1400                1405                1410

Ile Thr Arg His Gly Val Asn Arg Gln Asp Thr Gly Pro Leu Met
1415                1420                1425

Lys Cys Ser Phe Glu Glu Thr Val Asp Val Leu Met Glu Ala Ala
1430                1435                1440

Ala His Gly Glu Ser Asp Pro Met Lys Gly Val Ser Glu Asn Ile
1445                1450                1455

Met Leu Gly Gln Leu Ala Pro Ala Gly Thr Gly Cys Phe Asp Leu
1460                1465                1470

Leu Leu Asp Ala Glu Lys Cys Lys Tyr Gly Met Glu Ile Pro Thr
1475                1480                1485

Asn Ile Pro Gly Leu Gly Ala Ala Gly Pro Thr Gly Met Phe Phe
1490                1495                1500

Gly Ser Ala Pro Ser Pro Met Gly Gly Ile Ser Pro Ala Met Thr
1505                1510                1515

Pro Trp Asn Gln Gly Ala Thr Pro Ala Tyr Gly Ala Trp Ser Pro
1520                1525                1530

Ser Val Gly Ser Gly Met Thr Pro Gly Ala Ala Gly Phe Ser Pro
1535                1540                1545

Ser Ala Ala Ser Asp Ala Ser Gly Phe Ser Pro Gly Tyr Xaa Pro
1550                1555                1560

Ala Trp Ser Pro Thr Pro Gly Ser Pro Gly Ser Pro Gly Pro Ser
1565                1570                1575

Ser Pro Tyr Ile Pro Ser Pro Gly Gly Ala Met Ser Pro Ser Tyr
1580                1585                1590

Xaa Pro Thr Ser Pro Ala Tyr Glu Pro Arg Ser Pro Gly Gly Tyr
1595                1600                1605

Thr Pro Gln Ser Pro Ser Tyr Xaa Pro Thr Ser Pro Ser Tyr Xaa
1610                1615                1620

Pro Thr Ser Pro Ser Tyr Xaa Pro Thr Ser Pro Asn Tyr Xaa Pro
1625                1630                1635

Thr Ser Pro Ser Tyr Xaa Pro Thr Ser Pro Ser Tyr Xaa Pro Thr
1640                1645                1650

Ser Pro Ser Tyr Xaa Pro Thr Ser Pro Ser Tyr Xaa Pro Thr Ser
1655                1660                1665

Pro Ser Tyr Xaa Pro Thr Ser Pro Ser Tyr Ser Pro Thr Ser Pro
1670                1675                1680

Ser Tyr Xaa Pro Thr Ser Pro Ser Tyr Xaa Pro Thr Ser Pro Ser
1685                1690                1695
```

```
Tyr Xaa Pro Thr Ser Pro Ser Tyr Xaa Pro Thr Ser Pro Ser Tyr
    1700                1705                1710

Xaa Pro Thr Ser Pro Ser Tyr Xaa Pro Thr Ser Pro Ser Tyr Xaa
    1715                1720                1725

Pro Thr Ser Pro Ser Tyr Xaa Pro Thr Ser Pro Ser Tyr Xaa Pro
    1730                1735                1740

Thr Ser Pro Asn Tyr Xaa Pro Thr Ser Pro Asn Tyr Thr Pro Thr
    1745                1750                1755

Ser Pro Ser Tyr Xaa Pro Thr Ser Pro Ser Tyr Xaa Pro Thr Ser
    1760                1765                1770

Pro Asn Tyr Thr Pro Thr Ser Pro Asn Tyr Xaa Pro Thr Ser Pro
    1775                1780                1785

Ser Tyr Xaa Pro Thr Ser Pro Ser Tyr Ser Pro Thr Ser Pro Ser
    1790                1795                1800

Tyr Xaa Pro Ser Ser Pro Arg Tyr Thr Pro Gln Ser Pro Thr Tyr
    1805                1810                1815

Thr Pro Ser Ser Pro Ser Tyr Xaa Pro Ser Ser Pro Ser Tyr Xaa
    1820                1825                1830

Pro Thr Ser Pro Lys Tyr Thr Pro Thr Ser Pro Ser Tyr Xaa Pro
    1835                1840                1845

Ser Ser Pro Glu Tyr Thr Pro Thr Ser Pro Lys Tyr Xaa Pro Thr
    1850                1855                1860

Ser Pro Lys Tyr Xaa Pro Thr Ser Pro Lys Tyr Xaa Pro Thr Ser
    1865                1870                1875

Pro Thr Tyr Xaa Pro Thr Thr Pro Lys Tyr Xaa Pro Thr Ser Pro
    1880                1885                1890

Thr Tyr Xaa Pro Thr Ser Pro Val Tyr Thr Pro Thr Ser Pro Lys
    1895                1900                1905

Tyr Xaa Pro Thr Ser Pro Thr Tyr Xaa Pro Thr Ser Pro Lys Tyr
    1910                1915                1920

Xaa Pro Thr Ser Pro Thr Tyr Xaa Pro Thr Ser Pro Lys Gly Ser
    1925                1930                1935

Thr Tyr Xaa Pro Thr Ser Pro Gly Tyr Xaa Pro Thr Ser Pro Thr
    1940                1945                1950

Tyr Xaa Leu Thr Ser Pro Ala Ile Ser Pro Asp Asp Ser Asp Glu
    1955                1960                1965

Glu Asn
    1970

<210> SEQ ID NO 61
<211> LENGTH: 317
<212> TYPE: PRT
<213> ORGANISM: Homo sapiens
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
```

<400> SEQUENCE: 61

Met Ser Cys Thr Arg Met Ile Gln Val Leu Asp Pro Arg Pro Leu Thr
1               5                   10                  15

Ser Ser Val Met Pro Val Asp Val Ala Met Arg Leu Cys Leu Ala His
            20                  25                  30

Ser Pro Pro Val Lys Ser Phe Leu Gly Pro Tyr Asp Glu Phe Gln Arg
        35                  40                  45

Arg His Phe Val Asn Lys Leu Lys Pro Leu Lys Ser Cys Leu Asn Ile
    50                  55                  60

Lys His Lys Ala Lys Ser Gln Asn Asp Trp Lys Cys Ser His Asn Gln
65                  70                  75                  80

Ala Lys Lys Arg Val Val Phe Ala Asp Xaa Lys Gly Leu Xaa Leu Xaa
                85                  90                  95

Ala Ile His Val Phe Xaa Asp Leu Pro Glu Pro Ala Trp Asp Leu
            100                 105                 110

Gln Phe Asp Leu Leu Asp Leu Asn Asp Ile Ser Ser Ala Leu Lys His
            115                 120                 125

His Glu Glu Lys Asn Leu Ile Leu Asp Phe Pro Gln Pro Ser Thr Asp
    130                 135                 140

Tyr Leu Ser Phe Arg Ser His Phe Gln Lys Asn Phe Val Cys Leu Glu
145                 150                 155                 160

Asn Cys Ser Leu Gln Glu Arg Thr Val Thr Gly Thr Val Lys Val Lys
                165                 170                 175

Asn Val Ser Phe Glu Lys Lys Val Gln Ile Arg Ile Thr Phe Asp Ser
            180                 185                 190

Trp Lys Asn Tyr Thr Asp Val Asp Cys Val Tyr Met Lys Asn Val Tyr
        195                 200                 205

Gly Gly Thr Asp Ser Asp Thr Phe Ser Phe Ala Ile Asp Leu Pro Pro
    210                 215                 220

Val Ile Pro Thr Glu Gln Lys Ile Glu Phe Cys Ile Ser Tyr His Ala
225                 230                 235                 240

Asn Gly Gln Val Phe Trp Asp Asn Asn Asp Gly Gln Asn Tyr Arg Ile
                245                 250                 255

Val His Val Gln Trp Lys Pro Asp Gly Val Gln Thr Gln Met Ala Pro
            260                 265                 270

Gln Asp Cys Ala Phe His Gln Thr Ser Pro Lys Thr Glu Leu Glu Ser
        275                 280                 285

Thr Ile Phe Gly Ser Pro Arg Leu Ala Ser Gly Leu Phe Pro Glu Trp
    290                 295                 300

Gln Ser Trp Gly Arg Met Glu Asn Leu Ala Ser Tyr Arg
305                 310                 315

<210> SEQ ID NO 62
<211> LENGTH: 928
<212> TYPE: PRT
<213> ORGANISM: Homo sapiens
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (252)..(252)
<223> OTHER INFORMATION: Xaa can be any naturally occurring amino acid
<220> FEATURE:
<221> NAME/KEY: misc_feature
<222> LOCATION: (373)..(373)
<223> OTHER INFORMATION: Xaa can be any naturally occurring amino acid
<220> FEATURE:

```
<221> NAME/KEY: misc_feature
<222> LOCATION: (807)..(807)
<223> OTHER INFORMATION: Xaa can be any naturally occurring amino acid
<220> FEATURE:
<221> NAME/KEY: misc_feature
<222> LOCATION: (811)..(811)
<223> OTHER INFORMATION: Xaa can be any naturally occurring amino acid
<220> FEATURE:
<221> NAME/KEY: misc_feature
<222> LOCATION: (821)..(821)
<223> OTHER INFORMATION: Xaa can be any naturally occurring amino acid
<220> FEATURE:
<221> NAME/KEY: misc_feature
<222> LOCATION: (826)..(826)
<223> OTHER INFORMATION: Xaa can be any naturally occurring amino acid

<400> SEQUENCE: 62

Met Pro Pro Lys Thr Pro Arg Lys Thr Ala Ala Thr Ala Ala Ala Ala
1               5                   10                  15

Ala Ala Glu Pro Pro Ala Pro Pro Pro Pro Pro Pro Glu Glu Asp
            20                  25                  30

Pro Glu Gln Asp Ser Gly Pro Glu Asp Leu Pro Leu Val Arg Leu Glu
            35                  40                  45

Phe Glu Glu Thr Glu Glu Pro Asp Phe Thr Ala Leu Cys Gln Lys Leu
50                  55                  60

Lys Ile Pro Asp His Val Arg Glu Arg Ala Trp Leu Thr Trp Glu Lys
65                  70                  75                  80

Val Ser Ser Val Asp Gly Val Leu Gly Gly Tyr Ile Gln Lys Lys Lys
                85                  90                  95

Glu Leu Trp Gly Ile Cys Ile Phe Ile Ala Ala Val Asp Leu Asp Glu
            100                 105                 110

Met Ser Phe Thr Phe Thr Glu Leu Gln Lys Asn Ile Glu Ile Ser Val
        115                 120                 125

His Lys Phe Phe Asn Leu Leu Lys Glu Ile Asp Thr Ser Thr Lys Val
    130                 135                 140

Asp Asn Ala Met Ser Arg Leu Leu Lys Lys Tyr Asp Val Leu Phe Ala
145                 150                 155                 160

Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
            180                 185                 190

Val Ser Trp Ile Thr Phe Leu Leu Ala Lys Gly Glu Val Leu Gln Met
        195                 200                 205

Glu Asp Asp Leu Val Ile Ser Phe Gln Leu Met Leu Cys Val Leu Asp
    210                 215                 220

Tyr Phe Ile Lys Leu Ser Pro Pro Met Leu Leu Lys Glu Pro Tyr Lys
225                 230                 235                 240

Thr Ala Val Ile Pro Ile Asn Gly Xaa Pro Arg Xaa Pro Arg Arg Gly
                245                 250                 255

Gln Asn Arg Ser Ala Arg Ile Ala Lys Gln Leu Glu Asn Asp Thr Arg
            260                 265                 270

Ile Ile Glu Val Leu Cys Lys Glu His Glu Cys Asn Ile Asp Glu Val
        275                 280                 285

Lys Asn Val Tyr Phe Lys Asn Phe Ile Pro Phe Met Asn Ser Leu Gly
    290                 295                 300

Leu Val Thr Ser Asn Gly Leu Pro Glu Val Glu Asn Leu Ser Lys Arg
305                 310                 315                 320

Tyr Glu Glu Ile Tyr Leu Lys Asn Lys Asp Leu Asp Ala Arg Leu Phe
                325                 330                 335
```

```
Leu Asp His Asp Lys Thr Leu Gln Thr Asp Ser Ile Asp Ser Phe Glu
        340                 345                 350

Thr Gln Arg Thr Pro Arg Lys Ser Asn Leu Asp Glu Glu Val Asn Val
            355                 360                 365

Ile Pro Pro His Xaa Pro Val Arg Thr Val Met Asn Thr Ile Gln Gln
370                 375                 380

Leu Met Met Ile Leu Asn Ser Ala Ser Asp Gln Pro Ser Glu Asn Leu
385                 390                 395                 400

Ile Ser Tyr Phe Asn Asn Cys Thr Val Asn Pro Lys Glu Ser Ile Leu
                405                 410                 415

Lys Arg Val Lys Asp Ile Gly Tyr Ile Phe Lys Glu Lys Phe Ala Lys
                420                 425                 430

Ala Val Gly Gln Gly Cys Val Glu Ile Gly Ser Gln Arg Tyr Lys Leu
            435                 440                 445

Gly Val Arg Leu Tyr Tyr Arg Val Met Glu Ser Met Leu Lys Ser Glu
        450                 455                 460

Glu Glu Arg Leu Ser Ile Gln Asn Phe Ser Lys Leu Leu Asn Asp Asn
465                 470                 475                 480

Ile Phe His Met Ser Leu Leu Ala Cys Ala Leu Glu Val Val Met Ala
                485                 490                 495

Thr Tyr Ser Arg Ser Thr Ser Gln Asn Leu Asp Ser Gly Thr Asp Leu
            500                 505                 510

Ser Phe Pro Trp Ile Leu Asn Val Leu Asn Leu Lys Ala Phe Asp Phe
        515                 520                 525

Tyr Lys Val Ile Glu Ser Phe Ile Lys Ala Glu Gly Asn Leu Thr Arg
        530                 535                 540

Glu Met Ile Lys His Leu Glu Arg Cys Glu His Arg Ile Met Glu Ser
545                 550                 555                 560

Leu Ala Trp Leu Ser Asp Ser Pro Leu Phe Asp Leu Ile Lys Gln Ser
                565                 570                 575

Lys Asp Arg Glu Gly Pro Thr Asp His Leu Glu Ser Ala Cys Pro Leu
            580                 585                 590

Asn Leu Pro Leu Gln Asn Asn His Thr Ala Ala Asp Met Tyr Leu Ser
        595                 600                 605

Pro Val Arg Ser Pro Lys Lys Lys Gly Ser Thr Thr Arg Val Asn Ser
        610                 615                 620

Thr Ala Asn Ala Glu Thr Gln Ala Thr Ser Ala Phe Gln Thr Gln Lys
625                 630                 635                 640

Pro Leu Lys Ser Thr Ser Leu Ser Leu Phe Tyr Lys Lys Val Tyr Arg
                645                 650                 655

Leu Ala Tyr Leu Arg Leu Asn Thr Leu Cys Glu Arg Leu Leu Ser Glu
                660                 665                 670

His Pro Glu Leu Glu His Ile Ile Trp Thr Leu Phe Gln His Thr Leu
            675                 680                 685

Gln Asn Glu Tyr Glu Leu Met Arg Asp Arg His Leu Asp Gln Ile Met
        690                 695                 700

Met Cys Ser Met Tyr Gly Ile Cys Lys Val Lys Asn Ile Asp Leu Lys
705                 710                 715                 720

Phe Lys Ile Ile Val Thr Ala Tyr Lys Asp Leu Pro His Ala Val Gln
                725                 730                 735

Glu Thr Phe Lys Arg Val Leu Ile Lys Glu Glu Glu Tyr Asp Ser Ile
            740                 745                 750

Ile Val Phe Tyr Asn Ser Val Phe Met Gln Arg Leu Lys Thr Asn Ile
```

```
                        755                 760                 765
Leu Gln Tyr Ala Ser Thr Arg Pro Pro Thr Leu Ser Pro Ile Pro His
        770                 775                 780
Ile Pro Arg Ser Pro Tyr Lys Phe Pro Ser Pro Leu Arg Ile Pro
785                 790                 795                 800
Gly Gly Asn Ile Tyr Ile Xaa Pro Leu Lys Xaa Pro Tyr Lys Ile Ser
            805                 810                 815
Glu Gly Leu Pro Xaa Pro Thr Lys Met Xaa Pro Arg Ser Arg Ile Leu
                820                 825                 830
Val Ser Ile Gly Glu Ser Phe Gly Thr Ser Glu Lys Phe Gln Lys Ile
            835                 840                 845
Asn Gln Met Val Cys Asn Ser Asp Arg Val Leu Lys Arg Ser Ala Glu
        850                 855                 860
Gly Ser Asn Pro Pro Lys Pro Leu Lys Lys Leu Arg Phe Asp Ile Glu
865                 870                 875                 880
Gly Ser Asp Glu Ala Asp Gly Ser Lys His Leu Pro Gly Glu Ser Lys
                885                 890                 895
Phe Gln Gln Lys Leu Ala Glu Met Thr Ser Thr Arg Thr Arg Met Gln
            900                 905                 910
Lys Gln Lys Met Asn Asp Ser Met Asp Thr Ser Asn Lys Glu Glu Lys
        915                 920                 925

<210> SEQ ID NO 63
<211> LENGTH: 1400
<212> TYPE: PRT
<213> ORGANISM: Homo sapiens
<220> FEATURE:
<221> NAME/KEY: misc_feature
<222> LOCATION: (1394)..(1394)
<223> OTHER INFORMATION: Xaa can be any naturally occurring amino acid

<400> SEQUENCE: 63

Met Glu Leu Leu Pro Pro Leu Pro Gln Ser Phe Leu Leu Leu Leu
1               5                   10                  15
Leu Pro Ala Lys Pro Ala Ala Gly Glu Asp Trp Gln Cys Pro Arg Thr
            20                  25                  30
Pro Tyr Ala Ala Ser Arg Asp Phe Asp Val Lys Tyr Val Val Pro Ser
        35                  40                  45
Phe Ser Ala Gly Gly Leu Val Gln Ala Met Val Thr Tyr Glu Gly Asp
    50                  55                  60
Arg Asn Glu Ser Ala Val Phe Val Ala Ile Arg Asn Arg Leu His Val
65                  70                  75                  80
Leu Gly Pro Asp Leu Lys Ser Val Gln Ser Leu Ala Thr Gly Pro Ala
                85                  90                  95
Gly Asp Pro Gly Cys Gln Thr Cys Ala Ala Cys Gly Pro Gly Pro His
            100                 105                 110
Gly Pro Pro Gly Asp Thr Asp Thr Lys Val Leu Val Leu Asp Pro Ala
        115                 120                 125
Leu Pro Ala Leu Val Ser Cys Gly Ser Ser Leu Gln Gly Arg Cys Phe
    130                 135                 140
Leu His Asp Leu Glu Pro Gln Gly Thr Ala Val His Leu Ala Ala Pro
145                 150                 155                 160
Ala Cys Leu Phe Ser Ala His His Asn Arg Pro Asp Asp Cys Pro Asp
                165                 170                 175
Cys Val Ala Ser Pro Leu Gly Thr Arg Val Thr Val Val Glu Gln Gly
            180                 185                 190
```

```
Gln Ala Ser Tyr Phe Tyr Val Ala Ser Ser Leu Asp Ala Val Ala
    195                 200                 205

Gly Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
                260                 265                 270

Pro Ser Ala Leu His Thr Arg Leu Ala Arg Leu Ser Ala Thr Glu Pro
                275                 280                 285

Glu Leu Gly Asp Tyr Arg Glu Leu Val Leu Asp Cys Arg Phe Ala Pro
                290                 295                 300

Lys Arg Arg Arg Arg Gly Ala Pro Glu Gly Gly Gln Pro Tyr Pro Val
305                 310                 315                 320

Leu Gln Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
                340                 345                 350

Gly Lys Asp Gly Gly Pro Gly Val Gly Pro Asn Ser Val Val Cys Ala
                355                 360                 365

Phe Pro Ile Asp Leu Leu Asp Thr Leu Ile Asp Glu Gly Val Glu Arg
                370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Pro Gly Leu Glu Ala Leu
                405                 410                 415

Ser Pro Asn Thr Ser Cys Arg His Phe Pro Leu Leu Val Ser Ser Ser
                420                 425                 430

Phe Ser Arg Val Asp Leu Phe Asn Gly Leu Leu Gly Pro Val Gln Val
                435                 440                 445

Thr Ala Leu Tyr Val Thr Arg Leu Asp Asn Val Thr Val Ala His Met
450                 455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
                500                 505                 510

Ser Gly Asp Gln Val Phe Gln Val Pro Ile Arg Gly Pro Gly Cys Arg
                515                 520                 525

His Phe Leu Thr Cys Gly Arg Cys Leu Arg Ala Trp His Phe Met Gly
                530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
                580                 585                 590

Asn Phe Tyr Leu His Pro Ser Gly Leu Val Pro Glu Gly Thr His Gln
                595                 600                 605

Val Thr Val Gly Gln Ser Pro Cys Arg Pro Leu Pro Lys Asp Ser Ser
610                 615                 620
```

```
Lys Leu Arg Pro Val Pro Arg Lys Asp Phe Val Glu Phe Glu Cys
625                 630                 635                 640

Glu Leu Glu Pro Leu Gly Thr Gln Ala Val Gly Pro Thr Asn Val Ser
            645                 650                 655

Leu Thr Val Thr Asn Met Pro Pro Gly Lys His Phe Arg Val Asp Gly
            660                 665                 670

Thr Ser Val Leu Arg Gly Phe Ser Phe Met Glu Pro Val Leu Ile Ala
        675                 680                 685

Val Gln Pro Leu Phe Gly Pro Arg Ala Gly Gly Thr Cys Leu Thr Leu
    690                 695                 700

Glu Gly Gln Ser Leu Ser Val Gly Thr Ser Arg Ala Val Leu Val Asn
705                 710                 715                 720

Gly Thr Glu Cys Leu Leu Ala Arg Val Ser Gly Gln Leu Leu Cys
                725                 730                 735

Ala Thr Pro Pro Gly Ala Thr Val Ala Ser Val Pro Leu Ser Leu Gln
            740                 745                 750

Val Gly Gly Ala Gln Val Pro Gly Ser Trp Thr Phe Gln Tyr Arg Glu
        755                 760                 765

Asp Pro Val Val Leu Ser Ile Ser Pro Asn Cys Gly Tyr Ile Asn Ser
    770                 775                 780

His Ile Thr Ile Cys Gly Gln His Leu Thr Ser Ala Trp His Leu Val
785                 790                 795                 800

Leu Ser Phe His Asp Gly Leu Arg Ala Val Glu Ser Arg Cys Glu Arg
                805                 810                 815

Gln Leu Pro Glu Gln Gln Leu Cys Arg Leu Pro Glu Tyr Val Val Arg
            820                 825                 830

Asp Pro Gln Gly Trp Val Ala Gly Asn Leu Ser Ala Arg Gly Asp Gly
        835                 840                 845

Ala Ala Gly Phe Thr Leu Pro Gly Phe Arg Phe Leu Pro Pro Pro His
    850                 855                 860

Pro Pro Ser Ala Asn Leu Val Pro Leu Lys Pro Glu Glu His Ala Ile
865                 870                 875                 880

Lys Phe Glu Tyr Ile Gly Leu Gly Ala Val Ala Asp Cys Val Gly Ile
                885                 890                 895

Asn Val Thr Val Gly Gly Glu Ser Cys Gln His Glu Phe Arg Gly Asp
            900                 905                 910

Met Val Val Cys Pro Leu Pro Pro Ser Leu Gln Leu Gly Gln Asp Gly
        915                 920                 925

Ala Pro Leu Gln Val Cys Val Asp Gly Glu Cys His Ile Leu Gly Arg
    930                 935                 940

Val Val Arg Pro Gly Pro Asp Gly Val Pro Gln Ser Thr Leu Leu Gly
945                 950                 955                 960

Ile Leu Leu Pro Leu Leu Leu Leu Val Ala Ala Leu Ala Thr Ala Leu
                965                 970                 975

Val Phe Ser Tyr Trp Trp Arg Arg Lys Gln Leu Val Leu Pro Pro Asn
            980                 985                 990

Leu Asn Asp Leu Ala Ser Leu Asp Gln Thr Ala Gly Ala Thr Pro Leu
        995                 1000                1005

Pro Ile Leu Tyr Ser Gly Ser Asp Tyr Arg Ser Gly Leu Ala Leu
    1010                1015                1020

Pro Ala Ile Asp Gly Leu Asp Ser Thr Thr Cys Val His Gly Ala
    1025                1030                1035

Ser Phe Ser Asp Ser Glu Asp Glu Ser Cys Val Pro Leu Leu Arg
```

```
                1040                1045                1050

Lys Glu Ser Ile Gln Leu Arg Asp Leu Asp Ser Ala Leu Leu Ala
    1055                1060                1065

Glu Val Lys Asp Val Leu Ile Pro His Glu Arg Val Val Thr His
    1070                1075                1080

Ser Asp Arg Val Ile Gly Lys Gly His Phe Gly Val Val Tyr His
    1085                1090                1095

Gly Glu Tyr Ile Asp Gln Ala Gln Asn Arg Ile Gln Cys Ala Ile
    1100                1105                1110

Lys Ser Leu Ser Arg Ile Thr Glu Met Gln Gln Val Glu Ala Phe
    1115                1120                1125

Leu Arg Glu Gly Leu Leu Met Arg Gly Leu Asn His Pro Asn Val
    1130                1135                1140

Leu Ala Leu Ile Gly Ile Met Leu Pro Pro Glu Gly Leu Pro His
    1145                1150                1155

Val Leu Leu Pro Tyr Met Cys His Gly Asp Leu Leu Gln Phe Ile
    1160                1165                1170

Arg Ser Pro Gln Arg Asn Pro Thr Val Lys Asp Leu Ile Ser Phe
    1175                1180                1185

Gly Leu Gln Val Ala Arg Gly Met Glu Tyr Leu Ala Glu Gln Lys
    1190                1195                1200

Phe Val His Arg Asp Leu Ala Ala Arg Asn Cys Met Leu Asp Glu
    1205                1210                1215

Ser Phe Thr Val Lys Val Ala Asp Phe Gly Leu Ala Arg Asp Ile
    1220                1225                1230

Leu Asp Arg Glu Tyr Tyr Ser Val Gln Gln His Arg His Ala Arg
    1235                1240                1245

Leu Pro Val Lys Trp Met Ala Leu Glu Ser Leu Gln Thr Tyr Arg
    1250                1255                1260

Phe Thr Thr Lys Ser Asp Val Trp Ser Phe Gly Val Leu Leu Trp
    1265                1270                1275

Glu Leu Leu Thr Arg Gly Ala Pro Pro Tyr Arg His Ile Asp Pro
    1280                1285                1290

Phe Asp Leu Thr His Phe Leu Ala Gln Gly Arg Arg Leu Pro Gln
    1295                1300                1305

Pro Glu Tyr Cys Pro Asp Ser Leu Tyr Gln Val Met Gln Gln Cys
    1310                1315                1320

Trp Glu Ala Asp Pro Ala Val Arg Pro Thr Phe Arg Val Leu Val
    1325                1330                1335

Gly Glu Val Glu Gln Ile Val Ser Ala Leu Leu Gly Asp His Tyr
    1340                1345                1350

Val Gln Leu Pro Ala Thr Tyr Met Asn Leu Gly Pro Ser Thr Ser
    1355                1360                1365

His Glu Met Asn Val Arg Pro Glu Gln Pro Gln Phe Ser Pro Met
    1370                1375                1380

Pro Gly Asn Val Arg Arg Pro Arg Pro Leu Xaa Glu Pro Pro Arg
    1385                1390                1395

Pro Thr
    1400

<210> SEQ ID NO 64
<211> LENGTH: 473
<212> TYPE: PRT
<213> ORGANISM: Homo sapiens
<220> FEATURE:
```

```
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
<222> LOCATION: (168)..(168)
<223> OTHER INFORMATION: Xaa can be any naturally occurring amino acid
<220> FEATURE:
<221> NAME/KEY: misc_feature
<222> LOCATION: (191)..(191)
<223> OTHER INFORMATION: Xaa can be any naturally occurring amino acid
<220> FEATURE:
<221> NAME/KEY: misc_feature
<222> LOCATION: (198)..(198)
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
<221> NAME/KEY: misc_feature
<222> LOCATION: (216)..(216)
<223> OTHER INFORMATION: Xaa can be any naturally occurring amino acid

<400> SEQUENCE: 64

Met Ser Thr Glu Leu Phe Ser Ser Thr Arg Glu Glu Gly Ser Gly
1               5                   10                  15

Ser Gly Pro Ser Phe Arg Ser Asn Gln Arg Lys Met Leu Asn Leu Leu
            20                  25                  30

Leu Glu Arg Asp Thr Ser Phe Thr Val Cys Pro Asp Val Pro Arg Xaa
        35                  40                  45

Pro Val Gly Lys Phe Leu Gly Asp Ser Ala Asn Leu Ser Ile Leu Ser
    50                  55                  60

Gly Gly Xaa Pro Lys Cys Cys Leu Asp Leu Ser Asn Leu Ser Ser Gly
65                  70                  75                  80

Glu Ile Thr Ala Thr Gln Leu Thr Thr Ser Ala Asp Leu Asp Glu Thr
                85                  90                  95

Gly His Leu Asp Ser Ser Gly Leu Gln Glu Val His Leu Ala Gly Met
            100                 105                 110

Asn His Asp Gln His Leu Met Lys Cys Xaa Pro Ala Gln Leu Leu Cys
        115                 120                 125

Ser Xaa Pro Asn Gly Leu Asp Arg Gly His Arg Lys Arg Asp Ala Met
    130                 135                 140

Cys Ser Ser Ser Ala Asn Lys Glu Asn Asp Asn Gly Asn Leu Val Asp
145                 150                 155                 160

Ser Glu Met Lys Tyr Leu Gly Xaa Pro Ile Thr Thr Val Pro Lys Leu
                165                 170                 175

Asp Lys Asn Pro Asn Leu Gly Glu Asp Gln Ala Glu Ile Xaa Asp
            180                 185                 190

Glu Leu Met Glu Phe Xaa Leu Lys Asp Gln Glu Ala Lys Val Ser Arg
        195                 200                 205

Ser Gly Leu Tyr Arg Xaa Pro Xaa Met Pro Glu Asn Leu Asn Arg Pro
    210                 215                 220
```

```
Arg Leu Lys Gln Val Glu Lys Phe Lys Asp Asn Thr Ile Pro Asp Lys
225                 230                 235                 240

Val Lys Lys Lys Tyr Phe Ser Gly Gln Gly Lys Leu Arg Lys Gly Leu
            245                 250                 255

Cys Leu Lys Lys Thr Val Ser Leu Cys Asp Ile Thr Ile Thr Gln Met
        260                 265                 270

Leu Glu Glu Asp Ser Asn Gln Gly His Leu Ile Gly Asp Phe Ser Lys
    275                 280                 285

Val Cys Ala Leu Pro Thr Val Ser Gly Lys His Gln Asp Leu Lys Tyr
290                 295                 300

Val Asn Pro Glu Thr Val Ala Ala Leu Leu Ser Gly Lys Phe Gln Gly
305                 310                 315                 320

Leu Ile Glu Lys Phe Tyr Val Ile Asp Cys Arg Tyr Pro Tyr Glu Tyr
            325                 330                 335

Leu Gly Gly His Ile Gln Gly Ala Leu Asn Leu Tyr Ser Gln Glu Glu
        340                 345                 350

Leu Phe Asn Phe Phe Leu Lys Lys Pro Ile Val Pro Leu Asp Thr Gln
    355                 360                 365

Lys Arg Ile Ile Ile Val Phe His Cys Glu Phe Ser Ser Glu Arg Gly
370                 375                 380

Pro Arg Met Cys Arg Cys Leu Arg Glu Glu Asp Arg Ser Leu Asn Gln
385                 390                 395                 400

Tyr Pro Ala Leu Tyr Tyr Pro Glu Leu Tyr Ile Leu Lys Gly Gly Tyr
            405                 410                 415

Arg Asp Phe Phe Pro Glu Tyr Met Glu Leu Cys Glu Pro Gln Ser Tyr
        420                 425                 430

Cys Pro Met His His Gln Asp His Lys Thr Glu Leu Leu Arg Cys Arg
    435                 440                 445

Ser Gln Ser Lys Val Gln Glu Gly Glu Arg Gln Leu Arg Glu Gln Ile
450                 455                 460

Ala Leu Leu Val Lys Asp Met Ser Pro
465                 470

<210> SEQ ID NO 65
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid

<400> SEQUENCE: 65

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Phe Cys Leu Ile Leu Ile Cys Leu Leu Ile Cys Ile Ile
        35                  40                  45

Val Met Leu Leu
    50

<210> SEQ ID NO 66
<211> LENGTH: 858
<212> TYPE: PRT
<213> ORGANISM: Homo sapiens
<220> FEATURE:
<221> NAME/KEY: misc_feature
<222> LOCATION: (54)..(54)
```

-continued

<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid

<400> SEQUENCE: 66

Met Val Asn Phe Thr Val Asp Gln Ile Arg Ala Ile Met Asp Lys Lys
1               5                   10                  15

Ala Asn Ile Arg Asn Met Ser Val Ile Ala His Val Asp His Gly Lys
            20                  25                  30

Ser Thr Leu Thr Asp Ser Leu Val Cys Lys Ala Gly Ile Ile Ala Ser
        35                  40                  45

Ala Arg Ala Gly Glu Xaa Arg Phe Xaa Asp Xaa Arg Lys Asp Glu Gln
    50                  55                  60

Glu Arg Cys Ile Thr Ile Lys Ser Thr Ala Ile Ser Leu Phe Tyr Glu
65                  70                  75                  80

Leu Ser Glu Asn Asp Leu Asn Phe Ile Lys Gln Ser Lys Asp Gly Ala
                85                  90                  95

Gly Phe Leu Ile Asn Leu Ile Asp Ser Pro Gly His Val Asp Phe Ser
            100                 105                 110

Ser Glu Val Thr Ala Ala Leu Arg Val Thr Asp Gly Ala Leu Val Val
        115                 120                 125

Val Asp Cys Val Ser Gly Val Cys Val Gln Thr Glu Thr Val Leu Arg
    130                 135                 140

Gln Ala Ile Ala Glu Arg Ile Lys Pro Val Leu Met Met Asn Lys Met
145                 150                 155                 160

Asp Arg Ala Leu Leu Glu Leu Gln Leu Glu Pro Glu Glu Leu Tyr Gln
                165                 170                 175

Thr Phe Gln Arg Ile Val Glu Asn Val Asn Val Ile Ile Ser Thr Tyr
            180                 185                 190

Gly Glu Gly Glu Ser Gly Pro Met Gly Asn Ile Met Ile Asp Pro Val
        195                 200                 205

Leu Gly Thr Val Gly Phe Gly Ser Gly Leu His Gly Trp Ala Phe Thr
    210                 215                 220

Leu Lys Gln Phe Ala Glu Met Tyr Val Ala Lys Phe Ala Ala Lys Gly
225                 230                 235                 240

Glu Gly Gln Leu Gly Pro Ala Glu Arg Ala Lys Lys Val Glu Asp Met
                245                 250                 255

Met Lys Lys Leu Trp Gly Asp Arg Tyr Phe Asp Pro Ala Asn Gly Lys
            260                 265                 270

Phe Ser Lys Ser Ala Thr Ser Pro Glu Gly Lys Lys Leu Pro Arg Thr
        275                 280                 285

Phe Cys Gln Leu Ile Leu Asp Pro Ile Phe Lys Val Phe Asp Ala Ile
    290                 295                 300

Met Asn Phe Lys Lys Glu Glu Thr Ala Lys Leu Ile Glu Lys Leu Asp
305                 310                 315                 320

Ile Lys Leu Asp Ser Glu Asp Lys Glu Gly Lys Pro Leu Leu
                325                 330                 335

Lys Ala Val Met Arg Arg Trp Leu Pro Ala Gly Asp Ala Leu Leu Gln
            340                 345                 350

Met Ile Thr Ile His Leu Pro Ser Pro Val Thr Ala Gln Lys Tyr Arg
        355                 360                 365

```
Cys Glu Leu Leu Tyr Glu Gly Pro Pro Asp Glu Ala Ala Met Gly
    370                 375                 380

Ile Lys Ser Cys Asp Pro Lys Gly Pro Leu Met Met Tyr Ile Ser Lys
385                 390                 395                 400

Met Val Pro Thr Ser Asp Lys Gly Arg Phe Tyr Ala Phe Gly Arg Val
                405                 410                 415

Phe Ser Gly Leu Val Ser Thr Gly Leu Lys Val Arg Ile Met Gly Pro
            420                 425                 430

Asn Tyr Thr Pro Gly Lys Lys Glu Asp Leu Tyr Leu Lys Pro Ile Gln
        435                 440                 445

Arg Thr Ile Leu Met Met Gly Arg Tyr Val Glu Pro Ile Glu Asp Val
    450                 455                 460

Pro Cys Gly Asn Ile Val Gly Leu Val Gly Val Asp Gln Phe Leu Val
465                 470                 475                 480

Lys Thr Gly Thr Ile Thr Thr Phe Glu His Ala His Asn Met Arg Val
                485                 490                 495

Met Lys Phe Ser Val Ser Pro Val Val Arg Val Ala Val Glu Ala Lys
            500                 505                 510

Asn Pro Ala Asp Leu Pro Lys Leu Val Glu Gly Leu Lys Arg Leu Ala
        515                 520                 525

Lys Ser Asp Pro Met Val Gln Cys Ile Ile Glu Glu Ser Gly Glu His
    530                 535                 540

Ile Ile Ala Gly Ala Gly Glu Leu His Leu Glu Ile Cys Leu Lys Asp
545                 550                 555                 560

Leu Glu Glu Asp His Ala Cys Ile Pro Ile Lys Lys Ser Asp Pro Val
                565                 570                 575

Val Ser Tyr Arg Glu Thr Val Ser Glu Glu Ser Asn Val Leu Cys Leu
            580                 585                 590

Ser Lys Ser Pro Asn Lys His Asn Arg Leu Tyr Met Lys Ala Arg Pro
        595                 600                 605

Phe Pro Asp Gly Leu Ala Glu Asp Ile Asp Lys Gly Glu Val Ser Ala
    610                 615                 620

Arg Gln Glu Leu Lys Gln Arg Ala Arg Tyr Leu Ala Glu Lys Tyr Glu
625                 630                 635                 640

Trp Asp Val Ala Glu Ala Arg Lys Ile Trp Cys Phe Gly Pro Asp Gly
                645                 650                 655

Thr Gly Pro Asn Ile Leu Thr Asp Ile Thr Lys Gly Val Gln Tyr Leu
            660                 665                 670

Asn Glu Ile Lys Asp Ser Val Val Ala Gly Phe Gln Trp Ala Thr Lys
        675                 680                 685

Glu Gly Ala Leu Cys Glu Glu Asn Met Arg Gly Val Arg Phe Asp Val
    690                 695                 700

His Asp Val Thr Leu His Ala Asp Ala Ile His Arg Gly Gly Gly Gln
705                 710                 715                 720

Ile Ile Pro Thr Ala Arg Arg Cys Leu Tyr Ala Ser Val Leu Thr Ala
                725                 730                 735

Gln Pro Arg Leu Met Glu Pro Ile Tyr Leu Val Glu Ile Gln Cys Pro
            740                 745                 750

Glu Gln Val Val Gly Gly Ile Tyr Gly Val Leu Asn Arg Lys Arg Gly
        755                 760                 765

His Val Phe Glu Glu Ser Gln Val Ala Gly Thr Pro Met Phe Val Val
    770                 775                 780

Lys Ala Tyr Leu Pro Val Asn Glu Ser Phe Gly Phe Thr Ala Asp Leu
```

```
                785                 790                 795                 800
Arg Ser Asn Thr Gly Gly Gln Ala Phe Pro Gln Cys Val Phe Asp His
                805                 810                 815
Trp Gln Ile Leu Pro Gly Asp Pro Phe Asp Asn Ser Ser Arg Pro Ser
                820                 825                 830
Gln Val Val Ala Glu Thr Arg Lys Arg Lys Gly Leu Lys Glu Gly Ile
            835                 840                 845
Pro Ala Leu Asp Asn Phe Leu Asp Lys Leu
        850                 855

<210> SEQ ID NO 67
<211> LENGTH: 93
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid

<400> SEQUENCE: 67

Val Asn Phe Thr Val Asp Gln Ile Arg Ala Ile Met Asp Lys Lys Ala
1               5                   10                  15
Asn Ile Arg Asn Met Ser Val Ile Ala His Val Asp His Gly Lys Ser
            20                  25                  30
Thr Leu Thr Asp Ser Leu Val Cys Lys Ala Gly Ile Ile Ala Ser Ala
        35                  40                  45
Arg Ala Gly Glu Xaa Arg Phe Xaa Asp Xaa Arg Lys Asp Glu Gln Glu
    50                  55                  60
Arg Cys Ile Thr Ile Lys Ser Thr Ala Ile Ser Leu Phe Tyr Glu Leu
65                  70                  75                  80
Ser Glu Asn Asp Leu Asn Phe Ile Lys Gln Ser Lys Asp
                85                  90

<210> SEQ ID NO 68
<211> LENGTH: 15
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: Xaa can be any naturally occurring amino acid

<400> SEQUENCE: 68

Arg Arg Thr Xaa Leu Cys Gly Thr Leu Asp Tyr Leu Pro Pro Glu
1               5                   10                  15

<210> SEQ ID NO 69
<211> LENGTH: 59
<212> TYPE: PRT
<213> ORGANISM: artificial sequence
<220> FEATURE:
<223> OTHER INFORMATION: synthetic
<220> FEATURE:
<221> NAME/KEY: misc_feature
```

```
<222> LOCATION: (8)..(8)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid

<400> SEQUENCE: 69

Glu Glu Pro Gln Ser Asp Pro Xaa Val Glu Pro Pro Leu Xaa Gln Glu
1               5                   10                  15

Xaa Phe Xaa Asp Leu Trp Lys Leu Leu Pro Glu Asn Asn Val Leu Xaa
            20                  25                  30

Pro Leu Pro Xaa Gln Ala Met Asp Asp Leu Met Leu Xaa Pro Asp Asp
        35                  40                  45

Ile Glu Gln Trp Phe Xaa Glu Asp Pro Gly Pro
    50                  55

<210> SEQ ID NO 70
<211> LENGTH: 60
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
```

```
<220> FEATURE:
<221> NAME/KEY: misc_feature
<222> LOCATION: (55)..(55)
<223> OTHER INFORMATION: Xaa can be any naturally occurring amino acid

<400> SEQUENCE: 70

Met Glu Glu Pro Gln Ser Asp Pro Xaa Val Glu Pro Pro Leu Xaa Gln
1               5                   10                  15

Glu Xaa Phe Xaa Asp Leu Trp Lys Leu Leu Pro Glu Asn Asn Val Leu
            20                  25                  30

Xaa Pro Leu Pro Xaa Gln Ala Met Asp Asp Leu Met Leu Xaa Pro Asp
        35                  40                  45

Asp Ile Glu Gln Trp Phe Xaa Glu Asp Pro Gly Pro
    50                  55                  60

<210> SEQ ID NO 71
<211> LENGTH: 60
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (20)..(20)
<223> OTHER INFORMATION: Xaa can be any naturally occurring amino acid

<400> SEQUENCE: 71

Met Lys Met Ala Asp Ala Lys Gln Lys Arg Asn Glu Gln Leu Lys Arg
1               5                   10                  15

Trp Ile Gly Xaa Glu Thr Asp Leu Glu Pro Pro Val Val Lys Arg Gln
            20                  25                  30

Lys Thr Lys Val Lys Phe Asp Asp Gly Ala Val Phe Leu Ala Ala Cys
        35                  40                  45

Ser Ser Gly Asp Thr Asp Glu Val Leu Lys Leu Leu
    50                  55                  60

<210> SEQ ID NO 72
<211> LENGTH: 59
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (19)..(19)
<223> OTHER INFORMATION: Xaa can be any naturally occurring amino acid

<400> SEQUENCE: 72

Lys Met Ala Asp Ala Lys Gln Lys Arg Asn Glu Gln Leu Lys Arg Trp
1               5                   10                  15

Ile Gly Xaa Glu Thr Asp Leu Glu Pro Pro Val Val Lys Arg Gln Lys
            20                  25                  30

Thr Lys Val Lys Phe Asp Asp Gly Ala Val Phe Leu Ala Ala Cys Ser
        35                  40                  45

Ser Gly Asp Thr Asp Glu Val Leu Lys Leu Leu
    50                  55

<210> SEQ ID NO 73
<211> LENGTH: 73
<212> TYPE: PRT
<213> ORGANISM: artificial sequence
<220> FEATURE:
<223> OTHER INFORMATION: synthetic
<220> FEATURE:
<221> NAME/KEY: misc_feature
```

```
<222> LOCATION: (67)..(67)
<223> OTHER INFORMATION: Xaa can be any naturally occurring amino acid

<400> SEQUENCE: 73

Pro Ala Val Arg Pro Thr Phe Arg Val Leu Val Gly Glu Val Glu Gln
1               5                   10                  15

Ile Val Ser Ala Leu Leu Gly Asp His Tyr Val Gln Leu Pro Ala Thr
            20                  25                  30

Tyr Met Asn Leu Gly Pro Ser Thr Ser His Glu Met Asn Val Arg Pro
        35                  40                  45

Glu Gln Pro Gln Phe Ser Pro Met Pro Gly Asn Val Arg Arg Pro Arg
    50                  55                  60

Pro Leu Xaa Glu Pro Pro Arg Pro Thr
65                  70

<210> SEQ ID NO 74
<211> LENGTH: 56
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid

<400> SEQUENCE: 74

Tyr Xaa Pro Thr Ser Pro Asn Tyr Xaa Pro Thr Ser Pro Asn Tyr Thr
1               5                   10                  15

Pro Thr Ser Pro Ser Tyr Xaa Pro Thr Ser Pro Ser Tyr Xaa Pro Thr
            20                  25                  30

Ser Pro Asn Tyr Thr Pro Thr Ser Pro Asn Tyr Xaa Pro Thr Ser Pro
        35                  40                  45

Ser Tyr Xaa Pro Thr Ser Pro Ser
    50                  55

<210> SEQ ID NO 75
<211> LENGTH: 84
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (28)..(28)
```

-continued

<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid

<400> SEQUENCE: 75

His Ile Pro Arg Ser Pro Tyr Lys Phe Pro Ser Ser Pro Leu Arg Ile
1               5                   10                  15

Pro Gly Gly Asn Ile Tyr Ile Xaa Pro Leu Lys Xaa Pro Tyr Lys Ile
            20                  25                  30

Ser Glu Gly Leu Pro Xaa Pro Thr Lys Met Xaa Pro Arg Ser Arg Ile
        35                  40                  45

Leu Val Ser Ile Gly Glu Ser Phe Gly Thr Ser Glu Lys Phe Gln Lys
    50                  55                  60

Ile Asn Gln Met Val Cys Asn Ser Asp Arg Val Leu Lys Arg Ser Ala
65                  70                  75                  80

Glu Gly Ser Asn

<210> SEQ ID NO 76
<211> LENGTH: 236
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (129)..(129)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (190)..(190)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid

<400> SEQUENCE: 76

Ser Thr Glu Leu Phe Ser Ser Thr Arg Glu Glu Gly Ser Ser Gly Ser
1               5                   10                  15

Gly Pro Ser Phe Arg Ser Asn Gln Arg Lys Met Leu Asn Leu Leu Leu
            20                  25                  30

```
Glu Arg Asp Thr Ser Phe Thr Val Cys Pro Asp Val Pro Arg Xaa Pro
             35                  40                  45

Val Gly Lys Phe Leu Gly Asp Ser Ala Asn Leu Ser Ile Leu Ser Gly
 50                  55                  60

Gly Xaa Pro Lys Cys Cys Leu Asp Leu Ser Asn Leu Ser Ser Gly Glu
 65                  70                  75                  80

Ile Thr Ala Thr Gln Leu Thr Thr Ser Ala Asp Leu Asp Glu Thr Gly
                 85                  90                  95

His Leu Asp Ser Ser Gly Leu Gln Glu Val His Leu Ala Gly Met Asn
                100                 105                 110

His Asp Gln His Leu Met Lys Cys Xaa Pro Ala Gln Leu Leu Cys Ser
                115                 120                 125

Xaa Pro Asn Gly Leu Asp Arg Gly His Arg Lys Arg Asp Ala Met Cys
            130                 135                 140

Ser Ser Ser Ala Asn Lys Glu Asn Asp Asn Gly Asn Leu Val Asp Ser
145                 150                 155                 160

Glu Met Lys Tyr Leu Gly Xaa Pro Ile Thr Thr Val Pro Lys Leu Asp
                165                 170                 175

Lys Asn Pro Asn Leu Gly Glu Asp Gln Ala Glu Glu Ile Xaa Asp Glu
                180                 185                 190

Leu Met Glu Phe Xaa Leu Lys Asp Gln Glu Ala Lys Val Ser Arg Ser
                195                 200                 205

Gly Leu Tyr Arg Xaa Pro Xaa Met Pro Glu Asn Leu Asn Arg Pro Arg
            210                 215                 220

Leu Lys Gln Val Glu Lys Phe Lys Asp Asn Thr Ile
225                 230                 235

<210> SEQ ID NO 77
<211> LENGTH: 237
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
<222> LOCATION: (168)..(168)
<223> OTHER INFORMATION: Xaa can be any naturally occurring amino acid
<220> FEATURE:
<221> NAME/KEY: misc_feature
<222> LOCATION: (191)..(191)
<223> OTHER INFORMATION: Xaa can be any naturally occurring amino acid
<220> FEATURE:
<221> NAME/KEY: misc_feature
<222> LOCATION: (198)..(198)
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
```

```
<221> NAME/KEY: misc_feature
<222> LOCATION: (216)..(216)
<223> OTHER INFORMATION: Xaa can be any naturally occurring amino acid

<400> SEQUENCE: 77
```

Met Ser Thr Glu Leu Phe Ser Ser Thr Arg Glu Glu Gly Ser Ser Gly
1               5                   10                  15

Ser Gly Pro Ser Phe Arg Ser Asn Gln Arg Lys Met Leu Asn Leu Leu
            20                  25                  30

Leu Glu Arg Asp Thr Ser Phe Thr Val Cys Pro Asp Val Pro Arg Xaa
        35                  40                  45

Pro Val Gly Lys Phe Leu Gly Asp Ser Ala Asn Leu Ser Ile Leu Ser
    50                  55                  60

Gly Gly Xaa Pro Lys Cys Cys Leu Asp Leu Ser Asn Leu Ser Ser Gly
65                  70                  75                  80

Glu Ile Thr Ala Thr Gln Leu Thr Thr Ser Ala Asp Leu Asp Glu Thr
                85                  90                  95

Gly His Leu Asp Ser Ser Gly Leu Gln Glu Val His Leu Ala Gly Met
            100                 105                 110

Asn His Asp Gln His Leu Met Lys Cys Xaa Pro Ala Gln Leu Leu Cys
        115                 120                 125

Ser Xaa Pro Asn Gly Leu Asp Arg Gly His Arg Lys Arg Asp Ala Met
    130                 135                 140

Cys Ser Ser Ser Ala Asn Lys Glu Asn Asp Asn Gly Asn Leu Val Asp
145                 150                 155                 160

Ser Glu Met Lys Tyr Leu Gly Xaa Pro Ile Thr Thr Val Pro Lys Leu
                165                 170                 175

Asp Lys Asn Pro Asn Leu Gly Glu Asp Gln Ala Glu Glu Ile Xaa Asp
            180                 185                 190

Glu Leu Met Glu Phe Xaa Leu Lys Asp Gln Glu Ala Lys Val Ser Arg
        195                 200                 205

Ser Gly Leu Tyr Arg Xaa Pro Xaa Met Pro Glu Asn Leu Asn Arg Pro
    210                 215                 220

Arg Leu Lys Gln Val Glu Lys Phe Lys Asp Asn Thr Ile
225                 230                 235

```
<210> SEQ ID NO 78
<211> LENGTH: 107
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid

<400> SEQUENCE: 78
```

Met Ser Cys Thr Arg Met Ile Gln Val Leu Asp Pro Arg Pro Leu Thr
1               5                   10                  15

```
Ser Ser Val Met Pro Val Asp Val Ala Met Arg Leu Cys Leu Ala His
        20                  25                  30

Ser Pro Pro Val Lys Ser Phe Leu Gly Pro Tyr Asp Glu Phe Gln Arg
            35                  40                  45

Arg His Phe Val Asn Lys Leu Lys Pro Leu Lys Ser Cys Leu Asn Ile
    50                  55                  60

Lys His Lys Ala Lys Ser Gln Asn Asp Trp Lys Cys Ser His Asn Gln
65                  70                  75                  80

Ala Lys Lys Arg Val Val Phe Ala Asp Xaa Lys Gly Leu Xaa Leu Xaa
                85                  90                  95

Ala Ile His Val Phe Xaa Asp Leu Pro Glu Glu
            100                 105
```

<210> SEQ ID NO 79
<211> LENGTH: 106
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid

<400> SEQUENCE: 79

```
Ser Cys Thr Arg Met Ile Gln Val Leu Asp Pro Arg Pro Leu Thr Ser
1               5                   10                  15

Ser Val Met Pro Val Asp Val Ala Met Arg Leu Cys Leu Ala His Ser
            20                  25                  30

Pro Pro Val Lys Ser Phe Leu Gly Pro Tyr Asp Glu Phe Gln Arg Arg
        35                  40                  45

His Phe Val Asn Lys Leu Lys Pro Leu Lys Ser Cys Leu Asn Ile Lys
    50                  55                  60

His Lys Ala Lys Ser Gln Asn Asp Trp Lys Cys Ser His Asn Gln Ala
65                  70                  75                  80

Lys Lys Arg Val Val Phe Ala Asp Xaa Lys Gly Leu Xaa Leu Xaa Ala
                85                  90                  95

Ile His Val Phe Xaa Asp Leu Pro Glu Glu
            100                 105
```

<210> SEQ ID NO 80
<211> LENGTH: 23
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (15)..(16)
<223> OTHER INFORMATION: Xaa can be any naturally occurring amino acid

<400> SEQUENCE: 80

```
Glu Lys Val Gln Tyr Leu Thr Arg Ser Ala Ile Arg Arg Ala Xaa Xaa
```

Ile Glu Met Pro Gln Gln Ala
            20

<210> SEQ ID NO 81
<211> LENGTH: 24
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(17)
<223> OTHER INFORMATION: Xaa can be any naturally occurring amino acid

<400> SEQUENCE: 81

Met Glu Lys Val Gln Tyr Leu Thr Arg Ser Ala Ile Arg Arg Ala Xaa
1               5                   10                  15

Xaa Ile Glu Met Pro Gln Gln Ala
            20

<210> SEQ ID NO 82
<211> LENGTH: 116
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid

```
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid

<400> SEQUENCE: 82

Tyr Xaa Pro Thr Ser Pro Ser Tyr Xaa Pro Thr Ser Pro Ser Tyr Xaa
1               5                   10                  15

Pro Thr Ser Pro Asn Tyr Xaa Pro Thr Ser Pro Ser Tyr Xaa Pro Thr
            20                  25                  30

Ser Pro Ser Tyr Xaa Pro Thr Ser Pro Ser Tyr Xaa Pro Thr Ser Pro
        35                  40                  45

Ser Tyr Xaa Pro Thr Ser Pro Ser Tyr Xaa Pro Thr Ser Pro Ser Tyr
    50                  55                  60

Xaa Pro Thr Ser Pro Ser Tyr Xaa Pro Thr Ser Pro Ser Tyr Xaa Pro
65                  70                  75                  80

Thr Ser Pro Ser Tyr Xaa Pro Thr Ser Pro Ser Tyr Xaa Pro Thr Ser
                85                  90                  95

Pro Ser Tyr Xaa Pro Thr Ser Pro Ser Tyr Xaa Pro Thr Ser Pro Ser
            100                 105                 110

Tyr Xaa Pro Thr
        115

<210> SEQ ID NO 83
<211> LENGTH: 351
<212> TYPE: PRT
<213> ORGANISM: Homo sapiens
<220> FEATURE:
<221> NAME/KEY: misc_feature
<222> LOCATION: (161)..(161)
<223> OTHER INFORMATION: Xaa can be any naturally occurring amino acid
<220> FEATURE:
<221> NAME/KEY: misc_feature
<222> LOCATION: (178)..(178)
<223> OTHER INFORMATION: Xaa can be any naturally occurring amino acid
<220> FEATURE:
<221> NAME/KEY: misc_feature
<222> LOCATION: (199)..(199)
<223> OTHER INFORMATION: Xaa can be any naturally occurring amino acid
<220> FEATURE:
<221> NAME/KEY: misc_feature
<222> LOCATION: (204)..(204)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (335)..(335)
<223> OTHER INFORMATION: Xaa can be any naturally occurring amino acid

<400> SEQUENCE: 83

Met Ala Ala Ala Ala Asn Ser Gly Ser Ser Leu Pro Leu Phe Asp Cys
```

```
  1               5                  10                 15
Pro Thr Trp Ala Gly Lys Pro Pro Gly Leu His Leu Asp Val Val
              20                 25                 30

Lys Gly Asp Lys Leu Ile Glu Lys Leu Ile Asp Glu Lys Lys Tyr
              35                 40                 45

Tyr Leu Phe Gly Arg Asn Pro Asp Leu Cys Asp Phe Thr Ile Asp His
 50                 55                 60

Gln Ser Cys Ser Arg Val His Ala Ala Leu Val Tyr His Lys His Leu
 65                 70                 75                 80

Lys Arg Val Phe Leu Ile Asp Leu Asn Ser Thr His Gly Thr Phe Leu
                    85                 90                 95

Gly His Ile Arg Leu Glu Pro His Lys Pro Gln Gln Ile Pro Ile Asp
                   100                105                110

Ser Thr Val Ser Phe Gly Ala Ser Thr Arg Ala Tyr Thr Leu Arg Glu
                   115                120                125

Lys Pro Gln Thr Leu Pro Ser Ala Val Lys Gly Asp Glu Lys Met Gly
                   130                135                140

Gly Glu Asp Asp Glu Leu Lys Gly Leu Leu Gly Leu Pro Glu Glu Glu
145                150                155                160

Xaa Glu Leu Asp Asn Leu Thr Glu Phe Asn Thr Ala His Asn Lys Arg
                   165                170                175

Ile Xaa Thr Leu Thr Ile Glu Glu Gly Asn Leu Asp Ile Gln Arg Pro
                   180                185                190

Lys Arg Lys Arg Lys Asn Xaa Arg Val Thr Phe Xaa Glu Asp Asp Glu
                   195                200                205

Ile Ile Asn Pro Glu Asp Val Asp Pro Ser Val Gly Arg Phe Arg Asn
                   210                215                220

Met Val Gln Thr Ala Val Pro Val Lys Lys Arg Val Glu Gly
225                230                235                240

Pro Gly Ser Leu Gly Leu Glu Glu Ser Gly Ser Arg Arg Met Gln Asn
                   245                250                255

Phe Ala Phe Ser Gly Gly Leu Xaa Gly Gly Leu Pro Pro Thr His Ser
                   260                265                270

Glu Ala Gly Ser Gln Pro His Gly Ile His Gly Thr Ala Leu Ile Gly
                   275                280                285

Gly Leu Pro Met Pro Tyr Pro Asn Leu Ala Pro Asp Val Asp Leu Thr
                   290                295                300

Pro Val Val Pro Ser Ala Val Asn Met Asn Pro Ala Pro Asn Pro Ala
305                310                315                320

Val Tyr Asn Pro Glu Ala Val Asn Glu Pro Lys Lys Lys Xaa Ala
                   325                330                335

Lys Glu Ala Trp Pro Gly Lys Lys Pro Thr Pro Ser Leu Leu Ile
                   340                345                350

<210> SEQ ID NO 84
<211> LENGTH: 518
<212> TYPE: PRT
<213> ORGANISM: Homo sapiens

<400> SEQUENCE: 84

Met Asp Gln Thr Pro Pro Ala Arg Pro Glu Tyr Leu Val Ser Gly Ile
 1               5                  10                 15

Arg Thr Pro Pro Val Arg Arg Asn Ser Lys Leu Ala Thr Leu Gly Arg
              20                 25                 30

Ile Phe Lys Pro Trp Lys Trp Arg Lys Lys Lys Asn Glu Lys Leu Lys
```

```
              35                  40                  45
Gln Thr Thr Ser Ala Leu Glu Lys Lys Met Ala Gly Arg Gln Gly Arg
 50                  55                  60

Glu Glu Leu Ile Lys Lys Gly Leu Leu Glu Met Met Glu Gln Asp Ala
 65                  70                  75                  80

Glu Ser Lys Thr Cys Asn Pro Asp Gly Pro Arg Ser Val Gln Ser
                 85                  90                  95

Glu Pro Pro Thr Pro Lys Ser Glu Thr Leu Thr Ser Glu Asp Ala Gln
                100                 105                 110

Pro Gly Ser Pro Leu Ala Thr Gly Thr Asp Gln Val Ser Leu Asp Lys
                115                 120                 125

Pro Leu Ser Ser Ala Ala His Leu Asp Asp Ala Lys Met Pro Ser
   130                 135                 140

Ala Ser Ser Gly Glu Glu Ala Asp Ala Gly Ser Leu Leu Pro Thr Thr
145                 150                 155                 160

Asn Glu Leu Ser Gln Ala Leu Ala Gly Ala Asp Ser Leu Asp Ser Pro
                165                 170                 175

Pro Arg Pro Leu Glu Arg Ser Val Gly Gln Leu Pro Ser Pro Pro Leu
                180                 185                 190

Leu Pro Thr Pro Pro Lys Ala Ser Ser Lys Thr Thr Lys Asn Val
   195                 200                 205

Thr Gly Gln Ala Thr Leu Phe Gln Ala Ser Ser Met Lys Ser Ala Asp
210                 215                 220

Pro Ser Leu Arg Gly Gln Leu Ser Thr Pro Thr Gly Ser Pro His Leu
225                 230                 235                 240

Thr Thr Val His Arg Pro Leu Pro Pro Ser Arg Val Ile Glu Glu Leu
                245                 250                 255

His Arg Ala Leu Ala Thr Lys His Arg Gln Asp Ser Phe Gln Gly Arg
                260                 265                 270

Glu Ser Lys Gly Ser Pro Lys Arg Arg Leu Asp Val Arg Leu Ser Arg
                275                 280                 285

Thr Ser Ser Val Glu Arg Gly Lys Glu Arg Glu Glu Ala Trp Ser Phe
290                 295                 300

Asp Gly Ala Leu Glu Asn Lys Arg Thr Ala Ala Lys Glu Ser Glu Glu
305                 310                 315                 320

Asn Lys Glu Asn Leu Ile Ile Asn Ser Glu Leu Lys Asp Asp Leu Leu
                325                 330                 335

Leu Tyr Gln Asp Glu Glu Ala Leu Asn Asp Ser Ile Ile Ser Gly Thr
                340                 345                 350

Leu Pro Arg Lys Cys Arg Lys Glu Leu Leu Ala Val Lys Leu Arg Asn
                355                 360                 365

Arg Pro Ser Lys Gln Glu Leu Glu Asp Arg Asn Ile Phe Pro Arg Arg
   370                 375                 380

Thr Asp Glu Glu Arg Gln Glu Ile Arg Gln Ile Glu Met Lys Leu
385                 390                 395                 400

Ser Lys Arg Leu Ser Gln Arg Pro Ala Val Glu Glu Leu Glu Arg Arg
                405                 410                 415

Asn Ile Leu Lys Gln Arg Asn Asp Gln Thr Glu Gln Glu Glu Arg Arg
                420                 425                 430

Glu Ile Lys Gln Arg Leu Thr Arg Lys Leu Asn Gln Arg Pro Thr Val
            435                 440                 445

Asp Glu Leu Arg Asp Arg Lys Ile Leu Ile Arg Phe Ser Asp Tyr Val
450                 455                 460
```

```
Glu Val Ala Lys Ala Gln Asp Tyr Asp Arg Arg Ala Asp Lys Pro Trp
465                 470                 475                 480

Thr Arg Leu Ser Ala Ala Asp Lys Ala Ala Ile Arg Lys Glu Leu Asn
            485                 490                 495

Glu Tyr Lys Ser Asn Glu Met Glu Val His Ala Ser Lys His Leu
        500                 505                 510

Thr Arg Phe His Arg Pro
        515

<210> SEQ ID NO 85
<211> LENGTH: 147
<212> TYPE: PRT
<213> ORGANISM: Homo sapiens
<220> FEATURE:
<221> NAME/KEY: misc_feature
<222> LOCATION: (38)..(38)
<223> OTHER INFORMATION: Xaa can be any naturally occurring amino acid

<400> SEQUENCE: 85

Met Ala Ala Gln Arg Leu Gly Lys Arg Val Leu Ser Lys Leu Gln Ser
1               5                   10                  15

Pro Ser Arg Ala Arg Gly Pro Gly Gly Ser Pro Gly Leu Gln Lys
            20                  25                  30

Arg His Ala Arg Val Xaa Val Lys Tyr Asp Arg Arg Glu Leu Gln Arg
        35                  40                  45

Arg Leu Asp Val Glu Lys Trp Ile Asp Gly Arg Leu Glu Glu Leu Tyr
    50                  55                  60

Arg Gly Met Glu Ala Asp Met Pro Asp Glu Ile Asn Ile Asp Glu Leu
65                  70                  75                  80

Leu Glu Leu Glu Ser Glu Glu Glu Arg Ser Arg Lys Ile Gln Gly Leu
                85                  90                  95

Leu Lys Ser Cys Gly Lys Pro Val Glu Asp Phe Ile Gln Glu Leu Leu
            100                 105                 110

Ala Lys Leu Gln Gly Leu His Arg Gln Pro Gly Leu Arg Gln Pro Ser
        115                 120                 125

Pro Ser His Asp Gly Ser Leu Ser Pro Leu Gln Asp Arg Ala Arg Thr
    130                 135                 140

Ala His Pro
145

<210> SEQ ID NO 86
<211> LENGTH: 204
<212> TYPE: PRT
<213> ORGANISM: Homo sapiens
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid

<400> SEQUENCE: 86

Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg
            20                  25                  30

Pro Xaa Pro Ala Met Leu Phe Arg Leu Ser Glu His Ser Ser Pro Glu
        35                  40                  45

Glu Glu Ala Ser Pro His Gln Arg Ala Ser Gly Glu Gly His His Leu
```

```
                  50                  55                  60
Lys Ser Lys Arg Pro Asn Pro Cys Ala Tyr Xaa Pro Pro Ser Leu Lys
 65                  70                  75                  80

Ala Val Gln Arg Ile Ala Glu Ser His Leu Gln Ser Ile Ser Asn Leu
                 85                  90                  95

Asn Glu Asn Gln Ala Ser Glu Glu Asp Glu Leu Gly Glu Leu Arg
            100                 105                 110

Glu Leu Gly Tyr Pro Arg Glu Glu Asp Glu Glu Glu Glu Asp Asp
        115                 120                 125

Glu Glu Glu Glu Glu Glu Asp Ser Gln Ala Glu Val Leu Lys Val
    130                 135                 140

Ile Arg Gln Ser Ala Gly Gln Lys Thr Thr Cys Gly Gln Gly Leu Glu
145                 150                 155                 160

Gly Pro Trp Glu Arg Pro Pro Leu Asp Glu Ser Glu Arg Asp Gly
            165                 170                 175

Gly Ser Glu Asp Gln Val Glu Asp Pro Ala Leu Ser Glu Pro Gly Glu
                180                 185                 190

Glu Pro Gln Arg Pro Ser Pro Ser Glu Pro Gly Thr
            195                 200

<210> SEQ ID NO 87
<211> LENGTH: 940
<212> TYPE: PRT
<213> ORGANISM: Homo sapiens

<400> SEQUENCE: 87

Met Gly Ser Gly Pro Ile Asp Pro Lys Glu Leu Leu Lys Gly Leu Asp
 1                   5                  10                  15

Ser Phe Leu Asn Arg Asp Gly Glu Val Lys Ser Val Asp Gly Ile Ser
                 20                  25                  30

Lys Ile Phe Ser Leu Met Lys Glu Ala Arg Lys Met Val Ser Arg Cys
             35                  40                  45

Thr Tyr Leu Asn Ile Leu Leu Gln Thr Arg Ser Pro Glu Ile Leu Val
         50                  55                  60

Lys Phe Ile Asp Val Gly Gly Tyr Lys Leu Leu Asn Asn Trp Leu Thr
 65                  70                  75                  80

Tyr Ser Lys Thr Thr Asn Asn Ile Pro Leu Leu Gln Gln Ile Leu Leu
                 85                  90                  95

Thr Leu Gln His Leu Pro Leu Thr Val Asp His Leu Lys Gln Asn Asn
            100                 105                 110

Thr Ala Lys Leu Val Lys Gln Leu Ser Lys Ser Ser Glu Asp Glu Glu
        115                 120                 125

Leu Arg Lys Leu Ala Ser Val Leu Val Ser Asp Trp Met Ala Val Ile
    130                 135                 140

Arg Ser Gln Ser Ser Thr Gln Pro Ala Glu Lys Asp Lys Lys Arg
145                 150                 155                 160

Lys Asp Glu Gly Lys Ser Arg Thr Thr Leu Pro Glu Arg Pro Leu Thr
                165                 170                 175

Glu Val Lys Ala Glu Thr Arg Ala Glu Ala Pro Glu Lys Lys Arg
            180                 185                 190

Glu Lys Pro Lys Ser Leu Arg Thr Thr Ala Pro Ser His Ala Lys Phe
        195                 200                 205

Arg Ser Thr Gly Leu Glu Leu Glu Thr Pro Ser Leu Val Pro Val Lys
    210                 215                 220

Lys Asn Ala Ser Thr Val Val Val Ser Asp Lys Tyr Asn Leu Lys Pro
```

```
               225                 230                 235                 240
    Ile Pro Leu Lys Arg Gln Ser Asn Val Ala Ala Pro Gly Asp Ala Thr
                     245                 250                 255

Pro Pro Ala Glu Lys Lys Tyr Lys Pro Leu Asn Thr Thr Pro Asn Ala
                     260                 265                 270

Thr Lys Glu Ile Lys Val Lys Ile Ile Pro Gln Pro Met Glu Gly
                     275                 280                 285

Leu Gly Phe Leu Asp Ala Leu Asn Ser Ala Pro Val Pro Gly Ile Lys
                     290                 295                 300

Ile Lys Lys Lys Lys Lys Val Leu Ser Pro Thr Ala Ala Lys Pro Ser
    305                 310                 315                 320

Pro Phe Glu Gly Lys Thr Ser Thr Glu Pro Ser Thr Ala Lys Pro Ser
                     325                 330                 335

Ser Pro Glu Pro Ala Pro Pro Ser Glu Ala Met Asp Ala Asp Arg Pro
                     340                 345                 350

Gly Thr Pro Val Pro Val Glu Val Pro Glu Leu Met Asp Thr Ala
                     355                 360                 365

Ser Leu Glu Pro Gly Ala Leu Asp Ala Lys Pro Val Glu Ser Pro Gly
                     370                 375                 380

Asp Pro Asn Gln Leu Thr Arg Lys Gly Arg Lys Arg Lys Ser Val Thr
    385                 390                 395                 400

Trp Pro Glu Glu Gly Lys Leu Arg Glu Tyr Phe Tyr Phe Glu Leu Asp
                     405                 410                 415

Glu Thr Glu Arg Val Asn Val Asn Lys Ile Lys Asp Phe Gly Glu Ala
                     420                 425                 430

Ala Lys Arg Glu Ile Leu Ser Asp Arg His Ala Phe Glu Thr Ala Arg
                     435                 440                 445

Arg Leu Ser His Asp Asn Met Glu Glu Lys Val Pro Trp Val Cys Pro
                     450                 455                 460

Arg Pro Leu Val Leu Pro Ser Pro Leu Val Thr Pro Gly Ser Asn Ser
    465                 470                 475                 480

Gln Glu Arg Tyr Ile Gln Ala Glu Arg Glu Lys Gly Ile Leu Gln Glu
                     485                 490                 495

Leu Phe Leu Asn Lys Glu Ser Pro His Glu Pro Asp Pro Glu Pro Tyr
                     500                 505                 510

Glu Pro Ile Pro Pro Lys Leu Ile Pro Leu Asp Glu Cys Ser Met
                     515                 520                 525

Asp Glu Thr Pro Tyr Val Glu Thr Leu Glu Pro Gly Gly Ser Gly Gly
                     530                 535                 540

Ser Pro Asp Gly Ala Gly Gly Ser Lys Leu Pro Pro Val Leu Ala Asn
    545                 550                 555                 560

Leu Met Gly Ser Met Gly Ala Gly Lys Gly Pro Gln Gly Pro Gly Gly
                     565                 570                 575

Gly Gly Ile Asn Val Gln Glu Ile Leu Thr Ser Ile Met Gly Ser Pro
                     580                 585                 590

Asn Ser His Pro Ser Glu Glu Leu Leu Lys Gln Pro Asp Tyr Ser Asp
                     595                 600                 605

Lys Ile Lys Gln Met Leu Val Pro His Gly Leu Leu Gly Pro Gly Pro
    610                 615                 620

Ile Ala Asn Gly Phe Pro Gly Gly Pro Gly Gly Pro Lys Gly Met
    625                 630                 635                 640

Gln His Phe Pro Pro Gly Pro Gly Gly Pro Met Pro Gly Pro His Gly
                     645                 650                 655
```

```
Gly Pro Gly Gly Pro Val Gly Pro Arg Leu Gly Pro Pro Pro
            660                 665                 670

Pro Arg Gly Gly Asp Pro Phe Trp Asp Gly Pro Gly Asp Pro Met Arg
            675                 680                 685

Gly Gly Pro Met Arg Gly Gly Pro Gly Pro Gly Pro Tyr His
        690                 695                 700

Arg Gly Arg Gly Gly Arg Gly Gly Asn Glu Pro Pro Pro Pro
705                 710                 715                 720

Pro Phe Arg Gly Ala Arg Gly Gly Arg Ser Gly Gly Pro Pro Asn
                725                 730                 735

Gly Arg Gly Gly Pro Gly Gly Gly Met Val Gly Gly Gly His Arg
        740                 745                 750

Pro His Glu Gly Pro Gly Gly Met Gly Asn Ser Ser Gly His Arg
    755                 760                 765

Pro His Glu Gly Pro Gly Gly Met Gly Ser Gly His Arg Pro His
    770                 775                 780

Glu Gly Pro Gly Gly Ser Met Gly Gly Gly His Arg Pro His
785                 790                 795                 800

Glu Gly Pro Gly Gly Gly Ile Ser Gly Gly Ser Gly His Arg Pro His
                805                 810                 815

Glu Gly Pro Gly Gly Gly Met Gly Ala Gly Gly His Arg Pro His
                820                 825                 830

Glu Gly Pro Gly Gly Ser Met Gly Gly Ser Gly His Arg Pro His
                835                 840                 845

Glu Gly Pro Gly His Gly Gly Pro His Gly His Arg Pro His Asp Val
                850                 855                 860

Pro Gly His Arg Gly His Asp His Arg Gly Pro Pro His Glu His
865                 870                 875                 880

Arg Gly His Asp Gly Pro Gly His Gly Gly His Arg Gly His
                885                 890                 895

Asp Gly Gly His Ser His Gly Gly Asp Met Ser Asn Arg Pro Val Cys
                900                 905                 910

Arg His Phe Met Met Lys Gly Asn Cys Arg Tyr Glu Asn Asn Cys Ala
                915                 920                 925

Phe Tyr His Pro Gly Val Asn Gly Pro Pro Leu Pro
    930                 935                 940

<210> SEQ ID NO 88
<211> LENGTH: 171
<212> TYPE: PRT
<213> ORGANISM: Homo sapiens
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid

<400> SEQUENCE: 88

Met Glu Gln Asp Asn Ser Pro Gln Lys Ile Gln Phe Thr Val Pro Leu
1               5                   10                  15

Leu Glu Pro His Leu Asp Pro Glu Ala Ala Glu Gln Ile Arg Arg Arg
                20                  25                  30
```

-continued

```
Arg Pro Xaa Pro Ala Thr Leu Val Leu Thr Ser Asp Gln Ser Ser Pro
            35                  40                  45

Glu Ile Asp Glu Asp Arg Ile Pro Asn Pro His Leu Lys Ser Thr Leu
 50                  55                  60

Ala Met Xaa Pro Arg Gln Arg Lys Lys Met Xaa Arg Ile Thr Pro Thr
 65                  70                  75                  80

Met Lys Glu Leu Gln Met Met Val Glu His His Leu Gly Gln Gln Gln
                 85                  90                  95

Gln Gly Glu Glu Pro Glu Gly Ala Ala Glu Ser Thr Gly Thr Gln Glu
            100                 105                 110

Ser Arg Pro Pro Gly Ile Pro Asp Thr Glu Val Glu Ser Arg Leu Gly
            115                 120                 125

Thr Ser Gly Thr Ala Lys Lys Thr Ala Glu Cys Ile Pro Lys Thr His
130                 135                 140

Glu Arg Gly Ser Lys Glu Pro Ser Thr Lys Glu Pro Ser Thr His Ile
145                 150                 155                 160

Pro Pro Leu Asp Ser Lys Gly Ala Asn Ser Val
            165                 170
```

<210> SEQ ID NO 89
<211> LENGTH: 815
<212> TYPE: PRT
<213> ORGANISM: Homo sapiens
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid

<400> SEQUENCE: 89

```
Met Met Lys Thr Glu Pro Arg Gly Pro Gly Gly Pro Leu Arg Ser Ala
 1               5                  10                  15

Ser Pro His Arg Ser Ala Tyr Glu Ala Gly Ile Gln Ala Leu Lys Pro
                 20                  25                  30

Pro Asp Ala Pro Gly Pro Asp Glu Ala Pro Lys Gly Ala His His Lys
             35                  40                  45

Lys Tyr Gly Ser Asn Val His Arg Ile Lys Ser Met Phe Leu Gln Met
 50                  55                  60

Gly Thr Thr Ala Gly Pro Ser Gly Glu Ala Gly Gly Ala Gly Leu
 65                  70                  75                  80

Ala Glu Ala Pro Arg Ala Ser Glu Arg Gly Val Arg Leu Xaa Leu Pro
                 85                  90                  95

Arg Ala Ser Xaa Leu Asn Glu Asn Val Asp His Ser Ala Leu Leu Lys
            100                 105                 110

Leu Gly Thr Ser Val Ser Glu Arg Val Ser Arg Phe Asp Ser Lys Pro
            115                 120                 125

Ala Pro Ser Ala Gln Pro Ala Pro Pro His Pro Pro Ser Arg Leu
130                 135                 140

Gln Glu Thr Arg Lys Leu Phe Glu Arg Ser Ala Pro Ala Ala Gly Gly
145                 150                 155                 160

Asp Lys Glu Ala Ala Arg Arg Leu Leu Arg Gln Glu Arg Ala Gly Leu
                165                 170                 175

Gln Asp Arg Lys Leu Asp Val Val Arg Phe Asn Gly Ser Thr Glu
            180                 185                 190

Ala Leu Asp Lys Leu Asp Ala Asp Ala Val Ser Pro Thr Val Ser Gln
```

195                 200                 205
Leu Ser Ala Val Phe Glu Lys Ala Asp Ser Arg Thr Gly Leu His Arg
210                 215                 220

Gly Pro Gly Leu Pro Arg Ala Ala Gly Val Pro Gln Val Asn Ser Lys
225                 230                 235                 240

Leu Val Ser Lys Arg Ser Arg Val Phe Gln Pro Pro Pro Pro Pro Pro
                245                 250                 255

Pro Ala Pro Ser Gly Asp Ala Pro Ala Glu Lys Glu Arg Cys Pro Ala
            260                 265                 270

Gly Gln Gln Pro Pro Gln His Arg Val Ala Pro Ala Arg Pro Pro Pro
        275                 280                 285

Lys Pro Arg Glu Val Arg Lys Ile Lys Pro Val Glu Val Glu Glu Ser
    290                 295                 300

Gly Glu Ser Glu Ala Glu Ser Ala Pro Gly Glu Val Ile Gln Ala Glu
305                 310                 315                 320

Val Thr Val His Ala Ala Leu Glu Asn Gly Ser Thr Val Ala Thr Ala
                325                 330                 335

Ala Ser Pro Ala Pro Glu Glu Pro Lys Ala Gln Ala Ala Pro Glu Lys
            340                 345                 350

Glu Ala Ala Val Ala Pro Pro Glu Arg Gly Val Gly Asn Gly Arg
        355                 360                 365

Ala Pro Asp Val Ala Pro Glu Val Asp Glu Ser Lys Lys Glu Asp
    370                 375                 380

Phe Ser Glu Ala Asp Leu Val Asp Val Ser Ala Tyr Ser Gly Leu Gly
385                 390                 395                 400

Glu Asp Ser Ala Gly Ser Ala Leu Glu Glu Asp Glu Asp Glu
                405                 410                 415

Glu Asp Gly Glu Pro Pro Tyr Glu Pro Glu Ser Gly Cys Val Glu Ile
            420                 425                 430

Pro Gly Leu Ser Glu Glu Asp Pro Ala Pro Ser Arg Lys Ile His
        435                 440                 445

Phe Ser Thr Ala Pro Ile Gln Val Phe Ser Thr Tyr Ser Asn Glu Asp
450                 455                 460

Tyr Asp Arg Arg Asn Glu Asp Val Asp Pro Met Ala Ala Ser Ala Glu
465                 470                 475                 480

Tyr Glu Leu Glu Lys Arg Val Glu Arg Leu Glu Leu Phe Pro Val Glu
                485                 490                 495

Leu Glu Lys Asp Ser Glu Gly Leu Gly Ile Ser Ile Ile Gly Met Gly
            500                 505                 510

Ala Gly Ala Asp Met Gly Leu Glu Lys Leu Gly Ile Phe Val Lys Thr
        515                 520                 525

Val Thr Glu Gly Gly Ala Ala His Arg Asp Gly Arg Ile Gln Val Asn
    530                 535                 540

Asp Leu Leu Val Glu Val Asp Gly Thr Ser Leu Val Gly Val Thr Gln
545                 550                 555                 560

Ser Phe Ala Ala Ser Val Leu Arg Asn Thr Lys Gly Arg Val Arg Phe
                565                 570                 575

Met Ile Gly Arg Glu Arg Pro Gly Glu Gln Ser Glu Val Ala Gln Leu
            580                 585                 590

Ile Gln Gln Thr Leu Glu Gln Glu Arg Trp Gln Arg Glu Met Met Glu
        595                 600                 605

Gln Arg Tyr Ala Gln Tyr Gly Glu Asp Asp Glu Thr Gly Glu Tyr
    610                 615                 620

```
Ala Thr Asp Glu Asp Glu Glu Leu Ser Pro Thr Phe Pro Gly Gly Glu
625                 630                 635                 640

Met Ala Ile Glu Val Phe Glu Leu Ala Glu Asn Glu Asp Ala Leu Ser
            645                 650                 655

Pro Val Asp Met Glu Pro Glu Lys Leu Val His Lys Phe Lys Glu Leu
        660                 665                 670

Gln Ile Lys His Ala Val Thr Glu Ala Glu Ile Gln Gln Leu Lys Arg
    675                 680                 685

Lys Leu Gln Ser Leu Glu Gln Glu Lys Gly Arg Trp Arg Val Glu Lys
690                 695                 700

Ala Gln Leu Glu Gln Ser Val Glu Glu Asn Lys Glu Arg Met Glu Lys
705                 710                 715                 720

Leu Glu Gly Tyr Trp Gly Glu Ala Gln Ser Leu Cys Gln Ala Val Asp
            725                 730                 735

Glu His Leu Arg Glu Thr Gln Ala Gln Tyr Gln Ala Leu Glu Arg Lys
        740                 745                 750

Tyr Ser Lys Ala Lys Arg Leu Ile Lys Asp Tyr Gln Gln Lys Glu Ile
    755                 760                 765

Glu Phe Leu Lys Lys Glu Thr Ala Gln Arg Arg Val Leu Glu Glu Ser
770                 775                 780

Glu Leu Ala Arg Lys Glu Glu Met Asp Lys Leu Leu Asp Lys Ile Ser
785                 790                 795                 800

Glu Leu Glu Gly Asn Leu Gln Thr Leu Arg Asn Ser Asn Ser Thr
            805                 810                 815

<210> SEQ ID NO 90
<211> LENGTH: 1098
<212> TYPE: PRT
<213> ORGANISM: Homo sapiens
<220> FEATURE:
<221> NAME/KEY: misc_feature
<222> LOCATION: (371)..(371)
<223> OTHER INFORMATION: Xaa can be any naturally occurring amino acid
<220> FEATURE:
<221> NAME/KEY: misc_feature
<222> LOCATION: (461)..(461)
<223> OTHER INFORMATION: Xaa can be any naturally occurring amino acid
<220> FEATURE:
<221> NAME/KEY: misc_feature
<222> LOCATION: (915)..(915)
<223> OTHER INFORMATION: Xaa can be any naturally occurring amino acid

<400> SEQUENCE: 90

Met Leu Lys Thr Glu Ser Ser Gly Glu Arg Thr Thr Leu Arg Ser Ala
1               5                   10                  15

Ser Pro His Arg Asn Ala Tyr Arg Thr Glu Phe Gln Ala Leu Lys Ser
            20                  25                  30

Thr Phe Asp Lys Pro Lys Ser Asp Gly Glu Gln Lys Thr Lys Glu Gly
        35                  40                  45

Glu Gly Ser Gln Gln Ser Arg Gly Arg Lys Tyr Gly Ser Asn Val Asn
    50                  55                  60

Arg Ile Lys Asn Leu Phe Met Gln Met Gly Met Glu Pro Asn Glu Asn
65                  70                  75                  80

Ala Ala Val Ile Ala Lys Thr Arg Gly Lys Gly Gly His Ser Ser Pro
                85                  90                  95

Gln Arg Arg Met Lys Pro Lys Glu Phe Leu Glu Lys Thr Asp Gly Ser
            100                 105                 110

Val Val Lys Leu Glu Ser Ser Val Ser Glu Arg Ile Ser Arg Phe Asp
        115                 120                 125
```

```
Thr Met Tyr Asp Gly Pro Ser Tyr Ser Lys Phe Thr Glu Thr Arg Lys
    130                 135                 140

Met Phe Glu Arg Ser Val His Glu Ser Gly Gln Asn Asn Arg Tyr Ser
145                 150                 155                 160

Pro Lys Lys Glu Lys Ala Gly Gly Ser Glu Pro Gln Asp Glu Trp Gly
                165                 170                 175

Gly Ser Lys Ser Asn Arg Gly Ser Thr Asp Ser Leu Asp Ser Leu Ser
            180                 185                 190

Ser Arg Thr Glu Ala Val Ser Pro Thr Val Ser Gln Leu Ser Ala Val
        195                 200                 205

Phe Glu Asn Thr Asp Ser Pro Ser Ala Ile Ile Ser Glu Lys Ala Glu
    210                 215                 220

Asn Asn Glu Tyr Ser Val Thr Gly His Tyr Pro Leu Asn Leu Pro Ser
225                 230                 235                 240

Val Thr Val Thr Asn Leu Asp Thr Phe Gly His Leu Lys Asp Ser Asn
                245                 250                 255

Ser Trp Pro Pro Ser Asn Lys Arg Gly Val Asp Thr Glu Asp Ala His
            260                 265                 270

Lys Ser Asn Ala Thr Pro Val Pro Glu Val Ala Ser Lys Ser Thr Ser
        275                 280                 285

Leu Ala Ser Ile Pro Gly Glu Glu Ile Gln Gln Ser Lys Glu Pro Glu
    290                 295                 300

Asp Ser Thr Ser Asn Gln Gln Thr Pro Asp Ser Ile Asp Lys Asp Gly
305                 310                 315                 320

Pro Glu Glu Pro Cys Ala Glu Ser Lys Ala Met Pro Lys Ser Glu Ile
                325                 330                 335

Pro Ser Pro Gln Ser Gln Leu Leu Glu Asp Ala Glu Ala Asn Leu Val
            340                 345                 350

Gly Arg Glu Ala Ala Lys Gln Gln Arg Lys Glu Leu Ala Gly Gly Asp
        355                 360                 365

Phe Thr Xaa Pro Asp Ala Ser Ala Ser Ser Cys Gly Lys Glu Val Pro
    370                 375                 380

Glu Asp Ser Asn Asn Phe Asp Gly Ser His Val Tyr Met His Ser Asp
385                 390                 395                 400

Tyr Asn Val Tyr Arg Val Arg Ser Arg Tyr Asn Ser Asp Trp Gly Glu
                405                 410                 415

Thr Gly Thr Glu Gln Asp Glu Glu Asp Ser Asp Glu Asn Ser Tyr
            420                 425                 430

Tyr Gln Pro Asp Met Glu Tyr Ser Glu Ile Val Gly Leu Pro Glu Glu
        435                 440                 445

Glu Glu Ile Pro Ala Asn Arg Lys Ile Lys Phe Ser Xaa Ala Pro Ile
    450                 455                 460

Lys Val Phe Asn Thr Tyr Ser Asn Glu Asp Tyr Asp Arg Arg Asn Asp
465                 470                 475                 480

Glu Val Asp Pro Val Ala Ala Ser Ala Glu Tyr Leu Glu Lys Arg
                485                 490                 495

Val Glu Lys Leu Glu Leu Phe Pro Val Glu Leu Glu Lys Asp Glu Asp
            500                 505                 510

Gly Leu Gly Ile Ser Ile Ile Gly Met Gly Val Gly Ala Asp Ala Gly
        515                 520                 525

Leu Glu Lys Leu Gly Ile Phe Val Lys Thr Val Thr Glu Gly Gly Ala
    530                 535                 540

Ala Gln Arg Asp Gly Arg Ile Gln Val Asn Asp Gln Ile Val Glu Val
545                 550                 555                 560
```

```
Asp Gly Ile Ser Leu Val Gly Val Thr Gln Asn Phe Ala Ala Thr Val
                565                 570                 575
Leu Arg Asn Thr Lys Gly Asn Val Arg Phe Val Ile Gly Arg Glu Lys
                580                 585                 590
Pro Gly Gln Val Ser Glu Val Ala Gln Leu Ile Ser Gln Thr Leu Glu
                595                 600                 605
Gln Glu Arg Arg Gln Arg Glu Leu Leu Glu Gln His Tyr Ala Gln Tyr
            610                 615                 620
Asp Ala Asp Asp Glu Thr Gly Glu Tyr Ala Thr Asp Glu Glu Glu
625                 630                 635                 640
Asp Glu Val Gly Pro Val Leu Pro Gly Ser Asp Met Ala Ile Glu Val
                645                 650                 655
Phe Glu Leu Pro Glu Asn Glu Asp Met Phe Ser Pro Ser Glu Leu Asp
                660                 665                 670
Thr Ser Lys Leu Ser His Lys Phe Lys Glu Leu Gln Ile Lys His Ala
            675                 680                 685
Val Thr Glu Ala Glu Ile Gln Lys Leu Lys Thr Lys Leu Gln Ala Ala
            690                 695                 700
Glu Asn Glu Lys Val Arg Trp Glu Leu Glu Lys Thr Gln Leu Gln Gln
705                 710                 715                 720
Asn Ile Glu Glu Asn Lys Glu Arg Met Leu Lys Leu Gly Ser Tyr Trp
                725                 730                 735
Ile Glu Ala Gln Thr Leu Cys His Thr Val Asn Glu His Leu Lys Glu
                740                 745                 750
Thr Gln Ser Gln Tyr Gln Ala Leu Glu Lys Lys Tyr Asn Lys Ala Lys
            755                 760                 765
Lys Leu Ile Lys Asp Phe Gln Gln Lys Glu Leu Asp Phe Ile Lys Arg
            770                 775                 780
Gln Glu Ala Glu Arg Lys Lys Ile Glu Asp Leu Glu Lys Ala His Leu
785                 790                 795                 800
Val Glu Val Gln Gly Leu Gln Val Arg Ile Arg Asp Leu Glu Ala Glu
                805                 810                 815
Val Phe Arg Leu Leu Lys Gln Asn Gly Thr Gln Val Asn Asn Asn Asn
                820                 825                 830
Asn Ile Phe Glu Arg Arg Thr Ser Leu Gly Glu Val Ser Lys Gly Asp
            835                 840                 845
Thr Met Glu Asn Leu Asp Gly Lys Gln Thr Ser Cys Gln Asp Gly Leu
850                 855                 860
Ser Gln Asp Leu Asn Glu Ala Val Pro Glu Thr Glu Arg Leu Asp Ser
865                 870                 875                 880
Lys Ala Leu Lys Thr Arg Ala Gln Leu Ser Val Lys Asn Arg Arg Gln
                885                 890                 895
Arg Pro Ser Arg Thr Arg Leu Tyr Asp Ser Val Ser Ser Thr Asp Gly
                900                 905                 910
Glu Asp Xaa Leu Glu Arg Lys Asn Phe Thr Phe Asn Asp Asp Phe Ser
            915                 920                 925
Pro Ser Ser Thr Ser Ser Ala Asp Leu Ser Gly Leu Gly Ala Glu Pro
            930                 935                 940
Lys Thr Pro Gly Leu Ser Gln Ser Leu Ala Leu Ser Ser Asp Glu Ser
945                 950                 955                 960
Leu Asp Met Ile Asp Asp Glu Ile Leu Asp Asp Gly Gln Ser Pro Lys
                965                 970                 975
His Ser Gln Cys Gln Asn Arg Ala Val Gln Glu Trp Ser Val Gln Gln
```

```
                  980             985             990
Val Ser His Trp Leu Met Ser Leu  Asn Leu Glu Gln Tyr  Val Ser Glu
                995             1000            1005

Phe Ser Ala Gln Asn Ile Thr  Gly Glu Gln Leu Leu  Gln Leu Asp
    1010            1015            1020

Gly Asn Lys Leu Lys Ala Leu  Gly Met Thr Ala Ser  Gln Asp Arg
    1025            1030            1035

Ala Val Val Lys Lys Lys Leu  Lys Glu Met Lys Met  Ser Leu Glu
    1040            1045            1050

Lys Ala Arg Lys Ala Gln Glu  Lys Met Glu Lys Gln  Arg Glu Lys
    1055            1060            1065

Leu Arg Arg Lys Glu Gln Glu  Gln Met Gln Arg Lys  Ser Lys Lys
    1070            1075            1080

Thr Glu Lys Met Thr Ser Thr  Thr Ala Glu Gly Ala  Gly Glu Gln
    1085            1090            1095

<210> SEQ ID NO 91
<211> LENGTH: 205
<212> TYPE: PRT
<213> ORGANISM: Homo sapiens
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (121)..(122)
<223> OTHER INFORMATION: Xaa can be any naturally occurring amino acid

<400> SEQUENCE: 91

Met Ala Ala Ser Thr Ala Ser His Arg Pro Ile Lys Gly Ile Leu Lys
1               5                   10                  15

Asn Lys Thr Ser Thr Thr Ser Ser Met Val Ala Ser Ala Glu Gln Pro
            20                  25                  30

Arg Gly Asn Val Asp Glu Glu Leu Ser Lys Lys Ser Gln Lys Trp Asp
        35                  40                  45

Glu Met Asn Ile Leu Ala Thr Tyr His Pro Ala Asp Lys Asp Tyr Gly
50                  55                  60

Leu Met Lys Ile Asp Glu Pro Ser Xaa Pro Tyr His Ser Met Met Gly
65                  70                  75                  80

Asp Asp Glu Asp Ala Cys Xaa Asp Thr Glu Ala Thr Glu Ala Met Ala
                85                  90                  95

Pro Asp Ile Leu Ala Arg Lys Leu Ala Ala Ala Glu Gly Leu Glu Pro
            100                 105                 110

Lys Tyr Arg Ile Gln Glu Gln Glu Xaa Xaa Gly Glu Glu Asp Ser Asp
        115                 120                 125

Leu Ser Pro Glu Glu Arg Glu Lys Lys Arg Gln Phe Glu Met Lys Arg
    130                 135                 140

Lys Leu His Tyr Asn Glu Gly Leu Asn Ile Lys Leu Ala Arg Gln Leu
145                 150                 155                 160

Ile Ser Lys Asp Leu His Asp Asp Glu Asp Glu Glu Met Leu Glu
                165                 170                 175

Thr Ala Asp Gly Glu Ser Met Asn Thr Glu Glu Ser Asn Gln Gly Ser
            180                 185                 190

Thr Pro Ser Asp Gln Gln Gln Asn Lys Leu Arg Ser Ser
```

```
          195                 200                 205

<210> SEQ ID NO 92
<211> LENGTH: 78
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid

<400> SEQUENCE: 92

Glu Asp Asp Glu Leu Lys Gly Leu Leu Gly Leu Pro Glu Glu Glu Xaa
1               5                   10                  15

Glu Leu Asp Asn Leu Thr Glu Phe Asn Thr Ala His Asn Lys Arg Ile
            20                  25                  30

Xaa Thr Leu Thr Ile Glu Glu Gly Asn Leu Asp Ile Gln Arg Pro Lys
        35                  40                  45

Arg Lys Arg Lys Asn Xaa Arg Val Thr Phe Xaa Glu Asp Asp Glu Ile
    50                  55                  60

Ile Asn Pro Glu Asp Val Asp Pro Ser Val Gly Arg Phe Arg
65                  70                  75

<210> SEQ ID NO 93
<211> LENGTH: 146
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (37)..(37)
<223> OTHER INFORMATION: Xaa can be any naturally occurring amino acid

<400> SEQUENCE: 93

Ala Ala Gln Arg Leu Gly Lys Arg Val Leu Ser Lys Leu Gln Ser Pro
1               5                   10                  15

Ser Arg Ala Arg Gly Pro Gly Gly Ser Pro Gly Gly Leu Gln Lys Arg
            20                  25                  30

His Ala Arg Val Xaa Val Lys Tyr Asp Arg Arg Glu Leu Gln Arg Arg
        35                  40                  45

Leu Asp Val Glu Lys Trp Ile Asp Gly Arg Leu Glu Glu Leu Tyr Arg
    50                  55                  60

Gly Met Glu Ala Asp Met Pro Asp Glu Ile Asn Ile Asp Glu Leu Leu
65                  70                  75                  80

Glu Leu Glu Ser Glu Glu Glu Arg Ser Arg Lys Ile Gln Gly Leu Leu
                85                  90                  95

Lys Ser Cys Gly Lys Pro Val Glu Asp Phe Ile Gln Glu Leu Leu Ala
            100                 105                 110

Lys Leu Gln Gly Leu His Arg Gln Pro Gly Leu Arg Gln Pro Ser Pro
        115                 120                 125
```

Ser His Asp Gly Ser Leu Ser Pro Leu Gln Asp Arg Ala Arg Thr Ala
            130                 135                 140

His Pro
145

<210> SEQ ID NO 94
<211> LENGTH: 147
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (38)..(38)
<223> OTHER INFORMATION: Xaa can be any naturally occurring amino acid

<400> SEQUENCE: 94

Met Ala Ala Gln Arg Leu Gly Lys Arg Val Leu Ser Lys Leu Gln Ser
1               5                   10                  15

Pro Ser Arg Ala Arg Gly Pro Gly Gly Ser Pro Gly Gly Leu Gln Lys
            20                  25                  30

Arg His Ala Arg Val Xaa Val Lys Tyr Asp Arg Glu Leu Gln Arg
        35                  40                  45

Arg Leu Asp Val Glu Lys Trp Ile Asp Gly Arg Leu Glu Glu Leu Tyr
50                  55                  60

Arg Gly Met Glu Ala Asp Met Pro Asp Glu Ile Asn Ile Asp Glu Leu
65                  70                  75                  80

Leu Glu Leu Glu Ser Glu Glu Arg Ser Arg Lys Ile Gln Gly Leu
                85                  90                  95

Leu Lys Ser Cys Gly Lys Pro Val Glu Asp Phe Ile Gln Glu Leu Leu
            100                 105                 110

Ala Lys Leu Gln Gly Leu His Arg Gln Pro Gly Leu Arg Gln Pro Ser
            115                 120                 125

Pro Ser His Asp Gly Ser Leu Ser Pro Leu Gln Asp Arg Ala Arg Thr
            130                 135                 140

Ala His Pro
145

<210> SEQ ID NO 95
<211> LENGTH: 79
<212> TYPE: PRT
<213> ORGANISM: artificial sequence
<220> FEATURE:
<223> OTHER INFORMATION: synthetic

<400> SEQUENCE: 95

Arg Lys Leu Asn Gln Arg Pro Thr Val Asp Glu Leu Arg Asp Arg Lys
1               5                   10                  15

Ile Leu Ile Arg Phe Ser Asp Tyr Val Glu Val Ala Lys Ala Gln Asp
            20                  25                  30

Tyr Asp Arg Arg Ala Asp Lys Pro Trp Thr Arg Leu Ser Ala Ala Asp
            35                  40                  45

Lys Ala Ala Ile Arg Lys Glu Leu Asn Glu Tyr Lys Ser Asn Glu Met
50                  55                  60

Glu Val His Ala Ser Ser Lys His Leu Thr Arg Phe His Arg Pro
65                  70                  75

<210> SEQ ID NO 96
<211> LENGTH: 99
<212> TYPE: PRT

-continued

```
<213> ORGANISM: artificial sequence
<220> FEATURE:
<223> OTHER INFORMATION: synthetic
<220> FEATURE:
<221> NAME/KEY: misc_feature
<222> LOCATION: (34)..(34)
<223> OTHER INFORMATION: Xaa can be any naturally occurring amino acid

<400> SEQUENCE: 96

Glu Gln Asp Asn Ser Pro Gln Lys Ile Gln Phe Thr Val Pro Leu Leu
1               5                   10                  15

Glu Pro His Leu Asp Pro Glu Ala Ala Glu Gln Ile Arg Arg Arg
            20                  25                  30

Pro Xaa Pro Ala Thr Leu Val Leu Thr Ser Asp Gln Ser Ser Pro Glu
        35                  40                  45

Ile Asp Glu Asp Arg Ile Pro Asn Pro His Leu Lys Ser Thr Leu Ala
    50                  55                  60

Met Ser Pro Arg Gln Arg Lys Lys Met Thr Arg Ile Thr Pro Thr Met
65                  70                  75                  80

Lys Glu Leu Gln Met Met Val Glu His His Leu Gly Gln Gln Gln Gln
                85                  90                  95

Gly Glu Glu

<210> SEQ ID NO 97
<211> LENGTH: 100
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid

<400> SEQUENCE: 97

Met Glu Gln Asp Asn Ser Pro Gln Lys Ile Gln Phe Thr Val Pro Leu
1               5                   10                  15

Leu Glu Pro His Leu Asp Pro Glu Ala Ala Glu Gln Ile Arg Arg Arg
            20                  25                  30

Arg Pro Xaa Pro Ala Thr Leu Val Leu Thr Ser Asp Gln Ser Ser Pro
        35                  40                  45

Glu Ile Asp Glu Asp Arg Ile Pro Asn Pro His Leu Lys Ser Thr Leu
    50                  55                  60

Ala Met Xaa Pro Arg Gln Arg Lys Lys Met Xaa Arg Ile Thr Pro Thr
65                  70                  75                  80

Met Lys Glu Leu Gln Met Met Val Glu His His Leu Gly Gln Gln Gln
                85                  90                  95

Gln Gly Glu Glu
            100

<210> SEQ ID NO 98
<211> LENGTH: 89
<212> TYPE: PRT
<213> ORGANISM: artificial sequence
<220> FEATURE:
<223> OTHER INFORMATION: synthetic
```

```
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid

<400> SEQUENCE: 98

Asp Pro Lys Asp Arg Lys Lys Ile Gln Phe Ser Val Pro Ala Pro Pro
1               5                   10                  15

Ser Gln Leu Asp Pro Arg Gln Val Glu Met Ile Arg Arg Arg Arg Pro
            20                  25                  30

Xaa Pro Ala Met Leu Phe Arg Leu Ser Glu His Ser Ser Pro Glu Glu
        35                  40                  45

Glu Ala Ser Pro His Gln Arg Ala Ser Gly Glu Gly His His Leu Lys
    50                  55                  60

Ser Lys Arg Pro Asn Pro Cys Ala Tyr Xaa Pro Pro Ser Leu Lys Ala
65                  70                  75                  80

Val Gln Arg Ile Ala Glu Ser His Leu
                85

<210> SEQ ID NO 99
<211> LENGTH: 90
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid

<400> SEQUENCE: 99

Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
            20                  25                  30

Pro Xaa Pro Ala Met Leu Phe Arg Leu Ser Glu His Ser Ser Pro Glu
        35                  40                  45

Glu Glu Ala Ser Pro His Gln Arg Ala Ser Gly Glu Gly His His Leu
    50                  55                  60

Lys Ser Lys Arg Pro Asn Pro Cys Ala Tyr Xaa Pro Pro Ser Leu Lys
65                  70                  75                  80

Ala Val Gln Arg Ile Ala Glu Ser His Leu
                85                  90

<210> SEQ ID NO 100
<211> LENGTH: 35
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (33)..(33)
<223> OTHER INFORMATION: Xaa can be any naturally occurring amino acid

<400> SEQUENCE: 100

Asp Pro Lys Asp Arg Lys Lys Ile Gln Phe Ser Val Pro Ala Pro Pro
```

```
                1               5                   10                  15
            Ser Gln Leu Asp Pro Arg Gln Val Glu Met Ile Arg Arg Arg Arg Pro
                            20                  25                  30

Xaa Pro Ala
                    35

<210> SEQ ID NO 101
<211> LENGTH: 66
<212> TYPE: PRT
<213> ORGANISM: artificial sequence
<220> FEATURE:
<223> OTHER INFORMATION: synthetic

<400> SEQUENCE: 101

Gly Asp Pro Asn Gln Leu Thr Arg Lys Gly Arg Lys Arg Lys Ser Val
1               5                   10                  15

Thr Trp Pro Glu Glu Gly Lys Leu Arg Glu Tyr Phe Tyr Phe Glu Leu
                20                  25                  30

Asp Glu Thr Glu Arg Val Asn Val Asn Lys Ile Lys Asp Phe Gly Glu
                35                  40                  45

Ala Ala Lys Arg Glu Ile Leu Ser Asp Arg His Ala Phe Glu Thr Ala
        50                  55                  60

Arg Arg
65

<210> SEQ ID NO 102
<211> LENGTH: 125
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid

<400> SEQUENCE: 102

Lys Thr Glu Pro Arg Gly Pro Gly Gly Pro Leu Arg Ser Ala Ser Pro
1               5                   10                  15

His Arg Ser Ala Tyr Glu Ala Gly Ile Gln Ala Leu Lys Pro Pro Asp
                20                  25                  30

Ala Pro Gly Pro Asp Glu Ala Pro Lys Gly Ala His His Lys Lys Tyr
            35                  40                  45

Gly Ser Asn Val His Arg Ile Lys Ser Met Phe Leu Gln Met Gly Thr
        50                  55                  60

Thr Ala Gly Pro Ser Gly Glu Ala Gly Gly Ala Gly Leu Ala Glu
65                  70                  75                  80

Ala Pro Arg Ala Ser Glu Arg Gly Val Arg Leu Xaa Leu Pro Arg Ala
                85                  90                  95

Ser Xaa Leu Asn Glu Asn Val Asp His Ser Ala Leu Leu Lys Leu Gly
            100                 105                 110

Thr Ser Val Ser Glu Arg Val Ser Arg Phe Asp Ser Lys
        115                 120                 125

<210> SEQ ID NO 103
<211> LENGTH: 127
<212> TYPE: PRT
<213> ORGANISM: artificial sequence
```

```
<220> FEATURE:
<223> OTHER INFORMATION: synthetic
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid

<400> SEQUENCE: 103
```

Met Met Lys Thr Glu Pro Arg Gly Pro Gly Gly Pro Leu Arg Ser Ala
1               5                   10                  15

Ser Pro His Arg Ser Ala Tyr Glu Ala Gly Ile Gln Ala Leu Lys Pro
            20                  25                  30

Pro Asp Ala Pro Gly Pro Asp Glu Ala Pro Lys Gly Ala His His Lys
        35                  40                  45

Lys Tyr Gly Ser Asn Val His Arg Ile Lys Ser Met Phe Leu Gln Met
    50                  55                  60

Gly Thr Thr Ala Gly Pro Ser Gly Glu Ala Gly Gly Ala Gly Leu
65                  70                  75                  80

Ala Glu Ala Pro Arg Ala Ser Glu Arg Gly Val Arg Leu Xaa Leu Pro
                85                  90                  95

Arg Ala Ser Xaa Leu Asn Glu Asn Val Asp His Ser Ala Leu Leu Lys
            100                 105                 110

Leu Gly Thr Ser Val Ser Glu Arg Val Ser Arg Phe Asp Ser Lys
        115                 120                 125

```
<210> SEQ ID NO 104
<211> LENGTH: 150
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (73)..(73)
<223> OTHER INFORMATION: Xaa can be any naturally occurring amino acid

<400> SEQUENCE: 104
```

Met Ala Ala Ser Thr Ala Ser His Arg Pro Ile Lys Gly Ile Leu Lys
1               5                   10                  15

Asn Lys Thr Ser Thr Thr Ser Ser Met Val Ala Ser Ala Glu Gln Pro
            20                  25                  30

Arg Gly Asn Val Asp Glu Glu Leu Ser Lys Lys Ser Gln Lys Trp Asp
        35                  40                  45

Glu Met Asn Ile Leu Ala Thr Tyr His Pro Ala Asp Lys Asp Tyr Gly
    50                  55                  60

Leu Met Lys Ile Asp Glu Pro Ser Xaa Pro Tyr His Ser Met Met Gly
65                  70                  75                  80

Asp Asp Glu Asp Ala Cys Ser Asp Thr Glu Ala Thr Glu Ala Met Ala
                85                  90                  95

Pro Asp Ile Leu Ala Arg Lys Leu Ala Ala Glu Gly Leu Glu Pro
            100                 105                 110

Lys Tyr Arg Ile Gln Glu Gln Glu Ser Ser Gly Glu Glu Asp Ser Asp
        115                 120                 125

Leu Ser Pro Glu Glu Arg Glu Lys Lys Arg Gln Phe Glu Met Lys Arg
    130                 135                 140

Lys Leu His Tyr Asn Glu
145                 150

<210> SEQ ID NO 105
<211> LENGTH: 149
<212> TYPE: PRT
<213> ORGANISM: artificial sequence
<220> FEATURE:
<223> OTHER INFORMATION: synthetic

<400> SEQUENCE: 105

Ala Ala Ser Thr Ala Ser His Arg Pro Ile Lys Gly Ile Leu Lys Asn
1               5                   10                  15

Lys Thr Ser Thr Thr Ser Ser Met Val Ala Ser Ala Glu Gln Pro Arg
            20                  25                  30

Gly Asn Val Asp Glu Glu Leu Ser Lys Lys Ser Gln Lys Trp Asp Glu
        35                  40                  45

Met Asn Ile Leu Ala Thr Tyr His Pro Ala Asp Lys Asp Tyr Gly Leu
50                  55                  60

Met Lys Ile Asp Glu Pro Ser Thr Pro Tyr His Ser Met Met Gly Asp
65                  70                  75                  80

Asp Glu Asp Ala Cys Ser Asp Thr Gly Ala Thr Glu Ala Met Ala Pro
                85                  90                  95

Asp Ile Leu Ala Arg Lys Leu Ala Ala Ala Glu Gly Leu Glu Pro Lys
            100                 105                 110

Tyr Arg Ile Gln Glu Gln Glu Ser Ser Gly Glu Asp Ser Asp Leu
        115                 120                 125

Ser Pro Glu Gly Arg Glu Lys Lys Arg Gln Phe Glu Met Lys Arg Lys
130                 135                 140

Leu His Tyr Asn Glu
145

<210> SEQ ID NO 106
<211> LENGTH: 99
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (77)..(77)
<223> OTHER INFORMATION: Xaa can be any naturally occurring amino acid

<400> SEQUENCE: 106

Glu Asp Ser Asn Asn Phe Asp Gly Ser His Val Tyr Met His Ser Asp
1               5                   10                  15

Tyr Asn Val Tyr Arg Val Arg Ser Arg Tyr Asn Ser Asp Trp Gly Glu
            20                  25                  30

Thr Gly Thr Glu Gln Asp Glu Glu Asp Ser Asp Glu Asn Ser Tyr
        35                  40                  45

Tyr Gln Pro Asp Met Glu Tyr Ser Glu Ile Val Gly Leu Pro Glu Glu
    50                  55                  60

Glu Glu Ile Pro Ala Asn Arg Lys Ile Lys Phe Ser Xaa Ala Pro Ile
65                  70                  75                  80

Lys Val Phe Asn Thr Tyr Ser Asn Glu Asp Tyr Asp Arg Arg Asn Asp
                85                  90                  95

Glu Val Asp

<210> SEQ ID NO 107
<211> LENGTH: 100
<212> TYPE: PRT
<213> ORGANISM: artificial sequence

```
<220> FEATURE:
<223> OTHER INFORMATION: synthetic
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid

<400> SEQUENCE: 107

Met Glu Gln Asp Asn Ser Pro Gln Lys Ile Gln Phe Thr Val Pro Leu
1               5                   10                  15

Leu Glu Pro His Leu Asp Pro Glu Ala Ala Glu Gln Ile Arg Arg Arg
                20                  25                  30

Arg Pro Xaa Pro Ala Thr Leu Val Leu Thr Ser Asp Gln Ser Ser Pro
            35                  40                  45

Glu Ile Asp Glu Asp Arg Ile Pro Asn Pro His Leu Lys Ser Thr Leu
50                  55                  60

Ala Met Xaa Pro Arg Gln Arg Lys Lys Met Xaa Arg Ile Thr Pro Thr
65                  70                  75                  80

Met Lys Glu Leu Gln Met Met Val Glu His His Leu Gly Gln Gln Gln
                85                  90                  95

Gln Gly Glu Glu
            100

<210> SEQ ID NO 108
<211> LENGTH: 99
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid

<400> SEQUENCE: 108

Glu Gln Asp Asn Ser Pro Gln Lys Ile Gln Phe Thr Val Pro Leu Leu
1               5                   10                  15

Glu Pro His Leu Asp Pro Glu Ala Ala Glu Gln Ile Arg Arg Arg Arg
                20                  25                  30

Pro Xaa Pro Ala Thr Leu Val Leu Thr Ser Asp Gln Ser Ser Pro Glu
            35                  40                  45

Ile Asp Glu Asp Arg Ile Pro Asn Pro His Leu Lys Ser Thr Leu Ala
50                  55                  60

Met Xaa Pro Arg Gln Arg Lys Lys Met Xaa Arg Ile Thr Pro Thr Met
65                  70                  75                  80

Lys Glu Leu Gln Met Met Val Glu His His Leu Gly Gln Gln Gln Gln
                85                  90                  95

Gly Glu Glu
```

<210> SEQ ID NO 109
<211> LENGTH: 64
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (34)..(34)
<223> OTHER INFORMATION: Xaa can be any naturally occurring amino acid

<400> SEQUENCE: 109

Glu Gln Asp Asn Ser Pro Gln Lys Ile Gln Phe Thr Val Pro Leu Leu
1               5                   10                  15

Glu Pro His Leu Asp Pro Glu Ala Ala Glu Gln Ile Arg Arg Arg Arg
            20                  25                  30

Pro Xaa Pro Ala Thr Leu Val Leu Thr Ser Asp Gln Ser Ser Pro Glu
        35                  40                  45

Ile Asp Glu Asp Arg Ile Pro Asn Pro His Leu Lys Ser Thr Leu Ala
    50                  55                  60

<210> SEQ ID NO 110
<211> LENGTH: 352
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (72)..(72)
<223> OTHER INFORMATION: Xaa can be any naturally occurring amino acid

<400> SEQUENCE: 110

Ala Ala Ser Thr Ala Ser His Arg Pro Ile Lys Gly Ile Leu Lys Asn
1               5                   10                  15

Lys Thr Ser Thr Thr Ser Ser Met Val Ala Ser Ala Glu Gln Pro Arg
            20                  25                  30

Gly Asn Val Asp Glu Glu Leu Ser Lys Lys Ser Gln Lys Trp Asp Glu
        35                  40                  45

Met Asn Ile Leu Ala Thr Tyr His Pro Ala Asp Lys Asp Tyr Gly Leu
    50                  55                  60

Met Lys Ile Asp Glu Pro Ser Xaa Pro Tyr His Ser Met Met Gly Asp
65                  70                  75                  80

Asp Glu Asp Ala Cys Ser Asp Thr Glu Ala Thr Glu Ala Met Ala Pro
                85                  90                  95

Asp Ile Leu Ala Arg Lys Leu Ala Ala Ala Glu Gly Leu Glu Pro Lys
            100                 105                 110

Tyr Arg Ile Gln Glu Gln Glu Ser Ser Gly Glu Asp Ser Asp Leu
        115                 120                 125

Ser Pro Glu Glu Arg Glu Lys Lys Arg Gln Phe Glu Met Lys Arg Lys
    130                 135                 140

Leu His Tyr Asn Glu Ala Ala Ser Thr Ala Ser His Arg Pro Ile Lys
145                 150                 155                 160

Gly Ile Leu Lys Asn Lys Thr Ser Thr Thr Ser Ser Met Val Ala Ser
                165                 170                 175

Ala Glu Gln Pro Arg Gly Asn Val Asp Glu Glu Leu Ser Lys Lys Ser
            180                 185                 190

Gln Lys Trp Asp Glu Met Asn Ile Leu Ala Thr Tyr His Pro Ala Asp
        195                 200                 205

Lys Asp Tyr Leu Met Lys Ile Asp Glu Pro Ser Glu Pro Tyr His Ser

```
                210                 215                 220
Met Met Gly Asp Asp Glu Asp Ala Cys Ser Asp Thr Glu Ala Thr Glu
225                 230                 235                 240

Ala Met Ala Pro Asp Ile Leu Ala Arg Lys Leu Ala Ala Ala Glu Gly
                245                 250                 255

Leu Glu Pro Lys Tyr Arg Ile Gln Glu Gln Glu Ser Ser Gly Glu Glu
            260                 265                 270

Asp Ser Asp Leu Ser Pro Glu Glu Arg Glu Lys Lys Arg Gln Phe Glu
            275                 280                 285

Met Lys Arg Lys Leu His Tyr Asn Glu Gly Leu Asn Ile Lys Leu Ala
        290                 295                 300

Arg Gln Leu Ile Ser Lys Asp Leu His Asp Asp Glu Asp Glu Glu
305                 310                 315                 320

Met Leu Glu Thr Ala Asp Gly Glu Ser Met Asn Thr Glu Glu Ser Asn
                325                 330                 335

Gln Gly Ser Thr Pro Ser Asp Gln Gln Asn Lys Leu Arg Ser Ser
            340                 345                 350

<210> SEQ ID NO 111
<211> LENGTH: 100
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid

<400> SEQUENCE: 111

Gln Thr Leu Pro Ser Ala Val Lys Gly Asp Glu Lys Met Gly Gly Glu
1               5                   10                  15

Asp Asp Glu Leu Lys Gly Leu Leu Gly Leu Pro Glu Glu Glu Xaa Glu
                20                  25                  30

Leu Asp Asn Leu Thr Glu Phe Asn Thr Ala His Asn Lys Arg Ile Xaa
            35                  40                  45

Thr Leu Thr Ile Glu Glu Gly Asn Leu Asp Ile Gln Arg Pro Lys Arg
    50                  55                  60

Lys Arg Lys Asn Xaa Arg Val Thr Phe Xaa Glu Asp Asp Glu Ile Ile
65                  70                  75                  80

Asn Pro Glu Asp Val Asp Pro Ser Val Gly Arg Phe Arg Asn Met Val
                85                  90                  95

Gln Thr Ala Val
            100

<210> SEQ ID NO 112
<211> LENGTH: 52
<212> TYPE: PRT
<213> ORGANISM: Homo sapiens

<400> SEQUENCE: 112
```

```
Met Glu Lys Val Gln Tyr Leu Thr Arg Ser Ala Ile Arg Arg Ala Ser
1               5                   10                  15

Thr Ile Glu Met Pro Gln Gln Ala Arg Gln Lys Leu Gln Asn Leu Phe
            20                  25                  30

Ile Asn Phe Cys Leu Ile Leu Ile Cys Leu Leu Leu Ile Cys Ile Ile
        35                  40                  45

Val Met Leu Leu
    50
```

```
<210> SEQ ID NO 113
<211> LENGTH: 66
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid

<400> SEQUENCE: 113
```

```
Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Phe Cys Leu Ile Leu Ile Cys Leu Leu Leu Ile Cys Ile Ile
        35                  40                  45

Val Met Leu Leu Pro Pro Ile Asn His Ile Asx Ile Thr Arg Ser Phe
    50                  55                  60

Leu Leu
65
```

```
<210> SEQ ID NO 114
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid

<400> SEQUENCE: 114
```

```
Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Phe Cys Leu Ile Leu Ile Cys Leu Leu Leu Ile Cys Ile Ile
        35                  40                  45

Val Met Leu Xaa
    50
```

```
<210> SEQ ID NO 115
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (51)..(51)
```

<223> OTHER INFORMATION: Xaa can be any naturally occurring amino acid

<400> SEQUENCE: 115

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Phe Cys Leu Ile Leu Ile Cys Leu Leu Leu Ile Cys Ile Ile
        35                  40                  45

Val Met Xaa Leu
    50

<210> SEQ ID NO 116
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid

<400> SEQUENCE: 116

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Phe Cys Leu Ile Leu Ile Cys Leu Leu Leu Ile Cys Ile Ile
        35                  40                  45

Val Xaa Leu Leu
    50

<210> SEQ ID NO 117
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid

<400> SEQUENCE: 117

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Phe Cys Leu Ile Leu Ile Cys Leu Leu Leu Ile Cys Ile Ile
        35                  40                  45

Xaa Met Leu Leu
    50

<210> SEQ ID NO 118
<211> LENGTH: 52
<212> TYPE: PRT
<213> ORGANISM: Homo sapiens
<220> FEATURE:
<221> NAME/KEY: misc_feature
<222> LOCATION: (16)..(17)

```
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid

<400> SEQUENCE: 118

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Phe Cys Leu Ile Leu Ile Cys Leu Leu Leu Ile Cys Ile Xaa
        35                  40                  45

Val Met Leu Leu
    50

<210> SEQ ID NO 119
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid

<400> SEQUENCE: 119

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Phe Cys Leu Ile Leu Ile Cys Leu Leu Leu Ile Cys Xaa Ile
        35                  40                  45

Val Met Leu Leu
    50

<210> SEQ ID NO 120
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid

<400> SEQUENCE: 120

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Phe Cys Leu Ile Leu Ile Cys Leu Leu Leu Ile Xaa Ile Ile
        35                  40                  45

Val Met Leu Leu
    50

<210> SEQ ID NO 121
<211> LENGTH: 52
<212> TYPE: PRT
```

<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid

<400> SEQUENCE: 121

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Phe Cys Leu Ile Leu Ile Cys Leu Leu Leu Xaa Cys Ile Ile
        35                  40                  45

Val Met Leu Leu
    50

<210> SEQ ID NO 122
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid

<400> SEQUENCE: 122

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Phe Cys Leu Ile Leu Ile Cys Leu Leu Xaa Ile Cys Ile Ile
        35                  40                  45

Val Met Leu Leu
    50

<210> SEQ ID NO 123
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid

<400> SEQUENCE: 123

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Phe Cys Leu Ile Leu Ile Cys Leu Xaa Leu Ile Cys Ile Ile
        35                  40                  45

Val Met Leu Leu
    50

```
<210> SEQ ID NO 124
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid

<400> SEQUENCE: 124

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Phe Cys Leu Ile Leu Ile Cys Xaa Leu Leu Ile Cys Ile Ile
        35                  40                  45

Val Met Leu Leu
    50

<210> SEQ ID NO 125
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid

<400> SEQUENCE: 125

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Phe Cys Leu Ile Leu Ile Xaa Leu Leu Leu Ile Cys Ile Ile
        35                  40                  45

Val Met Leu Leu
    50

<210> SEQ ID NO 126
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid

<400> SEQUENCE: 126

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Phe Cys Leu Ile Leu Xaa Cys Leu Leu Leu Ile Cys Ile Ile
        35                  40                  45
```

Val Met Leu Leu
    50

<210> SEQ ID NO 127
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid

<400> SEQUENCE: 127

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Phe Cys Leu Ile Xaa Ile Cys Leu Leu Leu Ile Cys Ile Ile
        35                  40                  45

Val Met Leu Leu
    50

<210> SEQ ID NO 128
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid

<400> SEQUENCE: 128

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Phe Cys Leu Xaa Leu Ile Cys Leu Leu Leu Ile Cys Ile Ile
        35                  40                  45

Val Met Leu Leu
    50

<210> SEQ ID NO 129
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid

<400> SEQUENCE: 129

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe

-continued

```
                20                  25                  30

Ile Asn Phe Cys Xaa Ile Leu Ile Cys Leu Leu Leu Ile Cys Ile Ile
        35                  40                  45

Val Met Leu Leu
        50

<210> SEQ ID NO 130
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid

<400> SEQUENCE: 130

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Phe Xaa Leu Ile Leu Ile Cys Leu Leu Leu Ile Cys Ile Ile
        35                  40                  45

Val Met Leu Leu
        50

<210> SEQ ID NO 131
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid

<400> SEQUENCE: 131

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Asn Xaa Cys Leu Ile Leu Ile Cys Leu Leu Leu Ile Cys Ile Ile
        35                  40                  45

Val Met Leu Leu
        50

<210> SEQ ID NO 132
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid

<400> SEQUENCE: 132
```

-continued

```
Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Ile Xaa Phe Cys Leu Ile Leu Ile Cys Leu Leu Leu Ile Cys Ile Ile
        35                  40                  45

Val Met Leu Leu
        50

<210> SEQ ID NO 133
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid

<400> SEQUENCE: 133

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Phe
            20                  25                  30

Xaa Asn Phe Cys Leu Ile Leu Ile Cys Leu Leu Leu Ile Cys Ile Ile
        35                  40                  45

Val Met Leu Leu
        50

<210> SEQ ID NO 134
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 134

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Leu Xaa
            20                  25                  30

Ile Asn Phe Cys Leu Ile Leu Ile Cys Leu Leu Leu Ile Cys Ile Ile
        35                  40                  45

Val Met Leu Leu
        50

<210> SEQ ID NO 135
<211> LENGTH: 52
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (31)..(31)
```

<223> OTHER INFORMATION: Xaa can be any naturally occurring amino acid

<400> SEQUENCE: 135

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Xaa Phe
            20                  25                  30

Ile Asn Phe Cys Leu Ile Leu Ile Cys Leu Leu Leu Ile Cys Ile Ile
        35                  40                  45

Val Met Leu Leu
    50

<210> SEQ ID NO 136
<211> LENGTH: 69
<212> TYPE: PRT
<213> ORGANISM: Homo sapiens
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid

<400> SEQUENCE: 136

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn Xaa Phe
            20                  25                  30

Ile Xaa Phe Cys Leu Ile Leu Ile Cys Leu Leu Leu Ile Cys Ile Ile
        35                  40                  45

Val Met Leu Leu Pro Pro Ile Asn His Ile Asx Ile Thr Arg Ser Met
    50                  55                  60

Asn Met Glu Arg Ser
65

<210> SEQ ID NO 137
<211> LENGTH: 30
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(16)
<223> OTHER INFORMATION: Xaa can be any naturally occurring amino acid

<400> SEQUENCE: 137

Met Glu Lys Val Gln Tyr Leu Thr Arg Ser Ala Ile Arg Arg Ala Xaa
1               5                   10                  15

Thr Ile Glu Met Pro Gln Gln Ala Arg Gln Lys Leu Gln Asn
            20                  25                  30

<210> SEQ ID NO 138
<211> LENGTH: 30
<212> TYPE: PRT
<213> ORGANISM: artificial sequence
<220> FEATURE:
<223> OTHER INFORMATION: synthetic
<220> FEATURE:
<221> NAME/KEY: misc_feature

```
<222> LOCATION: (17)..(17)
<223> OTHER INFORMATION: Xaa can be any naturally occurring amino acid

<400> SEQUENCE: 138

Met Glu Lys Val Gln Tyr Leu Thr Arg Ser Ala Ile Arg Arg Ala Ser
1               5                   10                  15

Xaa Ile Glu Met Pro Gln Gln Ala Arg Gln Lys Leu Gln Asn
            20                  25                  30

<210> SEQ ID NO 139
<211> LENGTH: 30
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(17)
<223> OTHER INFORMATION: Xaa can be any naturally occurring amino acid

<400> SEQUENCE: 139

Met Glu Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn
            20                  25                  30

<210> SEQ ID NO 140
<211> LENGTH: 30
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(17)
<223> OTHER INFORMATION: Xaa can be any naturally occurring amino acid

<400> SEQUENCE: 140

Met Asp Lys Val Gln Tyr Leu Thr Arg Ser Ala Ile Arg Arg Ala Xaa
1               5                   10                  15

Xaa Ile Glu Met Pro Gln Gln Ala Arg Gln Lys Leu Gln Asn
            20                  25                  30

<210> SEQ ID NO 141
<211> LENGTH: 30
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(17)
<223> OTHER INFORMATION: Xaa can be any naturally occurring amino acid

<400> SEQUENCE: 141

Met Glu Lys Val Gln Tyr Ile Thr Arg Ser Ala Ile Arg Arg Ala Xaa
1               5                   10                  15

Xaa Ile Glu Met Pro Gln Gln Ala Arg Gln Lys Leu Gln Asn
            20                  25                  30

<210> SEQ ID NO 142
<211> LENGTH: 30
<212> TYPE: PRT
<213> ORGANISM: artificial sequence
<220> FEATURE:
<223> OTHER INFORMATION: synthetic
<220> FEATURE:
<221> NAME/KEY: misc_feature
```

```
<222> LOCATION: (16)..(17)
<223> OTHER INFORMATION: Xaa can be any naturally occurring amino acid

<400> SEQUENCE: 142

Met Glu Lys Val Gln Tyr Leu Thr Arg Ser Ala Leu Arg Arg Ala Xaa
1               5                   10                  15

Xaa Ile Glu Met Pro Gln Gln Ala Arg Gln Lys Leu Gln Asn
            20                  25                  30

<210> SEQ ID NO 143
<211> LENGTH: 20
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(16)
<223> OTHER INFORMATION: Xaa can be any naturally occurring amino acid

<400> SEQUENCE: 143

Met Glu Lys Val Gln Tyr Leu Thr Arg Ser Ala Ile Arg Arg Ala Xaa
1               5                   10                  15

Thr Ile Glu Met
            20

<210> SEQ ID NO 144
<211> LENGTH: 20
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (17)..(17)
<223> OTHER INFORMATION: Xaa can be any naturally occurring amino acid

<400> SEQUENCE: 144

Met Glu Lys Val Gln Tyr Leu Thr Arg Ser Ala Ile Arg Arg Ala Ser
1               5                   10                  15

Xaa Ile Glu Met
            20

<210> SEQ ID NO 145
<211> LENGTH: 20
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(17)
<223> OTHER INFORMATION: Xaa can be any naturally occurring amino acid

<400> SEQUENCE: 145

Met Glu Lys Val Gln Tyr Leu Thr Arg Ser Ala Ile Arg Arg Ala Xaa
1               5                   10                  15

Xaa Ile Glu Met
            20

<210> SEQ ID NO 146
<211> LENGTH: 20
<212> TYPE: PRT
<213> ORGANISM: artificial sequence
<220> FEATURE:
<223> OTHER INFORMATION: synthetic
<220> FEATURE:
<221> NAME/KEY: misc_feature
```

```
<222> LOCATION: (16)..(17)
<223> OTHER INFORMATION: Xaa can be any naturally occurring amino acid

<400> SEQUENCE: 146

Met Asp Lys Val Gln Tyr Leu Thr Arg Ser Ala Ile Arg Arg Ala Xaa
1               5                   10                  15

Xaa Ile Glu Met
            20

<210> SEQ ID NO 147
<211> LENGTH: 20
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(17)
<223> OTHER INFORMATION: Xaa can be any naturally occurring amino acid

<400> SEQUENCE: 147

Met Glu Lys Val Gln Tyr Ile Thr Arg Ser Ala Ile Arg Arg Ala Xaa
1               5                   10                  15

Xaa Ile Glu Met
            20

<210> SEQ ID NO 148
<211> LENGTH: 20
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(17)
<223> OTHER INFORMATION: Xaa can be any naturally occurring amino acid

<400> SEQUENCE: 148

Met Glu Lys Val Gln Tyr Leu Thr Arg Ser Ala Leu Arg Arg Ala Xaa
1               5                   10                  15

Xaa Ile Glu Met
            20

<210> SEQ ID NO 149
<211> LENGTH: 20
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(17)
<223> OTHER INFORMATION: Xaa can be any naturally occurring amino acid

<400> SEQUENCE: 149

Met Glu Lys Val Gln Tyr Leu Thr Arg Ser Gly Ile Arg Arg Ala Xaa
1               5                   10                  15

Xaa Ile Glu Met
            20

<210> SEQ ID NO 150
<211> LENGTH: 20
<212> TYPE: PRT
<213> ORGANISM: artificial sequence
<220> FEATURE:
<223> OTHER INFORMATION: synthetic
<220> FEATURE:
<221> NAME/KEY: misc_feature
```

```
<222> LOCATION: (16)..(17)
<223> OTHER INFORMATION: Xaa can be any naturally occurring amino acid

<400> SEQUENCE: 150

Met Asp Lys Val Gln Tyr Leu Thr Arg Ser Gly Ile Arg Arg Ala Xaa
1               5                   10                  15

Xaa Ile Glu Met
            20

<210> SEQ ID NO 151
<211> LENGTH: 20
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(17)
<223> OTHER INFORMATION: Xaa can be any naturally occurring amino acid

<400> SEQUENCE: 151

Met Glu Lys Val Gln Tyr Ile Thr Arg Ser Gly Ile Arg Arg Ala Xaa
1               5                   10                  15

Xaa Ile Glu Met
            20

<210> SEQ ID NO 152
<211> LENGTH: 19
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(17)
<223> OTHER INFORMATION: Xaa can be any naturally occurring amino acid

<400> SEQUENCE: 152

Met Glu Lys Val Gln Tyr Leu Thr Arg Ser Ala Ile Arg Arg Ala Xaa
1               5                   10                  15

Xaa Ile Glu

<210> SEQ ID NO 153
<211> LENGTH: 19
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(17)
<223> OTHER INFORMATION: Xaa can be any naturally occurring amino acid

<400> SEQUENCE: 153

Met Asp Lys Val Gln Tyr Leu Thr Arg Ser Ala Ile Arg Arg Ala Xaa
1               5                   10                  15

Xaa Ile Glu

<210> SEQ ID NO 154
<211> LENGTH: 19
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(17)
<223> OTHER INFORMATION: Xaa can be any naturally occurring amino acid
```

```
<400> SEQUENCE: 154

Met Glu Lys Val Gln Tyr Ile Thr Arg Ser Ala Ile Arg Arg Ala Xaa
1               5                   10                  15

Xaa Ile Glu

<210> SEQ ID NO 155
<211> LENGTH: 19
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(17)
<223> OTHER INFORMATION: Xaa can be any naturally occurring amino acid

<400> SEQUENCE: 155

Met Glu Lys Val Gln Tyr Leu Thr Arg Ser Ala Leu Arg Arg Ala Xaa
1               5                   10                  15

Xaa Ile Glu

<210> SEQ ID NO 156
<211> LENGTH: 19
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(17)
<223> OTHER INFORMATION: Xaa can be any naturally occurring amino acid

<400> SEQUENCE: 156

Met Glu Lys Val Gln Tyr Leu Thr Arg Ser Gly Ile Arg Arg Ala Xaa
1               5                   10                  15

Xaa Ile Glu

<210> SEQ ID NO 157
<211> LENGTH: 21
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(8)
<223> OTHER INFORMATION: Xaa can be any naturally occurring amino acid

<400> SEQUENCE: 157

Ser Ala Ile Arg Arg Ala Xaa Xaa Ile Glu Met Pro Gln Gln Ala Arg
1               5                   10                  15

Gln Lys Leu Gln Asn
            20

<210> SEQ ID NO 158
<211> LENGTH: 21
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(8)
<223> OTHER INFORMATION: Xaa can be any naturally occurring amino acid

<400> SEQUENCE: 158
```

```
Ser Gly Ile Arg Arg Ala Xaa Xaa Ile Glu Met Pro Gln Gln Ala Arg
1               5                   10                  15

Gln Lys Leu Gln Asn
            20

<210> SEQ ID NO 159
<211> LENGTH: 21
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(8)
<223> OTHER INFORMATION: Xaa can be any naturally occurring amino acid

<400> SEQUENCE: 159

Ser Ala Ile Arg Arg Ala Xaa Xaa Ile Glu Met Pro Gln Gln Gly Arg
1               5                   10                  15

Gln Lys Leu Gln Asn
            20

<210> SEQ ID NO 160
<211> LENGTH: 21
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(8)
<223> OTHER INFORMATION: Xaa can be any naturally occurring amino acid

<400> SEQUENCE: 160

Ser Ala Ile Arg Arg Ala Xaa Xaa Ile Glu Met Pro Gln Gln Ala Arg
1               5                   10                  15

Gln Lys Ile Gln Asn
            20

<210> SEQ ID NO 161
<211> LENGTH: 19
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (6)..(7)
<223> OTHER INFORMATION: Xaa can be any naturally occurring amino acid

<400> SEQUENCE: 161

Ala Ile Arg Arg Ala Xaa Xaa Ile Glu Met Pro Gln Gln Ala Arg Gln
1               5                   10                  15

Lys Leu Gln

<210> SEQ ID NO 162
<211> LENGTH: 19
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (6)..(7)
<223> OTHER INFORMATION: Xaa can be any naturally occurring amino acid

<400> SEQUENCE: 162

Gly Ile Arg Arg Ala Xaa Xaa Ile Glu Met Pro Gln Gln Ala Arg Gln
```

Lys Leu Gln

<210> SEQ ID NO 163
<211> LENGTH: 19
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (6)..(7)
<223> OTHER INFORMATION: Xaa can be any naturally occurring amino acid

<400> SEQUENCE: 163

Ala Ile Arg Arg Ala Xaa Xaa Ile Glu Met Pro Gln Gln Gly Arg Gln
1               5                   10                  15

Lys Leu Gln

<210> SEQ ID NO 164
<211> LENGTH: 19
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (6)..(7)
<223> OTHER INFORMATION: Xaa can be any naturally occurring amino acid

<400> SEQUENCE: 164

Ala Ile Arg Arg Ala Xaa Xaa Ile Glu Met Pro Gln Gln Ala Arg Gln
1               5                   10                  15

Lys Ile Gln

<210> SEQ ID NO 165
<211> LENGTH: 86
<212> TYPE: PRT
<213> ORGANISM: artificial sequence
<220> FEATURE:
<223> OTHER INFORMATION: synthetic

<400> SEQUENCE: 165

Met Glu Lys Val Gln Tyr Leu Thr Arg Ser Ala Ile Arg Arg Ala Glu
1               5                   10                  15

Asp Ile Glu Met Pro Gln Gln Ala Arg Gln Lys Leu Gln Asn Gly Gly
            20                  25                  30

Gly Gly Met Glu Lys Val Gln Tyr Leu Thr Arg Ser Ala Ile Arg Arg
        35                  40                  45

Ala Asp Glu Ile Glu Met Pro Gln Gln Ala Arg Gln Lys Leu Gln Asn
    50                  55                  60

Ala Phe Ile Ala Phe Cys Leu Ile Leu Ile Cys Leu Leu Ile Cys
65                  70                  75                  80

Ile Ile Val Met Leu Leu
                85

<210> SEQ ID NO 166
<211> LENGTH: 258
<212> TYPE: DNA
<213> ORGANISM: artificial sequence
<220> FEATURE:
<223> OTHER INFORMATION: synthetic

<400> SEQUENCE: 166

```
atggagaagg tgcagtacct gaccaggagc gccatcagga gggccgagga catcgagatg    60
ccccagcagg ccaggcagaa gctccagaac ggcggcggcg gcatggagaa ggtgcagtac   120
ctgaccagga gcgccatcag gagggccgac gagatcgaga tgccccagca ggccaggcag   180
aagctccaga acgccttcat cgccttctgc ctgatcctga tctgcctgct gctgatctgc   240
atcatcgtga tgctgctg                                                 258
```

<210> SEQ ID NO 167
<211> LENGTH: 292
<212> TYPE: DNA
<213> ORGANISM: artificial sequence
<220> FEATURE:
<223> OTHER INFORMATION: synthetic

<400> SEQUENCE: 167

```
gctagcgccg gcatggagaa ggtgcagtac ctgaccagga gcgccatcag gagggccgag    60
gacatcgaga tgccccagca ggccaggcag aagctccaga acggcggcgg cggcatggag   120
aaggtgcagt acctgaccag gagcgccatc aggagggccg acgagatcga gatgccccag   180
caggccaggc agaagctcca gaacgccttc atcgccttct gcctgatcct gatctgcctg   240
ctgctgatct gcatcatcgt gatgctgctg cccggggag gcggaatcga tt            292
```

<210> SEQ ID NO 168
<211> LENGTH: 301
<212> TYPE: DNA
<213> ORGANISM: artificial sequence
<220> FEATURE:
<223> OTHER INFORMATION: synthetic

<400> SEQUENCE: 168

```
gctagcgcca ccatggccgg catggagaag gtgcagtacc tgaccaggag cgccatcagg    60
agggccgagg acatcgagat gccccagcag gccaggcaga agctccagaa cggcggcggc   120
ggcatggaga aggtgcagta cctgaccagg agcgccatca ggagggccga cgagatcgag   180
atgccccagc aggccaggca gaagctccag aacgccttca tcgccttctg cctgatcctg   240
atctgcctgc tgctgatctg catcatcgtg atgctgctgc cggggggagg cggaatcgat   300
t                                                                   301
```

<210> SEQ ID NO 169
<211> LENGTH: 75
<212> TYPE: PRT
<213> ORGANISM: artificial sequence
<220> FEATURE:
<223> OTHER INFORMATION: synthetic

<400> SEQUENCE: 169

Met Glu Lys Val Gln Tyr Leu Thr Arg Ser Ala Ile Arg Arg Ala Asp
1               5                   10                  15

Glu Ile Glu Gly Gly Gly Gly Met Glu Lys Val Gln Tyr Leu Thr Arg
            20                  25                  30

Ser Ala Ile Arg Arg Ala Asp Glu Ile Glu Met Pro Gln Gln Ala Arg
        35                  40                  45

Gln Lys Leu Gln Asn Ala Phe Ile Ala Phe Cys Leu Ile Leu Ile Cys
    50                  55                  60

Leu Leu Leu Ile Cys Ile Ile Val Met Leu Leu
65                  70                  75

<210> SEQ ID NO 170
<211> LENGTH: 225

```
<212> TYPE: DNA
<213> ORGANISM: artificial sequence
<220> FEATURE:
<223> OTHER INFORMATION: synthetic

<400> SEQUENCE: 170
atggagaagg tgcagtacct gaccaggagc gccatcagga gggccgacga gatcgagggc      60
ggcggcggca tggagaaggt gcagtacctg accaggagcg ccatcaggag ggccgacgag     120
atcgagatgc cccagcaggc caggcagaag ctccagaacg ccttcatcgc cttctgcctg     180
atcctgatct gcctgctgct gatctgcatc atcgtgatgc tgctg                     225

<210> SEQ ID NO 171
<211> LENGTH: 259
<212> TYPE: DNA
<213> ORGANISM: artificial sequence
<220> FEATURE:
<223> OTHER INFORMATION: synthetic

<400> SEQUENCE: 171
gctagcgccg gcatggagaa ggtgcagtac ctgaccagga gcgccatcag gagggccgac      60
gagatcgagg gcggcggcgg catggagaag gtgcagtacc tgaccaggag cgccatcagg     120
agggccgacg agatcgagat gccccagcag gccaggcaga agctccagaa cgccttcatc     180
gccttctgcc tgatcctgat ctgcctgctg ctgatctgca tcatcgtgat gctgctgccc     240
gggggaggcg gaatcgatt                                                  259

<210> SEQ ID NO 172
<211> LENGTH: 268
<212> TYPE: DNA
<213> ORGANISM: artificial sequence
<220> FEATURE:
<223> OTHER INFORMATION: synthetic

<400> SEQUENCE: 172
gctagcgcca ccatggccgg catggagaag gtgcagtacc tgaccaggag cgccatcagg      60
agggccgacg agatcgaggg cggcggcggc atggagaagg tgcagtacct gaccaggagc     120
gccatcagga gggccgacga gatcgagatg ccccagcagg ccaggcagaa gctccagaac     180
gccttcatcg ccttctgcct gatcctgatc tgcctgctgc tgatctgcat catcgtgatg     240
ctgctgcccg ggggaggcgg aatcgatt                                        268

<210> SEQ ID NO 173
<211> LENGTH: 91
<212> TYPE: PRT
<213> ORGANISM: artificial sequence
<220> FEATURE:
<223> OTHER INFORMATION: synthetic

<400> SEQUENCE: 173

Met Glu Lys Val Gln Tyr Leu Thr Arg Ser Ala Ile Arg Arg Ala Asp
 1               5                  10                  15

Glu Ile Glu Met Gly Gly Gly Gly Ser Ala Ile Arg Arg Ala Asp Glu
            20                  25                  30

Ile Glu Met Pro Gln Gln Ala Arg Gln Lys Leu Gln Asn Gly Gly Gly
        35                  40                  45

Gly Ala Ile Arg Arg Ala Glu Asp Ile Glu Met Pro Gln Gln Ala Arg
    50                  55                  60

Gln Lys Leu Gln Gly Gly Gly Gly Ala Ile Arg Arg Ala Asp Glu Ile
65                  70                  75                  80
```

Glu Met Pro Gln Gln Ala Arg Gln Lys Ile Gln
            85                  90

<210> SEQ ID NO 174
<211> LENGTH: 273
<212> TYPE: DNA
<213> ORGANISM: artificial sequence
<220> FEATURE:
<223> OTHER INFORMATION: synthetic

<400> SEQUENCE: 174
atggagaagg tgcagtacct gaccaggagc gccatcagga gggccgacga gatcgagatg    60
ggcggcggcg gcagcgccat caggagggcc gacgagatcg agatgcccca gcaggccagg   120
cagaagctcc agaacggcgg cggcggcgcc atcaggaggg ccgaggacat cgagatgccc   180
cagcaggcca ggcagaagct ccagggcggc ggcggcgcca tcaggagggc cgacgagatc   240
gagatgcccc agcaggccag gcagaagatc cag                                273

<210> SEQ ID NO 175
<211> LENGTH: 307
<212> TYPE: DNA
<213> ORGANISM: artificial sequence
<220> FEATURE:
<223> OTHER INFORMATION: synthetic

<400> SEQUENCE: 175
gctagcgccg gcatggagaa ggtgcagtac ctgaccagga gcgccatcag gagggccgac    60
gagatcgaga tgggcggcgg cggcagcgcc atcaggaggg ccgacgagat cgagatgccc   120
cagcaggcca ggcagaagct ccagaacggc ggcggcggcg ccatcaggag ggccgaggac   180
atcgagatgc cccagcaggc caggcagaag ctccagggcg gcggcggcgc catcaggagg   240
gccgacgaga tcgagatgcc ccagcaggcc aggcagaaga tccagcccgg gggaggcgga   300
atcgatt                                                             307

<210> SEQ ID NO 176
<211> LENGTH: 316
<212> TYPE: DNA
<213> ORGANISM: artificial sequence
<220> FEATURE:
<223> OTHER INFORMATION: synthetic

<400> SEQUENCE: 176
gctagcgcca ccatggccgg catggagaag gtgcagtacc tgaccaggag cgccatcagg    60
agggccgacg agatcgagat gggcggcggc ggcagcgcca tcaggagggc cgacgagatc   120
gagatgcccc agcaggccag gcagaagctc cagaacggcg gcggcggcgc catcaggagg   180
gccgaggaca tcgagatgcc ccagcaggcc aggcagaagc tccagggcgg cggcggcgcc   240
atcaggaggg ccgacgagat cgagatgccc cagcaggcca ggcagaagat ccagcccggg   300
ggaggcggaa tcgatt                                                   316

<210> SEQ ID NO 177
<211> LENGTH: 73
<212> TYPE: PRT
<213> ORGANISM: artificial sequence
<220> FEATURE:
<223> OTHER INFORMATION: synthetic

<400> SEQUENCE: 177

Gly Leu Ile Thr Pro Asn Lys His Gly Leu Leu Gln Asn Pro Tyr Arg
1               5                   10                  15

```
Ile Pro Pro Leu Phe Pro Ile Lys Asp Phe Val Lys Thr Lys Cys Lys
         20                  25                  30

Lys Asn Leu Leu Glu Glu Asn Phe Glu Glu His Ala Val Leu Leu Pro
             35                  40                  45

Lys Lys Thr Ser Ala Thr Val Gly Pro Lys Ala Pro Ser Gly Gly Lys
 50                      55                  60

Lys Ala Thr Gln Ala Asp Gln Glu Tyr
 65                  70
```

<210> SEQ ID NO 178
<211> LENGTH: 219
<212> TYPE: DNA
<213> ORGANISM: artificial sequence
<220> FEATURE:
<223> OTHER INFORMATION: synthetic

<400> SEQUENCE: 178

```
ggcctgatca cccccaacaa gcacggcctc ctgcagaacc cctacaggat tccccccctg      60
ttccccatca aggacttcgt gaagaccaag tgcaagaaga acctcctgga ggagaacttc     120
gaggagcacg ccgtcctgct gcccaagaag accagcgcca ccgtgggccc caaggccccc     180
agcggcggca agaaggccac ccaagccgac caggagtac                            219
```

<210> SEQ ID NO 179
<211> LENGTH: 253
<212> TYPE: DNA
<213> ORGANISM: artificial sequence
<220> FEATURE:
<223> OTHER INFORMATION: synthetic

<400> SEQUENCE: 179

```
gctagcgccg gcggcctgat cacccccaac aagcacggcc tcctgcagaa cccctacagg      60 attcccccc tgttccccat caaggacttc gtgaagacca agtgcaagaa gaacctcctg     120
gaggagaact cgaggagca cgccgtcctg ctgcccaaga gaccagcgc accgtgggc      180 cccaaggccc cagcggcgg caagaaggcc acccaagccg accaggagta ccccggggga     240
ggcggaatcg att                                                       253
```

<210> SEQ ID NO 180
<211> LENGTH: 262
<212> TYPE: DNA
<213> ORGANISM: artificial sequence
<220> FEATURE:
<223> OTHER INFORMATION: synthetic

<400> SEQUENCE: 180

```
gctagcgcca ccatggccgg cggcctgatc acccccaaca agcacggcct cctgcagaac      60
ccctacagga ttcccccct gttccccatc aaggacttcg tgaagaccaa gtgcaagaag     120
aacctcctgg aggagaactt cgaggagcac gccgtcctgc tgcccaagaa gaccagcgcc     180
accgtgggcc ccaaggcccc cagcggcggc aagaaggccc ccaagccga ccaggagtac     240 cccgggggag gcggaatcga tt                                             262
```

<210> SEQ ID NO 181
<211> LENGTH: 74
<212> TYPE: PRT
<213> ORGANISM: artificial sequence
<220> FEATURE:
<223> OTHER INFORMATION: synthetic

<400> SEQUENCE: 181

```
Ala Val Glu Ile Arg Ser Arg His Ser Glu Tyr Pro Ala Gly Thr Glu
1               5                   10                  15

Asp Asp Glu Gly Met Gly Glu Glu Pro Ser Pro Phe Arg Gly Arg Ser
            20                  25                  30

Arg Glu Ala Pro Pro Asn Leu Trp Ala Ala Gln Arg Ala Val Leu Leu
        35                  40                  45

Pro Lys Lys Thr Ser Ala Thr Val Gly Pro Lys Ala Pro Ser Gly Gly
    50                  55                  60

Lys Lys Ala Thr Gln Ala Asp Gln Glu Tyr
65                  70
```

<210> SEQ ID NO 182
<211> LENGTH: 222
<212> TYPE: DNA
<213> ORGANISM: artificial sequence
<220> FEATURE:
<223> OTHER INFORMATION: synthetic

<400> SEQUENCE: 182

```
gccgtggaga tcaggagcag gcacagcgag taccccgccg gaaccgagga cgacgagggc      60
atgggcgagg agcccagccc cttcaggggc aggagcaggg aggcccccccc caacctgtgg    120
gccgcccaga gagccgtgct gctgcccaag aagaccagcg ccaccgtggg ccccaaggcc    180
cccagcggcg gcaagaaggc cacccaagcc gaccaggagt ac                       222
```

<210> SEQ ID NO 183
<211> LENGTH: 256
<212> TYPE: DNA
<213> ORGANISM: artificial sequence
<220> FEATURE:
<223> OTHER INFORMATION: synthetic

<400> SEQUENCE: 183

```
gctagcgccg cgccgtggag atcaggagca ggcacagcg agtaccccgc cggaaccgag       60
gacgacgagg gcatgggcga ggagcccagc cccttcaggg gcaggagcag ggaggccccc    120
cccaacctgt gggccgccca gagagccgtg ctgctgccca agaagaccag cgccaccgtg    180
ggccccaagg cccccagcgg cggcaagaag gccacccaag ccgaccagga gtaccccggg    240
ggaggcggaa tcgatt                                                    256
```

<210> SEQ ID NO 184
<211> LENGTH: 265
<212> TYPE: DNA
<213> ORGANISM: artificial sequence
<220> FEATURE:
<223> OTHER INFORMATION: synthetic

<400> SEQUENCE: 184

```
gctagcgcca ccatggccgg cgccgtggag atcaggagca ggcacagcga gtaccccgcc      60
ggaaccgagg acgacgaggg catgggcgag gagcccagcc ccttcagggg caggagcagg    120
gaggcccccc ccaacctgtg ggccgcccag agagccgtgc tgctgcccaa gaagaccagc    180
gccaccgtgg gccccaaggc ccccagcggc ggcaagaagg cacccaagc cgaccaggag    240
taccccgggg gaggcggaat cgatt                                          265
```

<210> SEQ ID NO 185
<211> LENGTH: 71
<212> TYPE: PRT
<213> ORGANISM: artificial sequence
<220> FEATURE:
<223> OTHER INFORMATION: synthetic

<400> SEQUENCE: 185

| | | | | | | | | | | | | |
|---|---|---|---|---|---|---|---|---|---|---|---|---|
|Glu|Ser|Glu|Arg|Ser|Val|Asp|Pro|Glu|Leu|Asp|Glu|Arg|Ala|Gly|
|1| | | |5| | | | |10| | | | |15|

Ser Pro Gln Leu Asp Asp Ile Arg Val Phe Gln Asn Gly Val Leu Gly
            20                  25                  30

Val Gln Lys Thr Ala Met Asn Trp Arg Leu Ser Ala Arg Asn Ala Ala
        35                  40                  45

Arg Arg Asp Glu Val Leu Ala Ala Ser Arg Asp Tyr Arg Asn Ile Ile
    50                  55                  60

Glu Arg Leu Gln Asp Ile Val
65                  70

<210> SEQ ID NO 186
<211> LENGTH: 213
<212> TYPE: DNA
<213> ORGANISM: artificial sequence
<220> FEATURE:
<223> OTHER INFORMATION: synthetic

<400> SEQUENCE: 186

```
gagagcgaga ggagcgtgga ccccgaggag ctggacgaga gggccggaag cccccagctg    60
gacgacatca gggtgttcca gaacgaggtg ctgggcgtgc agaagaccgc catgaactgg   120
aggctgtccg ccaggaacgc cgccaggagg gacgaggtgc tggccgccag cagggactac   180
aggaacatca tcgagaggct gcaggacatc gtg                               213
```

<210> SEQ ID NO 187
<211> LENGTH: 247
<212> TYPE: DNA
<213> ORGANISM: artificial sequence
<220> FEATURE:
<223> OTHER INFORMATION: synthetic

<400> SEQUENCE: 187

```
gctagcgccg cgagagcga gaggagcgtg accccgagg agctggacga gagggccgga     60
agcccccagc tggacgacat cagggtgttc agaacgagg tgctgggcgt gcagaagacc   120
gccatgaact ggaggctgtc cgccaggaac gccgccagga gggacgaggt gctggccgcc   180
agcagggact acaggaacat catcgagagg ctgcaggaca tcgtgcccgg gggaggcgga   240
atcgatt                                                            247
```

<210> SEQ ID NO 188
<211> LENGTH: 256
<212> TYPE: DNA
<213> ORGANISM: artificial sequence
<220> FEATURE:
<223> OTHER INFORMATION: synthetic

<400> SEQUENCE: 188

```
gctagcgcca ccatggccgg cgagagcgag aggagcgtgg accccgagga gctggacgag    60
agggccggaa gcccccagct ggacgacatc agggtgttcc agaacgaggt gctgggcgtg   120
cagaagaccg ccatgaactg gaggctgtcc gccaggaacg ccgccaggag ggacgaggtg   180
ctggccgcca gcagggacta caggaacatc atcgagaggc tgcaggacat cgtgcccggg   240
ggaggcggaa tcgatt                                                   256
```

<210> SEQ ID NO 189
<211> LENGTH: 74
<212> TYPE: PRT

<213> ORGANISM: artificial sequence
<220> FEATURE:
<223> OTHER INFORMATION: synthetic

<400> SEQUENCE: 189

```
Lys Ile Ala Asp Phe Gly Trp Ser Val His Ala Pro Ser Ser Arg Arg
1               5                   10                  15

Thr Asp Leu Cys Gly Thr Leu Asp Tyr Leu Pro Pro Glu Met Ile Glu
            20                  25                  30

Gly Arg Met His Asp Glu Lys Val Ala Lys Gln Lys Arg Asn Glu Gln
        35                  40                  45

Leu Lys Arg Trp Ile Gly Asp Glu Thr Asp Leu Glu Pro Pro Val Val
    50                  55                  60

Lys Arg Gln Lys Thr Lys Val Lys Phe Asp
65                  70
```

<210> SEQ ID NO 190
<211> LENGTH: 222
<212> TYPE: DNA
<213> ORGANISM: artificial sequence
<220> FEATURE:
<223> OTHER INFORMATION: synthetic

<400> SEQUENCE: 190

```
aagatcgccg acttcggctg gagcgtccac gcccccagca gcaggaggac cgacctgtgc      60
ggcaccctgg actacctccc ccccgagatg atcgagggca ggatgcacga cgagaaggtg     120
gccaagcaga aaaggaacga gcagctgaaa aggtggatcg gcgacgagac cgacctggag     180 cccccccgtgg tgaaaaggca agagaccaag gtgaagttcg ac                      222
```

<210> SEQ ID NO 191
<211> LENGTH: 256
<212> TYPE: DNA
<213> ORGANISM: artificial sequence
<220> FEATURE:
<223> OTHER INFORMATION: synthetic

<400> SEQUENCE: 191

```
gctagcgccg gcaagatcgc cgacttcggc tggagcgtcc acgcccccag cagcaggagg      60
accgacctgt gcggcaccct ggactacctc ccccccgaga tgatcgaggg caggatgcac     120
gacgagaagg tggccaagca gaaaaggaac gagcagctga aaaggtggat cggcgacgag     180
accgacctgg agcccccccgt ggtgaaaagg cagaagacca aggtgaagtt cgaccccggg     240
ggaggcggaa tcgatt                                                    256
```

<210> SEQ ID NO 192
<211> LENGTH: 265
<212> TYPE: DNA
<213> ORGANISM: artificial sequence
<220> FEATURE:
<223> OTHER INFORMATION: synthetic

<400> SEQUENCE: 192

```
gctagcgcca ccatggccgg caagatcgcc gacttcggct ggagcgtcca cgcccccagc      60
agcaggagga ccgacctgtg cggcaccctg gactacctcc ccccccgagat gatcgagggc     120 aggatgcacg acgagaaggt ggccaagcag aaaaggaacg agcagctgaa aaggtggatc     180
ggcgacgaga ccgacctgga gcccccccgtg gtgaaaaggc agaagaccaa ggtgaagttc     240
gaccccgggg gaggcggaat cgatt                                          265
```

```
<210> SEQ ID NO 193
<211> LENGTH: 116
<212> TYPE: PRT
<213> ORGANISM: artificial sequence
<220> FEATURE:
<223> OTHER INFORMATION: synthetic

<400> SEQUENCE: 193

Ile Gln Phe Thr Val Pro Leu Leu Glu Pro His Leu Asp Pro Glu Ala
1               5                   10                  15

Ala Glu Gln Ile Arg Arg Arg Pro Ala Pro Ala Thr Leu Val Leu
            20                  25                  30

Thr Ser Asp Gln Ser Ser Pro Glu Ile Asp Glu Asp Arg Ile Pro Asn
        35                  40                  45

Pro His Leu Gly Glu Thr Gly Thr Glu Gln Asp Glu Glu Asp Ser
    50                  55                  60

Asp Glu Asn Ser Tyr Tyr Gln Pro Asp Met Glu Tyr Ser Glu Ile Val
65                  70                  75                  80

Gly Leu Pro Glu Glu Glu Ile Pro Ala Asn Arg Lys Ile Lys Phe
                85                  90                  95

Ser Ala Ala Pro Ile Lys Val Phe Asn Thr Tyr Ser Asn Glu Asp Tyr
                100                 105                 110

Asp Arg Arg Asn
        115

<210> SEQ ID NO 194
<211> LENGTH: 348
<212> TYPE: DNA
<213> ORGANISM: artificial sequence
<220> FEATURE:
<223> OTHER INFORMATION: synthetic

<400> SEQUENCE: 194
atccagttca ccgtgcccct gctggagccc cacctggacc ccgaggccgc cgagcagatc      60
aggaggagga ggcccgcccc cgccaccctg gtgctgacca gcgaccagag cagccccgag     120
atcgacgagg acaggattcc caaccccac ctgggcgaga ccggcaccga gcaggacgag     180
gaggaggaca gcgacgagaa cagctactac cagcccgaca tggagtacag cgagatcgtg     240
ggcctgcccg aggaggagga gatccccgcc aacaggaaga tcaagttcag cgccgccccc     300
atcaaggtgt tcaacaccta cagcaacgag gactacgaca ggaggaac                 348

<210> SEQ ID NO 195
<211> LENGTH: 382
<212> TYPE: DNA
<213> ORGANISM: artificial sequence
<220> FEATURE:
<223> OTHER INFORMATION: synthetic

<400> SEQUENCE: 195
gctagcgccg gcatccagtt caccgtgccc ctgctggagc ccacctggac cccgaggcc      60 gccgagcaga tcaggaggag gaggcccgcc ccgccaccc tggtgctgac cagcgaccag     120
agcagccccg agatcgacga ggacaggatt cccaaccccc acctgggcga ccggcacc     180 gagcaggacg aggaggagga cagcgacgag aacagctact accagcccga catggagtac     240
agcgagatcg tgggcctgcc cgaggaggag gatccccg ccaacaggaa gatcaagttc     300
agcgccgccc ccatcaaggt gttcaacacc tacagcaacg aggactacga caggaggaac     360
cccgggggag gcggaatcga tt                                             382
```

```
<210> SEQ ID NO 196
<211> LENGTH: 391
<212> TYPE: DNA
<213> ORGANISM: artificial sequence
<220> FEATURE:
<223> OTHER INFORMATION: synthetic

<400> SEQUENCE: 196
gctagcgcca ccatggccgg catccagttc accgtgcccc tgctggagcc ccacctggac      60
cccgaggccg ccgagcagat caggaggagg aggcccgccc ccgccaccct ggtgctgacc     120
agcgaccaga gcagccccga gatcgacgag gacaggattc ccaaccccca cctgggcgag     180
accggcaccg agcaggacga ggaggaggac agcgacgaga cagctacta ccagcccgac      240 atggagtaca gcgagatcgt gggcctgccc gaggaggagg agatccccgc caacaggaag     300
atcaagttca gcgccgcccc catcaaggtg ttcaacacct acagcaacga ggactacgac     360
aggaggaacc ccggggagg cggaatcgat t                                     391

<210> SEQ ID NO 197
<211> LENGTH: 123
<212> TYPE: PRT
<213> ORGANISM: artificial sequence
<220> FEATURE:
<223> OTHER INFORMATION: synthetic

<400> SEQUENCE: 197

Gly Asp Pro Asn Gln Leu Thr Arg Lys Gly Arg Lys Arg Ser Val
1               5                  10                  15

Thr Trp Pro Glu Glu Gly Lys Leu Arg Glu Tyr Phe Tyr Phe Glu Leu
            20                  25                  30

Asp Glu Thr Glu Arg Val Asn Val Asn Lys Ile Lys Asp Phe Gly Glu
        35                  40                  45

Ala Ala Lys Arg Glu Ile Leu Ser Asp Arg His Ala Phe Glu Thr Ala
    50                  55                  60

Arg Arg Leu Arg Asp Arg Lys Ile Leu Ile Arg Phe Ser Asp Tyr Val
65                  70                  75                  80

Glu Val Ala Lys Ala Gln Asp Tyr Asp Arg Arg Ala Asp Lys Pro Trp
                85                  90                  95

Thr Arg Leu Ser Ala Ala Asp Lys Ala Ala Ile Arg Lys Glu Leu Asn
            100                 105                 110

Glu Tyr Lys Ser Asn Glu Met Glu Val His Ala
        115                 120

<210> SEQ ID NO 198
<211> LENGTH: 369
<212> TYPE: DNA
<213> ORGANISM: artificial sequence
<220> FEATURE:
<223> OTHER INFORMATION: synthetic

<400> SEQUENCE: 198
ggcgacccca accagctgac caggaagggc aggaaaagga aaagcgtgac ctggcccgag      60
gagggcaagc tgagggagta cttctacttc gagctggacg agaccgagag ggtgaacgtg     120
aacaagatca aggacttcgg cgaggccgcc aagagggaga tcctgagcga caggcacgcc     180
ttcgagaccg ccaggaggct gagggacagg aagatcctga tcaggttcag cgactacgtg     240
gaggtggcca aggcccagga ctacgacagg agggccgaca agccctggac caggctgtcc     300
gccgccgaca agccgccat caggaaggag ctgaacgagt acaagagcaa cgagatggag      360
gtccacgcc                                                             369
```

<210> SEQ ID NO 199
<211> LENGTH: 403
<212> TYPE: DNA
<213> ORGANISM: artificial sequence
<220> FEATURE:
<223> OTHER INFORMATION: synthetic

<400> SEQUENCE: 199

```
gctagcgccg gcggcgaccc caaccagctg accaggaagg gcaggaaaag gaaaagcgtg      60
acctggcccg aggagggcaa gctgagggag tacttctact tcgagctgga cgagaccgag     120
agggtgaacg tgaacaagat caaggacttc ggcgaggccg ccaagaggga gatcctgagc     180
gacaggcacg ccttcgagac cgccaggagg ctgagggaca ggaagatcct gatcaggttc     240
agcgactacg tggaggtggc caaggcccag gactacgaca ggagggccga caagccctgg     300
accaggctgt ccgccgccga caaagccgcc atcaggaagg agctgaacga gtacaagagc     360
aacgagatgg aggtccacgc ccccggggga ggcggaatcg att                       403
```

<210> SEQ ID NO 200
<211> LENGTH: 412
<212> TYPE: DNA
<213> ORGANISM: artificial sequence
<220> FEATURE:
<223> OTHER INFORMATION: synthetic

<400> SEQUENCE: 200

```
gctagcgcca ccatggccgg cggcgacccc aaccagctga ccaggaaggg caggaaaagg      60
aaaagcgtga cctggcccga ggagggcaag ctgagggagt acttctactt cgagctggac     120
gagaccgaga gggtgaacgt gaacaagatc aaggacttcg gcgaggccgc caagagggag     180
atcctgagcg acaggcacgc cttcgagacc gccaggaggc tgagggacag gaagatcctg     240
atcaggttca gcgactacgt ggaggtggcc aaggcccagg actacgacag gagggccgac     300
aagccctgga ccaggctgtc cgccgccgac aaagccgcca tcaggaagga gctgaacgag     360
tacaagagca acgagatgga ggtccacgcc cccgggggag gcggaatcga tt             412
```

<210> SEQ ID NO 201
<211> LENGTH: 403
<212> TYPE: PRT
<213> ORGANISM: Homo sapiens
<220> FEATURE:
<221> NAME/KEY: misc_feature
<222> LOCATION: (288)..(288)
<223> OTHER INFORMATION: Xaa can be any naturally occurring amino acid

<400> SEQUENCE: 201

```
Met Asp Arg Ser Lys Glu Asn Cys Ile Ser Gly Pro Val Lys Ala Thr
1               5                   10                  15

Ala Pro Val Gly Gly Pro Lys Arg Val Leu Val Thr Gln Gln Phe Pro
            20                  25                  30

Cys Gln Asn Pro Leu Pro Val Asn Ser Gly Gln Ala Gln Arg Val Leu
        35                  40                  45

Cys Pro Ser Asn Ser Ser Gln Arg Ile Pro Leu Gln Ala Gln Lys Leu
    50                  55                  60

Val Ser Ser His Lys Pro Val Gln Asn Lys Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu
```

```
                    100                 105                 110
Glu Leu Ala Ser Lys Gln Lys Asn Glu Glu Ser Lys Lys Arg Gln Trp
            115                 120                 125
Ala Leu Glu Asp Phe Glu Ile Gly Arg Pro Leu Gly Lys Gly Lys Phe
        130                 135                 140
Gly Asn Val Tyr Leu Ala Arg Glu Lys Gln Ser Lys Phe Ile Leu Ala
145                 150                 155                 160
Leu Lys Val Leu Phe Lys Ala Gln Leu Glu Lys Ala Gly Val Glu His
                165                 170                 175
Gln Leu Arg Arg Glu Val Glu Ile Gln Ser His Leu Arg His Pro Asn
            180                 185                 190
Ile Leu Arg Leu Tyr Gly Tyr Phe His Asp Ala Thr Arg Val Tyr Leu
        195                 200                 205
Ile Leu Glu Tyr Ala Pro Leu Gly Thr Val Tyr Arg Glu Leu Gln Lys
210                 215                 220
Leu Ser Lys Phe Asp Glu Gln Arg Thr Ala Thr Tyr Ile Thr Glu Leu
225                 230                 235                 240
Ala Asn Ala Leu Ser Tyr Cys His Ser Lys Arg Val Ile His Arg Asp
                245                 250                 255
Ile Lys Pro Glu Asn Leu Leu Leu Gly Ser Ala Gly Glu Leu Lys Ile
            260                 265                 270
Ala Asp Phe Gly Trp Ser Val His Ala Pro Ser Ser Arg Arg Thr Xaa
        275                 280                 285
Leu Cys Gly Thr Leu Asp Tyr Leu Pro Pro Glu Met Ile Glu Gly Arg
    290                 295                 300
Met His Asp Glu Lys Val Asp Leu Trp Ser Leu Gly Val Leu Cys Tyr
305                 310                 315                 320
Glu Phe Leu Val Gly Lys Pro Pro Phe Glu Ala Asn Thr Tyr Gln Glu
                325                 330                 335
Thr Tyr Lys Arg Ile Ser Arg Val Glu Phe Thr Phe Pro Asp Phe Val
            340                 345                 350
Thr Glu Gly Ala Arg Asp Leu Ile Ser Arg Leu Leu Lys His Asn Pro
        355                 360                 365
Ser Gln Arg Pro Met Leu Arg Glu Val Leu Glu His Pro Trp Ile Thr
    370                 375                 380
Ala Asn Ser Ser Lys Pro Ser Asn Cys Gln Asn Lys Glu Ser Ala Ser
385                 390                 395                 400
Lys Gln Ser

<210> SEQ ID NO 202
<211> LENGTH: 1030
<212> TYPE: PRT
<213> ORGANISM: Homo sapiens
<220> FEATURE:
<221> NAME/KEY: misc_feature
<222> LOCATION: (20)..(20)
<223> OTHER INFORMATION: Xaa can be any naturally occurring amino acid

<400> SEQUENCE: 202

Met Lys Met Ala Asp Ala Lys Gln Lys Arg Asn Glu Gln Leu Lys Arg
1               5                   10                  15
Trp Ile Gly Xaa Glu Thr Asp Leu Glu Pro Pro Val Val Lys Arg Gln
                20                  25                  30
Lys Thr Lys Val Lys Phe Asp Asp Gly Ala Val Phe Leu Ala Ala Cys
            35                  40                  45
Ser Ser Gly Asp Thr Asp Glu Val Leu Lys Leu Leu His Arg Gly Ala
```

```
              50                  55                  60
Asp Ile Asn Tyr Ala Asn Val Asp Gly Leu Thr Ala Leu His Gln Ala
 65                  70                  75                  80

Cys Ile Asp Asp Asn Val Asp Met Val Lys Phe Leu Val Glu Asn Gly
                 85                  90                  95

Ala Asn Ile Asn Gln Pro Asp Asn Glu Gly Trp Ile Pro Leu His Ala
            100                 105                 110

Ala Ala Ser Cys Gly Tyr Leu Asp Ile Ala Glu Phe Leu Ile Gly Gln
        115                 120                 125

Gly Ala His Val Gly Ala Val Asn Ser Glu Gly Asp Thr Pro Leu Asp
    130                 135                 140

Ile Ala Glu Glu Ala Met Glu Glu Leu Leu Gln Asn Glu Val Asn
145                 150                 155                 160

Arg Gln Gly Val Asp Ile Glu Ala Ala Arg Lys Glu Glu Arg Ile
                165                 170                 175

Met Leu Arg Asp Ala Arg Gln Trp Leu Asn Ser Gly His Ile Asn Asp
                180                 185                 190

Val Arg His Ala Lys Ser Gly Gly Thr Ala Leu His Val Ala Ala Ala
                195                 200                 205

Lys Gly Tyr Thr Glu Val Leu Lys Leu Leu Ile Gln Ala Gly Tyr Asp
    210                 215                 220

Val Asn Ile Lys Asp Tyr Asp Gly Trp Thr Pro Leu His Ala Ala Ala
225                 230                 235                 240

His Trp Gly Lys Glu Glu Ala Cys Arg Ile Leu Val Asp Asn Leu Cys
                245                 250                 255

Asp Met Glu Met Val Asn Lys Val Gly Gln Thr Ala Phe Asp Val Ala
            260                 265                 270

Asp Glu Asp Ile Leu Gly Tyr Leu Glu Glu Leu Gln Lys Lys Gln Asn
        275                 280                 285

Leu Leu His Ser Glu Lys Arg Asp Lys Lys Ser Pro Leu Ile Glu Ser
    290                 295                 300

Thr Ala Asn Met Asp Asn Asn Gln Ser Gln Lys Thr Phe Lys Asn Lys
305                 310                 315                 320

Glu Thr Leu Ile Ile Glu Pro Glu Lys Asn Ala Ser Arg Ile Glu Ser
                325                 330                 335

Leu Glu Gln Glu Lys Val Asp Glu Glu Glu Gly Lys Lys Asp Glu
            340                 345                 350

Ser Ser Cys Ser Ser Glu Glu Asp Glu Glu Asp Asp Ser Glu Ser Glu
        355                 360                 365

Ala Glu Thr Asp Lys Thr Lys Pro Leu Ala Ser Val Thr Asn Ala Asn
    370                 375                 380

Thr Ser Ser Thr Gln Ala Ala Pro Val Ala Val Thr Thr Pro Thr Val
385                 390                 395                 400

Ser Ser Gly Gln Ala Thr Pro Thr Ser Pro Ile Lys Lys Phe Pro Thr
                405                 410                 415

Thr Ala Thr Lys Ile Ser Pro Lys Glu Glu Arg Lys Asp Glu Ser
            420                 425                 430

Pro Ala Thr Trp Arg Leu Gly Leu Arg Lys Thr Gly Ser Tyr Gly Ala
        435                 440                 445

Leu Ala Glu Ile Thr Ala Ser Lys Glu Gly Gln Lys Glu Lys Asp Thr
    450                 455                 460

Ala Gly Val Thr Arg Ser Ala Ser Ser Pro Arg Leu Ser Ser Ser Leu
465                 470                 475                 480
```

```
Asp Asn Lys Glu Lys Glu Lys Asp Ser Lys Gly Thr Arg Leu Ala Tyr
            485                 490                 495

Val Ala Pro Thr Ile Pro Arg Arg Leu Ala Ser Thr Ser Asp Ile Glu
        500                 505                 510

Glu Lys Glu Asn Arg Asp Ser Ser Leu Arg Thr Ser Ser Ser Tyr
        515                 520                 525

Thr Arg Arg Lys Trp Glu Asp Asp Leu Lys Lys Asn Ser Ser Val Asn
        530                 535                 540

Glu Gly Ser Thr Tyr His Lys Ser Cys Ser Phe Gly Arg Arg Gln Asp
545                 550                 555                 560

Asp Leu Ile Ser Ser Val Pro Ser Thr Thr Ser Thr Pro Thr Val
                565                 570                 575

Thr Ser Ala Ala Gly Leu Gln Lys Ser Leu Leu Ser Ser Thr Ser Thr
            580                 585                 590

Thr Thr Lys Ile Thr Thr Gly Ser Ser Ala Gly Thr Gln Ser Ser
            595                 600                 605

Thr Ser Asn Arg Leu Trp Ala Glu Asp Ser Thr Glu Lys Glu Lys Asp
            610                 615                 620

Ser Val Pro Thr Ala Val Thr Ile Pro Val Ala Pro Thr Val Val Asn
625                 630                 635                 640

Ala Ala Ala Ser Thr Thr Thr Leu Thr Thr Thr Thr Ala Gly Thr Val
                645                 650                 655

Ser Ser Thr Thr Glu Val Arg Glu Arg Arg Arg Ser Tyr Leu Thr Pro
                660                 665                 670

Val Arg Asp Glu Glu Ser Glu Ser Gln Arg Lys Ala Arg Ser Arg Gln
            675                 680                 685

Ala Arg Gln Ser Arg Arg Ser Thr Gln Gly Val Thr Leu Thr Asp Leu
            690                 695                 700

Gln Glu Ala Glu Lys Thr Ile Gly Arg Ser Arg Ser Thr Arg Thr Arg
705                 710                 715                 720

Glu Gln Glu Asn Glu Glu Lys Glu Lys Glu Lys Glu Lys Gln Asp
                725                 730                 735

Lys Glu Lys Gln Glu Glu Lys Lys Glu Ser Glu Thr Ser Arg Glu Asp
            740                 745                 750

Glu Tyr Lys Gln Lys Tyr Ser Arg Thr Tyr Asp Glu Thr Tyr Gln Arg
            755                 760                 765

Tyr Arg Pro Val Ser Thr Ser Ser Thr Thr Pro Ser Ser Ser Leu
770                 775                 780

Ser Thr Met Ser Ser Ser Leu Tyr Ala Ser Gln Leu Asn Arg Pro
785                 790                 795                 800

Asn Ser Leu Val Gly Ile Thr Ser Ala Tyr Ser Arg Gly Ile Thr Lys
            805                 810                 815

Glu Asn Glu Arg Glu Gly Glu Lys Arg Glu Glu Lys Glu Gly Glu
                820                 825                 830

Asp Lys Ser Gln Pro Lys Ser Ile Arg Glu Arg Arg Pro Arg Glu
        835                 840                 845

Lys Arg Arg Ser Thr Gly Val Ser Phe Trp Thr Gln Asp Ser Asp Glu
        850                 855                 860

Asn Glu Gln Glu Gln Gln Ser Asp Thr Glu Glu Gly Ser Asn Lys Lys
865                 870                 875                 880

Glu Thr Gln Thr Asp Ser Ile Ser Arg Tyr Glu Thr Ser Ser Thr Ser
                885                 890                 895

Ala Gly Asp Arg Tyr Asp Ser Leu Leu Gly Arg Ser Gly Ser Tyr Ser
            900                 905                 910
```

```
Tyr Leu Glu Glu Arg Lys Pro Tyr Ser Ser Arg Leu Glu Lys Asp Asp
            915                 920                 925

Ser Thr Asp Phe Lys Lys Leu Tyr Glu Gln Ile Leu Ala Glu Asn Glu
    930                 935                 940

Lys Leu Lys Ala Gln Leu His Asp Thr Asn Met Glu Leu Thr Asp Leu
945                 950                 955                 960

Lys Leu Gln Leu Glu Lys Ala Thr Gln Arg Gln Glu Arg Phe Ala Asp
                965                 970                 975

Arg Ser Leu Leu Glu Met Glu Lys Arg Glu Arg Ala Leu Glu Arg
            980                 985                 990

Arg Ile Ser Glu Met Glu Glu Glu Leu Lys Met Leu Pro Asp Leu Lys
            995                 1000                1005

Ala Asp Asn Gln Arg Leu Lys Asp Glu Asn Gly Ala Leu Ile Arg
    1010                1015                1020

Val Ile Ser Lys Leu Ser Lys
    1025                1030

<210> SEQ ID NO 203
<211> LENGTH: 168
<212> TYPE: PRT
<213> ORGANISM: mouse
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid

<400> SEQUENCE: 203

Met Phe Gln Ile Pro Glu Phe Glu Pro Ser Glu Gln Glu Asp Ser Ser
1               5                   10                  15

Ser Ala Glu Arg Gly Leu Gly Pro Ser Pro Ala Gly Asp Gly Pro Ser
            20                  25                  30

Gly Ser Gly Lys His His Arg Gln Ala Pro Gly Leu Leu Trp Asp Ala
        35                  40                  45

Ser His Gln Gln Glu Gln Pro Thr Ser Ser His His Gly Gly Ala
    50                  55                  60

Gly Ala Val Glu Ile Arg Ser Arg His Ser Xaa Tyr Pro Ala Gly Thr
65                  70                  75                  80

Glu Asp Asp Glu Gly Met Gly Glu Glu Pro Ser Pro Phe Arg Gly Arg
                85                  90                  95

Ser Arg Xaa Ala Pro Pro Asn Leu Trp Ala Ala Gln Arg Tyr Gly Arg
            100                 105                 110

Glu Leu Arg Arg Met Ser Asp Glu Phe Val Asp Ser Phe Lys Lys Gly
        115                 120                 125

Leu Pro Arg Pro Lys Ser Ala Gly Thr Ala Thr Gln Met Arg Gln Ser
    130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165

<210> SEQ ID NO 204
<211> LENGTH: 1863
<212> TYPE: PRT
<213> ORGANISM: Homo sapiens
<220> FEATURE:
```

```
<221> NAME/KEY: misc_feature
<222> LOCATION: (988)..(988)
<223> OTHER INFORMATION: Xaa can be any naturally occurring amino acid

<400> SEQUENCE: 204
```

| Met | Asp | Leu | Ser | Ala | Leu | Arg | Val | Glu | Glu | Val | Gln | Asn | Val | Ile | Asn |
|---|---|---|---|---|---|---|---|---|---|---|---|---|---|---|---|
| 1 | | | | 5 | | | | | 10 | | | | | 15 | |

| Ala | Met | Gln | Lys | Ile | Leu | Glu | Cys | Pro | Ile | Cys | Leu | Glu | Leu | Ile | Lys |
|---|---|---|---|---|---|---|---|---|---|---|---|---|---|---|---|
| | | | 20 | | | | | 25 | | | | | 30 | | |

| Glu | Pro | Val | Ser | Thr | Lys | Cys | Asp | His | Ile | Phe | Cys | Lys | Phe | Cys | Met |
|---|---|---|---|---|---|---|---|---|---|---|---|---|---|---|---|
| | | | 35 | | | | | 40 | | | | | 45 | | |

| Leu | Lys | Leu | Leu | Asn | Gln | Lys | Lys | Gly | Pro | Ser | Gln | Cys | Pro | Leu | Cys |
|---|---|---|---|---|---|---|---|---|---|---|---|---|---|---|---|
| | 50 | | | | | 55 | | | | | 60 | | | | |

| Lys | Asn | Asp | Ile | Thr | Lys | Arg | Ser | Leu | Gln | Glu | Ser | Thr | Arg | Phe | Ser |
|---|---|---|---|---|---|---|---|---|---|---|---|---|---|---|---|
| 65 | | | | | 70 | | | | | 75 | | | | | 80 |

| Gln | Leu | Val | Glu | Glu | Leu | Leu | Lys | Ile | Ile | Cys | Ala | Phe | Gln | Leu | Asp |
|---|---|---|---|---|---|---|---|---|---|---|---|---|---|---|---|
| | | | | 85 | | | | | 90 | | | | | 95 | |

| Thr | Gly | Leu | Glu | Tyr | Ala | Asn | Ser | Tyr | Asn | Phe | Ala | Lys | Lys | Glu | Asn |
|---|---|---|---|---|---|---|---|---|---|---|---|---|---|---|---|
| | | | 100 | | | | | 105 | | | | | 110 | | |

| Asn | Ser | Pro | Glu | His | Leu | Lys | Asp | Glu | Val | Ser | Ile | Ile | Gln | Ser | Met |
|---|---|---|---|---|---|---|---|---|---|---|---|---|---|---|---|
| | | 115 | | | | | 120 | | | | | 125 | | | |

| Gly | Tyr | Arg | Asn | Arg | Ala | Lys | Arg | Leu | Leu | Gln | Ser | Glu | Pro | Glu | Asn |
|---|---|---|---|---|---|---|---|---|---|---|---|---|---|---|---|
| | 130 | | | | | 135 | | | | | 140 | | | | |

| Pro | Ser | Leu | Gln | Glu | Thr | Ser | Leu | Ser | Val | Gln | Leu | Ser | Asn | Leu | Gly |
|---|---|---|---|---|---|---|---|---|---|---|---|---|---|---|---|
| 145 | | | | | 150 | | | | | 155 | | | | | 160 |

| Thr | Val | Arg | Thr | Leu | Arg | Thr | Lys | Gln | Arg | Ile | Gln | Pro | Gln | Lys | Thr |
|---|---|---|---|---|---|---|---|---|---|---|---|---|---|---|---|
| | | | | 165 | | | | | 170 | | | | | 175 | |

| Ser | Val | Tyr | Ile | Glu | Leu | Gly | Ser | Asp | Ser | Ser | Glu | Asp | Thr | Val | Asn |
|---|---|---|---|---|---|---|---|---|---|---|---|---|---|---|---|
| | | | 180 | | | | | 185 | | | | | 190 | | |

| Lys | Ala | Thr | Tyr | Cys | Ser | Val | Gly | Asp | Gln | Glu | Leu | Leu | Gln | Ile | Thr |
|---|---|---|---|---|---|---|---|---|---|---|---|---|---|---|---|
| | | | 195 | | | | | 200 | | | | | 205 | | |

| Pro | Gln | Gly | Thr | Arg | Asp | Glu | Ile | Ser | Leu | Asp | Ser | Ala | Lys | Lys | Ala |
|---|---|---|---|---|---|---|---|---|---|---|---|---|---|---|---|
| | 210 | | | | | 215 | | | | | 220 | | | | |

| Ala | Cys | Glu | Phe | Ser | Glu | Thr | Asp | Val | Thr | Asn | Thr | Glu | His | His | Gln |
|---|---|---|---|---|---|---|---|---|---|---|---|---|---|---|---|
| 225 | | | | | 230 | | | | | 235 | | | | | 240 |

| Pro | Ser | Asn | Asn | Asp | Leu | Asn | Thr | Thr | Glu | Lys | Arg | Ala | Ala | Glu | Arg |
|---|---|---|---|---|---|---|---|---|---|---|---|---|---|---|---|
| | | | | 245 | | | | | 250 | | | | | 255 | |

| His | Pro | Glu | Lys | Tyr | Gln | Gly | Ser | Ser | Val | Ser | Asn | Leu | His | Val | Glu |
|---|---|---|---|---|---|---|---|---|---|---|---|---|---|---|---|
| | | | | 260 | | | | | 265 | | | | | 270 | |

| Pro | Cys | Gly | Thr | Asn | Thr | His | Ala | Ser | Ser | Leu | Gln | His | Glu | Asn | Ser |
|---|---|---|---|---|---|---|---|---|---|---|---|---|---|---|---|
| | | | 275 | | | | | 280 | | | | | 285 | | |

| Ser | Leu | Leu | Leu | Thr | Lys | Asp | Arg | Met | Asn | Val | Glu | Lys | Ala | Glu | Phe |
|---|---|---|---|---|---|---|---|---|---|---|---|---|---|---|---|
| | 290 | | | | | 295 | | | | | 300 | | | | |

| Cys | Asn | Lys | Ser | Lys | Gln | Pro | Gly | Leu | Ala | Arg | Ser | Gln | His | Asn | Arg |
|---|---|---|---|---|---|---|---|---|---|---|---|---|---|---|---|
| 305 | | | | | 310 | | | | | 315 | | | | | 320 |

| Trp | Ala | Gly | Ser | Lys | Glu | Thr | Cys | Asn | Asp | Arg | Arg | Thr | Pro | Ser | Thr |
|---|---|---|---|---|---|---|---|---|---|---|---|---|---|---|---|
| | | | | 325 | | | | | 330 | | | | | 335 | |

| Glu | Lys | Lys | Val | Asp | Leu | Asn | Ala | Asp | Pro | Leu | Cys | Glu | Arg | Lys | Glu |
|---|---|---|---|---|---|---|---|---|---|---|---|---|---|---|---|
| | | | 340 | | | | | 345 | | | | | 350 | | |

| Trp | Asn | Lys | Gln | Lys | Leu | Pro | Cys | Ser | Glu | Asn | Pro | Arg | Asp | Thr | Glu |
|---|---|---|---|---|---|---|---|---|---|---|---|---|---|---|---|
| | | 355 | | | | | 360 | | | | | 365 | | | |

| Asp | Val | Pro | Trp | Ile | Thr | Leu | Asn | Ser | Ser | Ile | Gln | Lys | Val | Asn | Glu |
|---|---|---|---|---|---|---|---|---|---|---|---|---|---|---|---|
| | 370 | | | | | 375 | | | | | 380 | | | | |

| Trp | Phe | Ser | Arg | Ser | Asp | Glu | Leu | Leu | Gly | Ser | Asp | Asp | Ser | His | Asp |
|---|---|---|---|---|---|---|---|---|---|---|---|---|---|---|---|
| 385 | | | | | 390 | | | | | 395 | | | | | 400 |

-continued

```
Gly Glu Ser Glu Ser Asn Ala Lys Val Ala Asp Val Leu Asp Val Leu
                405                 410                 415
Asn Glu Val Asp Glu Tyr Ser Gly Ser Ser Glu Lys Ile Asp Leu Leu
                420                 425                 430
Ala Ser Asp Pro His Glu Ala Leu Ile Cys Lys Ser Glu Arg Val His
                435                 440                 445
Ser Lys Ser Val Glu Ser Asn Ile Glu Asp Lys Ile Phe Gly Lys Thr
                450                 455                 460
Tyr Arg Lys Lys Ala Ser Leu Pro Asn Leu Ser His Val Thr Glu Asn
465                 470                 475                 480
Leu Ile Ile Gly Ala Phe Val Thr Glu Pro Gln Ile Gln Glu Arg
                    485                 490                 495
Pro Leu Thr Asn Lys Leu Lys Arg Lys Arg Pro Thr Ser Gly Leu
                500                 505                 510
His Pro Glu Asp Phe Ile Lys Lys Ala Asp Leu Ala Val Gln Lys Thr
                515                 520                 525
Pro Glu Met Ile Asn Gln Gly Thr Asn Gln Thr Glu Gln Asn Gly Gln
                530                 535                 540
Val Met Asn Ile Thr Asn Ser Gly His Glu Asn Lys Thr Lys Gly Asp
545                 550                 555                 560
Ser Ile Gln Asn Glu Lys Asn Pro Asn Pro Ile Glu Ser Leu Glu Lys
                565                 570                 575
Glu Ser Ala Phe Lys Thr Lys Ala Glu Pro Ile Ser Ser Ser Ile Ser
                580                 585                 590
Asn Met Glu Leu Glu Leu Asn Ile His Asn Ser Lys Ala Pro Lys Lys
                595                 600                 605
Asn Arg Leu Arg Arg Lys Ser Ser Thr Arg His Ile His Ala Leu Glu
                610                 615                 620
Leu Val Val Ser Arg Asn Leu Ser Pro Pro Asn Cys Thr Glu Leu Gln
625                 630                 635                 640
Ile Asp Ser Cys Ser Ser Ser Glu Glu Ile Lys Lys Lys Lys Tyr Asn
                645                 650                 655
Gln Met Pro Val Arg His Ser Arg Asn Leu Gln Leu Met Glu Gly Lys
                660                 665                 670
Glu Pro Ala Thr Gly Ala Lys Lys Ser Asn Lys Pro Asn Glu Gln Thr
                675                 680                 685
Ser Lys Arg His Asp Ser Asp Thr Phe Pro Glu Leu Lys Leu Thr Asn
                690                 695                 700
Ala Pro Gly Ser Phe Thr Lys Cys Ser Asn Thr Ser Glu Leu Lys Glu
705                 710                 715                 720
Phe Val Asn Pro Ser Leu Pro Arg Glu Glu Lys Glu Glu Lys Leu Glu
                725                 730                 735
Thr Val Lys Val Ser Asn Asn Ala Glu Asp Pro Lys Asp Leu Met Leu
                740                 745                 750
Ser Gly Glu Arg Val Leu Gln Thr Glu Arg Ser Val Glu Ser Ser Ser
                755                 760                 765
Ile Ser Leu Val Pro Gly Thr Asp Tyr Gly Thr Gln Glu Ser Ile Ser
                770                 775                 780
Leu Leu Glu Val Ser Thr Leu Gly Lys Ala Lys Thr Glu Pro Asn Lys
785                 790                 795                 800
Cys Val Ser Gln Cys Ala Ala Phe Glu Asn Pro Lys Gly Leu Ile His
                805                 810                 815
Gly Cys Ser Lys Asp Asn Arg Asn Asp Thr Glu Gly Phe Lys Tyr Pro
```

```
                    820              825                   830
Leu Gly His Glu Val Asn His Ser Arg Glu Thr Ser Ile Glu Met Glu
            835                 840              845
Glu Ser Glu Leu Asp Ala Gln Tyr Leu Gln Asn Thr Phe Lys Val Ser
850                 855                   860
Lys Arg Gln Ser Phe Ala Pro Phe Ser Asn Pro Gly Asn Ala Glu Glu
865                 870                   875                 880
Glu Cys Ala Thr Phe Ser Ala His Ser Gly Ser Leu Lys Lys Gln Ser
            885                   890                 895
Pro Lys Val Thr Phe Glu Cys Glu Gln Lys Glu Glu Asn Gln Gly Lys
            900                   905                 910
Asn Glu Ser Asn Ile Lys Pro Val Gln Thr Val Asn Ile Thr Ala Gly
            915                 920                   925
Phe Pro Val Val Gly Gln Lys Asp Lys Pro Val Asp Asn Ala Lys Cys
            930               935                     940
Ser Ile Lys Gly Gly Ser Arg Phe Cys Leu Ser Ser Gln Phe Arg Gly
945                 950                   955                 960
Asn Glu Thr Gly Leu Ile Thr Pro Asn Lys His Gly Leu Leu Gln Asn
            965                 970                   975
Pro Tyr Arg Ile Pro Pro Leu Phe Pro Ile Lys Xaa Phe Val Lys Thr
            980                 985                   990
Lys Cys Lys Lys Asn Leu Leu Glu  Glu Asn Phe Glu Glu  His Ser Met
            995                 1000                  1005
Ser Pro  Glu Arg Glu Met Gly  Asn Glu Asn Ile Pro  Ser Thr Val
       1010               1015                  1020
Ser Thr  Ile Ser Arg Asn Asn  Ile Arg Glu Asn Val  Phe Lys Glu
       1025               1030                  1035
Ala Ser  Ser Ser Asn Ile Asn  Glu Val Gly Ser Ser  Thr Asn Glu
       1040               1045                  1050
Val Gly  Ser Ser Ile Asn Glu  Ile Gly Ser Ser Asp  Glu Asn Ile
       1055               1060                  1065
Gln Ala  Glu Leu Gly Arg Asn  Arg Gly Pro Lys Leu  Asn Ala Met
       1070               1075                  1080
Leu Arg  Leu Gly Val Leu Gln  Pro Glu Val Tyr Lys  Gln Ser Leu
       1085               1090                  1095
Pro Gly  Ser Asn Cys Lys His  Pro Glu Ile Lys Lys  Gln Glu Tyr
       1100               1105                  1110
Glu Glu  Val Val Gln Thr Val  Asn Thr Asp Phe Ser  Pro Tyr Leu
       1115               1120                  1125
Ile Ser  Asp Asn Leu Glu Gln  Pro Met Gly Ser Ser  His Ala Ser
       1130               1135                  1140
Gln Val  Cys Ser Glu Thr Pro  Asp Asp Leu Leu Asp  Asp Gly Glu
       1145               1150                  1155
Ile Lys  Glu Asp Thr Ser Phe  Ala Glu Asn Asp Ile  Lys Glu Ser
       1160               1165                  1170
Ser Ala  Val Phe Ser Lys Ser  Val Gln Lys Gly Glu  Leu Ser Arg
       1175               1180                  1185
Ser Pro  Ser Pro Phe Thr His  Thr His Leu Ala Gln  Gly Tyr Arg
       1190               1195                  1200
Arg Gly  Ala Lys Lys Leu Glu  Ser Ser Glu Glu Asn  Leu Ser Ser
       1205               1210                  1215
Glu Asp  Glu Glu Leu Pro Cys  Phe Gln His Leu Leu  Phe Gly Lys
       1220               1225                  1230
```

-continued

```
Val Asn Asn Ile Pro Ser Gln Ser Thr Arg His Ser Thr Val Ala
    1235            1240            1245

Thr Glu Cys Leu Ser Lys Asn Thr Glu Glu Asn Leu Leu Ser Leu
    1250            1255            1260

Lys Asn Ser Leu Asn Asp Cys Ser Asn Gln Val Ile Leu Ala Lys
    1265            1270            1275

Ala Ser Gln Glu His His Leu Ser Glu Glu Thr Lys Cys Ser Ala
    1280            1285            1290

Ser Leu Phe Ser Ser Gln Cys Ser Glu Leu Glu Asp Leu Thr Ala
    1295            1300            1305

Asn Thr Asn Thr Gln Asp Pro Phe Leu Ile Gly Ser Ser Lys Gln
    1310            1315            1320

Met Arg His Gln Ser Glu Ser Gln Gly Val Gly Leu Ser Asp Lys
    1325            1330            1335

Glu Leu Val Ser Asp Asp Glu Arg Gly Thr Gly Leu Glu Glu
    1340            1345            1350

Asn Asn Gln Glu Glu Gln Ser Met Asp Ser Asn Leu Gly Glu Ala
    1355            1360            1365

Ala Ser Gly Cys Glu Ser Glu Thr Ser Val Ser Glu Asp Cys Ser
    1370            1375            1380

Gly Leu Ser Ser Gln Ser Asp Ile Leu Thr Thr Gln Gln Arg Asp
    1385            1390            1395

Thr Met Gln His Asn Leu Ile Lys Leu Gln Gln Glu Met Ala Glu
    1400            1405            1410

Leu Glu Ala Val Leu Glu Gln His Gly Ser Gln Pro Ser Asn Ser
    1415            1420            1425

Tyr Pro Ser Ile Ile Ser Asp Ser Ser Ala Leu Glu Asp Leu Arg
    1430            1435            1440

Asn Pro Glu Gln Ser Thr Ser Glu Lys Ala Val Leu Thr Ser Gln
    1445            1450            1455

Lys Ser Ser Glu Tyr Pro Ile Ser Gln Asn Pro Glu Gly Leu Ser
    1460            1465            1470

Ala Asp Lys Phe Glu Val Ser Ala Asp Ser Ser Thr Ser Lys Asn
    1475            1480            1485

Lys Glu Pro Gly Val Glu Arg Ser Ser Pro Ser Lys Cys Pro Ser
    1490            1495            1500

Leu Asp Asp Arg Trp Tyr Met His Ser Cys Ser Gly Ser Leu Gln
    1505            1510            1515

Asn Arg Asn Tyr Pro Ser Gln Glu Glu Leu Ile Lys Val Val Asp
    1520            1525            1530

Val Glu Glu Gln Gln Leu Glu Glu Ser Gly Pro His Asp Leu Thr
    1535            1540            1545

Glu Thr Ser Tyr Leu Pro Arg Gln Asp Leu Glu Gly Thr Pro Tyr
    1550            1555            1560

Leu Glu Ser Gly Ile Ser Leu Phe Ser Asp Asp Pro Glu Ser Asp
    1565            1570            1575

Pro Ser Glu Asp Arg Ala Pro Glu Ser Ala Arg Val Gly Asn Ile
    1580            1585            1590

Pro Ser Ser Thr Ser Ala Leu Lys Val Pro Gln Leu Lys Val Ala
    1595            1600            1605

Glu Ser Ala Gln Ser Pro Ala Ala Ala His Thr Thr Asp Thr Ala
    1610            1615            1620

Gly Tyr Asn Ala Met Glu Glu Ser Val Ser Arg Glu Lys Pro Glu
    1625            1630            1635
```

Leu Thr Ala Ser Thr Glu Arg Val Asn Lys Arg Met Ser Met Val
            1640                1645                1650

Val Ser Gly Leu Thr Pro Glu Glu Phe Met Leu Val Tyr Lys Phe
        1655                1660                1665

Ala Arg Lys His His Ile Thr Leu Thr Asn Leu Ile Thr Glu Glu
    1670                1675                1680

Thr Thr His Val Val Met Lys Thr Asp Ala Glu Phe Val Cys Glu
    1685                1690                1695

Arg Thr Leu Lys Tyr Phe Leu Gly Ile Ala Gly Gly Lys Trp Val
    1700                1705                1710

Val Ser Tyr Phe Trp Val Thr Gln Ser Ile Lys Glu Arg Lys Met
    1715                1720                1725

Leu Asn Glu His Asp Phe Glu Val Arg Gly Asp Val Val Asn Gly
    1730                1735                1740

Arg Asn His Gln Gly Pro Lys Arg Ala Arg Glu Ser Gln Asp Arg
    1745                1750                1755

Lys Ile Phe Arg Gly Leu Glu Ile Cys Cys Tyr Gly Pro Phe Thr
    1760                1765                1770

Asn Met Pro Thr Asp Gln Leu Glu Trp Met Val Gln Leu Cys Gly
    1775                1780                1785

Ala Ser Val Val Lys Glu Leu Ser Ser Phe Thr Leu Gly Thr Gly
    1790                1795                1800

Val His Pro Ile Val Val Val Gln Pro Asp Ala Trp Thr Glu Asp
    1805                1810                1815

Asn Gly Phe His Ala Ile Gly Gln Met Cys Glu Ala Pro Val Val
    1820                1825                1830

Thr Arg Glu Trp Val Leu Asp Ser Val Ala Leu Tyr Gln Cys Gln
    1835                1840                1845

Glu Leu Asp Thr Tyr Leu Ile Pro Gln Ile Pro His Ser His Tyr
    1850                1855                1860

<210> SEQ ID NO 205
<211> LENGTH: 716
<212> TYPE: PRT
<213> ORGANISM: Rattus norvegicus
<220> FEATURE:
<221> NAME/KEY: misc_feature
<222> LOCATION: (535)..(535)
<223> OTHER INFORMATION: Xaa can be any naturally occurring amino acid

<400> SEQUENCE: 205

Met Ala Ala Thr Ala Ala Val Pro Ser Ala Val Gly Gly Arg Ala Asn
1               5                   10                  15

Lys Arg Gly Gly Gly Ser Gly Gly Gly Thr Gln Gly Ala Glu Glu
            20                  25                  30

Glu Pro Pro Pro Pro Leu Gln Ala Val Leu Val Ala Asp Ser Phe Asp
        35                  40                  45

Arg Arg Phe Phe Pro Ile Ser Lys Asp Gln Pro Arg Val Leu Leu Pro
    50                  55                  60

Leu Ala Asn Val Ala Leu Ile Asp Tyr Thr Leu Glu Phe Leu Thr Ala
65                  70                  75                  80

Thr Gly Val Gln Glu Thr Phe Val Phe Cys Cys Trp Lys Ala Ala Gln
                85                  90                  95

Ile Lys Glu His Leu Gln Lys Ser Lys Trp Cys His Pro Thr Ser Leu
            100                 105                 110

Asn Val Val Arg Ile Thr Thr Ser Asp Leu Tyr Arg Ser Leu Gly Asp

```
            115                 120                 125
Val Leu Arg Asp Val Asp Ala Lys Ala Leu Val Arg Ser Asp Phe Leu
        130                 135                 140

Leu Ile Tyr Gly Asp Val Val Ser Asn Ile Asn Ile Ser Lys Ala Leu
145                 150                 155                 160

Glu Glu His Arg Leu Arg Arg Lys Leu Glu Lys Asn Val Ser Val Met
                165                 170                 175

Thr Met Val Phe Lys Glu Ser Ser Pro Ser His Pro Thr Arg Cys His
            180                 185                 190

Glu Asp Asn Val Val Leu Ala Val Asp Ser Thr Thr Asn Arg Ile Leu
        195                 200                 205

His Phe Gln Lys Thr Gln Gly Leu Arg His Phe Ser Phe Pro Leu Gly
    210                 215                 220

Leu Phe Gln Gly Ser Leu Asp Gly Val Glu Ile Arg Tyr Asp Leu Leu
225                 230                 235                 240

Asp Cys His Ile Ser Ile Cys Ser Pro Gln Val Ala Gln Leu Phe Thr
                245                 250                 255

Asp Asn Phe Asp Tyr Gln Thr Arg Asp Asp Phe Val Arg Gly Leu Leu
            260                 265                 270

Val Asn Glu Glu Ile Leu Gly Asn Gln Ile His Leu His Val Thr Ser
        275                 280                 285

Arg Glu Tyr Gly Ser Arg Val Ser Asn Leu His Met Tyr Ser Ala Val
    290                 295                 300

Cys Thr Asp Val Ile Arg Arg Trp Val Tyr Pro Leu Thr Pro Glu Val
305                 310                 315                 320

Asn Phe Thr Asp Ser Ser Thr Gln Ser Tyr Thr His Ser Arg His Asn
                325                 330                 335

Ile Tyr Arg Gly Pro Glu Val Ser Leu Gly His Gly Ser Val Leu Glu
            340                 345                 350

Glu Asn Val Leu Leu Gly Ala Gly Thr Val Val Gly Ser Asn Cys Ser
        355                 360                 365

Ile Thr Asn Ser Val Ile Gly Pro Asn Cys His Ile Gly Asp Asn Val
    370                 375                 380

Val Leu Asp Gln Ala Tyr Leu Trp Gln Gly Val Arg Val Ala Ala Gly
385                 390                 395                 400

Ala Gln Ile His Gln Ser Leu Leu Cys Asp Arg Ala Glu Val Lys Glu
                405                 410                 415

Arg Val Ile Leu Lys Pro His Cys Val Leu Thr Ser Gly Val Val Val
            420                 425                 430

Gly Pro Asp Ile Ile Leu Pro Glu Gly Ser Val Ile Ser Leu His Pro
        435                 440                 445

Pro Asp Ala Glu Glu Asp Glu Asp Asp Gly Gln Phe Ser Asp Asp Ser
    450                 455                 460

Gly Ala Asp Gln Glu Lys Glu Lys Val Lys Leu Lys Gly Tyr Asn Pro
465                 470                 475                 480

Ala Glu Val Gly Pro Glu Gly Gln Gly Tyr Leu Trp Lys Ala Glu Asp
                485                 490                 495

Val Asp Glu Lys Glu Asp Glu Glu Leu Arg Gln Ser Leu Trp Gly Leu
            500                 505                 510

Met Ile Asn Met Glu Glu Glu Ser Glu Thr Glu Ser Glu Arg Ser Val
        515                 520                 525

Asp Pro Glu Glu Leu Asp Xaa Arg Ala Gly Ser Pro Gln Leu Asp Asp
    530                 535                 540
```

```
Ile Arg Val Phe Gln Asn Glu Val Leu Gly Thr Leu Gln Arg Gly Arg
545                 550                 555                 560

Glu Glu Asn Ile Ser Cys Asp Asn Leu Val Leu Glu Ile Asn Ser Leu
                565                 570                 575

Lys Tyr Ala Tyr Asn Ile Ser Leu Lys Glu Val Met Gln Val Leu Ser
            580                 585                 590

His Val Val Leu Glu Phe Pro Leu Gln Gln Val Asp Gly Val Leu Asp
        595                 600                 605

Pro Asn Arg Tyr Cys Ala Leu Leu Pro Leu Leu Lys Ala Trp Ser
610                 615                 620

Pro Val Phe Arg Asn Tyr Ile Lys Arg Ala Ala Asp His Leu Glu Ala
625                 630                 635                 640

Leu Ala Ala Ile Glu Asp Phe Phe Leu Glu His Glu Thr Leu Val Pro
                645                 650                 655

Ser Leu Ala Lys Val Leu Met Ala Phe Tyr Gln Leu Glu Ile Leu Ala
            660                 665                 670

Glu Glu Thr Ile Leu Ser Trp Phe Ser Gln Arg Asp Ile Thr Asp Lys
        675                 680                 685

Gly Gln Gln Leu Arg Lys Asn Gln Gln Leu Gln Arg Phe Ile Gln Trp
690                 695                 700

Leu Arg Glu Ala Glu Glu Ser Ser Asp Asp
705                 710                 715

<210> SEQ ID NO 206
<211> LENGTH: 143
<212> TYPE: PRT
<213> ORGANISM: Homo sapiens
<220> FEATURE:
<221> NAME/KEY: misc_feature
<222> LOCATION: (140)..(140)
<223> OTHER INFORMATION: Xaa can be any naturally occurring amino acid

<400> SEQUENCE: 206

Met Ser Gly Arg Gly Lys Thr Gly Gly Lys Ala Arg Ala Lys Ala Lys
1               5                   10                  15

Ser Arg Ser Ser Arg Ala Gly Leu Gln Phe Pro Val Gly Arg Val His
            20                  25                  30

Arg Leu Leu Arg Lys Gly His Tyr Ala Glu Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Gly Val Thr Ile Ala Gln Gly Gly Val Leu Pro Asn Ile
            100                 105                 110

Gln Ala Val Leu Leu Pro Lys Lys Thr Ser Ala Thr Val Gly Pro Lys
        115                 120                 125

Ala Pro Ser Gly Gly Lys Lys Ala Thr Gln Ala Xaa Gln Glu Tyr
    130                 135                 140

<210> SEQ ID NO 207
<211> LENGTH: 2773
<212> TYPE: PRT
<213> ORGANISM: Rattus norvegicus
<220> FEATURE:
<221> NAME/KEY: misc_feature
<222> LOCATION: (1589)..(1589)
```

```
<223> OTHER INFORMATION: Xaa can be any naturally occurring amino acid
<220> FEATURE:
<221> NAME/KEY: misc_feature
<222> LOCATION: (1755)..(1755)
<223> OTHER INFORMATION: Xaa can be any naturally occurring amino acid

<400> SEQUENCE: 207
```

| | | | | | | | | | | | | | | | |
|---|---|---|---|---|---|---|---|---|---|---|---|---|---|---|---|
| Met | Ser | Asp | Lys | Met | Ser | Ser | Phe | Leu | His | Ile | Gly | Asp | Ile | Cys | Ser |
| 1 | | | | 5 | | | | | 10 | | | | | 15 | |
| Leu | Tyr | Ala | Glu | Gly | Ser | Thr | Asn | Gly | Phe | Ile | Ser | Thr | Leu | Gly | Leu |
| | | | 20 | | | | | 25 | | | | | 30 | | |
| Val | Asp | Asp | Arg | Cys | Val | Val | Gln | Pro | Glu | Ala | Gly | Asp | Leu | Asn | Asn |
| | | 35 | | | | | 40 | | | | | 45 | | | |
| Pro | Pro | Lys | Lys | Phe | Arg | Asp | Cys | Leu | Phe | Lys | Leu | Cys | Pro | Met | Asn |
| | 50 | | | | | 55 | | | | | 60 | | | | |
| Arg | Tyr | Ser | Ala | Gln | Lys | Gln | Phe | Trp | Lys | Ala | Ala | Lys | Pro | Gly | Ala |
| 65 | | | | | 70 | | | | | 75 | | | | | 80 |
| Asn | Ser | Thr | Thr | Asp | Ala | Val | Leu | Leu | Asn | Lys | Leu | His | His | Ala | Ala |
| | | | | 85 | | | | | 90 | | | | | 95 | |
| Asp | Leu | Glu | Lys | Lys | Gln | Asn | Glu | Thr | Glu | Asn | Arg | Lys | Leu | Leu | Gly |
| | | | 100 | | | | | 105 | | | | | 110 | | |
| Thr | Val | Ile | Gln | Tyr | Gly | Asn | Val | Ile | Gln | Leu | Leu | His | Leu | Lys | Ser |
| | | 115 | | | | | 120 | | | | | 125 | | | |
| Asn | Lys | Tyr | Leu | Thr | Val | Asn | Lys | Arg | Leu | Pro | Ala | Leu | Leu | Glu | Lys |
| | 130 | | | | | 135 | | | | | 140 | | | | |
| Asn | Ala | Met | Arg | Val | Thr | Leu | Asp | Glu | Ala | Gly | Asn | Glu | Gly | Ser | Trp |
| 145 | | | | | 150 | | | | | 155 | | | | | 160 |
| Phe | Tyr | Ile | Gln | Pro | Phe | Tyr | Lys | Leu | Arg | Ser | Ile | Gly | Asp | Ser | Val |
| | | | | 165 | | | | | 170 | | | | | 175 | |
| Val | Ile | Gly | Asp | Lys | Val | Val | Leu | Asn | Pro | Val | Asn | Ala | Gly | Gln | Pro |
| | | | 180 | | | | | 185 | | | | | 190 | | |
| Leu | His | Ala | Ser | Ser | His | Gln | Leu | Val | Asp | Asn | Pro | Gly | Cys | Asn | Glu |
| | | | | 195 | | | | | 200 | | | | | 205 | |
| Val | Asn | Ser | Val | Asn | Cys | Asn | Thr | Ser | Trp | Lys | Ile | Val | Leu | Phe | Met |
| | 210 | | | | | 215 | | | | | 220 | | | | |
| Lys | Trp | Ser | Asp | Asn | Lys | Asp | Asp | Ile | Leu | Lys | Gly | Gly | Asp | Val | Val |
| 225 | | | | | 230 | | | | | 235 | | | | | 240 |
| Arg | Leu | Phe | His | Ala | Glu | Gln | Glu | Lys | Phe | Leu | Thr | Cys | Asp | Glu | His |
| | | | | 245 | | | | | 250 | | | | | 255 | |
| Arg | Lys | Lys | Gln | His | Val | Phe | Leu | Arg | Thr | Thr | Gly | Arg | Gln | Ser | Ala |
| | | | 260 | | | | | 265 | | | | | 270 | | |
| Thr | Ser | Ala | Thr | Ser | Ser | Lys | Ala | Leu | Trp | Glu | Val | Glu | Val | Val | Gln |
| | | | | 275 | | | | | 280 | | | | | 285 | |
| His | Asp | Pro | Cys | Arg | Gly | Gly | Ala | Gly | Tyr | Trp | Asn | Ser | Leu | Phe | Arg |
| | | 290 | | | | | 295 | | | | | 300 | | | |
| Phe | Lys | His | Leu | Ala | Thr | Gly | His | Tyr | Leu | Ala | Ala | Glu | Val | Asp | Pro |
| 305 | | | | | 310 | | | | | 315 | | | | | 320 |
| Asp | Phe | Glu | Glu | Glu | Cys | Leu | Glu | Phe | Gln | Pro | Ser | Val | Asp | Pro | Asp |
| | | | | 325 | | | | | 330 | | | | | 335 | |
| Gln | Asp | Ala | Ser | Arg | Ser | Arg | Leu | Arg | Asn | Ala | Gln | Glu | Lys | Met | Val |
| | | | 340 | | | | | 345 | | | | | 350 | | |
| Tyr | Ser | Leu | Val | Ser | Val | Pro | Glu | Gly | Asn | Asp | Ile | Ser | Ser | Ile | Phe |
| | | | 355 | | | | | 360 | | | | | 365 | | |
| Glu | Leu | Asp | Pro | Thr | Thr | Leu | Arg | Gly | Gly | Asp | Ser | Leu | Val | Pro | Arg |
| | 370 | | | | | 375 | | | | | 380 | | | | |

-continued

```
Asn Ser Tyr Val Arg Leu Arg His Leu Cys Thr Asn Thr Trp Val His
385                 390                 395                 400

Ser Thr Asn Ile Pro Ile Asp Lys Glu Glu Lys Pro Val Met Leu
            405                 410                 415

Lys Ile Gly Thr Ser Pro Leu Lys Glu Asp Lys Glu Ala Phe Ala Ile
                420                 425                 430

Val Pro Val Ser Pro Ala Glu Val Arg Asp Leu Asp Phe Ala Asn Asp
        435                 440                 445

Ala Ser Lys Val Leu Gly Ser Ile Ala Gly Lys Leu Glu Lys Gly Thr
450                 455                 460

Ile Thr Gln Asn Glu Arg Arg Ser Val Thr Lys Leu Leu Glu Asp Leu
465                 470                 475                 480

Val Tyr Phe Val Thr Gly Gly Thr Asn Ser Gly Gln Asp Val Leu Glu
                485                 490                 495

Val Val Phe Ser Lys Pro Asn Arg Glu Arg Gln Lys Leu Met Arg Glu
                500                 505                 510

Gln Asn Ile Leu Lys Gln Ile Phe Lys Leu Leu Gln Ala Pro Phe Thr
            515                 520                 525

Asp Cys Gly Asp Gly Pro Met Leu Arg Leu Glu Glu Leu Gly Asp Gln
530                 535                 540

Arg His Ala Pro Phe Arg His Ile Cys Arg Leu Cys Tyr Arg Val Leu
545                 550                 555                 560

Arg His Ser Gln Gln Asp Tyr Arg Lys Asn Gln Glu Tyr Ile Ala Lys
                565                 570                 575

Gln Phe Gly Phe Met Gln Lys Gln Ile Gly Tyr Asp Val Leu Ala Glu
                580                 585                 590

Asp Thr Ile Thr Ala Leu Leu His Asn Asn Arg Lys Leu Leu Glu Lys
            595                 600                 605

His Ile Thr Ala Ala Glu Ile Asp Thr Phe Val Ser Leu Val Arg Lys
610                 615                 620

Asn Arg Glu Pro Arg Phe Leu Asp Tyr Leu Ser Asp Leu Cys Val Ser
625                 630                 635                 640

Met Asn Lys Ser Ile Pro Val Thr Gln Glu Leu Ile Cys Lys Ala Val
                645                 650                 655

Leu Asn Pro Thr Asn Ala Asp Ile Leu Ile Glu Thr Lys Leu Val Leu
            660                 665                 670

Ser Arg Phe Glu Phe Glu Gly Val Ser Thr Gly Glu Asn Ala Leu Glu
        675                 680                 685

Ala Gly Glu Asp Glu Glu Val Trp Leu Phe Trp Arg Asp Ser Asn
690                 695                 700

Lys Glu Ile Arg Ser Lys Ser Val Arg Glu Leu Ala Gln Asp Ala Lys
705                 710                 715                 720

Glu Gly Gln Lys Glu Asp Arg Asp Val Leu Ser Tyr Tyr Arg Tyr Gln
            725                 730                 735

Leu Asn Leu Phe Ala Arg Met Cys Leu Asp Arg Gln Tyr Leu Ala Ile
                740                 745                 750

Asn Glu Ile Ser Gly Gln Leu Asp Val Asp Leu Ile Leu Arg Cys Met
            755                 760                 765

Ser Asp Glu Asn Leu Pro Tyr Asp Leu Arg Ala Ser Phe Cys Arg Leu
770                 775                 780

Met Leu His Met His Val Asp Arg Asp Pro Gln Glu Gln Val Thr Pro
785                 790                 795                 800

Val Lys Tyr Ala Arg Leu Trp Ser Glu Ile Pro Ser Glu Ile Ala Ile
                805                 810                 815
```

Asp Asp Tyr Asp Ser Ser Gly Ala Ser Lys Asp Glu Ile Lys Glu Arg
            820                 825                 830

Phe Ala Gln Thr Met Glu Phe Val Glu Glu Tyr Leu Arg Asp Val Val
            835                 840                 845

Cys Gln Arg Phe Pro Phe Ser Asp Lys Glu Lys Asn Lys Leu Thr Phe
            850                 855                 860

Glu Val Val Asn Leu Ala Arg Asn Leu Ile Tyr Phe Gly Phe Tyr Asn
865                 870                 875                 880

Phe Ser Asp Leu Leu Arg Leu Thr Lys Ile Leu Leu Ala Ile Leu Asp
                885                 890                 895

Cys Val His Val Thr Thr Ile Phe Pro Ile Ser Lys Met Thr Lys Gly
            900                 905                 910

Glu Glu Asn Lys Gly Ser Asn Val Met Arg Ser Ile His Gly Val Gly
            915                 920                 925

Glu Leu Met Thr Gln Val Val Leu Arg Gly Gly Phe Leu Pro Met
            930                 935                 940

Thr Pro Met Ala Ala Ala Pro Glu Gly Asn Val Lys Gln Ala Glu Pro
945                 950                 955                 960

Glu Lys Glu Asp Ile Met Val Met Asp Thr Lys Leu Lys Ile Ile Glu
                965                 970                 975

Ile Leu Gln Phe Ile Leu Asn Val Arg Leu Asp Tyr Arg Ile Ser Cys
            980                 985                 990

Leu Leu Cys Ile Phe Lys Arg Glu  Phe Asp Glu Ser Asn  Ser Gln Ser
            995                 1000                1005

Ser Glu  Thr Ser Ser Gly Asn  Ser Ser Gln Glu Gly  Pro Ser Asn
    1010                1015                1020

Val Pro  Gly Ala Leu Asp Phe  Glu His Ile Glu Glu  Gln Ala Glu
    1025                1030                1035

Gly Ile  Phe Gly Gly Ser Glu  Glu Asn Thr Pro Leu  Asp Leu Asp
    1040                1045                1050

Asp His  Gly Gly Arg Thr Phe  Leu Arg Val Leu Leu  His Leu Thr
    1055                1060                1065

Met His  Asp Tyr Pro Pro Leu  Val Ser Gly Ala Leu  Gln Leu Leu
    1070                1075                1080

Phe Arg  His Phe Ser Gln Arg  Gln Glu Val Leu Gln  Ala Phe Lys
    1085                1090                1095

Gln Val  Gln Leu Leu Val Thr  Ser Gln Asp Val Asp  Asn Tyr Lys
    1100                1105                1110

Gln Ile  Lys Gln Asp Leu Asp  Gln Leu Arg Ser Ile  Val Glu Lys
    1115                1120                1125

Ser Glu  Leu Trp Val Tyr Lys  Gly Gln Gly Pro Asp  Glu Pro Met
    1130                1135                1140

Asp Gly  Ala Ser Gly Glu Asn  Glu His Lys Lys Thr  Glu Glu Gly
    1145                1150                1155

Thr Ser  Lys Pro Leu Lys His  Glu Ser Thr Ser Ser  Tyr Asn Tyr
    1160                1165                1170

Arg Val  Val Lys Glu Ile Leu  Ile Arg Leu Ser Lys  Leu Cys Val
    1175                1180                1185

Gln Glu  Ser Ala Ser Val Arg  Lys Ser Arg Lys Gln  Gln Gln Arg
    1190                1195                1200

Leu Leu  Arg Asn Met Gly Ala  His Ala Val Val Leu  Glu Leu Leu
    1205                1210                1215

Gln Ile  Pro Tyr Glu Lys Ala  Glu Asp Thr Lys Met  Gln Glu Ile

-continued

```
          1220                1225                1230
Met Arg Leu Ala His Glu Phe Leu Gln Asn Phe Cys Ala Gly Asn
    1235                1240                1245

Gln Gln Asn Gln Ala Leu Leu His Lys His Ile Asn Leu Phe Leu
    1250                1255                1260

Asn Pro Gly Ile Leu Glu Ala Val Thr Met Gln His Ile Phe Met
    1265                1270                1275

Asn Asn Phe Gln Leu Cys Ser Glu Ile Asn Glu Arg Val Val Gln
    1280                1285                1290

His Phe Val His Cys Ile Glu Thr His Gly Arg Asn Val Gln Tyr
    1295                1300                1305

Ile Lys Phe Leu Gln Thr Ile Val Lys Ala Glu Gly Lys Phe Ile
    1310                1315                1320

Lys Lys Cys Gln Asp Met Val Met Ala Glu Leu Val Asn Ser Gly
    1325                1330                1335

Glu Asp Val Leu Val Phe Tyr Asn Asp Arg Ala Ser Phe Gln Thr
    1340                1345                1350

Leu Ile Gln Met Met Arg Ser Glu Arg Asp Arg Met Asp Glu Asn
    1355                1360                1365

Ser Pro Leu Phe Met Tyr His Ile His Leu Val Glu Leu Leu Ala
    1370                1375                1380

Val Cys Thr Glu Gly Lys Asn Val Tyr Thr Glu Ile Lys Cys Asn
    1385                1390                1395

Ser Leu Leu Pro Leu Asp Asp Ile Val Arg Val Val Thr His Glu
    1400                1405                1410

Asp Cys Ile Pro Glu Val Lys Ile Ala Tyr Ile Asn Phe Leu Asn
    1415                1420                1425

His Cys Tyr Val Asp Thr Glu Val Glu Met Lys Glu Ile Tyr Thr
    1430                1435                1440

Ser Asn His Met Trp Lys Leu Phe Glu Asn Phe Leu Val Asp Ile
    1445                1450                1455

Cys Arg Ala Cys Asn Asn Thr Ser Asp Arg Lys His Ala Asp Ser
    1460                1465                1470

Val Leu Glu Lys Tyr Val Thr Glu Ile Val Met Ser Ile Val Thr
    1475                1480                1485

Thr Phe Phe Ser Ser Pro Phe Ser Asp Gln Ser Thr Thr Leu Gln
    1490                1495                1500

Thr Arg Gln Pro Val Phe Val Gln Leu Leu Gln Gly Val Phe Arg
    1505                1510                1515

Val Tyr His Cys Asn Trp Leu Met Pro Ser Gln Lys Ala Ser Val
    1520                1525                1530

Glu Ser Cys Ile Arg Val Leu Ser Asp Val Ala Lys Ser Arg Ala
    1535                1540                1545

Ile Ala Ile Pro Val Asp Leu Asp Ser Gln Val Asn Asn Leu Phe
    1550                1555                1560

Leu Lys Ser His Asn Ile Val Gln Lys Thr Ala Met Asn Trp Arg
    1565                1570                1575

Leu Ser Ala Arg Asn Ala Ala Arg Arg Asp Xaa Val Leu Ala Ala
    1580                1585                1590

Ser Arg Asp Tyr Arg Asn Ile Ile Glu Arg Leu Gln Asp Ile Val
    1595                1600                1605

Ser Ala Leu Glu Asp Arg Leu Arg Pro Leu Val Gln Ala Glu Leu
    1610                1615                1620
```

| | | | | | | | | | | | |
|---|---|---|---|---|---|---|---|---|---|---|---|
| Ser | Val | Leu | Val | Asp | Val | Leu | His | Arg | Pro | Glu | Leu | Leu | Phe | Pro |
| 1625 | | | | | 1630 | | | | | 1635 | | | | |
| Glu | Asn | Thr | Asp | Ala | Arg | Arg | Lys | Cys | Glu | Ser | Gly | Gly | Phe | Ile |
| 1640 | | | | | 1645 | | | | | 1650 | | | | |
| Cys | Lys | Leu | Ile | Lys | His | Thr | Lys | Gln | Leu | Leu | Glu | Glu | Asn | Glu |
| 1655 | | | | | 1660 | | | | | 1665 | | | | |
| Glu | Lys | Leu | Cys | Ile | Lys | Val | Leu | Gln | Thr | Leu | Arg | Glu | Met | Met |
| 1670 | | | | | 1675 | | | | | 1680 | | | | |
| Thr | Lys | Asp | Arg | Gly | Tyr | Gly | Glu | Lys | Gln | Ile | Ser | Ile | Asp | Glu |
| 1685 | | | | | 1690 | | | | | 1695 | | | | |
| Leu | Glu | Asn | Ala | Glu | Leu | Pro | Gln | Pro | Pro | Glu | Ala | Glu | Asn | Ser |
| 1700 | | | | | 1705 | | | | | 1710 | | | | |
| Thr | Glu | Glu | Leu | Glu | Pro | Ser | Pro | Pro | Leu | Arg | Gln | Leu | Glu | Asp |
| 1715 | | | | | 1720 | | | | | 1725 | | | | |
| His | Lys | Arg | Gly | Glu | Ala | Leu | Arg | Gln | Ile | Leu | Val | Asn | Arg | Tyr |
| 1730 | | | | | 1735 | | | | | 1740 | | | | |
| Tyr | Gly | Asn | Ile | Arg | Pro | Ser | Gly | Arg | Arg | Glu | Xaa | Leu | Thr | Ser |
| 1745 | | | | | 1750 | | | | | 1755 | | | | |
| Phe | Gly | Asn | Gly | Pro | Leu | Ser | Pro | Gly | Gly | Pro | Ser | Lys | Pro | Gly |
| 1760 | | | | | 1765 | | | | | 1770 | | | | |
| Gly | Gly | Gly | Gly | Gly | Pro | Gly | Ser | Gly | Ser | Thr | Ser | Arg | Gly | Glu |
| 1775 | | | | | 1780 | | | | | 1785 | | | | |
| Met | Ser | Leu | Ala | Glu | Val | Gln | Cys | His | Leu | Asp | Lys | Glu | Gly | Ala |
| 1790 | | | | | 1795 | | | | | 1800 | | | | |
| Ser | Asn | Leu | Val | Ile | Asp | Leu | Ile | Met | Asn | Ala | Ser | Ser | Asp | Arg |
| 1805 | | | | | 1810 | | | | | 1815 | | | | |
| Val | Phe | His | Glu | Ser | Ile | Leu | Leu | Ala | Ile | Ala | Leu | Leu | Glu | Gly |
| 1820 | | | | | 1825 | | | | | 1830 | | | | |
| Gly | Asn | Thr | Thr | Ile | Gln | His | Ser | Phe | Phe | Cys | Arg | Leu | Thr | Glu |
| 1835 | | | | | 1840 | | | | | 1845 | | | | |
| Asp | Lys | Lys | Ser | Glu | Lys | Phe | Phe | Lys | Val | Phe | Tyr | Asp | Arg | Met |
| 1850 | | | | | 1855 | | | | | 1860 | | | | |
| Lys | Val | Ala | Gln | Gln | Glu | Ile | Lys | Ala | Thr | Val | Thr | Val | Asn | Thr |
| 1865 | | | | | 1870 | | | | | 1875 | | | | |
| Ser | Asp | Leu | Gly | Asn | Lys | Lys | Lys | Asp | Asp | Glu | Val | Asp | Arg | Asp |
| 1880 | | | | | 1885 | | | | | 1890 | | | | |
| Ala | Pro | Ser | Arg | Lys | Lys | Ala | Lys | Glu | Pro | Thr | Thr | Gln | Ile | Thr |
| 1895 | | | | | 1900 | | | | | 1905 | | | | |
| Glu | Glu | Val | Arg | Asp | Gln | Leu | Leu | Glu | Ala | Ser | Ala | Ala | Thr | Arg |
| 1910 | | | | | 1915 | | | | | 1920 | | | | |
| Lys | Ala | Phe | Thr | Thr | Phe | Arg | Arg | Glu | Ala | Asp | Pro | Asp | Asp | His |
| 1925 | | | | | 1930 | | | | | 1935 | | | | |
| Tyr | Gln | Ser | Gly | Glu | Gly | Thr | Gln | Ala | Thr | Thr | Asp | Lys | Ala | Lys |
| 1940 | | | | | 1945 | | | | | 1950 | | | | |
| Asp | Asp | Leu | Glu | Met | Ser | Ala | Val | Ile | Thr | Ile | Met | Gln | Pro | Ile |
| 1955 | | | | | 1960 | | | | | 1965 | | | | |
| Leu | Arg | Phe | Leu | Gln | Leu | Leu | Cys | Glu | Asn | His | Asn | Arg | Asp | Leu |
| 1970 | | | | | 1975 | | | | | 1980 | | | | |
| Gln | Asn | Phe | Leu | Arg | Cys | Gln | Asn | Asn | Lys | Thr | Asn | Tyr | Asn | Leu |
| 1985 | | | | | 1990 | | | | | 1995 | | | | |
| Val | Cys | Glu | Thr | Leu | Gln | Phe | Leu | Asp | Cys | Ile | Cys | Gly | Ser | Thr |
| 2000 | | | | | 2005 | | | | | 2010 | | | | |
| Thr | Gly | Gly | Leu | Gly | Leu | Leu | Gly | Leu | Tyr | Ile | Asn | Glu | Lys | Asn |
| 2015 | | | | | 2020 | | | | | 2025 | | | | |

```
Val Ala Leu Ile Asn Gln Thr Leu Glu Ser Leu Thr Glu Tyr Cys
    2030                2035                2040

Gln Gly Pro Cys His Glu Asn Gln Asn Cys Ile Ala Thr His Glu
    2045                2050                2055

Ser Asn Gly Ile Asp Ile Ile Thr Ala Leu Ile Leu Asn Asp Ile
    2060                2065                2070

Asn Pro Leu Gly Lys Lys Arg Met Asp Leu Val Leu Glu Leu Lys
    2075                2080                2085

Asn Asn Ala Ser Lys Leu Leu Leu Ala Ile Met Glu Ser Arg His
    2090                2095                2100

Asp Ser Glu Asn Ala Glu Arg Ile Leu Tyr Asn Met Arg Pro Lys
    2105                2110                2115

Glu Leu Val Glu Val Ile Lys Lys Ala Tyr Met Gln Gly Glu Val
    2120                2125                2130

Glu Phe Glu Asp Gly Glu Asn Gly Glu Asp Gly Ala Ala Ser Pro
    2135                2140                2145

Arg Asn Val Gly His Asn Ile Tyr Ile Leu Ala His Gln Leu Ala
    2150                2155                2160

Arg His Asn Lys Glu Leu Gln Thr Met Leu Lys Pro Gly Gly Gln
    2165                2170                2175

Val Asp Gly Asp Glu Ala Leu Glu Phe Tyr Ala Lys His Thr Ala
    2180                2185                2190

Gln Ile Glu Ile Val Arg Leu Asp Arg Thr Met Glu Gln Ile Val
    2195                2200                2205

Phe Pro Val Pro Ser Ile Cys Glu Phe Leu Thr Lys Glu Ser Lys
    2210                2215                2220

Leu Arg Ile Tyr Tyr Thr Thr Glu Arg Asp Glu Gln Gly Ser Lys
    2225                2230                2235

Ile Asn Asp Phe Phe Leu Arg Ser Glu Asp Leu Phe Asn Glu Met
    2240                2245                2250

Asn Trp Gln Lys Lys Leu Arg Ala Gln Pro Val Leu Tyr Trp Cys
    2255                2260                2265

Ala Arg Asn Met Ser Phe Trp Ser Ser Ile Ser Phe Asn Leu Ala
    2270                2275                2280

Val Leu Met Asn Leu Leu Val Ala Phe Phe Tyr Pro Phe Lys Gly
    2285                2290                2295

Val Arg Gly Gly Thr Leu Glu Pro His Trp Ser Gly Leu Leu Trp
    2300                2305                2310

Thr Ala Met Leu Ile Ser Leu Ala Ile Val Ile Ala Leu Pro Lys
    2315                2320                2325

Pro His Gly Ile Arg Ala Leu Ile Ala Ser Thr Ile Leu Arg Leu
    2330                2335                2340

Ile Phe Ser Val Gly Leu Gln Pro Thr Leu Phe Leu Leu Gly Ala
    2345                2350                2355

Phe Asn Val Cys Asn Lys Ile Ile Phe Leu Met Ser Phe Val Gly
    2360                2365                2370

Asn Cys Gly Thr Phe Thr Arg Gly Tyr Arg Ala Met Val Leu Asp
    2375                2380                2385

Val Glu Phe Leu Tyr His Leu Tyr Leu Leu Ile Cys Ala Met
    2390                2395                2400

Gly Leu Phe Val His Glu Phe Phe Tyr Ser Leu Leu Leu Phe Asp
    2405                2410                2415

Leu Val Tyr Arg Glu Glu Thr Leu Leu Asn Val Ile Lys Ser Val
```

```
                   2420                2425                2430

Thr  Arg  Asn  Gly  Arg  Pro  Ile  Ile  Leu  Thr  Ala  Ala  Leu  Ala  Leu
     2435                2440                2445

Ile  Leu  Val  Tyr  Leu  Phe  Ser  Ile  Val  Gly  Tyr  Leu  Phe  Phe  Lys
     2450                2455                2460

Asp  Asp  Phe  Ile  Leu  Glu  Val  Asp  Arg  Leu  Pro  Asn  Glu  Thr  Ala
     2465                2470                2475

Gly  Pro  Glu  Thr  Gly  Glu  Ser  Leu  Ala  Asn  Asp  Phe  Leu  Tyr  Ser
     2480                2485                2490

Asp  Val  Cys  Arg  Val  Glu  Thr  Gly  Glu  Asn  Cys  Thr  Ser  Pro  Ala
     2495                2500                2505

Pro  Lys  Glu  Glu  Leu  Leu  Pro  Val  Glu  Glu  Thr  Glu  Gln  Asp  Lys
     2510                2515                2520

Glu  His  Thr  Cys  Glu  Thr  Leu  Leu  Met  Cys  Ile  Val  Thr  Val  Leu
     2525                2530                2535

Ser  His  Gly  Leu  Arg  Ser  Gly  Gly  Gly  Val  Gly  Asp  Val  Leu  Arg
     2540                2545                2550

Lys  Pro  Ser  Lys  Glu  Glu  Pro  Leu  Phe  Ala  Ala  Arg  Val  Ile  Tyr
     2555                2560                2565

Asp  Leu  Leu  Phe  Phe  Phe  Met  Val  Ile  Ile  Val  Leu  Asn  Leu
     2570                2575                2580

Ile  Phe  Gly  Val  Ile  Ile  Asp  Thr  Phe  Ala  Asp  Leu  Arg  Ser  Glu
     2585                2590                2595

Lys  Gln  Lys  Lys  Glu  Glu  Ile  Leu  Lys  Thr  Thr  Cys  Phe  Ile  Cys
     2600                2605                2610

Gly  Leu  Glu  Arg  Asp  Lys  Phe  Asp  Asn  Lys  Thr  Val  Thr  Phe  Glu
     2615                2620                2625

Glu  His  Ile  Lys  Glu  Glu  His  Asn  Met  Trp  His  Tyr  Leu  Cys  Phe
     2630                2635                2640

Ile  Val  Leu  Val  Lys  Val  Lys  Asp  Ser  Thr  Glu  Tyr  Thr  Gly  Pro
     2645                2650                2655

Glu  Ser  Tyr  Val  Ala  Glu  Met  Ile  Arg  Glu  Arg  Asn  Leu  Asp  Trp
     2660                2665                2670

Phe  Pro  Arg  Met  Arg  Ala  Met  Ser  Leu  Val  Ser  Ser  Asp  Ser  Glu
     2675                2680                2685

Gly  Glu  Gln  Asn  Glu  Leu  Arg  Asn  Leu  Gln  Glu  Lys  Leu  Glu  Ser
     2690                2695                2700

Thr  Met  Lys  Leu  Val  Thr  Asn  Leu  Ser  Gly  Gln  Leu  Ser  Glu  Leu
     2705                2710                2715

Lys  Asp  Gln  Met  Thr  Glu  Gln  Arg  Lys  Gln  Lys  Gln  Arg  Ile  Gly
     2720                2725                2730

Leu  Leu  Gly  His  Pro  Pro  His  Met  Asn  Val  Asn  Pro  Gln  Gln  Pro
     2735                2740                2745

Ala  Phe  Leu  Leu  Leu  Glu  Asn  Gly  Thr  His  Arg  Glu  Gly  Leu  Ala
     2750                2755                2760

Thr  Arg  Ser  Glu  Gln  Glu  Asn  Cys  Glu  Ser
     2765                2770

<210> SEQ ID NO 208
<211> LENGTH: 518
<212> TYPE: PRT
<213> ORGANISM: Homo sapiens

<400> SEQUENCE: 208

Met Asp Gln Thr Pro Pro Ala Arg Pro Glu Tyr Leu Val Ser Gly Ile
```

-continued

```
1               5               10              15
Arg Thr Pro Pro Val Arg Arg Asn Ser Lys Leu Ala Thr Leu Gly Arg
                20              25              30

Ile Phe Lys Pro Trp Lys Trp Arg Lys Lys Lys Asn Glu Lys Leu Lys
                35              40              45

Gln Thr Thr Ser Ala Leu Glu Lys Lys Met Ala Gly Arg Gln Gly Arg
                50              55              60

Glu Glu Leu Ile Lys Lys Gly Leu Leu Glu Met Met Glu Gln Asp Ala
65                      70              75              80

Glu Ser Lys Thr Cys Asn Pro Asp Gly Gly Pro Arg Ser Val Gln Ser
                        85              90              95

Glu Pro Pro Thr Pro Lys Ser Glu Thr Leu Thr Ser Glu Asp Ala Gln
                100             105             110

Pro Gly Ser Pro Leu Ala Thr Gly Thr Asp Gln Val Ser Leu Asp Lys
                115             120             125

Pro Leu Ser Ser Ala Ala His Leu Asp Asp Ala Ala Lys Met Pro Ser
                130             135             140

Ala Ser Ser Gly Glu Glu Ala Asp Ala Gly Ser Leu Leu Pro Thr Thr
145                     150             155             160

Asn Glu Leu Ser Gln Ala Leu Ala Gly Ala Asp Ser Leu Asp Ser Pro
                        165             170             175

Pro Arg Pro Leu Glu Arg Ser Val Gly Gln Leu Pro Ser Pro Pro Leu
                180             185             190

Leu Pro Thr Pro Pro Lys Ala Ser Ser Lys Thr Thr Lys Asn Val
                195             200             205

Thr Gly Gln Ala Thr Leu Phe Gln Ala Ser Ser Met Lys Ser Ala Asp
                210             215             220

Pro Ser Leu Arg Gly Gln Leu Ser Thr Pro Thr Gly Ser Pro His Leu
225                     230             235             240

Thr Thr Val His Arg Pro Leu Pro Pro Ser Arg Val Ile Glu Glu Leu
                        245             250             255

His Arg Ala Leu Ala Thr Lys His Arg Gln Asp Ser Phe Gln Gly Arg
                260             265             270

Glu Ser Lys Gly Ser Pro Lys Arg Arg Leu Asp Val Arg Leu Ser Arg
                275             280             285

Thr Ser Ser Val Glu Arg Gly Lys Glu Arg Glu Ala Trp Ser Phe
                290             295             300

Asp Gly Ala Leu Glu Asn Lys Arg Thr Ala Lys Glu Ser Glu Glu
305                     310             315             320

Asn Lys Glu Asn Leu Ile Ile Asn Ser Glu Leu Lys Asp Asp Leu Leu
                        325             330             335

Leu Tyr Gln Asp Glu Glu Ala Leu Asn Asp Ser Ile Ile Ser Gly Thr
                340             345             350

Leu Pro Arg Lys Cys Arg Lys Glu Leu Leu Ala Val Lys Leu Arg Asn
                355             360             365

Arg Pro Ser Lys Gln Glu Leu Glu Asp Arg Asn Ile Phe Pro Arg Arg
                370             375             380

Thr Asp Glu Glu Arg Gln Glu Ile Arg Gln Ile Glu Met Lys Leu
385                     390             395             400

Ser Lys Arg Leu Ser Gln Arg Pro Ala Val Glu Leu Glu Arg Arg
                        405             410             415

Asn Ile Leu Lys Gln Arg Asn Asp Gln Thr Glu Gln Glu Glu Arg Arg
                420             425             430
```

```
Glu Ile Lys Gln Arg Leu Thr Arg Lys Leu Asn Gln Arg Pro Thr Val
        435                 440                 445

Asp Glu Leu Arg Asp Arg Lys Ile Leu Ile Arg Phe Ser Asp Tyr Val
        450                 455                 460

Glu Val Ala Lys Ala Gln Asp Tyr Asp Arg Arg Ala Asp Lys Pro Trp
465                 470                 475                 480

Thr Arg Leu Ser Ala Ala Asp Lys Ala Ala Ile Arg Lys Glu Leu Asn
                485                 490                 495

Glu Tyr Lys Ser Asn Glu Met Glu Val His Ala Ser Ser Lys His Leu
                500                 505                 510

Thr Arg Phe His Arg Pro
        515

<210> SEQ ID NO 209
<211> LENGTH: 940
<212> TYPE: PRT
<213> ORGANISM: Homo sapiens

<400> SEQUENCE: 209

Met Gly Ser Gly Pro Ile Asp Pro Lys Glu Leu Leu Lys Gly Leu Asp
1               5                   10                  15

Ser Phe Leu Asn Arg Asp Gly Glu Val Lys Ser Val Asp Gly Ile Ser
                20                  25                  30

Lys Ile Phe Ser Leu Met Lys Glu Ala Arg Lys Met Val Ser Arg Cys
            35                  40                  45

Thr Tyr Leu Asn Ile Leu Leu Gln Thr Arg Ser Pro Glu Ile Leu Val
        50                  55                  60

Lys Phe Ile Asp Val Gly Gly Tyr Lys Leu Leu Asn Asn Trp Leu Thr
65                  70                  75                  80

Tyr Ser Lys Thr Thr Asn Asn Ile Pro Leu Leu Gln Gln Ile Leu Leu
                85                  90                  95

Thr Leu Gln His Leu Pro Leu Thr Val Asp His Leu Lys Gln Asn Asn
            100                 105                 110

Thr Ala Lys Leu Val Lys Gln Leu Ser Lys Ser Ser Glu Asp Glu Glu
        115                 120                 125

Leu Arg Lys Leu Ala Ser Val Leu Val Ser Asp Trp Met Ala Val Ile
    130                 135                 140

Arg Ser Gln Ser Ser Thr Gln Pro Ala Glu Lys Asp Lys Lys Lys Arg
145                 150                 155                 160

Lys Asp Glu Gly Lys Ser Arg Thr Thr Leu Pro Glu Arg Pro Leu Thr
                165                 170                 175

Glu Val Lys Ala Glu Thr Arg Ala Glu Glu Ala Pro Glu Lys Lys Arg
            180                 185                 190

Glu Lys Pro Lys Ser Leu Arg Thr Thr Ala Pro Ser His Ala Lys Phe
        195                 200                 205

Arg Ser Thr Gly Leu Glu Leu Gly Thr Pro Ser Leu Val Pro Val Lys
    210                 215                 220

Lys Asn Ala Ser Thr Val Val Ser Asp Lys Tyr Asn Leu Lys Pro
225                 230                 235                 240

Ile Pro Leu Lys Arg Gln Ser Asn Val Ala Ala Pro Gly Asp Ala Thr
                245                 250                 255

Pro Pro Ala Glu Lys Lys Tyr Lys Pro Leu Asn Thr Pro Asn Ala
            260                 265                 270

Thr Lys Glu Ile Lys Val Lys Ile Ile Pro Pro Gln Pro Met Glu Gly
        275                 280                 285
```

```
Leu Gly Phe Leu Asp Ala Leu Asn Ser Ala Pro Val Pro Gly Ile Lys
    290                 295                 300

Ile Lys Lys Lys Lys Val Leu Ser Pro Thr Ala Ala Lys Pro Ser
305                 310                 315                 320

Pro Phe Glu Gly Lys Thr Ser Thr Glu Pro Ser Thr Ala Lys Pro Ser
                325                 330                 335

Ser Pro Glu Pro Ala Pro Ser Glu Ala Met Asp Ala Asp Arg Pro
    340                 345                 350

Gly Thr Pro Val Pro Val Glu Val Pro Glu Leu Met Asp Thr Ala
            355                 360                 365

Ser Leu Glu Pro Gly Ala Leu Asp Ala Lys Pro Val Glu Ser Pro Gly
    370                 375                 380

Asp Pro Asn Gln Leu Thr Arg Lys Gly Arg Lys Arg Lys Ser Val Thr
385                 390                 395                 400

Trp Pro Glu Glu Gly Lys Leu Arg Glu Tyr Phe Tyr Phe Glu Leu Asp
                405                 410                 415

Glu Thr Glu Arg Val Asn Val Asn Lys Ile Lys Asp Phe Gly Glu Ala
            420                 425                 430

Ala Lys Arg Glu Ile Leu Ser Asp Arg His Ala Phe Glu Thr Ala Arg
            435                 440                 445

Arg Leu Ser His Asp Asn Met Glu Glu Lys Val Pro Trp Val Cys Pro
    450                 455                 460

Arg Pro Leu Val Leu Pro Ser Pro Leu Val Thr Pro Gly Ser Asn Ser
465                 470                 475                 480

Gln Glu Arg Tyr Ile Gln Ala Glu Arg Glu Lys Gly Ile Leu Gln Glu
                485                 490                 495

Leu Phe Leu Asn Lys Glu Ser Pro His Glu Pro Asp Pro Glu Pro Tyr
            500                 505                 510

Glu Pro Ile Pro Pro Lys Leu Ile Pro Leu Asp Glu Glu Cys Ser Met
            515                 520                 525

Asp Glu Thr Pro Tyr Val Glu Thr Leu Glu Pro Gly Gly Ser Gly Gly
    530                 535                 540

Ser Pro Asp Gly Ala Gly Gly Ser Lys Leu Pro Pro Val Leu Ala Asn
545                 550                 555                 560

Leu Met Gly Ser Met Gly Ala Gly Lys Gly Pro Gln Gly Pro Gly Gly
                565                 570                 575

Gly Gly Ile Asn Val Gln Glu Ile Leu Thr Ser Ile Met Gly Ser Pro
            580                 585                 590

Asn Ser His Pro Ser Glu Glu Leu Leu Lys Gln Pro Asp Tyr Ser Asp
    595                 600                 605

Lys Ile Lys Gln Met Leu Val Pro His Gly Leu Leu Gly Pro Gly Pro
610                 615                 620

Ile Ala Asn Gly Phe Pro Pro Gly Pro Gly Gly Pro Lys Gly Met
625                 630                 635                 640

Gln His Phe Pro Pro Gly Pro Gly Gly Pro Met Pro Gly Pro His Gly
                645                 650                 655

Gly Pro Gly Gly Pro Val Gly Pro Arg Leu Leu Gly Pro Pro Pro
            660                 665                 670

Pro Arg Gly Gly Asp Pro Phe Trp Asp Gly Pro Gly Asp Pro Met Arg
                675                 680                 685

Gly Gly Pro Met Arg Gly Gly Pro Gly Pro Gly Pro Tyr His
            690                 695                 700

Arg Gly Arg Gly Gly Arg Gly Asn Glu Pro Pro Pro Pro Pro
705                 710                 715                 720
```

```
Pro Phe Arg Gly Ala Arg Gly Gly Arg Ser Gly Gly Pro Pro Asn
            725                 730                 735

Gly Arg Gly Gly Pro Gly Gly Met Val Gly Gly Gly His Arg
            740                 745                 750

Pro His Glu Gly Pro Gly Gly Met Gly Asn Ser Ser Gly His Arg
            755                 760                 765

Pro His Glu Gly Pro Gly Gly Met Gly Ser Gly His Arg Pro His
            770                 775                 780

Glu Gly Pro Gly Gly Ser Met Gly Gly Gly Gly His Arg Pro His
785                 790                 795                 800

Glu Gly Pro Gly Gly Gly Ile Ser Gly Ser Gly His Arg Pro His
            805                 810                 815

Glu Gly Pro Gly Gly Gly Met Gly Ala Gly Gly His Arg Pro His
            820                 825                 830

Glu Gly Pro Gly Gly Ser Met Gly Gly Ser Gly Gly His Arg Pro His
            835                 840                 845

Glu Gly Pro Gly His Gly Gly Pro His Gly His Arg Pro His Asp Val
            850                 855                 860

Pro Gly His Arg Gly His Asp His Arg Gly Pro Pro His Glu His
865                 870                 875                 880

Arg Gly His Asp Gly Pro Gly His Gly Gly Gly His Arg Gly His
            885                 890                 895

Asp Gly Gly His Ser His Gly Gly Asp Met Ser Asn Arg Pro Val Cys
            900                 905                 910

Arg His Phe Met Met Lys Gly Asn Cys Arg Tyr Glu Asn Asn Cys Ala
            915                 920                 925

Phe Tyr His Pro Gly Val Asn Gly Pro Pro Leu Pro
            930                 935                 940

<210> SEQ ID NO 210
<211> LENGTH: 171
<212> TYPE: PRT
<213> ORGANISM: Homo sapiens
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid

<400> SEQUENCE: 210

Met Glu Gln Asp Asn Ser Pro Gln Lys Ile Gln Phe Thr Val Pro Leu
1               5                   10                  15

Leu Glu Pro His Leu Asp Pro Glu Ala Ala Glu Gln Ile Arg Arg Arg
                20                  25                  30

Arg Pro Xaa Pro Ala Thr Leu Val Leu Thr Ser Asp Gln Ser Ser Pro
            35                  40                  45

Glu Ile Asp Glu Asp Arg Ile Pro Asn Pro His Leu Lys Ser Thr Leu
        50                  55                  60

Ala Met Xaa Pro Arg Gln Arg Lys Lys Met Xaa Arg Ile Thr Pro Thr
65                  70                  75                  80

Met Lys Glu Leu Gln Met Met Val Glu His His Leu Gly Gln Gln Gln
                85                  90                  95
```

-continued

Gln Gly Glu Glu Pro Glu Gly Ala Ala Glu Ser Thr Gly Thr Gln Glu
            100                 105                 110

Ser Arg Pro Pro Gly Ile Pro Asp Thr Glu Val Glu Ser Arg Leu Gly
        115                 120                 125

Thr Ser Gly Thr Ala Lys Lys Thr Ala Glu Cys Ile Pro Lys Thr His
    130                 135                 140

Glu Arg Gly Ser Lys Glu Pro Ser Thr Lys Glu Pro Ser Thr His Ile
145                 150                 155                 160

Pro Pro Leu Asp Ser Lys Gly Ala Asn Ser Val
                165                 170

<210> SEQ ID NO 211
<211> LENGTH: 1098
<212> TYPE: PRT
<213> ORGANISM: Homo sapiens
<220> FEATURE:
<221> NAME/KEY: misc_feature
<222> LOCATION: (371)..(371)
<223> OTHER INFORMATION: Xaa can be any naturally occurring amino acid
<220> FEATURE:
<221> NAME/KEY: misc_feature
<222> LOCATION: (461)..(461)
<223> OTHER INFORMATION: Xaa can be any naturally occurring amino acid
<220> FEATURE:
<221> NAME/KEY: misc_feature
<222> LOCATION: (915)..(915)
<223> OTHER INFORMATION: Xaa can be any naturally occurring amino acid

<400> SEQUENCE: 211

Met Leu Lys Thr Glu Ser Ser Gly Glu Arg Thr Thr Leu Arg Ser Ala
1               5                   10                  15

Ser Pro His Arg Asn Ala Tyr Arg Thr Glu Phe Gln Ala Leu Lys Ser
            20                  25                  30

Thr Phe Asp Lys Pro Lys Ser Asp Gly Glu Gln Lys Thr Lys Glu Gly
        35                  40                  45

Glu Gly Ser Gln Gln Ser Arg Gly Arg Lys Tyr Gly Ser Asn Val Asn
    50                  55                  60

Arg Ile Lys Asn Leu Phe Met Gln Met Gly Met Glu Pro Asn Glu Asn
65                  70                  75                  80

Ala Ala Val Ile Ala Lys Thr Arg Gly Lys Gly Gly His Ser Ser Pro
                85                  90                  95

Gln Arg Arg Met Lys Pro Lys Glu Phe Leu Glu Lys Thr Asp Gly Ser
            100                 105                 110

Val Val Lys Leu Glu Ser Ser Val Ser Glu Arg Ile Ser Arg Phe Asp
        115                 120                 125

Thr Met Tyr Asp Gly Pro Ser Tyr Ser Lys Phe Thr Glu Thr Arg Lys
    130                 135                 140

Met Phe Glu Arg Ser Val His Glu Ser Gly Gln Asn Asn Arg Tyr Ser
145                 150                 155                 160

Pro Lys Lys Glu Lys Ala Gly Gly Ser Glu Pro Gln Asp Glu Trp Gly
            165                 170                 175

Gly Ser Lys Ser Asn Arg Gly Ser Thr Asp Ser Leu Asp Ser Leu Ser
        180                 185                 190

Ser Arg Thr Glu Ala Val Ser Pro Thr Val Ser Gln Leu Ser Ala Val
    195                 200                 205

Phe Glu Asn Thr Asp Ser Pro Ser Ala Ile Ile Ser Glu Lys Ala Glu
    210                 215                 220

Asn Asn Glu Tyr Ser Val Thr Gly His Tyr Pro Leu Asn Leu Pro Ser
225                 230                 235                 240

```
Val Thr Val Thr Asn Leu Asp Thr Phe Gly His Leu Lys Asp Ser Asn
            245                 250                 255

Ser Trp Pro Pro Ser Asn Lys Arg Gly Val Asp Thr Glu Asp Ala His
            260                 265                 270

Lys Ser Asn Ala Thr Pro Val Pro Glu Val Ala Ser Lys Ser Thr Ser
            275                 280                 285

Leu Ala Ser Ile Pro Gly Glu Glu Ile Gln Gln Ser Lys Glu Pro Glu
            290                 295                 300

Asp Ser Thr Ser Asn Gln Gln Thr Pro Asp Ser Ile Asp Lys Asp Gly
305                 310                 315                 320

Pro Glu Glu Pro Cys Ala Glu Ser Lys Ala Met Pro Lys Ser Glu Ile
                325                 330                 335

Pro Ser Pro Gln Ser Gln Leu Leu Glu Asp Ala Glu Ala Asn Leu Val
            340                 345                 350

Gly Arg Glu Ala Ala Lys Gln Gln Arg Lys Glu Leu Ala Gly Gly Asp
            355                 360                 365

Phe Thr Xaa Pro Asp Ala Ser Ala Ser Ser Cys Gly Lys Glu Val Pro
            370                 375                 380

Glu Asp Ser Asn Asn Phe Asp Gly Ser His Val Tyr Met His Ser Asp
385                 390                 395                 400

Tyr Asn Val Tyr Arg Val Arg Ser Arg Tyr Asn Ser Asp Trp Gly Glu
                405                 410                 415

Thr Gly Thr Glu Gln Asp Glu Glu Asp Ser Asp Glu Asn Ser Tyr
            420                 425                 430

Tyr Gln Pro Asp Met Glu Tyr Ser Glu Ile Val Gly Leu Pro Glu Glu
            435                 440                 445

Glu Glu Ile Pro Ala Asn Arg Lys Ile Lys Phe Ser Xaa Ala Pro Ile
450                 455                 460

Lys Val Phe Asn Thr Tyr Ser Asn Glu Asp Tyr Asp Arg Arg Asn Asp
465                 470                 475                 480

Glu Val Asp Pro Val Ala Ala Ser Ala Glu Tyr Glu Leu Glu Lys Arg
            485                 490                 495

Val Glu Lys Leu Glu Leu Phe Pro Val Glu Leu Glu Lys Asp Glu Asp
            500                 505                 510

Gly Leu Gly Ile Ser Ile Ile Gly Met Gly Val Gly Ala Asp Ala Gly
            515                 520                 525

Leu Glu Lys Leu Gly Ile Phe Val Lys Thr Val Thr Glu Gly Gly Ala
            530                 535                 540

Ala Gln Arg Asp Gly Arg Ile Gln Val Asn Asp Gln Ile Val Glu Val
545                 550                 555                 560

Asp Gly Ile Ser Leu Val Gly Val Thr Gln Asn Phe Ala Ala Thr Val
                565                 570                 575

Leu Arg Asn Thr Lys Gly Asn Val Arg Phe Val Ile Gly Arg Glu Lys
            580                 585                 590

Pro Gly Gln Val Ser Glu Val Ala Gln Leu Ile Ser Gln Thr Leu Glu
            595                 600                 605

Gln Glu Arg Arg Gln Arg Glu Leu Leu Glu Gln His Tyr Ala Gln Tyr
            610                 615                 620

Asp Ala Asp Asp Asp Glu Thr Gly Glu Tyr Ala Thr Asp Glu Glu
625                 630                 635                 640

Asp Glu Val Gly Pro Val Leu Pro Gly Ser Asp Met Ala Ile Glu Val
            645                 650                 655

Phe Glu Leu Pro Glu Asn Glu Asp Met Phe Ser Pro Ser Glu Leu Asp
```

```
                    660                665                670
Thr Ser Lys Leu Ser His Lys Phe Lys Glu Leu Gln Ile Lys His Ala
            675                680                685
Val Thr Glu Ala Glu Ile Gln Lys Leu Lys Thr Lys Leu Gln Ala Ala
            690                695                700
Glu Asn Glu Lys Val Arg Trp Glu Leu Glu Lys Thr Gln Leu Gln Gln
705                710                715                720
Asn Ile Glu Glu Asn Lys Glu Arg Met Leu Lys Leu Glu Ser Tyr Trp
            725                730                735
Ile Glu Ala Gln Thr Leu Cys His Thr Val Asn Glu His Leu Lys Glu
            740                745                750
Thr Gln Ser Gln Tyr Gln Ala Leu Glu Lys Lys Tyr Asn Lys Ala Lys
            755                760                765
Lys Leu Ile Lys Asp Phe Gln Gln Lys Glu Leu Asp Phe Ile Lys Arg
            770                775                780
Gln Glu Ala Glu Arg Lys Lys Ile Glu Asp Leu Glu Lys Ala His Leu
785                790                795                800
Val Glu Val Gln Gly Leu Gln Val Arg Ile Arg Asp Leu Glu Ala Glu
            805                810                815
Val Phe Arg Leu Leu Lys Gln Asn Gly Thr Gln Val Asn Asn Asn Asn
            820                825                830
Asn Ile Phe Glu Arg Arg Thr Ser Leu Gly Val Ser Lys Gly Asp
            835                840                845
Thr Met Glu Asn Leu Asp Gly Lys Gln Thr Ser Cys Gln Asp Gly Leu
850                855                860
Ser Gln Asp Leu Asn Glu Ala Val Pro Glu Thr Glu Arg Leu Asp Ser
865                870                875                880
Lys Ala Leu Lys Thr Arg Ala Gln Leu Ser Val Lys Asn Arg Arg Gln
            885                890                895
Arg Pro Ser Arg Thr Arg Leu Tyr Asp Ser Val Ser Ser Thr Asp Gly
            900                905                910
Glu Asp Xaa Leu Glu Arg Lys Asn Phe Thr Phe Asn Asp Asp Phe Ser
            915                920                925
Pro Ser Ser Thr Ser Ser Ala Asp Leu Ser Gly Leu Gly Ala Glu Pro
            930                935                940
Lys Thr Pro Gly Leu Ser Gln Ser Leu Ala Leu Ser Ser Asp Glu Ser
945                950                955                960
Leu Asp Met Ile Asp Asp Glu Ile Leu Asp Asp Gly Gln Ser Pro Lys
            965                970                975
His Ser Gln Cys Gln Asn Arg Ala Val Gln Glu Trp Ser Val Gln Gln
            980                985                990
Val Ser His Trp Leu Met Ser Leu  Asn Leu Glu Gln Tyr  Val Ser Glu
            995                1000                1005
Phe Ser  Ala Gln Asn Ile Thr  Gly Glu Gln Leu Leu  Gln Leu Asp
            1010                1015                1020
Gly Asn  Lys Leu Lys Ala Leu  Gly Met Thr Ala Ser  Gln Asp Arg
            1025                1030                1035
Ala Val  Val Lys Lys Leu  Lys Glu Met Lys Met  Ser Leu Glu
            1040                1045                1050
Lys Ala  Arg Lys Ala Gln Glu  Lys Met Glu Lys Gln  Arg Glu Lys
            1055                1060                1065
Leu Arg  Arg Lys Glu Gln Glu  Gln Met Gln Arg Lys  Ser Lys Lys
            1070                1075                1080
```

Thr Glu Lys Met Thr Ser Thr Thr Ala Glu Gly Ala Gly Glu Gln
        1085                1090                1095

<210> SEQ ID NO 212
<211> LENGTH: 40
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (18)..(18)
<223> OTHER INFORMATION: Xaa can be any naturally occurring amino acid

<400> SEQUENCE: 212

Lys Ile Ala Asp Phe Gly Trp Ser Val His Ala Pro Ser Ser Arg Arg
1               5                   10                  15

Thr Xaa Leu Cys Gly Thr Leu Asp Tyr Leu Pro Pro Glu Met Ile Glu
            20                  25                  30

Gly Arg Met His Asp Glu Lys Val
        35                  40

<210> SEQ ID NO 213
<211> LENGTH: 34
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (15)..(15)
<223> OTHER INFORMATION: Xaa can be any naturally occurring amino acid

<400> SEQUENCE: 213

Ala Lys Gln Lys Arg Asn Glu Gln Leu Lys Arg Trp Ile Gly Xaa Glu
1               5                   10                  15

Thr Asp Leu Glu Pro Pro Val Val Lys Arg Gln Lys Thr Lys Val Lys
            20                  25                  30

Phe Asp

<210> SEQ ID NO 214
<211> LENGTH: 44
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid

<400> SEQUENCE: 214

Ala Val Glu Ile Arg Ser Arg His Ser Xaa Tyr Pro Ala Gly Thr Glu
1               5                   10                  15

Asp Asp Glu Gly Met Gly Glu Glu Pro Ser Pro Phe Arg Gly Arg Ser
            20                  25                  30

Arg Xaa Ala Pro Pro Asn Leu Trp Ala Ala Gln Arg
        35                  40

<210> SEQ ID NO 215
<211> LENGTH: 43
<212> TYPE: PRT
<213> ORGANISM: artificial sequence

```
<220> FEATURE:
<223> OTHER INFORMATION: synthetic
<220> FEATURE:
<221> NAME/KEY: misc_feature
<222> LOCATION: (25)..(25)
<223> OTHER INFORMATION: Xaa can be any naturally occurring amino acid

<400> SEQUENCE: 215

Gly Leu Ile Thr Pro Asn Lys His Gly Leu Leu Gln Asn Pro Tyr Arg
1               5                   10                  15

Ile Pro Pro Leu Phe Pro Ile Lys Xaa Phe Val Lys Thr Lys Cys Lys
            20                  25                  30

Lys Asn Leu Leu Glu Glu Asn Phe Glu Glu His
        35                  40

<210> SEQ ID NO 216
<211> LENGTH: 32
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (13)..(13)
<223> OTHER INFORMATION: Xaa can be any naturally occurring amino acid

<400> SEQUENCE: 216

Glu Ser Glu Arg Ser Val Asp Pro Glu Glu Leu Asp Xaa Arg Ala Gly
1               5                   10                  15

Ser Pro Gln Leu Asp Asp Ile Arg Val Phe Gln Asn Glu Val Leu Gly
            20                  25                  30

<210> SEQ ID NO 217
<211> LENGTH: 30
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (27)..(27)
<223> OTHER INFORMATION: Xaa can be any naturally occurring amino acid

<400> SEQUENCE: 217

Ala Val Leu Leu Pro Lys Lys Thr Ser Ala Thr Val Gly Pro Lys Ala
1               5                   10                  15

Pro Ser Gly Gly Lys Lys Ala Thr Gln Ala Xaa Gln Glu Tyr
            20                  25                  30

<210> SEQ ID NO 218
<211> LENGTH: 39
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (20)..(20)
<223> OTHER INFORMATION: Xaa can be any naturally occurring amino acid

<400> SEQUENCE: 218

Val Gln Lys Thr Ala Met Asn Trp Arg Leu Ser Ala Arg Asn Ala Ala
1               5                   10                  15

Arg Arg Asp Xaa Val Leu Ala Ala Ser Arg Asp Tyr Arg Asn Ile Ile
            20                  25                  30

Glu Arg Leu Gln Asp Ile Val
        35
```

<210> SEQ ID NO 219
<211> LENGTH: 35
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (17)..(17)
<223> OTHER INFORMATION: Xaa can be any naturally occurring amino acid

<400> SEQUENCE: 219

Leu Val Asn Arg Tyr Tyr Gly Asn Ile Arg Pro Ser Gly Arg Arg Glu
1               5                   10                  15

Xaa Leu Thr Ser Phe Gly Asn Gly Pro Leu Ser Pro Gly Gly Pro Ser
            20                  25                  30

Lys Pro Gly
        35

<210> SEQ ID NO 220
<211> LENGTH: 57
<212> TYPE: PRT
<213> ORGANISM: artificial sequence
<220> FEATURE:
<223> OTHER INFORMATION: synthetic

<400> SEQUENCE: 220

Leu Arg Asp Arg Lys Ile Leu Ile Arg Phe Ser Asp Tyr Val Glu Val
1               5                   10                  15

Ala Lys Ala Gln Asp Tyr Asp Arg Arg Ala Asp Lys Pro Trp Thr Arg
            20                  25                  30

Leu Ser Ala Ala Asp Lys Ala Ile Arg Lys Glu Leu Asn Glu Tyr
        35                  40                  45

Lys Ser Asn Glu Met Glu Val His Ala
    50                  55

<210> SEQ ID NO 221
<211> LENGTH: 66
<212> TYPE: PRT
<213> ORGANISM: artificial sequence
<220> FEATURE:
<223> OTHER INFORMATION: synthetic

<400> SEQUENCE: 221

Gly Asp Pro Asn Gln Leu Thr Arg Lys Gly Lys Arg Lys Ser Val
1               5                   10                  15

Thr Trp Pro Glu Glu Gly Lys Leu Arg Glu Tyr Phe Tyr Phe Glu Leu
            20                  25                  30

Asp Glu Thr Glu Arg Val Asn Val Asn Lys Ile Lys Asp Phe Gly Glu
        35                  40                  45

Ala Ala Lys Arg Glu Ile Leu Ser Asp Arg His Ala Phe Glu Thr Ala
    50                  55                  60

Arg Arg
65

<210> SEQ ID NO 222
<211> LENGTH: 65
<212> TYPE: PRT
<213> ORGANISM: artificial sequence
<220> FEATURE:
<223> OTHER INFORMATION: synthetic
<220> FEATURE:
<221> NAME/KEY: misc_feature

```
<222> LOCATION: (47)..(47)
<223> OTHER INFORMATION: Xaa can be any naturally occurring amino acid

<400> SEQUENCE: 222

Gly Glu Thr Gly Thr Glu Gln Asp Glu Glu Asp Ser Asp Glu Asn
1               5                   10                  15

Ser Tyr Tyr Gln Pro Asp Met Glu Tyr Ser Glu Ile Val Gly Leu Pro
            20                  25                  30

Glu Glu Glu Glu Ile Pro Ala Asn Arg Lys Ile Lys Phe Ser Xaa Ala
            35                  40                  45

Pro Ile Lys Val Phe Asn Thr Tyr Ser Asn Glu Asp Tyr Asp Arg Arg
    50                  55                  60

Asn
65

<210> SEQ ID NO 223
<211> LENGTH: 51
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (26)..(26)
<223> OTHER INFORMATION: Xaa can be any naturally occurring amino acid

<400> SEQUENCE: 223

Ile Gln Phe Thr Val Pro Leu Leu Glu Pro His Leu Asp Pro Glu Ala
1               5                   10                  15

Ala Glu Gln Ile Arg Arg Arg Arg Pro Xaa Pro Ala Thr Leu Val Leu
            20                  25                  30

Thr Ser Asp Gln Ser Ser Pro Glu Ile Asp Glu Asp Arg Ile Pro Asn
            35                  40                  45

Pro His Leu
    50

<210> SEQ ID NO 224
<211> LENGTH: 145
<212> TYPE: PRT
<213> ORGANISM: artificial sequence
<220> FEATURE:
<223> OTHER INFORMATION: synthetic

<400> SEQUENCE: 224

Glu Arg Ile Met Leu Arg Asp Ala Arg Gln Trp Leu Asn Ser Gly His
1               5                   10                  15

Ile Asn Asp Val Arg His Ala Lys Ser Gly Gly Thr Ala Leu His Val
            20                  25                  30

Ala Ala Ala Lys Gly Tyr Thr Glu Val Leu Lys Leu Leu Ile Gln Ala
            35                  40                  45

Arg Tyr Asp Val Asn Ile Lys Asp Tyr Asp Gly Trp Thr Pro Leu His
    50                  55                  60

Ala Ala Ala His Trp Gly Lys Glu Glu Ala Cys Arg Ile Leu Val Glu
65                  70                  75                  80

Asn Leu Cys Asp Met Glu Ala Val Asn Lys Val Gly Gln Thr Ala Phe
                85                  90                  95

Asp Val Ala Asp Gly Pro Gly Gly Ser Pro Gly Gly Leu Gln Lys Arg
            100                 105                 110

His Ala Arg Thr Val Lys Tyr Asp Arg Arg Glu Leu Gln Arg Arg Leu
            115                 120                 125
```

```
Asp Val Glu Lys Trp Ile Asp Gly Arg Leu Glu Glu Leu Tyr Arg Glu
    130                 135                 140

Ala
145

<210> SEQ ID NO 225
<211> LENGTH: 435
<212> TYPE: DNA
<213> ORGANISM: artificial sequence
<220> FEATURE:
<223> OTHER INFORMATION: synthetic

<400> SEQUENCE: 225
gagagaatca tgctgagaga tgctaggcaa tggctcaact ccggccatat caatgacgtc      60
aggcacgcca aaagcggagg cacagccctc cacgtcgccg ctgccaaagg ctataccgaa     120
gtgctcaagc tcctgattca ggctaggtat gacgtcaaca ttaaggatta cgatggctgg     180
acccctctgc acgccgctgc ccattgggga aaggaagaag cttgcagaat cctcgtggaa     240
aacctctgcg atatggaagc cgtcaacaaa gtgggacaga cagccttgga cgtcgccgat     300
ggccctggcg aagccctgg cggactgcaa aagagacacg ctaggacagt gaaatacgat     360
aggagagagc tgcagagaag gctcgacgtc gagaaatgga ttgacggaag gctcgaagaa     420
ctgtataggg aagcc                                                     435

<210> SEQ ID NO 226
<211> LENGTH: 503
<212> TYPE: DNA
<213> ORGANISM: artificial sequence
<220> FEATURE:
<223> OTHER INFORMATION: synthetic

<400> SEQUENCE: 226
ggcgcgccac gcgtgggggg ggggggcta gcgccaccat ggccggcgag agaatcatgc      60
tgagagatgc taggcaatgg ctcaactccg gccatatcaa tgacgtcagg cacgccaaaa     120
gcggaggcac agcccctcac gtcgccgctg ccaaaggcta taccgaagtg ctcaagctcc     180
tgattcaggc taggtatgac gtcaacatta aggattacga tggctggacc cctctgcacg     240
ccgctgccca ttggggaaag gaagaagctt gcagaatcct cgtggaaaac ctctgcgata     300
tggaagccgt caacaaagtg ggacagacag cctttgacgt cgccgatggc cctggcggaa     360
gccctggcgg actgcaaaag agacacgcta ggacagtgaa atacgatagg agagagctgc     420
agagaaggct cgacgtcgag aaatggattg acggaaggct cgaagaactg tatagggaag     480 ccccggggg aggcggaatc gat                                             503

<210> SEQ ID NO 227
<211> LENGTH: 125
<212> TYPE: PRT
<213> ORGANISM: artificial sequence
<220> FEATURE:
<223> OTHER INFORMATION: synthetic

<400> SEQUENCE: 227

Ala Asp Ala Lys Gln Lys Arg Asn Glu Gln Leu Lys Arg Trp Ile Gly
1               5                   10                  15

Ser Glu Thr Asp Leu Glu Pro Pro Val Val Lys Arg Lys Lys Thr Lys
            20                  25                  30

Val Lys Phe Asp Asp Gly Ala Val Phe Leu Ala Ala Cys Ser Ser Gly
        35                  40                  45

Asp Thr Glu Glu Val Leu Arg Leu Leu Glu Arg Gly Ala Asp Ile Asn
```

```
                50                  55                  60
Tyr Ala Asn Val Asp Gly Leu Thr Ala Leu His Gln Ala Cys Ile Asp
 65                  70                  75                  80

Gly Pro Gly Gly Ser Pro Gly Gly Leu Gln Lys Arg His Ala Arg Thr
                 85                  90                  95

Val Lys Tyr Asp Arg Arg Glu Leu Gln Arg Arg Leu Asp Val Glu Lys
                100                 105                 110

Trp Ile Asp Gly Arg Leu Glu Glu Leu Tyr Arg Glu Ala
            115                 120                 125

<210> SEQ ID NO 228
<211> LENGTH: 375
<212> TYPE: DNA
<213> ORGANISM: artificial sequence
<220> FEATURE:
<223> OTHER INFORMATION: synthetic

<400> SEQUENCE: 228
gccgatgcca aacagaaaag gaatgagcaa ctgaaaaggt ggatcggaag cgaaaccgat      60
ctggaacccc ctgtggtcaa gagaaagaaa accaaagtga aattcgatga cggagccgtc     120
ttcctcgccg cttgctccag cggagacaca gaggaagtgc tcaggctcct ggaaggggga     180
gccgatatta attacgctaa cgtcgatgga ctgacagccc tccaccaagc tgtatcgac      240 ggccctggcg gaagccctgg cggactgcaa agagacacg ctaggacagt gaaatacgat     300
aggagagagc tgcagagaag gctcgacgtc gagaaatgga ttgacggaag gctcgaagaa     360
ctgtataggg aagcc                                                     375

<210> SEQ ID NO 229
<211> LENGTH: 443
<212> TYPE: DNA
<213> ORGANISM: artificial sequence
<220> FEATURE:
<223> OTHER INFORMATION: synthetic

<400> SEQUENCE: 229
ggcgcgccac gcgtgggggg ggggggggcta gcgccaccat ggccggcgcc gatgccaaac      60
agaaaaggaa tgagcaactg aaaaggtgga tcggaagcga aaccgatctg gaaccccctg     120
tggtcaagag aaagaaaacc aaagtgaaat tcgatgacgg agccgtcttc ctcgccgctt     180
gctccagcgg agacacagag gaagtgctca ggctcctgga aggggagcc gatattaatt     240 acgctaacgt cgatggactg acagcccctcc accaagcctg tatcgacggc cctggcggaa     300
gccctggcgg actgcaaaag agacacgcta ggacagtgaa atacgatagg agagagctgc     360
agagaaggct cgacgtcgag aaatggattg acggaaggct cgaagaactg tatagggaag     420
cccccggggg aggcggaatc gat                                            443

<210> SEQ ID NO 230
<211> LENGTH: 70
<212> TYPE: PRT
<213> ORGANISM: artificial sequence
<220> FEATURE:
<223> OTHER INFORMATION: synthetic

<400> SEQUENCE: 230

Ala Arg Val Thr Val Lys Tyr Asp Arg Arg Glu Leu Gln Arg Arg Leu
  1               5                  10                  15

Asp Val Glu Lys Trp Ile Asp Gly Arg Leu Glu Glu Leu Tyr Arg Glu
             20                  25                  30
```

Ala Met Ala Asp Ala Lys Gln Lys Arg Asn Glu Gln Leu Lys Arg Trp
            35                  40                  45

Ile Gly Ser Glu Thr Asp Leu Glu Pro Pro Val Val Lys Arg Lys Lys
 50                  55                  60

Thr Lys Val Lys Phe Asp
 65                  70

<210> SEQ ID NO 231
<211> LENGTH: 210
<212> TYPE: DNA
<213> ORGANISM: artificial sequence
<220> FEATURE:
<223> OTHER INFORMATION: synthetic

<400> SEQUENCE: 231
gccagagtga cagtgaaata cgataggaga gagctgcaga gaaggctcga cgtcgagaaa      60
tggattgacg gaaggctcga agaactgtat agggaagcca tggccgatgc aaacagaaaa     120
aggaatgagc aactgaaaag gtggatcgga agcgaaaccg atctggaacc ccctgtggtc     180
aagagaaaga aaccaaagt gaaattcgac                                       210

<210> SEQ ID NO 232
<211> LENGTH: 257
<212> TYPE: DNA
<213> ORGANISM: artificial sequence
<220> FEATURE:
<223> OTHER INFORMATION: synthetic

<400> SEQUENCE: 232
ggcgcgccac gcgtgggggg ggggggcta gcgccaccat ggccagagtg acagtgaaat       60
acgataggag agagctgcag agaaggctcg acgtcgagaa atggattgac ggaaggctcg     120
aagaactgta tagggaagcc atggccgatg ccaaacagaa aaggaatgag caactgaaaa     180
ggtggatcgg aagcgaaacc gatctggaac cccctgtggt caagagaaag aaaccaaag     240 tgaaattcga catcgat                                                    257

<210> SEQ ID NO 233
<211> LENGTH: 82
<212> TYPE: PRT
<213> ORGANISM: artificial sequence
<220> FEATURE:
<223> OTHER INFORMATION: synthetic

<400> SEQUENCE: 233

Ala Arg Val Thr Val Lys Tyr Asp Arg Arg Glu Leu Gln Arg Arg Leu
 1               5                  10                  15

Asp Val Glu Lys Trp Ile Asp Gly Arg Leu Glu Glu Leu Tyr Arg Glu
             20                  25                  30

Ala Met Ala Asp Ala Lys Gln Lys Arg Asn Glu Gln Leu Lys Arg Trp
            35                  40                  45

Ile Gly Ser Glu Thr Asp Leu Glu Pro Pro Val Val Lys Arg Lys Lys
 50                  55                  60

Thr Lys Val Lys Phe Asp Asp Gly Ala Val Phe Leu Ala Ala Cys Ser
 65                  70                  75                  80

Ser Gly

<210> SEQ ID NO 234
<211> LENGTH: 246
<212> TYPE: DNA
<213> ORGANISM: artificial sequence
<220> FEATURE:

-continued

<223> OTHER INFORMATION: synthetic

<400> SEQUENCE: 234

```
gccagagtga cagtgaaata cgataggaga gagctgcaga gaaggctcga cgtcgagaaa    60
tggattgacg gaaggctcga agaactgtat agggaagcca tggccgatgc caaacagaaa   120
aggaatgagc aactgaaaag gtggatcgga agcgaaaccg atctggaacc ccctgtggtc   180
aagagaaaga aaaccaaagt gaaattcgat gacggagccg tcttcctcgc cgcttgctcc   240
agcgga                                                              246
```

<210> SEQ ID NO 235
<211> LENGTH: 293
<212> TYPE: DNA
<213> ORGANISM: artificial sequence
<220> FEATURE:
<223> OTHER INFORMATION: synthetic

<400> SEQUENCE: 235

```
ggcgcgccac gcgtgggggg ggggggcta gcgccaccat ggccagagtg acagtgaaat    60
acgataggag agagctgcag agaaggctcg acgtcgagaa atggattgac ggaaggctcg   120
aagaactgta tagggaagcc atggccgatg ccaaacagaa aaggaatgag caactgaaaa   180
ggtggatcgg aagcgaaacc gatctggaac cccctgtggt caagagaaag aaaaccaaag   240
tgaaattcga tgacggagcc gtcttcctcg ccgcttgctc cagcggaatc gat          293
```

<210> SEQ ID NO 236
<211> LENGTH: 107
<212> TYPE: PRT
<213> ORGANISM: artificial sequence
<220> FEATURE:
<223> OTHER INFORMATION: synthetic

<400> SEQUENCE: 236

```
Ala Asp Ala Lys Gln Lys Arg Asn Glu Gln Leu Lys Arg Trp Ile Gly
  1               5                  10                  15

Ser Glu Thr Asp Leu Glu Pro Pro Val Val Lys Arg Lys Lys Thr Lys
             20                  25                  30

Val Lys Phe Asp Asp Gly Ala Val Phe Leu Ala Ala Cys Ser Ser Gly
         35                  40                  45

Asp Thr Glu Glu Val Leu Arg Leu Leu Glu Arg Gly Ala Asp Ile Asn
     50                  55                  60

Tyr Ala Asn Val Asp Gly Leu Thr Ala Leu His Gln Ala Cys Ile Asp
 65                  70                  75                  80

Gly Pro Gly Gly Asp Pro Glu Ala Ala Glu Gln Ile Arg Arg Arg
                 85                  90                  95

Pro Thr Pro Ala Thr Leu Val Ser Pro Gly Gly
            100                 105
```

<210> SEQ ID NO 237
<211> LENGTH: 321
<212> TYPE: DNA
<213> ORGANISM: artificial sequence
<220> FEATURE:
<223> OTHER INFORMATION: synthetic

<400> SEQUENCE: 237

```
gccgatgcca aacagaaaag gaatgagcaa ctgaaaaggt ggatcggaag cgaaaccgat    60
ctggaacccc ctgtggtcaa gagaaagaaa accaaagtga aattcgatga cggagccgtc   120
ttcctcgccg cttgctccag cggagacaca gaggaagtgc tcaggctcct ggaaggggga   180
```

```
gccgatatta attacgctaa cgtcgatgga ctgacagccc tccaccaagc ctgtatcgac      240
ggccctggcg gagaccctga ggctgccgaa cagattagga gaaggagacc cacacccgct      300
accctcgtgt cccccggagg c                                                321
```

<210> SEQ ID NO 238
<211> LENGTH: 368
<212> TYPE: DNA
<213> ORGANISM: artificial sequence
<220> FEATURE:
<223> OTHER INFORMATION: synthetic

<400> SEQUENCE: 238

```
ggcgcgccac gcgtgggggg ggggggcta gcgccaccat ggccgatgcc aaacagaaaa       60
ggaatgagca actgaaaagg tggatcggaa gcgaaaccga tctggaaccc cctgtggtca      120
agagaaagaa aaccaaagtg aaattcgatg acggagccgt cttcctcgcc gcttgctcca      180
gcggagacac agaggaagtg ctcaggctcc tggaaggggg agccgatatt aattacgcta      240
acgtcgatgg actgacagcc ctccaccaag cctgtatcga cggccctggc ggagaccctg      300
aggctgccga acagattagg agaaggagac ccacacccgc taccctcgtg tcccccggag      360
gcatcgat                                                               368
```

<210> SEQ ID NO 239
<211> LENGTH: 80
<212> TYPE: PRT
<213> ORGANISM: artificial sequence
<220> FEATURE:
<223> OTHER INFORMATION: synthetic

<400> SEQUENCE: 239

```
Ala Asp Ala Lys Gln Lys Arg Asn Glu Gln Leu Lys Arg Trp Ile Gly
1               5                   10                  15

Ser Glu Thr Asp Leu Glu Pro Pro Val Val Lys Arg Lys Lys Thr Lys
            20                  25                  30

Val Lys Phe Asp Asp Gly Ala Val Phe Leu Ala Ala Cys Ala Leu His
        35                  40                  45

Gln Ala Cys Ile Asp Gly Pro Gly Gly Asp Pro Glu Ala Ala Glu Gln
    50                  55                  60

Ile Arg Arg Arg Arg Pro Thr Pro Ala Thr Leu Val Ser Pro Gly Gly
65                  70                  75                  80
```

<210> SEQ ID NO 240
<211> LENGTH: 240
<212> TYPE: DNA
<213> ORGANISM: artificial sequence
<220> FEATURE:
<223> OTHER INFORMATION: synthetic

<400> SEQUENCE: 240

```
gccgatgcca aacagaaaag gaatgagcaa ctgaaaaggt ggatcggaag cgaaaccgat       60
ctggaacccc ctgtggtcaa gagaaagaaa accaaagtga aattcgatga cggagccgtc      120
ttcctcgccg cttgcgctct gcatcaggct tgcattgacg gacccggagg cgatcccgaa      180
gccgctgaac aaatcagaag gagaaggccc acccctgcca cactggtcag ccctggcgga      240
```

<210> SEQ ID NO 241
<211> LENGTH: 287
<212> TYPE: DNA
<213> ORGANISM: artificial sequence
<220> FEATURE:

<223> OTHER INFORMATION: synthetic

<400> SEQUENCE: 241

```
ggcgcgccac gcgtgggggg ggggggggcta gcgccaccat ggccgatgcc aaacagaaaa    60
ggaatgagca actgaaaagg tggatcggaa gcgaaaccga tctggaaccc cctgtggtca   120
agagaaagaa aaccaaagtg aaattcgatg acggagccgt cttcctcgcc gcttgcgctc   180
tgcatcaggc ttgcattgac ggacccggag gcgatcccga agccgctgaa caaatcagaa   240
ggagaaggcc cacccctgcc acactggtca gccctggcgg aatcgat               287
```

<210> SEQ ID NO 242
<211> LENGTH: 145
<212> TYPE: PRT
<213> ORGANISM: artificial sequence
<220> FEATURE:
<223> OTHER INFORMATION: synthetic

<400> SEQUENCE: 242

```
Glu Arg Ile Met Leu Arg Asp Ala Arg Gln Trp Leu Asn Ser Gly His
1               5                   10                  15

Ile Asn Asp Val Arg His Ala Lys Ser Gly Gly Thr Ala Leu His Val
            20                  25                  30

Ala Ala Ala Lys Gly Tyr Thr Glu Val Leu Lys Leu Leu Ile Gln Ala
        35                  40                  45

Arg Tyr Asp Val Asn Ile Lys Asp Tyr Asp Gly Trp Thr Pro Leu His
    50                  55                  60

Ala Ala Ala His Trp Gly Lys Glu Glu Ala Cys Arg Ile Leu Val Glu
65                  70                  75                  80

Asn Leu Cys Asp Met Glu Ala Val Asn Lys Val Gly Gln Thr Ala Phe
                85                  90                  95

Asp Val Ala Asp Gly Pro Gly Gly Ser Pro Gly Gly Leu Gln Lys Arg
            100                 105                 110

His Ala Arg Asp Val Lys Tyr Asp Arg Arg Glu Leu Gln Arg Arg Leu
        115                 120                 125

Asp Val Glu Lys Trp Ile Asp Gly Arg Leu Glu Glu Leu Tyr Arg Glu
    130                 135                 140

Ala
145
```

<210> SEQ ID NO 243
<211> LENGTH: 435
<212> TYPE: DNA
<213> ORGANISM: artificial sequence
<220> FEATURE:
<223> OTHER INFORMATION: synthetic

<400> SEQUENCE: 243

```
gagagaatca tgctgagaga tgctaggcaa tggctcaact ccggccatat caatgacgtc    60
aggcacgcca aaagcggagg cacagccctc acgtcgccg ctgccaaagg ctataccgaa   120
gtgctcaagc tcctgattca ggctaggtat gacgtcaaca ttaaggatta cgatggctgg   180 accctctgc acgccgctgc ccattgggga aggaagaag cttgcagaat cctcgtggaa   240
aacctctgcg atatggaagc cgtcaacaaa gtgggacaga cagcctttga cgtcgccgat   300
ggccctggcg gaagccctgg cggactgcaa aagagacacg ctagggatgt gaaatacgat   360
aggagagagc tgcagagaag gctcgacgtc gagaaatgga ttgacggaag gctcgaagaa   420
ctgtataggg aagcc                                                   435
```

```
<210> SEQ ID NO 244
<211> LENGTH: 503
<212> TYPE: DNA
<213> ORGANISM: artificial sequence
<220> FEATURE:
<223> OTHER INFORMATION: synthetic

<400> SEQUENCE: 244
ggcgcgccac gcgtgggggg ggggggggcta gcgccaccat ggccggcgag agaatcatgc      60
tgagagatgc taggcaatgg ctcaactccg gccatatcaa tgacgtcagg cacgccaaaa     120
gcggaggcac agccctccac gtcgccgctg ccaaaggcta taccgaagtg ctcaagctcc     180
tgattcaggc taggtatgac gtcaacatta aggattacga tggctggacc cctctgcacg     240
ccgctgccca ttggggaaag gaagaagctt gcagaatcct cgtggaaaac ctctgcgata     300
tggaagccgt caacaaagtg gacagacag cctttgacgt cgccgatggc cctggcggaa      360
gccctggcgg actgcaaaag agacacgcta gggatgtgaa atacgatagg agagagctgc     420
agagaaggct cgacgtcgag aaatggattg acggaaggct cgaagaactg tatagggaag     480
ccccccgggg aggcggaatc gat                                             503

<210> SEQ ID NO 245
<211> LENGTH: 82
<212> TYPE: PRT
<213> ORGANISM: artificial sequence
<220> FEATURE:
<223> OTHER INFORMATION: synthetic

<400> SEQUENCE: 245

Ala Arg Val Asp Val Lys Tyr Asp Arg Arg Glu Leu Gln Arg Arg Leu
1               5                  10                  15

Asp Val Glu Lys Trp Ile Asp Gly Arg Leu Glu Glu Leu Tyr Arg Glu
            20                  25                  30

Ala Met Ala Asp Ala Lys Gln Lys Arg Asn Glu Gln Leu Lys Arg Trp
        35                  40                  45

Ile Gly Ser Glu Thr Asp Leu Glu Pro Pro Val Val Lys Arg Lys Lys
    50                  55                  60

Thr Lys Val Lys Phe Asp Asp Gly Ala Val Phe Leu Ala Ala Cys Ser
65                  70                  75                  80

Ser Gly

<210> SEQ ID NO 246
<211> LENGTH: 246
<212> TYPE: DNA
<213> ORGANISM: artificial sequence
<220> FEATURE:
<223> OTHER INFORMATION: synthetic

<400> SEQUENCE: 246
gccagagtgg atgtgaaata cgataggaga gagctgcaga aaggctcga cgtcgagaaa       60 tggattgacg gaaggctcga agaactgtat agggaagcca tggccgatgc caaacagaaa     120
aggaatgagc aactgaaaag gtggatcgga agcgaaaccg atctggaacc ccctgtggtc     180
aagagaaaga aaaccaaagt gaaattcgat gacggagccg tcttcctcgc cgcttgctcc     240
agcgga                                                                246

<210> SEQ ID NO 247
<211> LENGTH: 293
<212> TYPE: DNA
<213> ORGANISM: artificial sequence
```

<220> FEATURE:
<223> OTHER INFORMATION: synthetic

<400> SEQUENCE: 247

```
ggcgcgccac gcgtgggggg ggggggggcta gcgccaccat ggccagagtg gatgtgaaat    60
acgataggag agagctgcag agaaggctcg acgtcgagaa atggattgac ggaaggctcg   120
aagaactgta tagggaagcc atggccgatg ccaaacagaa aaggaatgag caactgaaaa   180
ggtggatcgg aagcgaaacc gatctggaac cccctgtggt caagagaaag aaaaccaaag   240
tgaaattcga tgacggagcc gtcttcctcg ccgcttgctc cagcggaatc gat          293
```

<210> SEQ ID NO 248
<211> LENGTH: 80
<212> TYPE: PRT
<213> ORGANISM: artificial sequence
<220> FEATURE:
<223> OTHER INFORMATION: synthetic

<400> SEQUENCE: 248

```
Ala Asp Ala Lys Gln Lys Arg Asn Glu Gln Leu Lys Arg Trp Ile Gly
1               5                   10                  15
Ser Glu Thr Asp Leu Glu Pro Pro Val Val Lys Arg Lys Lys Thr Lys
            20                  25                  30
Val Lys Phe Asp Asp Gly Ala Val Phe Leu Ala Ala Cys Ala Leu His
        35                  40                  45
Gln Ala Cys Ile Asp Gly Pro Gly Gly Asp Pro Glu Ala Ala Glu Gln
    50                  55                  60
Ile Arg Arg Arg Arg Pro Asp Pro Ala Asp Leu Val Ser Pro Gly Gly
65                  70                  75                  80
```

<210> SEQ ID NO 249
<211> LENGTH: 240
<212> TYPE: DNA
<213> ORGANISM: artificial sequence
<220> FEATURE:
<223> OTHER INFORMATION: synthetic

<400> SEQUENCE: 249

```
gccgatgcca acagaaaag gaatgagcaa ctgaaaaggt ggatcggaag cgaaaccgat     60
ctggaacccc ctgtggtcaa gagaaagaaa accaaagtga aattcgatga cggagccgtc   120
ttcctcgccg cttgcgctct gcatcaggct tgcattgacg acccggagg cgatcccgaa    180
gccgctgaac aaatcagaag gagaaggccc gaccctgccg atctggtcag ccctggcgga   240
```

<210> SEQ ID NO 250
<211> LENGTH: 287
<212> TYPE: DNA
<213> ORGANISM: artificial sequence
<220> FEATURE:
<223> OTHER INFORMATION: synthetic

<400> SEQUENCE: 250

```
ggcgcgccac gcgtgggggg ggggggggcta gcgccaccat ggccgatgcc aaacagaaaa    60
ggaatgagca actgaaaagg tggatcggaa gcgaaaccga tctggaaccc cctgtggtca   120
agagaaagaa aaccaaagtg aaattcgatg acggagccgt cttcctcgcc gcttgcgctc   180
tgcatcaggc ttgcattgac ggacccggag gcgatcccga agccgctgaa caaatcagaa   240
ggagaaggcc cgaccctgcc gatctggtca gccctggcgg aatcgat                287
```

<210> SEQ ID NO 251

-continued

```
<211> LENGTH: 100
<212> TYPE: PRT
<213> ORGANISM: artificial sequence
<220> FEATURE:
<223> OTHER INFORMATION: synthetic

<400> SEQUENCE: 251

Glu Arg Ile Met Leu Arg Asp Ala Arg Gln Trp Leu Asn Ser Gly His
1               5                   10                  15

Ile Asn Asp Val Arg His Ala Lys Ser Gly Gly Thr Ala Leu His Val
            20                  25                  30

Ala Ala Ala Lys Gly Tyr Thr Glu Val Leu Lys Leu Leu Ile Gln Ala
        35                  40                  45

Arg Tyr Asp Val Asn Ile Lys Asp Tyr Asp Gly Trp Thr Pro Leu His
    50                  55                  60

Ala Ala Ala His Trp Gly Lys Glu Glu Ala Cys Arg Ile Leu Val Glu
65                  70                  75                  80

Asn Leu Cys Asp Met Glu Ala Val Asn Lys Val Gly Gln Thr Ala Phe
                85                  90                  95

Asp Val Ala Asp
            100

<210> SEQ ID NO 252
<211> LENGTH: 80
<212> TYPE: PRT
<213> ORGANISM: artificial sequence
<220> FEATURE:
<223> OTHER INFORMATION: synthetic

<400> SEQUENCE: 252

Ala Asp Ala Lys Gln Lys Arg Asn Glu Gln Leu Lys Arg Trp Ile Gly
1               5                   10                  15

Ser Glu Thr Asp Leu Glu Pro Pro Val Val Lys Arg Lys Lys Thr Lys
            20                  25                  30

Val Lys Phe Asp Asp Gly Ala Val Phe Leu Ala Ala Cys Ser Ser Gly
        35                  40                  45

Asp Thr Glu Glu Val Leu Arg Leu Leu Glu Arg Gly Ala Asp Ile Asn
    50                  55                  60

Tyr Ala Asn Val Asp Gly Leu Thr Ala Leu His Gln Ala Cys Ile Asp
65                  70                  75                  80

<210> SEQ ID NO 253
<211> LENGTH: 37
<212> TYPE: PRT
<213> ORGANISM: artificial sequence
<220> FEATURE:
<223> OTHER INFORMATION: synthetic

<400> SEQUENCE: 253

Met Ala Asp Ala Lys Gln Lys Arg Asn Glu Gln Leu Lys Arg Trp Ile
1               5                   10                  15

Gly Ser Glu Thr Asp Leu Glu Pro Pro Val Val Lys Arg Lys Lys Thr
            20                  25                  30

Lys Val Lys Phe Asp
        35

<210> SEQ ID NO 254
<211> LENGTH: 49
<212> TYPE: PRT
<213> ORGANISM: artificial sequence
<220> FEATURE:
<223> OTHER INFORMATION: synthetic
```

<400> SEQUENCE: 254

Met Ala Asp Ala Lys Gln Lys Arg Asn Glu Gln Leu Lys Arg Trp Ile
1               5                   10                  15

Gly Ser Glu Thr Asp Leu Glu Pro Pro Val Val Lys Arg Lys Lys Thr
            20                  25                  30

Lys Val Lys Phe Asp Asp Gly Ala Val Phe Leu Ala Ala Cys Ser Ser
        35                  40                  45

Gly

<210> SEQ ID NO 255
<211> LENGTH: 53
<212> TYPE: PRT
<213> ORGANISM: artificial sequence
<220> FEATURE:
<223> OTHER INFORMATION: synthetic

<400> SEQUENCE: 255

Ala Asp Ala Lys Gln Lys Arg Asn Glu Gln Leu Lys Arg Trp Ile Gly
1               5                   10                  15

Ser Glu Thr Asp Leu Glu Pro Pro Val Val Lys Arg Lys Lys Thr Lys
            20                  25                  30

Val Lys Phe Asp Asp Gly Ala Val Phe Leu Ala Ala Cys Ala Leu His
        35                  40                  45

Gln Ala Cys Ile Asp
    50

<210> SEQ ID NO 256
<211> LENGTH: 17
<212> TYPE: PRT
<213> ORGANISM: artificial sequence
<220> FEATURE:
<223> OTHER INFORMATION: synthetic

<400> SEQUENCE: 256

Leu Gln Lys Arg His Ala Arg Thr Val Lys Tyr Asp Arg Arg Glu Leu
1               5                   10                  15

Gln

<210> SEQ ID NO 257
<211> LENGTH: 13
<212> TYPE: PRT
<213> ORGANISM: artificial sequence
<220> FEATURE:
<223> OTHER INFORMATION: synthetic

<400> SEQUENCE: 257

Ala Arg Val Thr Val Lys Tyr Asp Arg Arg Glu Leu Gln
1               5                   10

<210> SEQ ID NO 258
<211> LENGTH: 19
<212> TYPE: PRT
<213> ORGANISM: artificial sequence
<220> FEATURE:
<223> OTHER INFORMATION: synthetic

<400> SEQUENCE: 258

Asp Pro Glu Ala Ala Glu Gln Ile Arg Arg Arg Pro Thr Pro Ala
1               5                   10                  15

Thr Leu Val

```
<210> SEQ ID NO 259
<211> LENGTH: 17
<212> TYPE: PRT
<213> ORGANISM: artificial sequence
<220> FEATURE:
<223> OTHER INFORMATION: synthetic

<400> SEQUENCE: 259

Leu Gln Lys Arg His Ala Arg Asp Val Lys Tyr Asp Arg Arg Glu Leu
1               5                   10                  15

Gln

<210> SEQ ID NO 260
<211> LENGTH: 13
<212> TYPE: PRT
<213> ORGANISM: artificial sequence
<220> FEATURE:
<223> OTHER INFORMATION: synthetic

<400> SEQUENCE: 260

Ala Arg Val Asp Val Lys Tyr Asp Arg Arg Glu Leu Gln
1               5                   10

<210> SEQ ID NO 261
<211> LENGTH: 19
<212> TYPE: PRT
<213> ORGANISM: artificial sequence
<220> FEATURE:
<223> OTHER INFORMATION: synthetic

<400> SEQUENCE: 261

Asp Pro Glu Ala Ala Glu Gln Ile Arg Arg Arg Pro Asp Pro Ala
1               5                   10                  15

Asp Leu Val

<210> SEQ ID NO 262
<211> LENGTH: 20
<212> TYPE: PRT
<213> ORGANISM: artificial sequence
<220> FEATURE:
<223> OTHER INFORMATION: synthetic

<400> SEQUENCE: 262

Arg Arg Leu Asp Val Glu Lys Trp Ile Asp Gly Arg Leu Glu Glu Leu
1               5                   10                  15

Tyr Arg Glu Ala
            20

<210> SEQ ID NO 263
<211> LENGTH: 8
<212> TYPE: PRT
<213> ORGANISM: artificial sequence
<220> FEATURE:
<223> OTHER INFORMATION: synthetic

<400> SEQUENCE: 263

Gly Pro Gly Gly Ser Pro Gly Gly
1               5

<210> SEQ ID NO 264
<211> LENGTH: 4
<212> TYPE: PRT
<213> ORGANISM: artificial sequence
<220> FEATURE:
<223> OTHER INFORMATION: synthetic

<400> SEQUENCE: 264
```

```
Gly Pro Gly Gly
  1

<210> SEQ ID NO 265
<211> LENGTH: 4
<212> TYPE: PRT
<213> ORGANISM: artificial sequence
<220> FEATURE:
<223> OTHER INFORMATION: synthetic

<400> SEQUENCE: 265

Ser Pro Gly Gly
  1

<210> SEQ ID NO 266
<211> LENGTH: 1004
<212> TYPE: PRT
<213> ORGANISM: Gallus gallus

<400> SEQUENCE: 266

Met Lys Met Ala Asp Ala Lys Gln Lys Arg Asn Glu Gln Leu Lys Arg
  1               5                  10                  15

Trp Ile Gly Ser Glu Thr Asp Leu Glu Pro Val Val Lys Arg Lys
                 20                  25                  30

Lys Thr Lys Val Lys Phe Asp Asp Gly Ala Val Phe Leu Ala Ala Cys
             35                  40                  45

Ser Ser Gly Asp Thr Glu Glu Val Leu Arg Leu Leu Glu Arg Gly Ala
         50                  55                  60

Asp Ile Asn Tyr Ala Asn Val Asp Gly Leu Thr Ala Leu His Gln Ala
 65                  70                  75                  80

Cys Ile Asp Asp Asn Val Asp Met Val Lys Phe Leu Val Glu Asn Gly
                 85                  90                  95

Ala Asn Ile Asn Gln Pro Asp Asn Glu Gly Trp Ile Pro Leu His Ala
                100                 105                 110

Ala Ala Ser Cys Gly Tyr Leu Asp Ile Ala Glu Tyr Leu Ile Ser Gln
            115                 120                 125

Gly Ala His Val Gly Ala Val Asn Ser Glu Gly Asp Thr Pro Leu Asp
        130                 135                 140

Ile Ala Glu Glu Glu Ala Met Glu Glu Leu Leu Gln Asn Glu Val Asn
145                 150                 155                 160

Arg Gln Gly Val Asp Ile Glu Ala Ala Arg Lys Glu Glu Arg Ile
                165                 170                 175

Met Leu Arg Asp Ala Arg Gln Trp Leu Asn Ser Gly His Ile Asn Asp
            180                 185                 190

Val Arg His Ala Lys Ser Gly Gly Thr Ala Leu His Val Ala Ala Ala
        195                 200                 205

Lys Gly Tyr Thr Glu Val Leu Lys Leu Leu Ile Gln Ala Arg Tyr Asp
    210                 215                 220

Val Asn Ile Lys Asp Tyr Asp Gly Trp Thr Pro Leu His Ala Ala Ala
225                 230                 235                 240

His Trp Gly Lys Glu Glu Ala Cys Arg Ile Leu Val Glu Asn Leu Cys
                245                 250                 255

Asp Met Glu Ala Val Asn Lys Val Gly Gln Thr Ala Phe Asp Val Ala
            260                 265                 270

Asp Glu Asp Ile Leu Gly Tyr Leu Glu Glu Leu Gln Lys Lys Gln Asn
        275                 280                 285

Leu Leu His Ser Glu Lys Arg Glu Lys Lys Ser Pro Leu Ile Glu Ser
```

```
            290                 295                 300
Thr Ala Asn Leu Asp Asn Asn Gln Thr Gln Lys Thr Phe Lys Asn Lys
305                 310                 315                 320

Glu Thr Leu Ile Met Glu Gln Glu Lys Asn Ala Ser Ser Ile Glu Ser
                325                 330                 335

Leu Glu His Glu Lys Ala Asp Glu Glu Glu Gly Lys Lys Asp Glu
            340                 345                 350

Ser Ser Cys Ser Ser Glu Glu Glu Asp Asp Ser Glu Ser Glu
            355                 360                 365

Ala Glu Thr Asp Lys Ala Lys Thr Leu Ala Asn Ala Asn Thr Thr Ser
        370                 375                 380

Thr Gln Ser Ala Ser Met Thr Ala Pro Ser Val Ala Gly Gly Gln Gly
385                 390                 395                 400

Thr Pro Thr Ser Pro Leu Lys Lys Phe Pro Thr Ser Thr Thr Lys Val
                405                 410                 415

Ser Pro Lys Glu Glu Arg Lys Asp Glu Ser Pro Ala Ser Trp Arg
            420                 425                 430

Leu Gly Leu Arg Lys Thr Gly Ser Tyr Gly Ala Leu Ala Glu Ile Thr
        435                 440                 445

Ala Ser Lys Glu Ala Gln Lys Glu Lys Asp Ser Ala Gly Val Ile Arg
450                 455                 460

Ser Ala Ser Ser Pro Arg Leu Ser Ser Ser Leu Asp Asn Lys Glu Lys
465                 470                 475                 480

Glu Lys Asp Gly Lys Gly Thr Arg Leu Ala Tyr Val Ala Pro Thr Ile
                485                 490                 495

Pro Arg Arg Leu Ala Ser Thr Ser Asp Ile Asp Glu Lys Glu Asn Arg
                500                 505                 510

Asp Ser Ser Ala Ser Ser Ile Arg Ser Gly Ser Ser Tyr Ala Arg Arg
            515                 520                 525

Lys Trp Glu Glu Asp Val Lys Lys Asn Ser Leu Asn Glu Gly Pro Thr
            530                 535                 540

Ser Leu Asn Thr Ser Tyr Gln Arg Ser Gly Ser Phe Gly Arg Arg Gln
545                 550                 555                 560

Asp Asp Leu Val Ser Ser Asn Val Pro Ser Thr Ala Ser Thr Val Thr
                565                 570                 575

Ser Ser Ala Gly Leu Gln Lys Thr Leu Pro Ala Ser Ala Asn Thr Thr
            580                 585                 590

Thr Lys Ser Thr Thr Gly Ser Thr Ser Ala Gly Val Gln Ser Ser Thr
            595                 600                 605

Ser Asn Arg Leu Trp Ala Glu Asp Ser Thr Glu Lys Glu Lys Asp Ser
        610                 615                 620

Val Pro Thr Ala Val Thr Val Pro Val Ala Pro Ser Val Val Asn Ala
625                 630                 635                 640

Ala Ala Thr Thr Thr Ala Met Thr Thr Ala Thr Ser Gly Thr Val Ser
                645                 650                 655

Ser Thr Ser Glu Val Arg Glu Arg Arg Ser Tyr Leu Thr Pro Val
            660                 665                 670

Arg Asp Glu Glu Ser Glu Ser Gln Arg Lys Ala Arg Ser Arg Gln Ala
        675                 680                 685

Arg Gln Ser Arg Arg Ser Thr Gln Gly Val Thr Leu Thr Asp Leu Gln
        690                 695                 700

Glu Ala Glu Lys Thr Ile Gly Arg Ser Arg Ser Thr Arg Thr Arg Glu
705                 710                 715                 720
```

-continued

```
Gln Glu Asn Glu Glu Lys Glu Lys Glu Lys Lys Gln Asp Lys
            725                 730                 735

Glu Lys Gln Glu Glu Lys Lys Glu Ser Glu Thr Lys Asp Asp Tyr
        740                 745                 750

Arg Gln Arg Tyr Ser Arg Thr Val Glu Glu Pro Tyr His Arg Tyr Arg
        755                 760                 765

Pro Thr Ser Thr Ser Thr Ser Thr Ser Thr Ser Ser Leu Ser Thr
    770                 775                 780

Ser Thr Ser Ser Leu Ser Ser Ser Ser Gln Leu Asn Arg Pro Asn Ser
785                 790                 795                 800

Leu Ile Gly Ile Thr Ser Ala Tyr Ser Arg Ser Gly Thr Lys Glu Ser
                805                 810                 815

Glu Arg Glu Gly Gly Lys Lys Glu Glu Glu Lys Glu Glu Asp Lys Ser
            820                 825                 830

Gln Pro Lys Ser Ile Arg Glu Arg Arg Pro Arg Glu Lys Arg Arg
            835                 840                 845

Ser Thr Gly Val Ser Phe Trp Thr Gln Asp Ser Asp Glu Asn Glu Gln
    850                 855                 860

Glu His Gln Ser Asp Ser Glu Glu Gly Thr Asn Lys Lys Glu Thr Gln
865                 870                 875                 880

Ser Asp Ser Leu Ser Arg Tyr Asp Thr Gly Ser Leu Ser Val Ser Ser
                885                 890                 895

Gly Asp Arg Tyr Asp Ser Ala Gln Gly Arg Ser Gly Ser Gln Ser Tyr
            900                 905                 910

Leu Glu Asp Arg Lys Pro Tyr Cys Ser Arg Leu Glu Lys Glu Asp Ser
            915                 920                 925

Thr Asp Phe Lys Lys Leu Tyr Glu Gln Ile Leu Ala Glu Asn Glu Lys
    930                 935                 940

Leu Lys Ala Gln Leu His Asp Thr Asn Met Glu Leu Thr Asp Leu Lys
945                 950                 955                 960

Leu Gln Leu Glu Lys Thr Thr Gln Arg Gln Glu Arg Phe Ala Asp Arg
                965                 970                 975

Ser Leu Leu Glu Met Glu Lys Arg Val Ser Gly Lys Ser Gln Tyr Leu
            980                 985                 990

Leu Gly Gly Lys Lys Ser Ser Arg  Lys Lys Asp Ile
        995                 1000

<210> SEQ ID NO 267
<211> LENGTH: 147
<212> TYPE: PRT
<213> ORGANISM: Homo sapiens

<400> SEQUENCE: 267

Met Ala Ala Gln Arg Leu Gly Lys Arg Val Leu Ser Lys Leu Gln Ser
1               5                   10                  15

Pro Ser Arg Ala Arg Gly Pro Gly Gly Ser Pro Gly Gly Leu Gln Lys
            20                  25                  30

Arg His Ala Arg Val Thr Val Lys Tyr Asp Arg Arg Glu Leu Gln Arg
        35                  40                  45

Arg Leu Asp Val Glu Lys Trp Ile Asp Gly Arg Leu Glu Glu Leu Tyr
    50                  55                  60

Arg Gly Met Glu Ala Asp Met Pro Asp Glu Ile Asn Ile Asp Glu Leu
65                  70                  75                  80

Leu Glu Leu Glu Ser Glu Glu Glu Arg Ser Arg Lys Ile Gln Gly Leu
                85                  90                  95
```

```
Leu Lys Ser Cys Gly Lys Pro Val Glu Asp Phe Ile Gln Glu Leu Leu
            100                 105                 110

Ala Lys Leu Gln Gly Leu His Arg Gln Pro Gly Leu Arg Gln Pro Ser
        115                 120                 125

Pro Ser His Asp Gly Ser Leu Ser Pro Leu Gln Asp Arg Ala Arg Thr
    130                 135                 140

Ala His Pro
145

<210> SEQ ID NO 268
<211> LENGTH: 185
<212> TYPE: PRT
<213> ORGANISM: Xenopus laevis

<400> SEQUENCE: 268

Met Glu Ala Asn Ser Pro Arg Lys Ile Gln Phe Thr Val Pro Phe Leu
1               5                   10                  15

Glu Pro His Leu Asp Pro Glu Ala Ala Glu Gln Ile Arg Arg Arg
            20                  25                  30

Pro Thr Pro Ala Thr Leu Val Leu Ser Ser Asp Gln Ser Ser Pro Glu
        35                  40                  45

Ile Asp Glu Glu Arg Val Pro Asn Pro Leu Gln Lys Ser Leu Ser Met
50                  55                  60

Ser Pro His Gln Arg Lys Lys Met Ser Arg Ile Thr Pro Thr Met Lys
65                  70                  75                  80

Glu Leu Gln Leu Leu Ala Glu His His Leu Cys Lys Gln Gly Ser Glu
                85                  90                  95

Glu Glu Lys Ile Pro His Leu Gln Asn Asn Leu Asp Asp Arg Pro Asp
            100                 105                 110

Leu Gly Cys Cys Cys His Gly Asn Thr Ala Ser Thr Gln Ala Ser Gln
        115                 120                 125

Ser His Ile Pro Cys Ser Cys Phe Thr Gln Asp Gly Asn His Asp Thr
    130                 135                 140

Asn Ser Leu Gly Ser Arg His Ser Ser Lys Glu Asp Ser Leu Asp Ser
145                 150                 155                 160

His Val Ser Asp Gly Asn Met Gln Ile Cys Glu Pro Lys Lys Gln Asn
                165                 170                 175

Ser His Ile Ser Phe Ile Glu Asp Lys
            180                 185

<210> SEQ ID NO 269
<211> LENGTH: 5
<212> TYPE: PRT
<213> ORGANISM: Artificial Sequence
<220> FEATURE:
<223> OTHER INFORMATION: S1 Spacer

<400> SEQUENCE: 269

Pro Gly Ala Gly Gly
1               5

<210> SEQ ID NO 270
<211> LENGTH: 5
<212> TYPE: PRT
<213> ORGANISM: Artificial Sequence
<220> FEATURE:
<223> OTHER INFORMATION: S2 Spacer

<400> SEQUENCE: 270

Pro Gly Ala Ala Gly
```

```
<210> SEQ ID NO 271
<211> LENGTH: 4
<212> TYPE: PRT
<213> ORGANISM: Artificial Sequence
<220> FEATURE:
<223> OTHER INFORMATION: S1 Spacer

<400> SEQUENCE: 271

Gly Gly Gly Gly
1

<210> SEQ ID NO 272
<211> LENGTH: 30
<212> TYPE: PRT
<213> ORGANISM: Artificial Sequence
<220> FEATURE:
<223> OTHER INFORMATION: SR Localization Sequence

<400> SEQUENCE: 272

Gln Ala Arg Gln Asn Leu Gln Asn Ala Phe Ile Ala Phe Cys Leu Ile
1               5                   10                  15

Leu Ile Cys Leu Leu Leu Ile Cys Ile Ile Val Met Leu Leu
            20                  25                  30

<210> SEQ ID NO 273
<211> LENGTH: 90
<212> TYPE: DNA
<213> ORGANISM: Artificial Sequence
<220> FEATURE:
<223> OTHER INFORMATION: SR Localization Sequence

<400> SEQUENCE: 273
caggccaggc agaacctcca gaatgctttc attgctttt gtctgattct catctgcctc      60
ctgctgattt gcattatcgt catgctcctg                                      90
```

PP1 LIGANDS

This application claims priority under 35 U.S.C. §120 to U.S. Provisional Patent Application Ser. No. 60/915,611, U.S. Provisional Patent Application Ser. No. 60/915,618, U.S. Provisional Patent Application Ser. No. 60/915,622, each filed May 2, 2007, and U.S. Provisional Patent Application Ser. No. 60/988,021, filed Nov. 14, 2007.

REFERENCE TO SEQUENCE LISTING SUBMITTED ELECTRONICALLY VIA EFS-WEB

This application includes a "SequenceListing.txt," 437,508 bytes, created on Jan. 31, 2013, and submitted electronically via EFS-Web, which is hereby incorporated by reference in its entirety.

FIELD OF INVENTION

The invention relates to mammalian PP1 ligands and modulators. In particular, the invention relates to polypeptides, polypeptide compositions and polynucleotides that encode polypeptides that are ligands and/or modulators of PP1. The invention also relates to polyligands that are homopolyligands or heteropolyligands that modulate PP1 activity. The invention also relates to ligands and polyligands localized to a region of a cell.

This application has subject matter related to application Nos. 60/915,611, 60/915,618, 60/915,622, 60/988,021, Ser. No. 10/724,532 (now U.S. Pat. No. 7,071,295), Ser. No. 10/682,764 (US2004/0185556, PCT/US2004/013517, WO2005/040336), Ser. No. 11/233,246, and US20040572011P (WO2005116231); U.S. Pat. No. 7,091,038; US 20040033600; US 20060200416; US 20060172377. Each of these patents and applications is hereby incorporated by reference.

BACKGROUND OF THE INVENTION

Phosphatases are enzymes that remove phosphate from a molecule. The removal of phosphate is called dephosphorylation. Kinases are enzymes that catalyze the addition of phosphate to a molecule. The addition of phosphate by a kinase is called phosphorylation. When the kinase substrate is a protein molecule, the amino acids commonly phosphorylated are serine, threonine and tyrosine. Kinases and phosphatases often represent competing forces within a cell to transmit, attenuate, or otherwise modulate cellular signals and cellular control mechanisms. Kinases and phosphatases have both overlapping and unique natural substrates. Cellular signals and control mechanisms, as regulated by kinases, phosphatases, and their natural substrates are a target of research tool design and drug design.

PP1 or protein phosphatase 1 is involved in regulation of numerous cellular processes, including heart function. Functional inactivation of the naturally occurring PP1 inhibitor 1 (INH-1) was shown to be associated with the heart failure in human patients (El-Armouche et al. 2004 Cardiovasc Res. 61:87-93). Inactivation of PP1 inhibitor results in the increased activity of PP1. Consistent with this notion, studies (Yamada et al. 2006 FASEB J 20:1197-9) showed that adenovirus-mediated expression of the naturally occurring inhibitor, INH-2, alleviated progression of heart failure and improved survival of the animals. Regulation of cardiac function by PP1 may occur via PP1 mediated dephosphorylation of phospholamban, which in turn regulates the activity of the calcium pump SERCA2 in the sarco(endo)plasmic reticulum (SR) of the muscle cells (Neumann 2002 Basic Res Cardiol. 97 Suppl 1:191-5). Additionally, transgenic animals overexpressing INH-2 had improved heart function and increased levels of phosphorylated PLB (Kirchhefer et al. 2005 Cardiovasc Res 68:98-108).

Mammalian Protein Phosphatase 1 is also known as PP1. The enzymatic activity of PP1 catalytic subunit has been studied (see Terrak et al. 2004 Nature 429:780-4). Unlike kinases, which have more distinct substrate specificites, PP1 catalytic subunit is capable of dephosphorylating many phospho-proteins. It is currently accepted that phosphatase substrate specificity is determined largely by phosphatase binding partners, non-catalytic subunits, and/or regulatory subunits (see for example, Cohen *J Cell Sci* 115:241-256, 2002; Ceulemans et al. *Physiol Rev* 84:1-39, 2004).

Numerous phosphoprotein substrates for PP1 have been identified, including, phospholamban, aurora beta kinase, TP53, MYPT1, RNA polymerase II, PPP1R3C, retinoblastoma, MST1R, cdc25, EF2, BAD, BRCA, histoneH2AX, and IP3 receptor. Furthermore, several cellular protein regulators of PP1 have been identified, including, scapinin, PNUTS, PPPIRA, neurabinI, NIPP1, CPI17, DARPP32, neurabinII, and PPPIR2. Some PP1 substrates, regulators and other research on PP1 biology are described in the following references: Ammosova et al. 2005 Retrovirology 2:47; Ayllon et al. 2000 EMBO J. 19:2237-2246; Carr et al. 2002 Mol. Cell Biol. 22:4124-4135; Egloff et al. 1997 EMBO J. 16:1876-1887; Eto et al. 2004 PNAS 101:8888-8893; Jideama et al. 2006 Int. J. Biol Sci. 2:1-9; Lees-Miller et al. 1991 Mol. Cell Biol. 12:5041-5049; Li et al. 2006 Oncogene 25:3006-3022; Liu et al. 2005 Eur. J. Neurosci. 22:1942-1950; Liu et al. 2002 Cancer Res. 62:6357-6361; Margolis et al. 2003 EMBO J. 22:5734-5745; Champion 2005 Circ. Res. 96:708-710; Ohki et al. 2003 J Mol Biol 326:1539-47; Pathak et al. 2005 Circ. Res. 96:756-766; Quevedo et al. 2003 J. Biol. Chem. 278: 16579-16586; Rubin et al. 2001 Oncogene 20:3776-3785; Santoro et al. 2003 Biochem. J. 376:587-594; Shmueli et al. 2006 Mol. Cell. Neurosci. 32:15-26; Strack et al. 1997 J. Neurochem. 68:2119-2128; Szatmari et al. 2005 J. Biol. Chem. 280:37526-37535; Tang et al. 2003 J. Neurosci. 23:403-415; Tsukada et al. 2006 BBRC 343:839-847; Uematsu et al. 2005 J. Neurochem. 95:1642-1652; Walter et al. 2000 Oncogene 19:4906-4916; Washington et al. 2002 J. Biol. Chem. 277:40442-40448; Yamada et al. 2006 FASEB J. 20:1197-9; Zhan et al. 2003 J. Immunology 171:3785-3793; Siino et al. 2002 BBRC 297:1318-1323; Welsh et al. 1997 Analyt. Biochem. 244:16-21; Rameau et al. 2004 J. Biol. Chem. 279:14307-14314; Toyoshima et al. 2003 PNAS 100: 467-472; Toyofuko et al. 1994 J. Biol. Chem. 269:22929-22932; Hagiwara et al. 1992 Cell 70: 105-113; Ji et al. 2003 J. Biol. Chem. 278:25063-25071; Kimura et al. 1998 FEBS Letters 425:509-512; Kimura et al. 1997 J. Biol. Chem. 272: 15061-15064; Kimura et al. 1996 J. Biol. Chem. 271:21726-21731; Haghighi et al. 2001 J. Biol. Chem. 276:24145-24152; Jin et al. 2003 J. Biol. Chem. 28:30677; Beullens et al. 2000 Biochem. J. 352:651; Sagara et al. 2003 J. Biol. Chem. 278:45611; Bibb et al. 1999 Nature 402:669; Huang et al. 1999 J. Biol. Chem. 274:7870; Landsverk et al. 2005 Biochem. J. 390:709; Kim et al. 2003 J. Biol. Chem. 278:13819; Endo et al. 1996 Biochemistry 35:5220; Weiser et al. 2004 J. Biol. Chem. 279:48904; Park et al. 1994 J. Biol. Chem. 269: 944; Oliver et al. 2002 Mol. Cell. Biol. 13:4690; Yamawaki et al. 2001 BBRC 285:1040-1045; Deng et al. 2002 Biochem. J. 36:17

Small molecule inhibitors of PP1 are known in the art and include okadaic acid and microstatin. Furthermore, kits for assaying PP1 activity are available commercially, such as those available from Sigma-Aldrich (St. Louis, Mo.), New England Biolabs (Ipswich, Mass.), and Promega (Madison, Wis.).

Description of Polypeptide and Polynucleotide Sequences

SEQ ID NOS:1-56 are examples of polyligands and polynucleotides encoding them.

Specifically, the PP1 polyligand of SEQ ID NO:1 is encoded by SEQ ID NO:2, SEQ ID NO:3, and SEQ ID NO:4, wherein codons are optimized for mammalian expression and vector insertion, and wherein SEQ ID NO:3 and SEQ ID NO:4 contain alternative flanking restriction sites applicable to modular cloning methods. SEQ ID NO:1 is an embodiment of a polyligand of the structure A-S1-B-S2-C, wherein A is SEQ ID NO:92 (wherein Xaa is Ala), B is SEQ ID NO:68 (wherein Xaa is Glu), C is SEQ ID NO:93 (wherein Xaa is Glu), and wherein S1 is a spacer of the amino acid sequence PGAGG (SEQ ID NO: 269) and S2 is a spacer of amino acid sequence PGAAG (SEQ ID NO: 270). A polyligand of structure A-S1-B-S2-C is also called herein a heteropolyligand, shown generically in FIG. 4G.

The PP1 polyligand of SEQ ID NO:5 is encoded by SEQ ID NO:6, SEQ ID NO:7, and SEQ ID NO:8, wherein codons are optimized for mammalian expression and vector insertion, and wherein SEQ ID NO:7 and SEQ ID NO:8 contain alternative flanking restriction sites applicable to modular cloning methods. SEQ ID NO:5 is an embodiment of a polyligand of the structure A-S1-B-S2-C, wherein A is SEQ ID NO:95, B is SEQ ID NO:69 (wherein Xaa is Ser), C is SEQ ID NO:96 (wherein Xaa is Thr), and wherein S1 is a spacer of the amino acid sequence PGAGG (SEQ ID NO: 269), and S2 is a spacer of amino acid sequence PGAAG (SEQ ID NO: 270). A polyligand of structure A-S1-B-S2-C is also called herein a heteropolyligand, shown generically in FIG. 4G.

The PP1 polyligand of SEQ ID NO:9 is encoded by SEQ ID NO:10, SEQ ID NO:11, and SEQ ID NO:12, wherein codons are optimized for mammalian expression and vector insertion, and wherein SEQ ID NO:11 and SEQ ID NO:12 contain alternative flanking restriction sites applicable to modular cloning methods. SEQ ID NO:9 is an embodiment of a polyligand of the structure X-S3-Y-S2-Z, wherein X is SEQ ID NO:102 (wherein Xaa is Ser), Y is SEQ ID NO:72 (wherein Xaa is Asp), Z is SEQ ID NO:100 (wherein Xaa is Thr), and wherein S3 is a spacer of the amino acid sequence PGGAG (SEQ ID NO: 269), and S2 is a spacer of amino acid sequence PGAAG (SEQ ID NO: 270. A polyligand of structure X-S3-Y-S2-Z is also called herein a heteropolyligand, shown generically in FIG. 4G.

The PP1 polyligand of SEQ ID NO:13 is encoded by SEQ ID NO:14, SEQ ID NO:15, and SEQ ID NO:16, wherein codons are optimized for mammalian expression and vector insertion, and wherein SEQ ID NO:15 and SEQ ID NO:16 contain alternative flanking restriction sites applicable to modular cloning methods. SEQ ID NO:13 is an embodiment of a polyligand of the structure X-S3-Y-S2-Z, wherein X is SEQ ID NO:101, Y is SEQ ID NO:74 (wherein Xaa is Asp), Z is SEQ ID NO:79 (wherein Xaa is Ser or Thr), and wherein S3 is a spacer of the amino acid sequence PGGAG (SEQ ID NO: 269), and S2 is a spacer of amino acid sequence PGAAG (SEQ ID NO: 270). A polyligand of structure X-S3-Y-S2-Z is also called herein a heteropolyligand, shown generically in FIG. 4G.

The PP1 polyligand of SEQ ID NO:17 is encoded by SEQ ID NO:18, SEQ ID NO:19, and SEQ ID NO:20, wherein codons are optimized for mammalian expression and vector insertion, and wherein SEQ ID NO:19 and SEQ ID NO:20 contain alternative flanking restriction sites applicable to modular cloning methods. SEQ ID NO:17 is an embodiment of a polyligand of the structure X-S4-Y-S2-Z, wherein X is SEQ ID NO:93 (wherein Xaa is Glu), Y is SEQ ID NO:75 (wherein Xaa is Ser or Asp), Z is SEQ ID NO:92 (wherein Xaa is Ala), and wherein S4 is a spacer of the amino acid sequence PPGAG (SEQ ID NO: 269), and S2 is a spacer of amino acid sequence PGAAG (SEQ ID NO: 270). A polyligand of structure X-S4-Y-S2-Z is also called herein a heteropolyligand, shown generically in FIG. 4G.

The PP1 polyligand of SEQ ID NO:21 is encoded by SEQ ID NO:22, SEQ ID NO:23, and SEQ ID NO:24, wherein codons are optimized for mammalian expression and vector insertion, and wherein SEQ ID NO:23 and SEQ ID NO:24 contain alternative flanking restriction sites applicable to modular cloning methods. SEQ ID NO:21 is an embodiment of a polyligand of the structure D-S3-E-S2-F, wherein D is SEQ ID NO:73 (wherein Xaa is Asp), E is SEQ ID NO:95, F is SEQ ID NO:98 (wherein Xaa is Glu or Thr), and wherein S3 is a spacer of the amino acid sequence PGGAG (SEQ ID NO: 269), and S2 is a spacer of amino acid sequence PGAAG (SEQ ID NO: 270). A polyligand of structure D-S3-E-S2-F is also called herein a heteropolyligand, shown generically in FIG. 4G.

The PP1 polyligand of SEQ ID NO:25 is encoded by SEQ ID NO:26, SEQ ID NO:27, and SEQ ID NO:28, wherein codons are optimized for mammalian expression and vector insertion, and wherein SEQ ID NO:27 and SEQ ID NO:28 contain alternative flanking restriction sites applicable to modular cloning methods. SEQ ID NO:25 is an embodiment of a polyligand of the structure D-S3-E-S2-F, wherein D is SEQ ID NO:101, E is SEQ ID NO:79 (wherein Xaa is Ser or Thr), F is SEQ ID NO:108 (wherein Xaa is Glu or Asp), and wherein S3 is a spacer of the amino acid sequence PGGAG (SEQ ID NO: 269), and S2 is a spacer of amino acid sequence PGAAG (SEQ ID NO: 270). A polyligand of structure D-S3-E-S2-F is also called herein a heteropolyligand, shown generically in FIG. 4G.

The PP1 polyligand of SEQ ID NO:29 is encoded by SEQ ID NO:30, SEQ ID NO:31, and SEQ ID NO:32, wherein codons are optimized for mammalian expression and vector insertion, and wherein SEQ ID NO:31 and SEQ ID NO:32 contain alternative flanking restriction sites applicable to modular cloning methods. SEQ ID NO:29 is an embodiment of a polyligand of the structure D-S3-E-S2-F, wherein D is SEQ ID NO:96 (wherein Xaa is Thr), E is SEQ ID NO:69 (wherein Xaa is Ser or Thr), F is SEQ ID NO:95, and wherein S3 is a spacer of the amino acid sequence PGGAG (SEQ ID NO: 269), and S2 is a spacer of amino acid sequence PGAAG (SEQ ID NO: 270). A polyligand of structure D-S3-E-S2-F is also called herein a heteropolyligand, shown generically in FIG. 4G.

The PP1 polyligand of SEQ ID NO:33 is encoded by SEQ ID NO:34, SEQ ID NO:35, and SEQ ID NO:36, wherein codons are optimized for mammalian expression and vector insertion, and wherein SEQ ID NO:35 and SEQ ID NO:36 contain alternative flanking restriction sites applicable to modular cloning methods. SEQ ID NO:33 is an embodiment of a polyligand of the structure H-S3-J-S2-K, wherein H is SEQ ID NO:80 (wherein Xaa is Asp or Ser or Thr), J is SEQ ID NO:109 (wherein Xaa is Glu), K is SEQ ID NO:110 (wherein Xaa is Glu), and wherein S3 is a spacer of the amino acid sequence PGGAG (SEQ ID NO: 269), and S2 is a spacer of amino acid sequence PGAAG (SEQ ID NO: 270). A polyligand of structure H-S3-J-S2-K is also called herein a heteropolyligand, shown generically in FIG. 4G.

The PP1 polyligand of SEQ ID NO:37 is encoded by SEQ ID NO:38, SEQ ID NO:39, and SEQ ID NO:40, wherein codons are optimized for mammalian expression and vector insertion, and wherein SEQ ID NO:39 and SEQ ID NO:40 contain alternative flanking restriction sites applicable to modular cloning methods. SEQ ID NO:37 is an embodiment of a polyligand of the structure H-S3-J-S2-K, wherein H is SEQ ID NO:80 (wherein Xaa is Glu or Ser or Thr), J is SEQ ID NO:109 (wherein Xaa is Glu), K is SEQ ID NO:110 (wherein Xaa is Glu), and wherein S3 is a spacer of the amino acid sequence PGGAG (SEQ ID NO: 269), and S2 is a spacer of amino acid sequence PGAAG (SEQ ID NO: 270). A polyligand of structure H-S3-J-S2-K is also called herein a heteropolyligand, shown generically in FIG. 4G.

The PP1 polyligand of SEQ ID NO:41 is encoded by SEQ ID NO:42, SEQ ID NO:43, and SEQ ID NO:44, wherein codons are optimized for mammalian expression and vector insertion, and wherein SEQ ID NO:43 and SEQ ID NO:44 contain alternative flanking restriction sites applicable to modular cloning methods. SEQ ID NO:41 is an embodiment of a polyligand of the structure A-S5-B-S2-C, wherein A is SEQ ID NO:92 (wherein Xaa is Ser or Thr), B is SEQ ID NO:68 (wherein Xaa is Glu), C is SEQ ID NO:93 (wherein Xaa is Glu), and wherein S5 is a spacer of the amino acid sequence PGAGG (SEQ ID NO: 269), and S2 is a spacer of amino acid sequence PGAAG (SEQ ID NO: 270). A polyligand of structure A-S5-B-S2-C is also called herein a heteropolyligand, shown generically in FIG. 4G.

The PP1 polyligand of SEQ ID NO:45 is encoded by SEQ ID NO:46, SEQ ID NO:47, and SEQ ID NO:48, wherein codons are optimized for mammalian expression and vector insertion, and wherein SEQ ID NO:47 and SEQ ID NO:48 contain alternative flanking restriction sites applicable to modular cloning methods. SEQ ID NO:45 is an embodiment of a polyligand of the structure A-S5-B-S2-C, wherein A is SEQ ID NO:93 (wherein Xaa is Glu), B is SEQ ID NO:82 (wherein Xaa is Glu), C is SEQ ID NO:111 (wherein Xaa is Ala), and wherein S5 is a spacer of the amino acid sequence PGAGG (SEQ ID NO: 269), and S2 is a spacer of amino acid sequence PGAAG (SEQ ID NO: 270). A polyligand of structure A-S5-B-S2-C is also called herein a heteropolyligand, shown generically in FIG. 4G.

The PP1 polyligand of SEQ ID NO:49 is encoded by SEQ ID NO:50, SEQ ID NO:51, and SEQ ID NO:52, wherein codons are optimized for mammalian expression and vector insertion, and wherein SEQ ID NO:51 and SEQ ID NO:52 contain alternative flanking restriction sites applicable to modular cloning methods. SEQ ID NO:49 is an embodiment of a polyligand of the structure A-S5-B-S2-C, wherein A is SEQ ID NO:105 (wherein Xaa is Glu), B is SEQ ID NO:76 (wherein Xaa is Ser), and wherein S5 is a spacer of the amino acid sequence PGAGG (SEQ ID NO: 269), and S2 is a spacer of amino acid sequence PGAAG (SEQ ID NO: 270). A polyligand of structure A-S5-B-S2-C is also called herein a heteropolyligand, shown generically in FIG. 4G.

The PP1 polyligand of SEQ ID NO:53 is encoded by SEQ ID NO:54, SEQ ID NO:55, and SEQ ID NO:56, wherein codons are optimized for mammalian expression and vector insertion, and wherein SEQ ID NO:55 and SEQ ID NO:56 contain alternative flanking restriction sites applicable to modular cloning methods. SEQ ID NO:53 is an embodiment of a polyligand of the structure A-S5-B-S2-C, wherein A is SEQ ID NO:108 (wherein Xaa is Asp or Glu or Ala), B is SEQ ID NO:67 (wherein Xaa is Glu), C is SEQ ID NO:100 (wherein Xaa is Glu), and wherein S5 is a spacer of the amino acid sequence PGAGG (SEQ ID NO: 269), and S2 is a spacer of amino acid sequence PGAAG (SEQ ID NO: 270). A polyligand of structure A-S5-B-S2-C is also called herein a heteropolyligand, shown generically in FIG. 4G.

SEQ ID NOS:57-66 and SEQ ID NOS:83-91 are full length PP1 protein substrates and regulators, respectively. These sequences have the following public database accession numbers: NP_054829, NP_003591, NP_150281, BAC82348, NP_000537, NP_006732, NP_115984, NP_002471, Q9UD71, NP_002705, NP_000928, NP_005389, NP_000312, NP_002438, NP_002658, NP_006232, NP_060120, NP_001952, and NP_001781. Each of the sequences represented by these accession numbers is incorporated by reference herein. In SEQ ID NOS:57-66, the positions of the amino acid(s) dephosphorylatable by PP1 are represented by Xaa. In a parental wild type reference sequence, Xaa is serine or threonine. In the ligands of the invention, Xaa is any amino acid. In some embodiments Xaa is alanine. Furthermore, in SEQ ID NOS:83-91, the positions of the amino acid(s) modified from a parental wild type reference sequence are represented by Xaa. In the ligands of the invention, Xaa is any amino acid. In some embodiments, Xaa is aspartate and/or glutamate.

SEQ ID NOS:67-82 are partial sequences of SEQ ID NOS: 57-66, which represent examples of polypeptide ligand sequences where the location(s) of the PP1 dephosphorylatable serine or threonine in the natural parental polypeptide is designated as Xaa.

SEQ ID NOS:92-111 are partial sequences of SEQ ID NOS:83-91, which represent examples of peptide ligand sequences where the location(s) of amino acid(s) modified from a parental wild type reference sequence are designated as Xaa.

Amino acid sequences containing Xaa encompass polypeptides where Xaa is any amino acid.

Below is a descriptive annotation of several heteropolyligand embodiments of the invention.

SEQ ID NO:1 Partial NIPP1-spacer-Partial Aurora beta Kinase-spacer-Partial CPI17

SEQ ID NO:5 Partial Scapinin-spacer-Partial TP53-spacer-Partial PPP1R1A

SEQ ID NO:9 Partial NeurabinII-spacer-Partial MYPT1-spacer-Partial DARPP32

SEQ ID NO:13 Partial PNUTS-spacer-Partial RNAPII-spacer-Partial PTG

SEQ ID NO:17 Partial CPI17-spacer-Partial Rb-spacer-Partial NIPP1

SEQ ID NO:21 Partial MST1R-spacer-Partial Scapinin-spacer-Partial DARPP32

SEQ ID NO:25 Partial PNUTS-spacer-Partial PTG-spacer-Partial PPPIR1A

SEQ ID NO:29 Partial PPPIR1A-spacer-Partial TP53-spacer-Partial Scapinin

SEQ ID NO:33 Partial PLN-spacer-Partial PPPIR1A-spacer-Partial PPPIR2

SEQ ID NO:37 Partial PLN-spacer-Partial PPPIR1A-spacer-Partial PPPIR2

SEQ ID NO:41 Partial NIPP1-spacer-Partial Aurora beta kinase-spacer-Partial CPI17

SEQ ID NO:45 Partial CPI17-spacer-Partial RNAPII-spacer-Partial NIPPI

SEQ ID NO:49 Partial PPPIR2-spacer-Partial CDC25-spacer-Partial NeurabinI

SEQ ID NO:53 Partial PPPIR1A-spacer-Partial EF2-spacer-Partial DARPP32

SEQ ID NO:112 is another example of a full length PP1 substrate, human phospholamban, database accession NP_002658.

SEQ ID NOS:113-136 are monomeric PP1 ligands, wherein Xaa at positions 16 or 17 are amino acids other than serine or threonine; and wherein X at other positions is an amino acid other than found in the corresponding position of SEQ ID NO:112.

SEQ ID NOS:137-156 are monomeric PP1 ligands, wherein Xaa at positions 16 or 17 are amino acids other than serine or threonine.

SEQ ID NOS:157-160 are monomeric PP1 ligands, wherein Xaa at positions 7 or 8 are amino acids other than serine or threonine.

SEQ ID NOS:161-164 are monomeric PP1 ligands, wherein Xaa at positions 6 or 7 are amino acids other than serine or threonine.

SEQ ID NOS:165-176 are further examples of polyligands and polynucleotides encoding them.

Specifically, the PP1 polyligand of SEQ ID NO:165 is encoded by SEQ ID NO:166, SEQ ID NO:167 and by SEQ ID NO:168, wherein codons are optimized for mammalian expression and vector insertion, and wherein SEQ ID NO:167 and SEQ ID NO:168 contain alternative flanking restriction sites applicable to modular cloning methods. SEQ ID NO:165 is an embodiment of a polyligand of the structure A-S1-B, wherein A is SEQ ID NO:139 (wherein Xaa is Asp, Glu, or Ala), B is SEQ ID NO:136 (wherein Xaa is Asp, Glu, or Ala), and wherein S1 is a spacer of the amino acid sequence GGGG (SEQ ID NO: 271). A polyligand of structure A-S1-B is also called herein a heteropolyligand, shown generically in FIG. 4A.

The PP1 polyligand of SEQ ID NO:169 is encoded by SEQ ID NO:170, SEQ ID NO:171 and by SEQ ID NO:172, wherein codons are optimized for mammalian expression and vector insertion, and wherein SEQ ID NO:171 and SEQ ID NO:172 contain alternative flanking restriction sites applicable to modular cloning methods. SEQ ID NO:165 is an embodiment of a polyligand of the structure A-S1-B, wherein A is SEQ ID NO:152 (wherein Xaa is Asp, Glu, or Ala), B is SEQ ID NO:136 (wherein Xaa is Asp, Glu, or Ala), and wherein S1 is a spacer of the amino acid sequence GGGG (SEQ ID NO: 271). A polyligand of structure A-S1-B is also called herein a hete opolyligand, shown generically in FIG. 4A.

The PP1 polyligand of SEQ ID NO:173 is encoded by SEQ ID NO:174, SEQ ID NO:175 and by SEQ ID NO:176, wherein codons are optimized for mammalian expression and vector insertion, and wherein SEQ ID NO:175 and SEQ ID NO:176 contain alternative flanking restriction sites applicable to modular cloning methods. SEQ ID NO:173 is an embodiment of a polyligand of the structure A-S1-B-S1-C-S1-D, wherein A is SEQ ID NO:145 (wherein Xaa is Asp or Glu), B is SEQ ID NO:157 (wherein Xaa is Asp or Glu), C is SEQ ID NO:161 (wherein Xaa is Asp or Glu), D is SEQ ID NO:164 (wherein Xaa is Asp or Glu), and wherein S1 is a spacer of the amino acid sequence GGGG (SEQ ID NO:271). A polyligand of structure A-S1-B-S1-C-S1-D is also called herein a heteropolyligand, shown generically in FIG. 4D.

In SEQ ID NOS:113-164, the positions of the amino acid(s) dephosphorylatable by PP1 correspond to positions 16 and 17 of SEQ ID NO:112 and are represented by Xaa. In wild-type proteins at positions corresponding to amino acid 16 and 17, Xaa is serine or threonine. In the ligands of the invention, Xaa is any amino acid. In some embodiments, Xaa is other than serine or threonine. In other embodiments, Xaa is Glu, Asp, or Ala.

SEQ ID NOS:113-136 represent examples of monomeric peptide ligand sequences containing a sarco(endo)plasmic reticulum localization signal at the C-terminal.

SEQ ID NOS:137-164 represent examples of monomeric peptide ligand sequences lacking a specific localization signal.

SEQ ID NOS:177-200 are further examples of polyligands and polynucleotides encoding them.

Specifically, the PP1 polyligand of SEQ ID NO:177 is encoded by SEQ ID NO:178, SEQ ID NO:179, and SEQ ID NO:180, wherein codons are optimized for mammalian expression and vector insertion, and wherein SEQ ID NO:179 and SEQ ID NO:180 contain alternative flanking restriction sites applicable to modular cloning methods. SEQ ID NO:177 is an embodiment of a polyligand of the structure A-B, wherein A is SEQ ID NO:215 (wherein Xaa is Asp) and B is SEQ ID NO:217 (wherein Xaa is Asp). A polyligand of structure A-B is also called herein a heteropolyligand, shown generically in FIG. 3A.

The PP1 polyligand of SEQ ID NO:181 is encoded by SEQ ID NO:182, SEQ ID NO:183, and SEQ ID NO:184, wherein codons are optimized for mammalian expression and vector insertion, and wherein SEQ ID NO:183 and SEQ ID NO:184 contain alternative flanking restriction sites applicable to modular cloning methods. SEQ ID NO:181 is an embodiment of a polyligand of the structure A-B, wherein A is SEQ ID NO:214 (wherein Xaa is Glu) and B is SEQ ID NO:217 (wherein Xaa is Asp). A polyligand of structure A-B is also called herein a heteropolyligand, shown generically in FIG. 3A.

The PP1 polyligand of SEQ ID NO:185 is encoded by SEQ ID NO:186, SEQ ID NO:187, and SEQ ID NO:188, wherein codons are optimized for mammalian expression and vector insertion, and wherein SEQ ID NO:187 and SEQ ID NO:188 contain alternative flanking restriction sites applicable to modular cloning methods. SEQ ID NO:185 is an embodiment of a polyligand of the structure A-B, wherein A is SEQ ID NO:216 (wherein Xaa is Glu) and B is SEQ ID NO:218 (wherein Xaa is Glu). A polyligand of structure A-B is also called herein a heteropolyligand, shown generically in FIG. 3A.

The PP1 polyligand of SEQ ID NO:189 is encoded by SEQ ID NO:190, SEQ ID NO:191, and SEQ ID NO:192, wherein codons are optimized for mammalian expression and vector insertion, and wherein SEQ ID NO:191 and SEQ ID NO:192 contain alternative flanking restriction sites applicable to modular cloning methods. SEQ ID NO:189 is an embodiment of a polyligand of the structure A-B, wherein A is SEQ ID NO:212 (wherein Xaa is Asp) and B is SEQ ID NO:213 (wherein Xaa is Asp). A polyligand of structure A-B is also called herein a heteropolyligand, shown generically in FIG. 3A.

The PP1 polyligand of SEQ ID NO:193 is encoded by SEQ ID NO:194, SEQ ID NO:195, and SEQ ID NO:196, wherein codons are optimized for mammalian expression and vector insertion, and wherein SEQ ID NO:195 and SEQ ID NO:196 contain alternative flanking restriction sites applicable to modular cloning methods. SEQ ID NO:193 is an embodiment of a polyligand of the structure A-B, wherein A is SEQ ID NO:223 (wherein Xaa is Ala) and B is SEQ ID NO:222 (wherein Xaa is Ala). A polyligand of structure A-B is also called herein a heteropolyligand, shown generically in FIG. 3A.

The PP1 polyligand of SEQ ID NO:197 is encoded by SEQ ID NO:198, SEQ ID NO:199, and SEQ ID NO:200, wherein codons are optimized for mammalian expression and vector insertion, and wherein SEQ ID NO:199 and SEQ ID NO:200 contain alternative flanking restriction sites applicable to modular cloning methods. SEQ ID NO:197 is an embodiment of a polyligand of the structure A-B, wherein A is SEQ ID NO:221 and B is SEQ ID NO:220. A polyligand of structure A-B is also called herein a heteropolyligand, shown generically in FIG. 3A.

SEQ ID NOS:201-207 and SEQ ID NOS:208-211 are full length PP1 protein substrates and regulators, respectively. These sequences have the following public database accession numbers: NP_003591, BAC82348, NP_006732, NP_002471, NP_002705, NP_060120, NP_004313, NP_620221, NP_002096, NP_001007236, and NP_009225. Each of the sequences represented by these accession numbers is incorporated by reference herein. In SEQ ID NOS:201-207 the positions of the amino acid(s) dephosphorylatable by PP1 are represented by Xaa. In a parental wild type reference sequence, Xaa is serine or threonine. In the ligands of the invention, Xaa is any amino acid. In some embodiments, Xaa is alanine. In other embodiments of the invention, Xaa is aspartate and/or glutamate.

Furthermore, in SEQ ID NOS:208-211, the positions of the amino acid(s) modified from a parental wild type reference sequence are represented by Xaa. In the ligands of the invention, Xaa is any amino acid. In some embodiments, Xaa is aspartate and/or glutamate.

SEQ ID NOS:212-219 are partial sequences of SEQ ID NOS:201-207, which represent examples of polypeptide ligand sequences where the location(s) of the PP1 dephosphorylatable serine or threonine in the natural parental polypeptide is designated as Xaa.

SEQ ID NOS:220-223 are partial sequences of SEQ ID NOS:208-211, which represent examples of peptide ligand sequences where the location(s) of amino acid(s) modified from a parental wild type reference sequence are designated as Xaa.

SEQ ID NOS:212-223 are further examples of monomeric PP1 ligands.

Amino acid sequences containing Xaa encompass polypeptides where Xaa is any amino acid.

SEQ ID NO:224-250 are further examples of polyligands and polynucleotides encoding them.

Specifically, the PP1 polyligand of SEQ ID NO:224 is encoded by SEQ ID NO:225 and SEQ ID NO:226, wherein codons are optimized for mammalian expression and vector insertion, and wherein SEQ ID NO:226 contains flanking restriction sites applicable to modular cloning methods. SEQ ID NO:224 is an embodiment of a polyligand of the structure A-S-B-C, wherein A is SEQ ID NO:251, B is SEQ ID NO:256, C is SEQ ID NO:262, and S is a spacer of SEQ ID NO:263. A polyligand of structure A-S-B-C is also called herein a heteropolyligand, shown generically in FIG. 4E.

The PP1 polyligand of SEQ ID NO:227 is encoded by SEQ ID NO:228 and SEQ ID NO:229, wherein codons are optimized for mammalian expression and vector insertion, and wherein SEQ ID NO:229 contains flanking restriction sites applicable to modular cloning methods. SEQ ID NO:227 is an embodiment of a polyligand of the structure A-S-B-C, wherein A is SEQ ID NO:252, B is SEQ ID NO:256, C is SEQ ID NO:262, and S is a spacer of SEQ ID NO:263. A polyligand of structure A-S-B-C is also called herein a heteropolyligand, shown generically in FIG. 4E.

The PP1 polyligand of SEQ ID NO:230 is encoded by SEQ ID NO:231 and SEQ ID NO:232, wherein codons are optimized for mammalian expression and vector insertion, and wherein SEQ ID NO:232 contains flanking restriction sites applicable to modular cloning methods. SEQ ID NO:230 is an embodiment of a polyligand of the structure A-B-C, wherein A is SEQ ID NO:257, B is SEQ ID NO:262 and C is SEQ ID NO:253. A polyligand of structure A-B-C is also called herein a heteropolyligand, shown generically in FIG. 3B.

The PP1 polyligand of SEQ ID NO:233 is encoded by SEQ ID NO:234 and SEQ ID NO:235, wherein codons are optimized for mammalian expression and vector insertion, and wherein SEQ ID NO:235 contains flanking restriction sites applicable to modular cloning methods. SEQ ID NO:233 is an embodiment of a polyligand of the structure A-B-C, wherein A is SEQ ID NO:257, B is SEQ ID NO:262 and C is SEQ ID NO:254. A polyligand of structure A-B-C is also called herein a heteropolyligand, shown generically in FIG. 3B.

The PP1 polyligand of SEQ ID NO:236 is encoded by SEQ ID NO:237 and SEQ ID NO:238, wherein codons are optimized for mammalian expression and vector insertion, and wherein SEQ ID NO:238 contains flanking restriction sites applicable to modular cloning methods. SEQ ID NO:236 is an embodiment of a polyligand of the structure A-S1-B-S2, wherein A is SEQ ID NO:252, B is SEQ ID NO:261, S1 is a spacer of SEQ ID NO:264, and S2 is a spacer of SEQ ID NO:265. A polyligand of structure A-S1-B-S2 is also called herein a heteropolyligand, shown generically in FIG. 4B.

The PP1 polyligand of SEQ ID NO:239 is encoded by SEQ ID NO:240 and SEQ ID NO:241, wherein codons are optimized for mammalian expression and vector insertion, and wherein SEQ ID NO:241 contains flanking restriction sites applicable to modular cloning methods. SEQ ID NO:239 is an embodiment of a polyligand of the structure A-S1-B-S2, wherein A is SEQ ID NO:255, B is SEQ ID NO:258, S1 is a spacer of SEQ ID NO:264, and S2 is a spacer of SEQ ID NO:265. A polyligand of structure A-S1-B-S2 is also called herein a heteropolyligand, shown generically in FIG. 4B.

The PP1 polyligand of SEQ ID NO:242 is encoded by SEQ ID NO:243 and SEQ ID NO:244, wherein codons are optimized for mammalian expression and vector insertion, and wherein SEQ ID NO:244 contains flanking restriction sites applicable to modular cloning methods. SEQ ID NO:242 is an embodiment of a polyligand of the structure A-S1-B-S2, wherein A is SEQ ID NO:255, B is SEQ ID NO:259, S1 is a spacer of SEQ ID NO:264, and S2 is a spacer of SEQ ID NO:265. A polyligand of structure A-S1-B-S2 is also called herein a heteropolyligand, shown generically in FIG. 4B.

The PP1 polyligand of SEQ ID NO:245 is encoded by SEQ ID NO:246 and SEQ ID NO:247, wherein codons are optimized for mammalian expression and vector insertion, and wherein SEQ ID NO:247 contains flanking restriction sites applicable to modular cloning methods. SEQ ID NO:245 is an embodiment of a polyligand of the structure A-B-C, wherein A is SEQ ID NO:256, B is SEQ ID NO:262 and C is SEQ ID NO:254. A polyligand of structure A-B-C is also called herein a heteropolyligand, shown generically in FIG. 3B.

The PP1 polyligand of SEQ ID NO:248 is encoded by SEQ ID NO:249 and SEQ ID NO:250, wherein codons are optimized for mammalian expression and vector insertion, and wherein SEQ ID NO:250 contains flanking restriction sites applicable to modular cloning methods. SEQ ID NO:248 is an embodiment of a polyligand of the structure A-S1-B-S2, wherein A is SEQ ID NO:255, B is SEQ ID NO:261, S1 is a spacer of SEQ ID NO:264, and S2 is a spacer of SEQ ID NO:265. A polyligand of structure A-S1-B-S2 is also called herein a heteropolyligand, shown generically in FIG. 4B.

SEQ ID NO:266-268 are full length PP1 catalytic subunit binding proteins. These sequences have the following public database accession numbers: NP_990454.1, NP_150281.1, NP_001082695.1. Each of the sequences represented by these accession numbers is incorporated by reference herein.

In one embodiment of the invention, where truncation fragments of SEQ ID NO:267 are utilized, amino acids corresponding to positions 38, 66 and 67 of SEQ ID NO:267 may be optionally mutated to any amino acid. In one embodiment, a mutation may generate a pseudophosphorylated polypeptide, such as by replacing with an acidic amino acid such as aspartate or glutamate. In a specific embodiment, the mutations are T38D and/or G66E and/or M67A.

In another embodiment of the invention, where fragments of SEQ ID NO:268 are utilized, amino acids corresponding to positions 35 and 38 of SEQ ID NO:268 may be optionally mutated to any amino acid. In one embodiment, a mutation may generate a pseudophosphorylated polypeptide, such as by replacing with an acidic amino acid such as aspartate or glutamate. In a specific embodiment, the mutations are T35D and/or T38D.

SEQ ID NOS:251-258 are partial sequences (truncation fragments) of SEQ ID NO:266-268.

SEQ ID NOS:259-262 are mutated partial sequences (mutated truncation fragments) of SEQ ID NOS:267-268.

SEQ ID NOS:263-265 are short peptide spacer amino acid sequences.

SEQ ID NOS:251-262 are further examples of monomeric PP1 ligands.

Three letter amino acid codes and one letter amino acid codes are used herein as is commonly known in the art.

DESCRIPTION OF DRAWINGS

The patent or application file contains at least one drawing executed in color. Copies of this patent or patent application publication with color drawing(s) will be provided by the Office upon request and payment of the necessary fee.

FIGS. 1A and 1B show examples of polyligands of the invention correlated with respective SEQ ID NOS.

FIGS. 4A-4I show examples of heteropolymeric ligands with spacers.

FIGS. 7A-7I show examples of ligands and polymeric ligands linked to an optional localization signal.

FIGS. 8A-8K show examples of ligands and polymeric ligands linked to an optional localization signal and an optional epitope tag.

FIGS. 9A-9G show examples of gene constructs where ligands and polyligands are linked to an optional localization signal, an optional epitope tag, and/or an optional reporter.

FIG. 30A shows undifferentiated P19 cells. FIG. 30B shows P19 cells after 48 hours exposure to DMSO. FIG. 30C is a still photograph of beating P19 cardiomyocytes after 8 days differentiation with DMSO. FIG. 30D shows differentiated P19 cardiomyocytes expressing cardiac muscle troponin (red). Rabbit anti-cardiac troponin I and goat anti-rabbit secondary antibody conjugated with AlexaFluor 546. Nuclei are counter stained with DAPI (blue). Specifically, P19 cells were plated in bacteriological Petri dishes and exposed to DMSO for 48 hours. The subsequent embryoid bodies (large cells masses) were transferred to mammalian tissue culture plates in regular medium. After 5 days, the cells reached confluency in the plate. By eight days, the cells synchronize and beat in the culture dish. Differentiated cells were fixed with 4% paraformaldehyde and incubated with rabbit anti-Troponin I, followed with AlexaFluor 546-conjugated goat anti-rabbit IgG secondary antibody. The cell nuclei were counterstained with DAPI. The cells were imaged on a Zeiss Axioscope fitted with appropriate filters and an Axiovision M2 camera.

FIG. 31 shows % Inhibition of PP1 in an in vitro assay. Polyligands were transcribed in vitro from plasmid DNA using Ambion's SP6 Megascript Kit (AM1330; according to manufacturer's protocol). RNA was subsequently translated in vitro using Ambion's Retic Lysate IVT Kit (AM1200; according to manufacturer's protocol) and immunoprecipitated from the reticulocyte lysate employing the Profound HA Tag IP Kit from Pierce (23610; according to manufacturer's protocol). Translation products were quantified using Pierce's Coomassie Plus Protein Reagent (1856210; microplate procedure). Following quantification, enzymatic reactions were performed in duplicate wells of a low-binding microtiter plate (TRP 96196). The PP1 substrate is p-nitrophenyl phosphate and appearance of a cleaved phosphate molecule results in chromogenic product formation that can be read at 405 nm.

µM activator drug for 24 hours. Red color shows location of phospholamban. Green illustrates localization of our polyligand (SEQ ID NO:239 fused to SR localization signal). Blue shows nuclei. Red and green overlap (yellow) in the merged image indicates co-localization. FIG. 33A is without activator drug. FIG. 33B is with activator drug. Merged fields are: cell nuclei stained with DAPI (Blue), HA-tagged polyligand imaged with rat anti-HA antibody and secondary antibody conjugated to AlexaFluor 488 (green), and phosphoPLB-Thr17 was imaged by staining with rabbit anti-PLB-Phosphothreonine antibody and secondary antibody conjugated to AlexaFluor 546 (red).

FIGS. 35C-35E show diagrams of PP1 ligands of the invention.

FIG. 36 shows sequence alignments of wild type phospholamban with PP1 inhibitor ligands, where amino acids corresponding to positions 16 and/or 17 of wild type phospholamban have been mutated to either aspartate or glutamate, and where amino acids corresponding to positions 31-52 (designated as X) are mutated to any amino acid other than wild type. In one embodiment, X is alanine or glycine.

FIG. 37 shows sequence alignments of wild type phospholamban with PP1 inhibitors, where amino acids corresponding to position 16 and/or position 17 of wild type phospholamban has been mutated to either aspartate or glutamate, and other amino acids have substitutions or have been deleted as indicated.

FIGS. 38A-38B show example diagrams of polyligand PP1 inhibitors. The PP1 inhibitor shown in FIG. 38B is SEQ ID NO: 145.

FIG. 39 shows results of an in vitro assay similar to the one used for generating the data of FIG. 31, using PP1 of rabbit origin.

BRIEF DESCRIPTION OF THE INVENTION

Figure 2A:
FIGS. 2A-2F show examples of homopolymeric ligands with and without spacers.
Figure 2B:
Figure 2C:
Figure 2D:
Figure 2E:
Figure 2F:
Figure 3A:
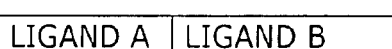
FIGS. 3A-3E show examples of heteropolymeric ligands without spacers.
Figure 3B:
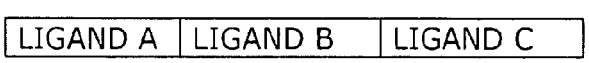
Figure 3C:
Figure 3D:
Figure 3E:
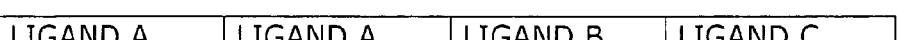
Figure 5A:
FIGS. 5A-5H show examples of ligands and polymeric ligands linked to an optional epitope tag.
Figure 5B:
Figure 5C:
Figure 5D:
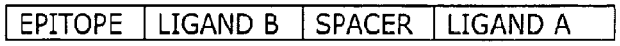
Figure 5E:
Figure 5F:
Figure 5G:
Figure 5H:
Figure 6A:
FIGS. 6A-6H show examples of ligands and polymeric ligands linked to an optional reporter.
Figure 6B:
Figure 6C:
Figure 6D:
Figure 6E:
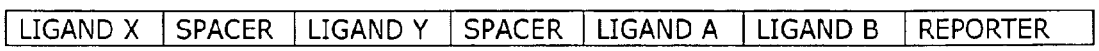
Figure 6F:
Figure 6G:
Figure 6H:
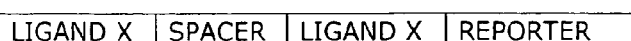

Novel PP1 polyligands and methods of making and using them are disclosed. The polyligand decoys are optionally linked to localization signals. In vitro enzymatic assays and live cell assays were used to test PP1 modulating activity.

Despite the fact that PP1 represents an attractive therapeutic target, the use of general PP1 inhibitors in human therapy is problematic because pancellular inhibition of PP1 causes deregulation of cell division cycle (Yan et al. 1999 J Biol Chem 274:31917-24). In order to overcome this problem, we made a novel class of PP1 ligands and location-targeted PP1 ligands. The sarco(endo)plasmic localization signal disclosed in U.S. Pat. No. 7,071,295 represents one way to localize PP1 ligands to the cardiac SR.

The PP1 ligands of the instant invention were compared to industry standard protein-based PP1 inhibitor, INH-2, in in vitro assays. Further, we linked the PP1 ligands to an SR localization signal (U.S. Pat. No. 7,071,295) and expressed them in P19 cardiomyocytes.

An aspect of the invention is to provide novel inhibitors of PP1 activity by modifying a natural substrate and/or regulator by truncation and/or by amino acid substitution. Another aspect of the invention is to provide modular polyligand inhibitors of PP1 activity by linking together novel inhibitors and variations thereof. A further aspect of the invention is the cellular localization of a PP1 inhibitor, ligand, or polyligand by linkage to a localization signal.

An aspect of the invention encompasses inhibition of PP1 as a way to enhance calcium uptake in cardiac tissue. By inhibiting PP1, inhibition of the sarco(endo)plasmic reticulum calcium pump will be relieved. Enhancement of calcium uptake into the sarco(endo)plasmic reticulum of a diseased heart represents a potential therapy of heart failure.

Additional aspects of the invention encompass PP1 inhibitors useful in any tissue. Additional embodiments of the invention encompass PP1 inhibitors localized to different cellular locations by linking to a localization signal targeted to a region of a cell.

The invention relates to polypeptide ligands and polyligands for PP1.

Various embodiments of the PP1 ligands and polyligands are represented in SEQ ID NOS:1-111. More specifically, the invention relates to ligands, homopolyligands, and heteropolyligands that comprise any one or more of SEQ ID NOS:67-82 and/or SEQ ID NOS:92-111. Additionally, the invention relates to ligands and polyligands comprising one or more partial sequences of SEQ ID NOS:57-66 and SEQ ID NOS:83-91 or any portion thereof. Furthermore, the invention relates to polyligands with at least about 80%, 85%, 90%, 95%, 96%, 97%, 98% and 99% sequence identity to a polyligand comprising one or more of SEQ ID NOS:67-82 and SEQ ID NOS:92-111 or any portion thereof. Furthermore, the invention relates to polyligands with at least about 80%, 85%, 90%, 95%, 96%, 97%, 98% and 99% sequence identity to a polyligand comprising one or more partial sequences of SEQ ID NOS:57-66 and SEQ ID NOS:83-91.

Further embodiments of the PP1 ligands and polyligands are represented in SEQ ID NOS:113-176. More specifically, the invention relates to ligands, homopolyligands, and heteropolyligands that comprise any one or more of SEQ ID NOS:113-164 or any portion thereof. Furthermore, the invention relates to polyligands with at least about 80%, 85%, 90%, 95%, 96%, 97%, 98% and 99% sequence identity to a polyligand comprising one or more of SEQ ID NOS:113-164 or any portion thereof.

Further embodiments of PP1 ligands and polyligands are represented in SEQ ID NOS:177-223. More specifically, the invention relates to ligands, homopolyligands, and heteropolyligands that comprise any one or more of SEQ ID NOS:212-223. Additionally, the invention relates to ligands and polyligands comprising one or more partial sequences of SEQ ID NOS:201-211 or any portion thereof. Furthermore, the invention relates to polyligands with at least about 80%, 85%, 90%, 95%, 96%, 97%, 98% and 99% sequence identity to a polyligand comprising one or more of SEQ ID NOS:212-223 or any portion thereof. Furthermore, the invention relates to polyligands with at least about 80%, 85%, 90%, 95%, 96%, 97%, 98% and 99% sequence identity to a polyligand comprising one or more partial sequences of SEQ ID NOS:201-211.

Further embodiments of PP1 ligands and polyligands are represented in SEQ ID NOS:224-262. More specifically, the invention relates to ligands, homopolyligands, and heteropolyligands that comprise any one or more of SEQ ID NOS:251-262. Additionally, the invention relates to ligands and polyligands comprising one or more partial sequences (truncation fragments) of SEQ ID NO:266-268 or any portion thereof. Furthermore, the invention relates to polyligands with at least about 80%, 85%, 90%, 95%, 96%, 97%, 98% and 99% sequence identity to a polyligand comprising one or more of SEQ ID NOS:251-262 or any portion thereof. Furthermore, the invention relates to polyligands with at least about 80%, 85%, 90%, 95%, 96%, 97%, 98% and 99% sequence identity to a polyligand comprising one or more partial sequences of SEQ ID NO:266-268.

Polyligands, which can be homopolyligands or heteropolyligands, are chimeric ligands composed of two or more monomeric polypeptide ligands. An example of a monomeric ligand is the polypeptide represented by SEQ ID NO:67, wherein Xaa is any amino acid. SEQ ID NO:67 is a selected partial sequence of parental full length SEQ ID NO:66, wherein the amino acid corresponding to Xaa in the parent sequence is a serine or threonine that may be dephosphorylatable by PP1. An example of a homopolyligand is a polypeptide comprising a dimer or multimer of SEQ ID NO:67, wherein Xaa is any amino acid. An example of a heteropolyligand is a polypeptide comprising SEQ ID NO:67 and one or more of SEQ ID NOS:68-82 or SEQ ID NOS:92-111, wherein Xaa is any amino acid. There are numerous ways to combine SEQ ID NOS:67-82 and SEQ ID NOS:92-111 into homopolymeric or heteropolymeric ligands. Furthermore, there are numerous ways to combine additional partial sequences of SEQ ID NOS:57-66 and SEQ ID NOS: 83-91 with each other and with SEQ ID NOS:67-82 and SEQ ID NOS:92-111 to make polymeric ligands.

Another example of a monomeric ligand is the polypeptide represented by SEQ ID NO:136, wherein Xaa is any amino acid. An example of a homopolyligand is a polypeptide comprising a dimer or multimer of SEQ ID NO:153, wherein Xaa is any amino acid. An example of a heteropolyligand is a polypeptide comprising SEQ ID NO:164 and one or more of SEQ ID NOS:113-163, wherein Xaa is any amino acid. There are numerous ways to combine SEQ ID NOS:113-164 into homopolymeric or heteropolymeric ligands. Furthermore, there are numerous ways to combine additional partial sequences of SEQ ID NO:113 with each other and with SEQ ID NOS:113-164 to make polymeric ligands.

Another example of a monomeric ligand is the polypeptide represented by SEQ ID NO:212, wherein Xaa is any amino acid. SEQ ID NO:212 is a selected partial sequence of parental full length SEQ ID NO:201, wherein the amino acid corresponding to Xaa in the parent sequence is a serine or threonine that may be dephosphorylatable by PP1. An example of a homopolyligand is a polypeptide comprising a dimer or multimer of SEQ ID NO:212, wherein Xaa is any amino acid. An example of a heteropolyligand is a polypeptide comprising SEQ ID NO:212 and one or more of SEQ ID NOS:37-47, wherein Xaa is any amino acid. There are numerous ways to combine SEQ ID NOS:212-223 into homopolymeric or heteropolymeric ligands. Furthermore, there are numerous ways to combine additional partial sequences of SEQ ID NOS:201-211 with each other and with SEQ ID NOS:212-223 to make polymeric ligands.

Another example of a monomeric ligand is the polypeptide represented by SEQ ID NO:251. SEQ ID NO:251 is a selected partial sequence of parental full length SEQ ID NO:266. An example of a homopolyligand is a polypeptide comprising a dimer or multimer of SEQ ID NO:251. An example of a heteropolyligand is a polypeptide comprising SEQ ID NO:251 and one or more of SEQ ID NOS:252-262. There are numerous ways to combine SEQ ID NOS:251-262 into homopolymeric or heteropolymeric ligands. Furthermore, there are numerous ways to combine additional partial sequences of SEQ ID NO:266-268 with each other and with SEQ ID NOS:251-262 to make polymeric ligands.

The polyligands of the invention optionally comprise spacer amino acids before, after, or between monomers. SEQ ID NO:1 is an embodiment of a polyligand of the structure A-S1-B-S2-C, wherein A is SEQ ID NO:92 (wherein Xaa is Ala), B is SEQ ID NO:68 (wherein Xaa is Glu), C is SEQ ID NO:93 (wherein Xaa is Glu), and wherein S1 is a five amino acid spacer of the amino acid sequence PGAGG (SEQ ID NO: 269) and S2 is a five amino acid spacer of amino acid sequence PGAAG (SEQ ID NO: 270). This invention intends to capture all combinations of homopolyligands and heteropolyligands without limitation to the examples given above or below. In this description, use of the term "ligand(s)" encompasses monomeric ligands, polymeric ligands, homopolymeric ligands and/or heteropolymeric ligands. The term ligand also encompasses the terms decoy, inhibitor, and modulator.

A monomeric ligand is a polypeptide where at least a portion of the polypeptide is capable of being recognized by PP1. The portion of the polypeptide capable of recognition is termed the recognition motif. In the present invention, recognition motifs can be natural or synthetic. Examples of recognition motifs are well known in the art and include, but are not limited to, naturally occurring PP1 substrates, pseudosubstrate motifs, and interaction domains present in PP1 regulatory binding proteins and modifications thereof.

A polymeric ligand (polyligand) comprises two or more monomeric ligands.

A homopolymeric ligand is a polymeric ligand where each of the monomeric ligands is identical in amino acid sequence, except that a dephosphorylatable residue, such as serine, threonine, or tyrosine, may be substituted or modified in one or more of the monomeric ligands. Modifications include, but are not limited to, substitution to a pseudophosphorylated residue (acidic amino acid) or substitution to a neutral residue.

A heteropolymeric ligand is a polymeric ligand where some of the monomeric ligands do not have an identical amino acid sequence.

The ligands of the invention are optionally linked to additional molecules or amino acids that provide an epitope tag, a reporter, and/or a cellular localization signal. The cellular localization signal targets the ligands to a region of a cell. The epitope tag and/or reporter and/or localization signal may be the same molecule. The epitope tag and/or reporter and/or localization signal may also be different molecules.

The invention also encompasses polynucleotides comprising a nucleotide sequence encoding ligands, homopolyligands, and heteropolyligands. The nucleic acids of the invention are optionally linked to additional nucleotide sequences encoding polypeptides with additional features, such as an epitope tag, a reporter, and/or a cellular localization signal. The polynucleotides are optionally flanked by nucleotide sequences comprising restriction endonuclease sites and other nucleotides needed for restriction endonuclese activity. The flanking sequences optionally provide unique cloning sites within a vector and optionally provide directionality of subsequence cloning. Further, the nucleic acids of the invention are optionally incorporated into vector polynucleotides. The ligands, polyligands, and polynucleotides of this invention have utility as research tools and/or therapeutics.

DETAILED DESCRIPTION OF THE INVENTION

The present invention relates to ligands and polyligands that are PP1 modulators. Various embodiments of ligands and polyligands are represented in SEQ ID NOS:1-111. Polyligands are chimeric ligands comprising two or more monomeric polypeptide ligands. An example of a monomeric ligand is the polypeptide represented by SEQ ID NO:92, wherein Xaa is any amino acid. SEQ ID NO:92 is a selected partial sequence of parental full length SEQ ID NO:83, wherein the amino acid corresponding to Xaa in the parent sequence is a serine or threonine. Another example of a monomeric ligand is the polypeptide represented by SEQ ID NO:75. Each of SEQ ID NOS:67-82 and SEQ ID NOS:92-111 represents an individual polypeptide ligand in monomeric form, wherein Xaa is any amino acid. SEQ ID NOS:67-82 and SEQ ID NOS:92-111 are selected examples of partial sequences of SEQ ID NOS:83-91 and SEQ ID NOS:57-66, respectively, however, other partial sequences of SEQ ID NOS:83-91 and/or SEQ ID NOS:57-66 may also be utilized as monomeric ligands. Monomeric partial sequences of SEQ ID NOS:83-91 and SEQ ID NOS:57-66 may be identical to a portion of a parent polypeptide. Additionally, monomeric partial sequences of SEQ ID NOS:83-91 and/or SEQ ID NOS:57-66 may have amino acid substitutions. Furthermore, monomeric ligands and polyligands may have at least about 80%, 85%, 90%, 95%, 96%, 97%, 98% or 99% sequence identity to a ligand comprising an amino acid sequence in one or more of SEQ ID NOS:67-82 and SEQ ID NOS:92-111. Furthermore, monomeric ligands and polyligands may have at least about 80%, 85%, 90%, 95%, 96%, 97%, 98% and 99% sequence identity to a partial sequence of SEQ ID NOS:83-91 and SEQ ID NOS:57-66.

Further embodiments of ligands and polyligands are represented in SEQ ID NOS:113-176. Polyligands are chimeric ligands comprising two or more monomeric polypeptide ligands. An example of a monomeric ligand is the polypeptide represented by SEQ ID NO:161, wherein Xaa is any amino acid. Another example of a monomeric ligand is the polypeptide represented by SEQ ID NO:137, wherein Xaa is any amino acid. Each of SEQ ID NOS:113-164 represents an individual polypeptide ligand in monomeric form, wherein Xaa is any amino acid. SEQ ID NOS:137-164 are selected examples of partial sequences of SEQ ID NO:113, however, other partial sequences of SEQ ID NO:113 may also be utilized as monomeric ligands. Monomeric ligand partial equences of SEQ ID NO:113 may be identical to a parent wild-type reference sequence. Additionally, monomeric ligand partial sequences of SEQ ID NO:113 may have the PP1 de-phosphorylatable amino acids replaced by other amino acids. Furthermore, monomeric ligands and polyligands may have at least about 80%, 85%, 90%, 95%, 96%, 97%, 98% or 99% sequence identity to a ligand comprising an amino acid sequence in one or more of SEQ ID NOS:113-164. Furthermore, monomeric ligands and polyligands may have at least about 80%, 85%, 90%, 95%, 96%, 97%, 98% and 99% sequence identity to a partial sequence of SEQ ID NO:113.

Further embodiments of ligands and polyligands are represented in SEQ ID NOS:177-223. Polyligands are chimeric ligands comprising two or more monomeric polypeptide ligands. An example of a monomeric ligand is the polypeptide represented by SEQ ID NO:223, wherein Xaa is any amino acid. SEQ ID NO:223 is a selected partial sequence of parental full length SEQ ID NO:210, wherein the amino acid corresponding to Xaa in the parent sequence is a serine or threonine. Another example of a monomeric ligand is the polypeptide represented by SEQ ID NO:219, wherein Xaa is any amino acid. Each of SEQ ID NOS:212-223 represents an individual polypeptide ligand in monomeric form, wherein Xaa is any amino acid. SEQ ID NOS:212-223 are selected examples of partial sequences of SEQ ID NOS:201-211, however, other partial sequences of SEQ ID NOS:201-211 may also be utilized as monomeric ligands. Monomeric partial sequences of SEQ ID NOS:201-211 may be identical to a portion of a parent polypeptide. Additionally, monomeric partial sequences of SEQ ID NOS:201-211 may have amino acid substitutions. Furthermore, monomeric ligands and polyligands may have at least about 80%, 85%, 90%, 95%, 96%, 97%, 98% or 99% sequence identity to a ligand comprising an amino acid sequence in one or more of SEQ ID NOS:212-223. Furthermore, monomeric ligands and polyligands may have at least about 80%, 85%, 90%, 95%, 96%, 97%, 98% and 99% sequence identity to a partial sequence of SEQ ID NOS:201-211.

Further embodiments of ligands and polyligands are represented in SEQ ID NOS:224-268. Polyligands are chimeric ligands comprising two or more monomeric polypeptide ligands. An example of a monomeric ligand is the polypeptide represented by SEQ ID NO:257. SEQ ID NO:257 is a selected partial sequence of parental full length SEQ ID NO:267. Another example of a monomeric ligand is the polypeptide represented by SEQ ID NO:261. Each of SEQ ID NOS:251-262 represents an individual polypeptide ligand in monomeric form, wherein Xaa is any amino acid. SEQ ID NOS:251-262 are selected examples of partial sequences of SEQ ID NO:266-268, however, other partial sequences of SEQ ID NO:266-268 may also be utilized as monomeric ligands. Monomeric partial sequences of SEQ ID NO:266-268 may be identical to a portion of a parent polypeptide. Additionally, partial sequences of SEQ ID NO:266-268 may have amino acid substitutions. Furthermore, monomeric ligands and polyligands may have at least about 80%, 85%, 90%, 95%, 96%, 97%, 98% or 99% sequence identity to a ligand comprising an amino acid sequence in one or more of SEQ ID NOS:251-262. Furthermore, monomeric ligands and polyligands may have at least about 80%, 85%, 90%, 95%, 96%, 97%, 98% and 99% sequence identity to a partial sequence of SEQ ID NO:266-268.

An example of a homopolyligand is a polypeptide comprising a dimer or multimer of SEQ ID NO:71, wherein Xaa is any amino acid. An example of a heteropolyligand is a polypeptide comprising SEQ ID NO:67 and one or more of SEQ ID NOS:68-82 or SEQ ID NOS:92-111, wherein Xaa is any amino acid. There are numerous ways to combine SEQ ID NOS:67-82 and SEQ ID NOS:92-111 into homopolymeric or heteropolymeric ligands. Furthermore, there are numerous ways to combine additional partial sequences of SEQ ID NOS:57-66 and/or SEQ ID NOS:83-91 with each other and with SEQ ID NOS:67-82 and/or SEQ ID NOS:92-111 to make polymeric ligands.

Another example of a homopolyligand is a polypeptide comprising a dimer or multimer of SEQ ID NO:154, wherein Xaa is any amino acid. An example of a heteropolyligand is a polypeptide comprising SEQ ID NO:164 and one or more of SEQ ID NOS:113-163, wherein Xaa is any amino acid. There are numerous ways to combine SEQ ID NOS:113-164 into homopolymeric or heteropolymeric ligands. Furthermore, there are numerous ways to combine additional subsequences of SEQ ID NO:113 with each other and with SEQ ID NOS:113-164 to make polymeric ligands.

Another example of a homopolyligand is a polypeptide comprising a dimer or multimer of SEQ ID NO:217, wherein Xaa is any amino acid. An example of a heteropolyligand is a polypeptide comprising SEQ ID NO:223 and one or more of SEQ ID NOS:212-222, wherein Xaa is any amino acid. There are numerous ways to combine SEQ ID NOS:212-223 into homopolymeric or heteropolymeric ligands. Furthermore, there are numerous ways to combine additional partial sequences of SEQ ID NOS:201-211 with each other and with SEQ ID NOS:212-223 to make polymeric ligands. The instant invention is directed to all possible combinations of homopolyligands and heteropolyligands without limitation.

Another example of a homopolyligand is a polypeptide comprising a dimer or multimer of SEQ ID NO:260. An example of a heteropolyligand is a polypeptide comprising SEQ ID NO:251 and one or more of SEQ ID NOS:252-262. There are numerous ways to combine SEQ ID NOS:251-262 into homopolymeric or heteropolymeric ligands. Furthermore, there are numerous ways to combine additional partial sequences of SEQ ID NO:266-268 with each other and with SEQ ID NOS:251-262 to make polymeric ligands. The instant invention is directed to all possible combinations of homopolyligands and heteropolyligands without limitation. The ligands and polyligands of the invention are designed to modulate the endogenous effects of one or more isoforms of PP1.

Polyligands may comprise any two or more of SEQ ID NOS:67-82 and/or SEQ ID NOS:92-111, wherein Xaa is any amino acid. A dimer or multimer of SEQ ID NO:109 is an example of a homopolyligand. An example of a heteropolyligand is a polypeptide comprising SEQ ID NO:111 and one or more of SEQ ID NOS:92-110 and/or SEQ ID NOS:67-82. Polyligands may further comprise any two or more of SEQ ID NOS:113-164, wherein Xaa is any amino acid. A dimer or multimer of SEQ ID NO:142 is an example of a homopolyligand. An example of a heteropolyligand is a polypeptide comprising SEQ ID NO:136 and one or more of SEQ ID NOS:137-164. Polyligands may further comprise any two or more of SEQ ID NOS:212-223, or any two or more of SEQ ID NOS:251-262, wherein Xaa is any amino acid. The instant invention is directed to all possible combinations of homopolyligands and heteropolyligands without limitation.

SEQ ID NOS:57-66 show proteins that contain at least one serine or threonine residue dephosphorylatable by PP1, the positions of which are represented by Xaa. SEQ ID NOS:67-82 are partial sequences of SEQ ID NOS:57-66 where the locations of the PP1 dephosphorylatable residues are represented by Xaa. SEQ ID NOS:113-164 show proteins that contain at least one serine or threonine residue de-phosphorylatable by PP1, the positions of which are represented by Xaa. SEQ ID NOS:137-164 are subsequences of SEQ ID NO:113 where the locations of the PP1 de-phosphorylatable residues are represented by Xaa. SEQ ID NOS:212-219 show proteins that contain at least one amino acid residue dephosphorylatable by PP1, the positions of which are represented by Xaa. SEQ ID NOS:212-219 are partial sequences of SEQ ID NOS:201-207 where the locations of the PP1 dephosphorylatable residues are represented by Xaa. In nature, Xaa is, generally speaking, serine or threonine. In one embodiment of the instant invention, Xaa can be any amino acid. Ligands where Xaa is serine or threonine can be used as part of a polyligand, however in one embodiment, at least one serine or threonine is replaced with another amino acid, such as one of the naturally occurring amino acids including, alanine, aspartate, asparagine, cysteine, glutamate, glutamine, phenylalanine, glycine, histidine, isoleucine, leucine, lysine, methionine, proline, arginine, valine, tryptophan, or tyrosine. The Xaa may also be a non-naturally occurring amino acid. In another embodiment, the PP1 dephosphorylatable serine(s) or threonine(s) are replaced by alanine. The ligands and polyligands of the invention are designed to modulate the endogenous effects of one or more isoforms of PP1.

In general, ligand monomers based on natural PP1 regulators are built by identifying and isolating a putative PP1 interaction domain recognition motif. Sometimes it is desirable to modify the interaction domain at serine and/or threonine residues which are affected by cellular kinases. Additional monomers include the PP1 recognition motif as well as amino acids adjacent and contiguous on either side of the PP1 interaction domain recognition motif. Monomeric ligands may therefore be any length provided the monomer includes the PP1 recognition motif. For example, the monomer may comprise a PP1 recognition motif and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 100 or more amino acids adjacent to the recognition motif. Further design considerations are taken from three-dimensional modeling of the ligands and modeling of binding interactions with PP1. Modifications of the primary sequence of a ligand or polyligand may be desirable based upon such modeling.

For example, in one embodiment, the invention comprises an inhibitor of PP1 comprising at least one copy of a peptide selected from the group consisting of:

a) a peptide at least 80%, 85%, 90%, 95%, 96%, 97%, 98% or 99% identical to a peptide comprising amino acid residues corresponding to amino acid residues 285-295 of SEQ ID NO:57, wherein the amino acid residue corresponding to amino acid residue 288 of SEQ ID NO:57 has been mutated to an amino acid residue other than serine or threonine;

b) a peptide at least 80%, 85%, 90%, 95%, 96%, 97%, 98% or 99% identical to a peptide comprising amino acid residues corresponding to amino acid residues 281-299 of SEQ ID NO:57, wherein the amino acid residue corresponding to amino acid residue 288 of SEQ ID NO:57 has been mutated to an amino acid residue other than serine or threonine;

c) a peptide at least 80%, 85%, 90%, 95%, 96%, 97%, 98% or 99% identical to a peptide comprising amino acid residues corresponding to amino acid residues 279-302 of SEQ ID NO:57, wherein the amino acid residue corresponding to amino acid residue 288 of SEQ ID NO:57 has been mutated to an amino acid residue other than serine or threonine; and d) a peptide at least 80%, 85%, 90%, 95%, 96%, 97%, 98% or 99% identical to a peptide comprising amino acid residues corresponding to amino acid residues 277-303 of SEQ ID NO:57, wherein the amino acid residue corresponding to amino acid residue 288 of SEQ ID NO:57 has been mutated to an amino acid residue other than serine or threonine.

In another embodiment, the invention comprises an inhibitor of PP1 comprising at least one copy of a peptide selected from the group consisting of:

a) a peptide at least 80%, 85%, 90%, 95%, 96%, 97%, 98% or 99% identical to a peptide comprising amino acid residues corresponding to amino acid residues 1-51 of SEQ ID NO:112, wherein the amino acid residues corresponding to amino acid residues 16 and 17 of SEQ ID NO:112 have been mutated to an amino acid residue other than serine or threonine;

b) a peptide at least 80%, 85%, 90%, 95%, 96%, 97%, 98% or 99% identical to a peptide comprising amino acid residues corresponding to amino acid residues 2-51 of SEQ ID NO:112, wherein the amino acid residues corresponding to amino acid residues 16 and 17 of SEQ ID NO:112 have been mutated to an amino acid residue other than serine or threonine;

c) a peptide at least 80%, 85%, 90%, 95%, 96%, 97%, 98% or 99% identical to a peptide comprising amino acid residues corresponding to amino acid residues 8-30 of SEQ ID NO:112, wherein the amino acid residues corresponding to amino acid residues 16 and 17 of SEQ ID NO:112 have been mutated to an amino acid residue other than serine or threonine; and d) a peptide at least 80%, 85%, 90%, 95%, 96%, 97%, 98% or 99% identical to a peptide comprising amino acid residues corresponding to amino acid residues 11-27 of SEQ ID NO:112, wherein the amino acid residues corresponding to amino acid residues 16 and 17 of SEQ ID NO:112 have been mutated to an amino acid residue other than serine or threonine.

In another embodiment, the invention comprises an inhibitor of PP1 comprising at least one copy of a peptide selected from the group consisting of:

a) a peptide at least 80%, 85%, 90%, 95%, 96%, 97%, 98% or 99% identical to a peptide comprising amino acid residues corresponding to amino acid residues 114-143 of SEQ ID NO:206, wherein the amino acid residue corresponding to amino acid residue 140 of SEQ ID NO:206 has been mutated to an amino acid residue other than serine or threonine;

b) a peptide at least 80%, 85%, 90%, 95%, 96%, 97%, 98% or 99% identical to a peptide comprising amino acid residues corresponding to amino acid residues 120-143 of SEQ ID NO:206, wherein the amino acid residue corresponding to amino acid residue 140 of SEQ ID NO:206 has been mutated to an amino acid residue other than serine or threonine;

c) a peptide at least 80%, 85%, 90%, 95%, 96%, 97%, 98% or 99% identical to a peptide comprising amino acid residues corresponding to amino acid residues 127-143 of SEQ ID NO:206, wherein the amino acid residue corresponding to amino acid residue 140 of SEQ ID NO:206 has been mutated to an amino acid residue other than serine or threonine; and d) a peptide at least 80%, 85%, 90%, 95%, 96%, 97%, 98% or 99% identical to a peptide comprising amino acid residues corresponding to amino acid residues 130-142 of SEQ ID NO:206, wherein the amino acid residue corresponding to amino acid residue 140 of SEQ ID NO:206 has been mutated to an amino acid residue other than serine or threonine.

In another embodiment, the invention comprises an inhibitor of PP1 comprising at least one copy of a peptide selected from the group consisting of:

a) a peptide at least 80%, 85%, 90%, 95%, 96%, 97%, 98% or 99% identical to a peptide comprising amino acid residues corresponding to amino acid residues 35-47 of SEQ ID NO:267, wherein the amino acid residue corresponding to amino acid residue 38 of SEQ ID NO:267 has been mutated to an amino acid residue other than serine or threonine;

b) a peptide at least 80%, 85%, 90%, 95%, 96%, 97%, 98% or 99% identical to a peptide comprising amino acid residues corresponding to amino acid residues 30-47 of SEQ ID NO:267, wherein the amino acid residue corresponding to amino acid residue 38 of SEQ ID NO:267 has been mutated to an amino acid residue other than serine or threonine;

c) a peptide at least 80%, 85%, 90%, 95%, 96%, 97%, 98% or 99% identical to a peptide comprising amino acid residues corresponding to amino acid residues 48-67 of SEQ ID NO:267, wherein the amino acid residue corresponding to amino acid residue 66 of SEQ ID NO:267 has been mutated to an amino acid residue other than glycine; and d) a peptide at least 80%, 85%, 90%, 95%, 96%, 97%, 98% or 99% identical to a peptide comprising amino acid residues corresponding to amino acid residues 48-67 of SEQ ID NO:267, wherein the amino acid residue corresponding to amino acid residue 67 of SEQ ID NO:267 has been mutated to an amino acid residue other than methionine.

As used herein, the terms "correspond(s) to" and "corresponding to," as they relate to sequence alignment, are intended to mean enumerated positions within a reference protein, e.g., PP1 subunit 14A NP_150281.1 (SEQ ID NO:267), and those positions that align with the positions on the reference protein. Thus, when the amino acid sequence of a subject peptide is aligned with the amino acid sequence of a reference peptide, e.g., SEQ ID NO:267, the amino acids in the subject peptide sequence that "correspond to" certain enumerated positions of the reference peptide sequence are those that align with these positions of the reference peptide sequence, but are not necessarily in these exact numerical positions of the reference sequence. Methods for aligning sequences for determining corresponding amino acids between sequences are described below.

Additional embodiments of the invention include monomers (as described above) based on any putative or real substrate or regulator for PP1 or PP1 binding protein, such as full length proteins identified by SEQ ID NOS:57-66, 83-91, 201-211, and 266-268. Furthermore, if the substrate has more than one recognition motif, then more than one monomer may be identified therein.

Figure 35A:
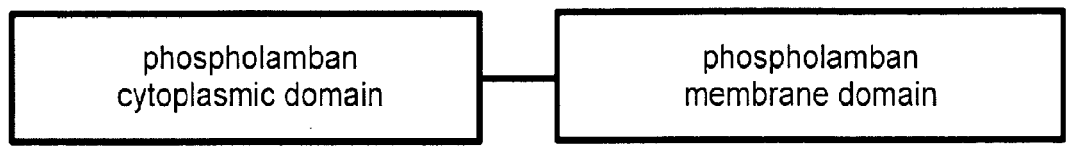
FIGS. 35A-35B show diagrams of wild type phospholamban and pseudophosphorylated phospholamban, respectively.
Figure 35B:
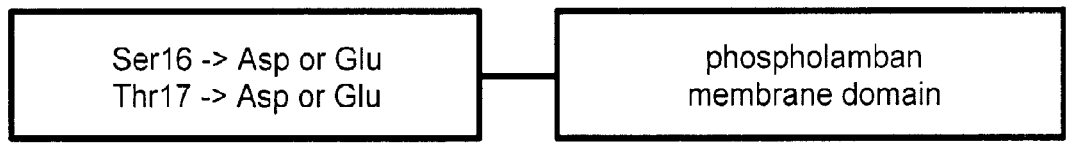

In another embodiment, PP1 inhibitors are based on phospholamban (FIG. 35A, SEQ ID NO:112), a 52 amino acid protein located in muscle sarco(endo)plasmic reticulum and can be phosphorylated by cellular kinases at serine 16 and threonine 17 in the cytoplasmic domain of the molecule. Phospholamban is a known reversible modulator of the cardiac sarco(endo)plasmic reticulum calcium pump. When dephosphorylated, phospholamban inhibits calcium uptake activity of the calcium pump; whereas phosphorylated phospholamban does not inhibit the sarco(endo)plasmic reticulum calcium pump. Defects in calcium uptake have been shown in studies of failing hearts. It is therefore desirable to modulate calcium handling in cardiac tissue by controlling the phosphorylation or pseudophosphorylation state of phospholamban. Pseudophosphorylated phospholamban is made by mutating amino acids corresponding to serine 16 and threonine 17 to acidic amino acids such as aspartate or glutamate (FIG. 35B). Expression of pseudophosphorylated phospholamban in cardiomyopathic hamsters was shown to enhance calcium uptake (Hoshijima et al. Nature Medicine 2002 8:864-71, ePub 2002 Jul. 22). PP1 ligands of the invention based on phospholambin are shown in FIGS. 35C-E and FIGS. 36-37.

Another embodiment of the invention is a nucleic acid molecule comprising a polynucleotide sequence encoding at least one copy of a ligand peptide.

Another embodiment of the invention is a nucleic acid molecule wherein the polynucleotide sequence encodes one or more copies of one or more peptide ligands.

Another embodiment of the invention is a nucleic acid molecule wherein the polynucleotide sequence encodes at least a number of copies of the peptide selected from the group consisting of 2, 3, 4, 5, 6, 7, 8, 9 or 10.

Another embodiment of the invention is a vector comprising a nucleic acid molecule encoding at least one copy of a ligand or polyligand.

Another embodiment of the invention is a recombinant host cell comprising a vector comprising a nucleic acid molecule encoding at least one copy of a ligand or polyligand.

Another embodiment of the invention is a method of inhibiting PP1 in a cell comprising transfecting a vector comprising a nucleic acid molecule encoding at least one copy of a ligand or polyligand into a host cell and culturing the transfected host cell under conditions suitable to produce at least one copy of the ligand or polyligand.

The invention also relates to modified inhibitors that are at least about 80%, 85%, 90% 95%, 96%, 97%, 98% or 99% identical to a reference inhibitor. A "modified inhibitor" is used to mean a peptide that can be created by addition, deletion or substitution of one or more amino acids in the primary structure (amino acid sequence) of a inhibitor protein or polypeptide. A "modified recognition motif" is a naturally occurring PP1 recognition motif that has been modified by addition, deletion, or substitution of one or more amino acids in the primary structure (amino acid sequence) of the motif. For example, a modified PP1 recognition motif may be a motif where the phosphorylatable amino acid has been modified to a non-phosphorylatable amino acid. The terms "protein" and "polypeptide" and "peptide" are used interchangeably herein. The reference inhibitor is not necessarily a wild-type protein or a portion thereof. Thus, the reference inhibitor may be a protein or peptide whose sequence was previously modified over a wild-type protein. The reference inhibitor may or may not be the wild-type protein from a particular organism.

A polypeptide having an amino acid sequence at least, for example, about 95% "identical" to a reference an amino acid sequence is understood to mean that the amino acid sequence of the polypeptide is identical to the reference sequence except that the amino acid sequence may include up to about five modifications per each 100 amino acids of the reference amino acid sequence encoding the reference peptide. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there exist several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., Current Protocols in Protein Science, Vol 1, John Wiley & Sons, Inc. (2000), which is incorporated by reference. In one embodiment of the present invention, the algorithm used to determine identity between two or more polypeptides is BLASTP.

In another embodiment of the present invention, the algorithm used to determine identity between two or more polypeptides is FASTDB, which is based upon the algorithm of Brutlag et al. (Comp. App. Biosci. 6:237-245 (1990), incorporated by reference). In a FASTDB sequence alignment, the query and subject sequences are amino sequences. The result of sequence alignment is in percent identity. Parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the subject sequence is shorter or longer than the query sequence because of N-terminus or C-terminus additions or deletions, not because of internal additions or deletions, a manual correction can be made, because the FASTDB program does not account for N-terminus and C-terminus truncations or additions of the subject sequence when calculating percent identity. For subject sequences truncated at both ends, relative to the query sequence, the percent identity is corrected by calculating the number of bases of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the query (subject) sequences or the reference sequence that extend past the N- or C-termini of the reference or subject sequence, respectively, may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue subject sequence is aligned with a 100 residue reference sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 reference sequence. This time the deletions are internal deletions so there are no residues at the N- or C-termini of the subject sequence which are not matched/aligned with the query. In this case the percent identity calculated by FASTDB is not manually corrected.

The polyligands of the invention optionally comprise spacer amino acids before, after, or between monomers. The length and composition of the spacer may vary. An example of a spacer is glycine, alanine, polyglycine, or polyalanine. Sometimes it is desirable to employ proline in a spacer for the purpose of interrupting secondary structure of a polypeptide.

Spacer amino acids may be any amino acid and are not limited to alanine, glycine and proline. The instant invention is directed to all combinations of homopolyligands and heteropolyligands, with or without spacers, and without limitation to the examples given above or below.

The ligands and polyligands of the invention are optionally linked to additional molecules or amino acids that provide an epitope tag, a reporter, and/or localize the ligand to a region of a cell (See FIGS. 5A-5H, FIGS. 6A-6H, FIGS. 7A-7I, and FIGS. 8A-8K). Non-limiting examples of epitope tags are FLAG™, HA (hemagluttinin), c-Myc and His6. Non-limiting examples of reporters are alkaline phosphatase, galactosidase, peroxidase, luciferase and fluorescent proteins. Non-limiting examples of cellular locations are sarcoplamic reticulum, endoplasmic reticulum, mitochondria, golgi apparatus, peroxisomes, lysosomes, nucleus, nucleolus, endosomes, exosomes, other intracellular vesicles, plasma membrane, apical membrane, and basolateral membrane. The epitopes, reporters and localization signals are given by way of example and without limitation. The epitope tag, reporter and/or localization signal may be the same molecule. The epitope tag, reporter and/or localization signal may also be different molecules.

Ligands and polyligands and optional amino acids linked thereto can be synthesized chemically or recombinantly using techniques known in the art. Chemical synthesis techniques include but are not limited to peptide synthesis which is often performed using an automated peptide synthesizer. Peptides can also be synthesized utilizing non-automated peptide synthesis methods known in the art. Recombinant techniques include insertion of ligand-encoding nucleic acids into expression vectors, wherein nucleic acid expression products are synthesized using cellular factors and processes.

Linkage of a cellular localization signal, epitope tag, or reporter to a ligand or polyligand can include covalent or enzymatic linkage to the ligand. When the localization signal comprises material other than a polypeptide, such as a lipid or carbohydrate, a chemical reaction to link molecules may be utilized. Additionally, non-standard amino acids and amino acids modified with lipids, carbohydrates, phosphate or other molecules may be used as precursors to peptide synthesis. The ligands of the invention have therapeutic utility with or without localization signals. However, ligands linked to localization signals have utility as subcellular tools or therapeutics. An example of a cellular localization signal which localizes a polypeptide cargo of interest to the sarco(endo) plasmic reticulum of cardiac tissue is disclosed in U.S. Pat. No. 7,071,295.

PP1 ligand-containing gene constructs are also delivered via gene therapy. FIGS. 10B and 10C depict embodiments of gene therapy vectors for delivering and controlling polypeptide expression in vivo. Polynucleotide sequences linked to the gene construct in FIGS. 10B and 10C include genome integration domains to facilitate integration of the transgene into a viral genome and/or host genome. AttP and AttB sequences are non-limiting examples of genome integration sequences.

Figure 10A:
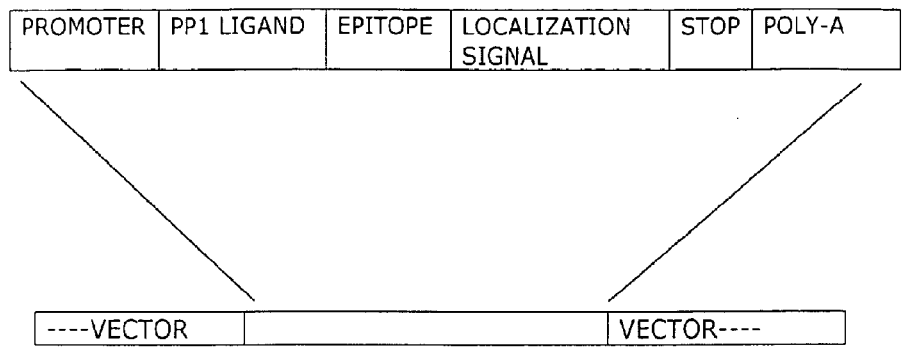
FIGS. 10A-10D show examples of vectors containing ligand gene constructs.
Figure 10B:
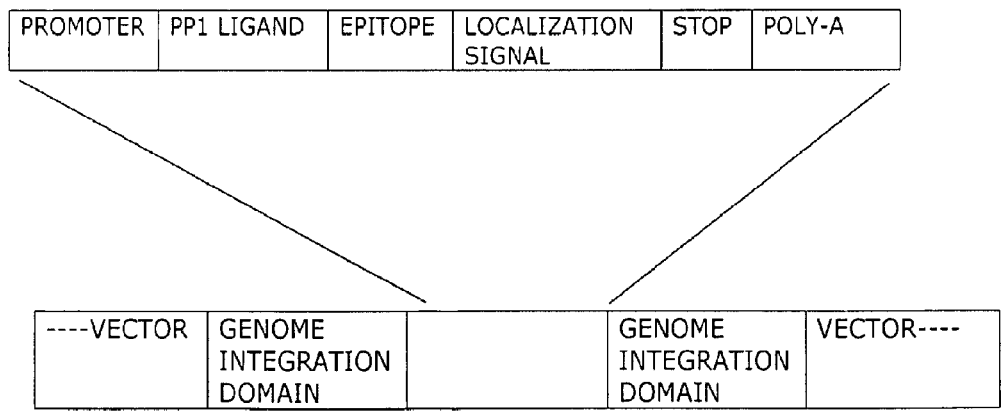
Figure 10C:
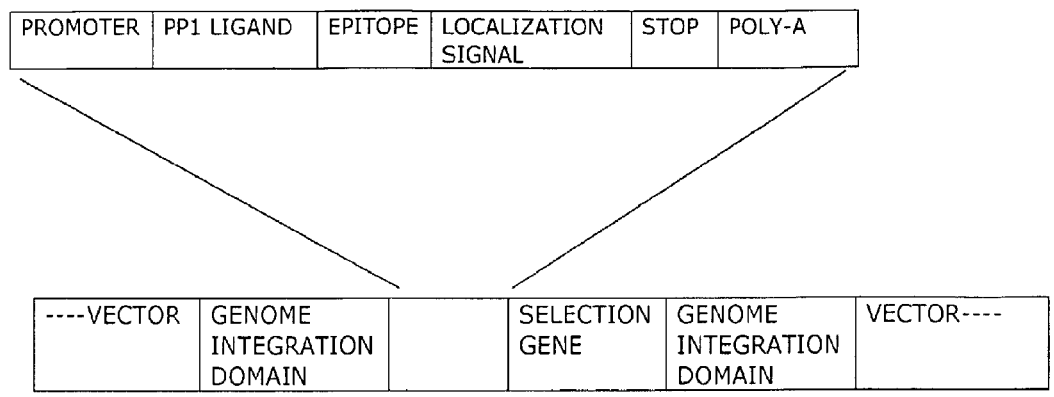

FIG. 10A shows a vector containing a PP1 ligand gene construct, wherein the ligand gene construct is releasable from the vector as a unit useful for generating transgenic animals. For example, the ligand gene construct, or transgene, is released from the vector backbone by restriction endonuclease digestion. The released transgene is then injected into pronuclei of fertilized mouse eggs; or the transgene is used to transform embryonic stem cells. The vector containing a ligand gene construct of FIG. 10A is also useful for transient transfection of the trangene, wherein the promoter and codons of the transgene are optimized for the host organism. The vector containing a ligand gene construct of FIG. 10A is also useful for recombinant expression of polypeptides in fermentable organisms adaptable for small or large scale production, wherein the promoter and codons of the transgene are optimized for the fermentation host organism.

Figure 10D:
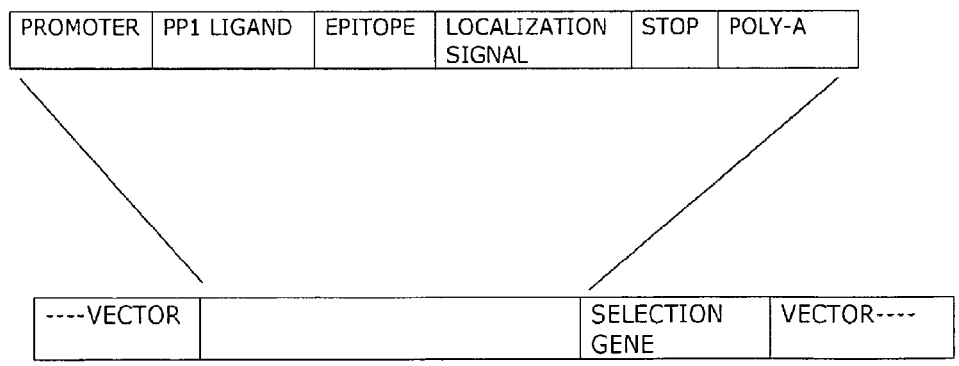

FIG. 10D shows a vector containing a PP1 ligand gene construct useful for generating stable cell lines.

The invention also encompasses polynucleotides comprising nucleotide sequences encoding ligands and polyligands. The polynucleotides of the invention are optionally linked to additional nucleotide sequences encoding epitopes, reporters and/or localization signals. Further, the nucleic acids of the invention are optionally incorporated into vector polynucleotides. The polynucleotides are optionally flanked by nucleotide sequences comprising restriction endonuclease sites and other nucleotides needed for restriction endonuclese activity. The flanking sequences optionally provide cloning sites within a vector. The restriction sites can include, but are not limited to, any of the commonly used sites in most commercially available cloning vectors. Sites for cleavage by other restriction enzymes, including homing endonucleases, are also used for this purpose. The polynucleotide flanking sequences also optionally provide directionality of subsequence cloning. It is preferred that 5' and 3' restriction endonuclease sites differ from each other so that double-stranded DNA can be directionally cloned into corresponding complementary sites of a cloning vector.

Ligands and polyligands with or without localization signals, epitopes or reporters are alternatively synthesized by recombinant techniques. Polynucleotide expression constructs are made containing desired components and inserted into an expression vector. The expression vector is then transfected into cells and the polypeptide products are expressed and isolated. Ligands made according to recombinant DNA techniques have utility as research tools and/or therapeutics.

The following is an example of how polynucleotides encoding ligands and polyligands are produced. Complimentary oligonucleotides encoding the ligands and flanking sequences are synthesized and annealled. The resulting double-stranded DNA molecule is inserted into a cloning vector using techniques known in the art. When the ligands and polyligands are placed in-frame adjacent to sequences within a transgenic gene construct that is translated into a protein product, they form part of a fusion protein when expressed in cells or transgenic animals.

Another embodiment of the invention relates to selective control of transgene expression in a desired cell or organism. The promotor portion of the recombinant gene can be a constitutive promotor, a non-constitutive promotor, a tissue-specific promotor (constitutive or non-constitutive) or a selectively controlled promotor. Different selectively controlled promotors are controlled by different mechanisms. For example, a tetracycline-inducible promotor is activated to express a downstream coding sequence when the cell containing the promotor and other necessary cellular factors is treated with tetracycline. Other inducible promotors are activated by other drugs or factors. RHEOSWITCH is an inducible promotor system available from New England BioLabs (Ipswich, Mass.). Temperature sensitive promotors can also be used to increase or decrease gene expression. An embodiment of the invention comprises a ligand or polyligand gene construct whose expression is controlled by an inducible promotor system. The vectors of FIGS. 21-29 incorporate the RHEOSWITCH inducible gene expression system.

Polyligands are modular in nature. An aspect of the instant invention is the combinatorial modularity of the disclosed polyligands. Another aspect of the invention are methods of making these modular polyligands easily and conveniently. In this regard, an embodiment of the invention comprises methods of modular cloning of genetic expression components. When the ligands, homopolyligands, heteropolyligands and optional amino acid expression components are synthesized recombinantly, one can consider each clonable element as a module. For speed and convenience of cloning, it is desirable to make modular elements that are compatible at cohesive ends and are easy to insert and clone sequentially. This is accomplished by exploiting the natural properties of restriction endonuclease site recognition and cleavage. One aspect of the invention encompasses module flanking sequences that, at one end of the module, are utilized for restriction enzyme digestion once, and at the other end, utilized for restriction enzyme digestion as many times as desired. In other words, a restriction site at one end of the module is utilized and destroyed in order to effect sequential cloning of modular elements. An example of restriction sites flanking a coding region module are sequences recognized by the restriction enzymes NgoM IV and Cla I; or Xma I and Cla I. Cutting a first circular DNA with NgoM IV and Cla I to yield linear DNA with a 5' NgoM IV overhang and a 3' Cla I overhang; and cutting a second circular DNA with Xma I and Cla I to yield linear DNA with a 5' Cla I overhang and a 3' Xma I overhang generates first and second DNA fragments with compatible cohesive ends. When these first and second DNA fragments are mixed together, annealed, and ligated to form a third circular DNA fragment, the NgoM IV site that was in the first DNA and the Xma I site that was in the second DNA are destroyed in the third circular DNA. Now this vestigial region of DNA is protected from further Xma I or NgoM IV digestion, but flanking sequences remaining in the third circular DNA still contain intact 5' NgoM IV and 3' Cla I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences.

Figure 11:
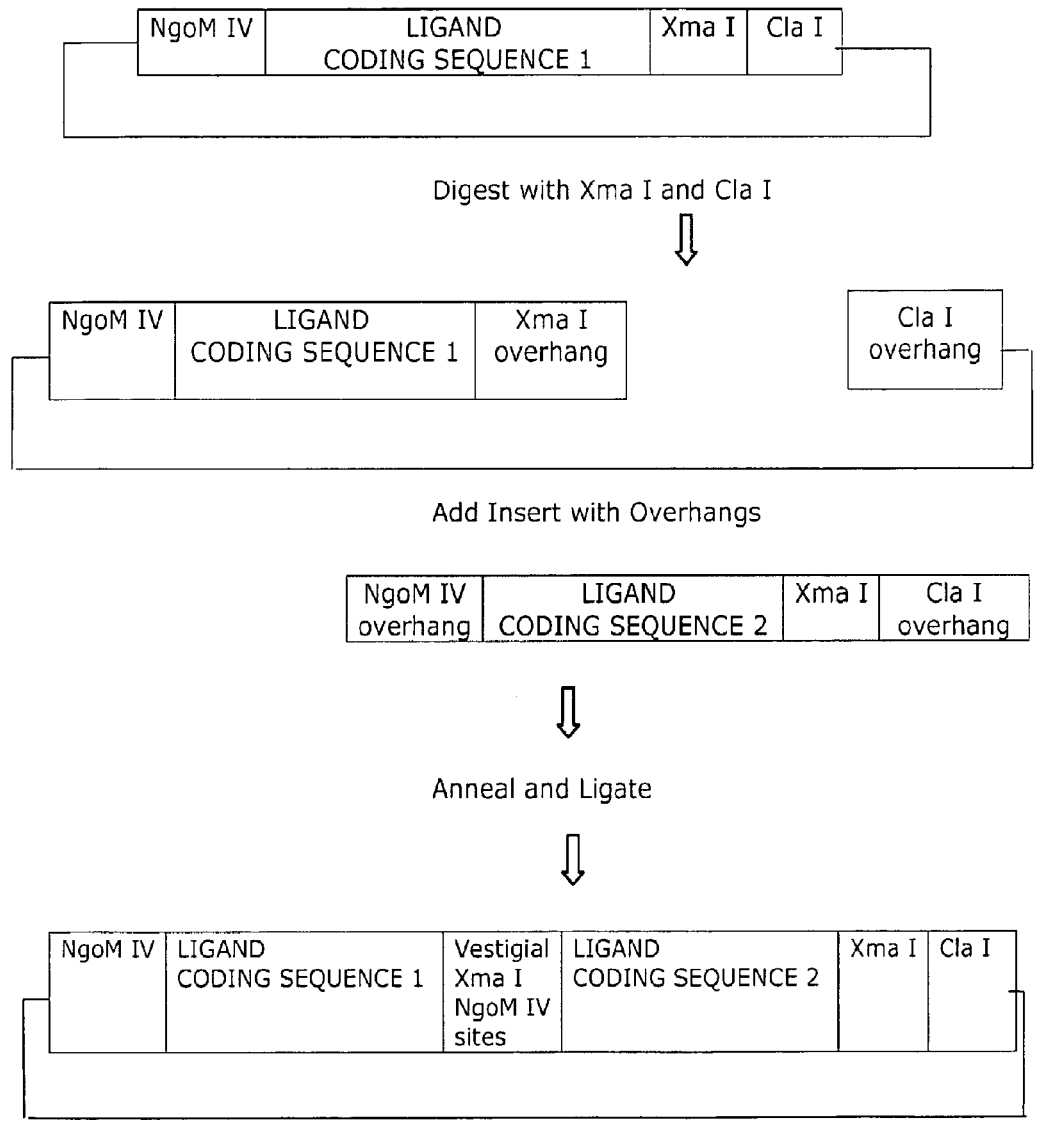
FIG. 11 shows an example of a sequential cloning process useful for combinatorial synthesis of polyligands.
Figure 12:
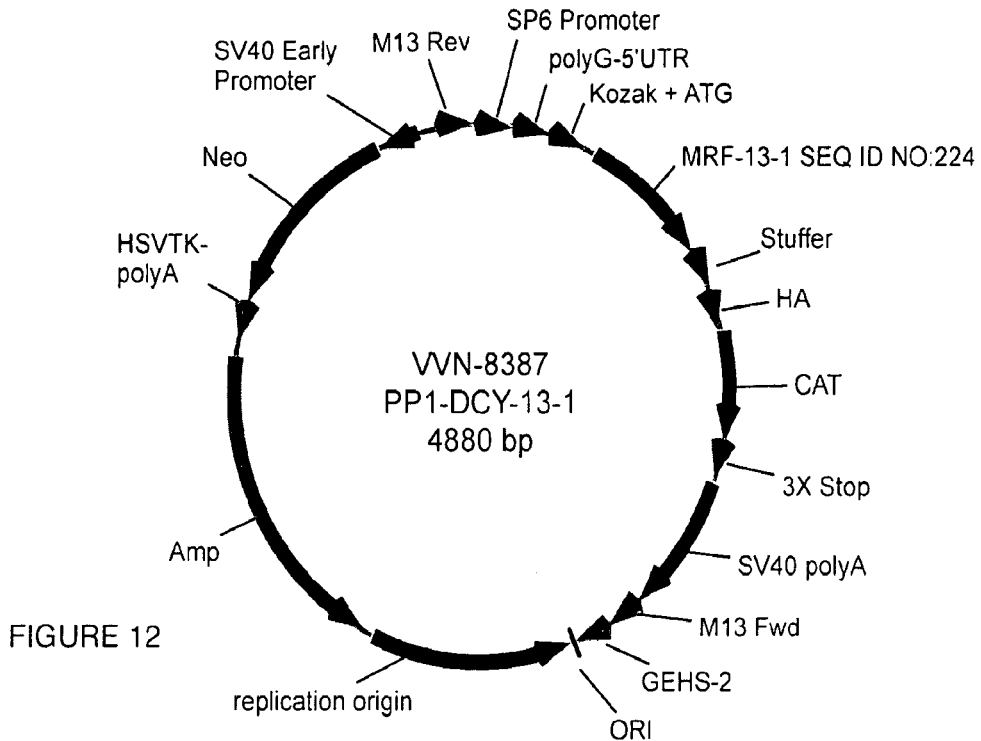
FIGS. 12-20 show vectors for in vitro transcription/translation used to generate the data of FIG. 31.
Figure 13:
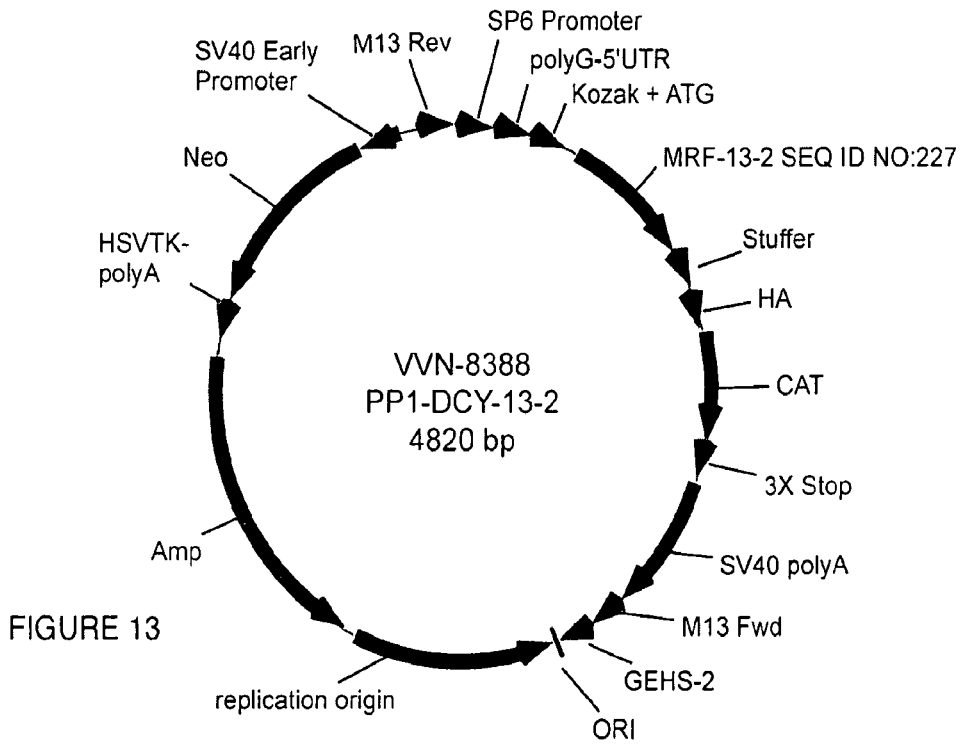
Figure 14:
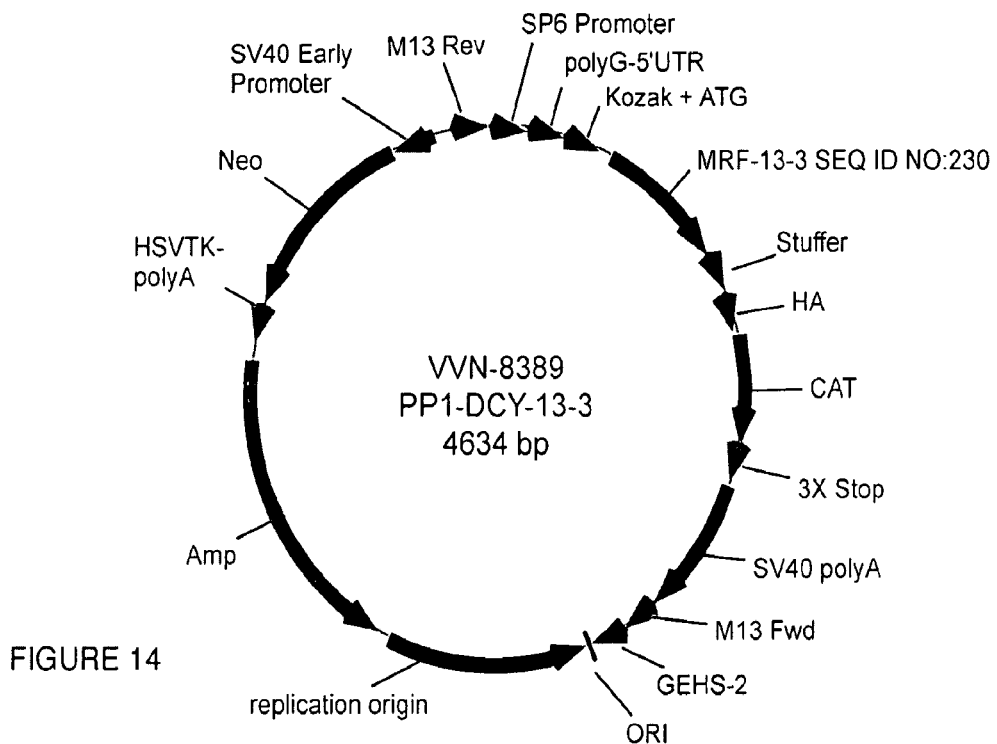
Figure 15:
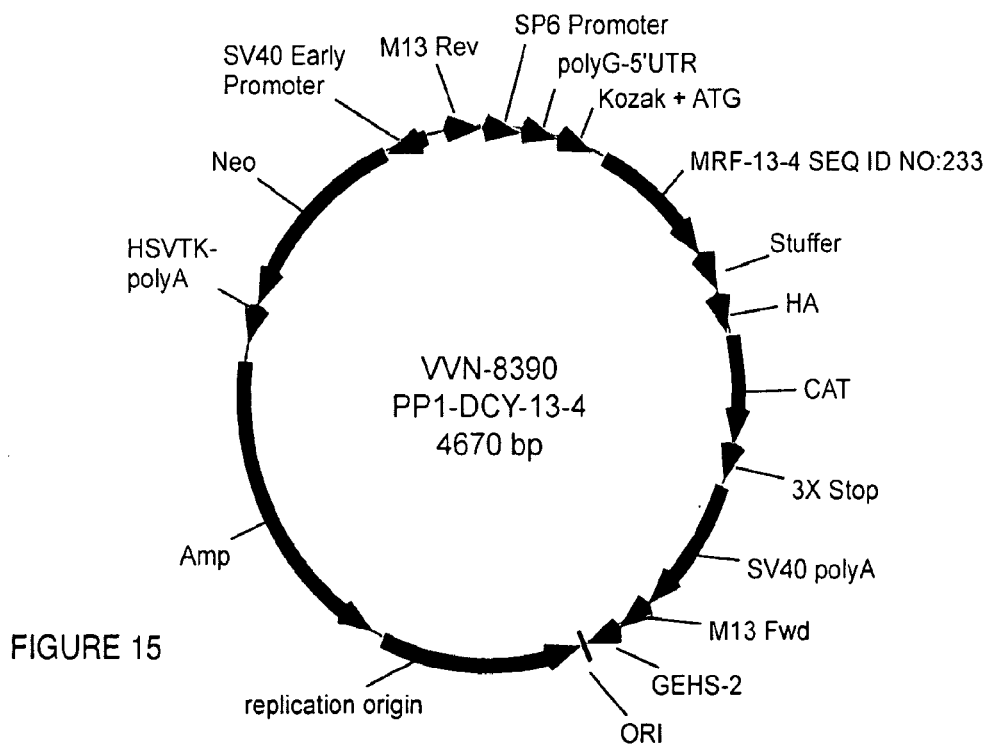
Figure 16:
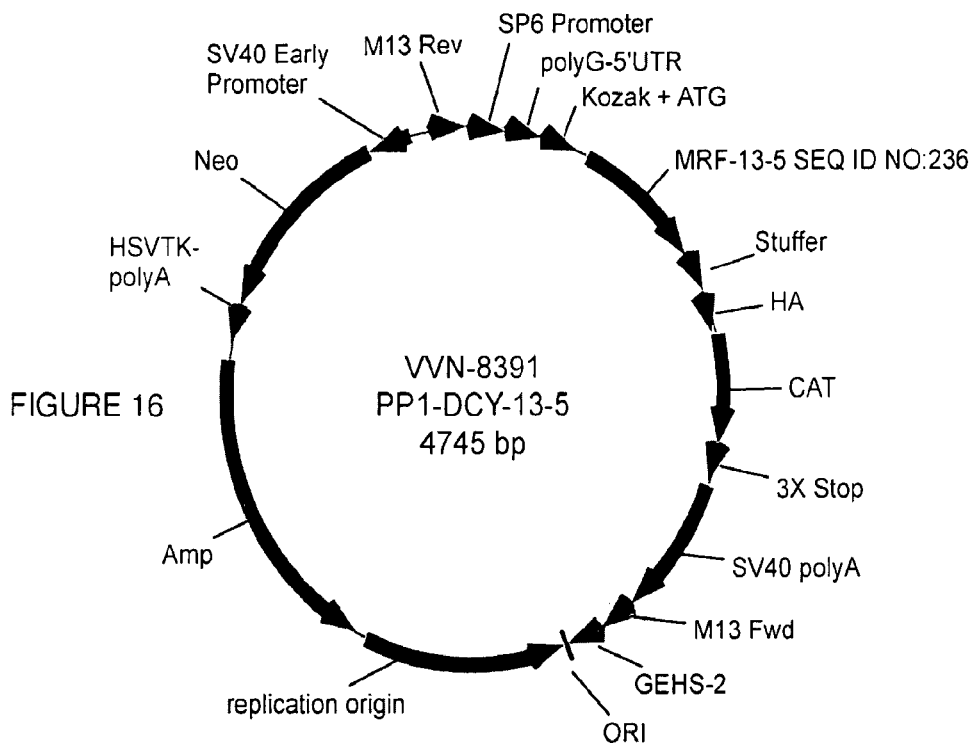
Figure 17:
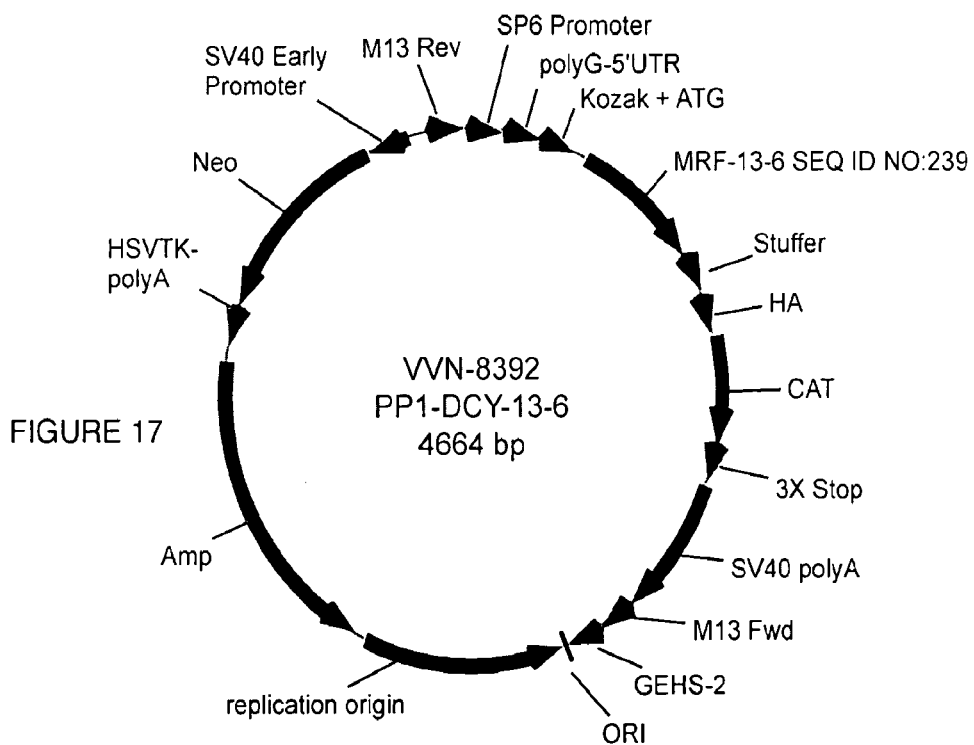
Figure 18:
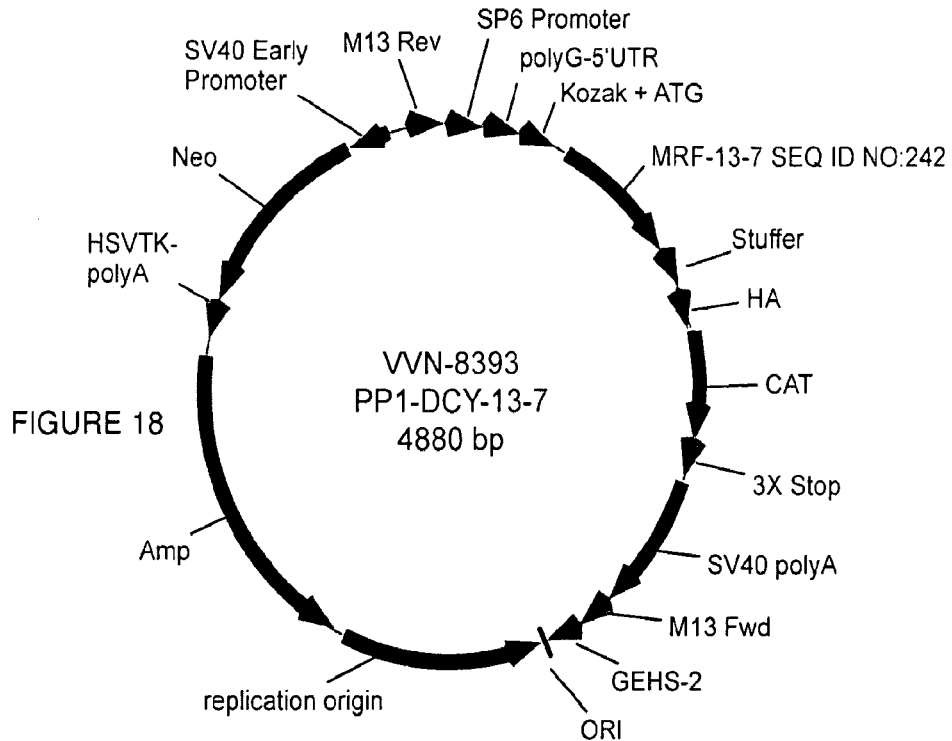
Figure 19:
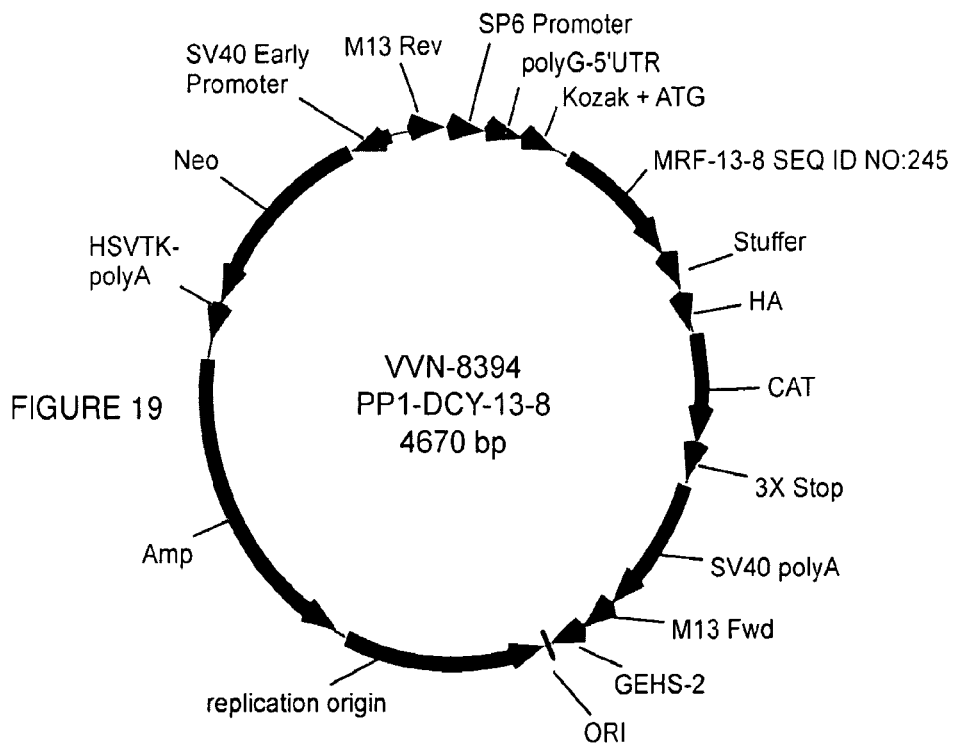
Figure 20:
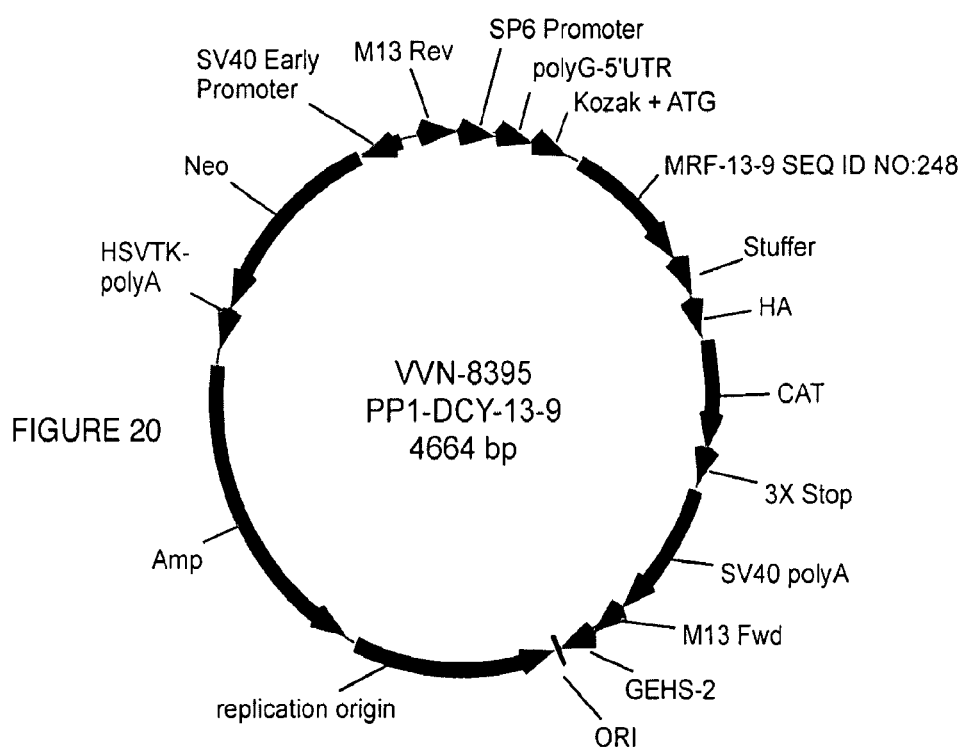
Figure 21:
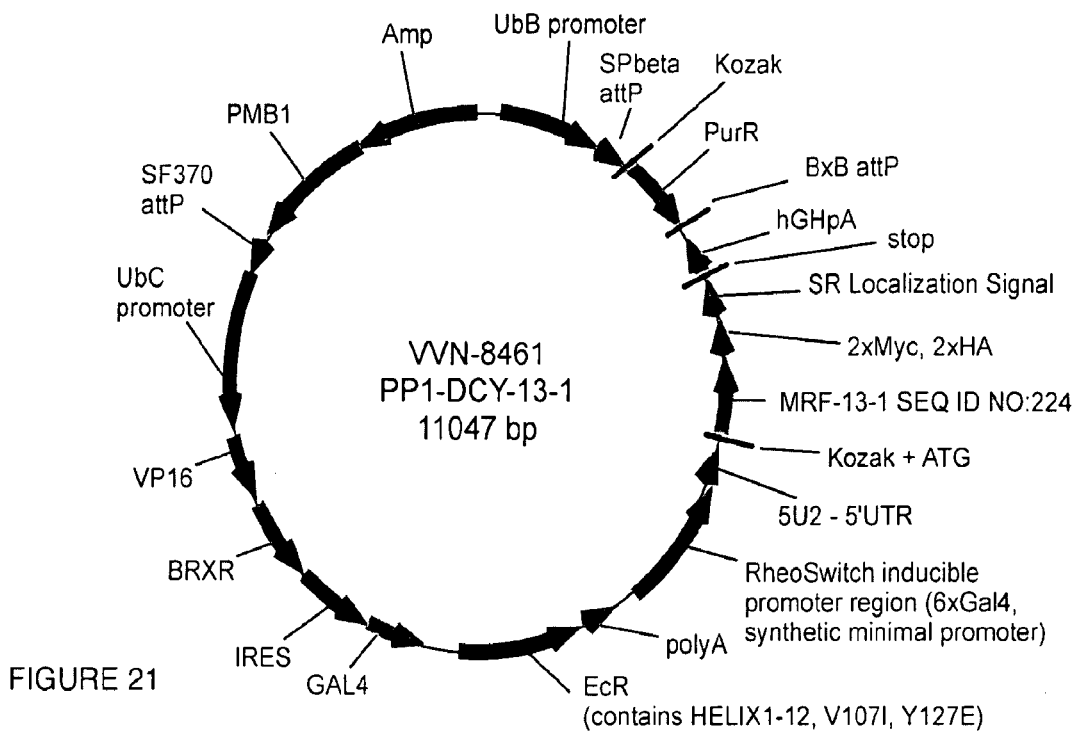
FIGS. 21-29 show vectors for AttSite-mediated genome integration and RheoSwitch inducible expression of the polyligands of the invention fused to a sarco(endo)plasmic reticulum localization signal.
Figure 22:
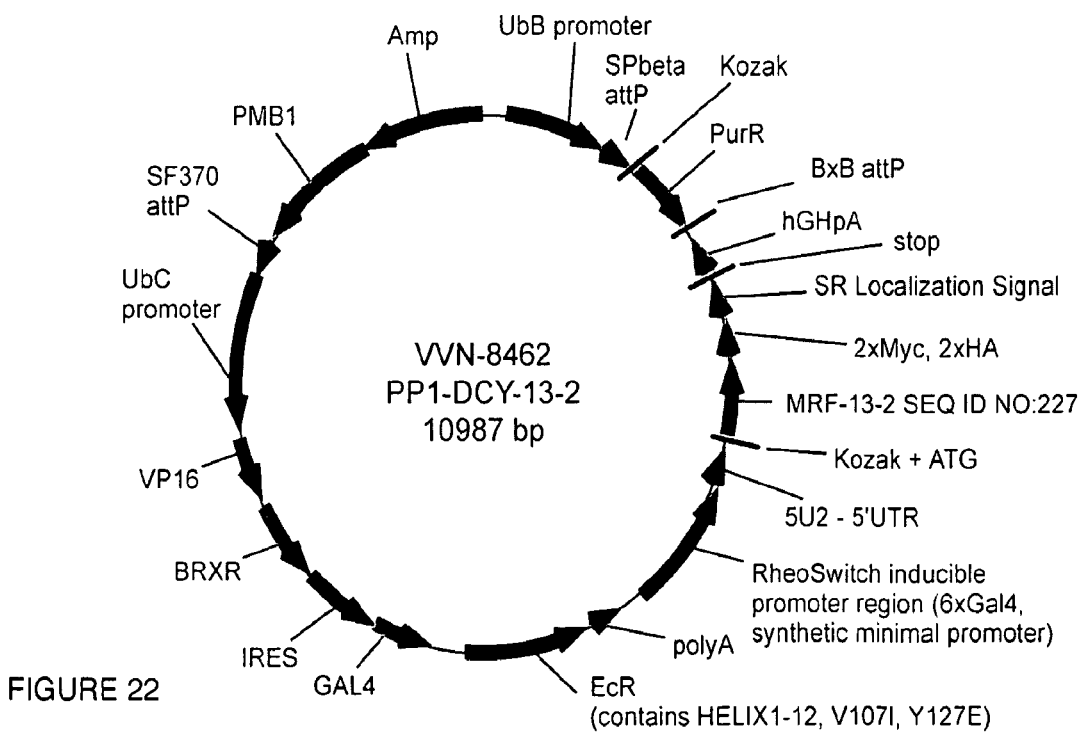
Figure 23:
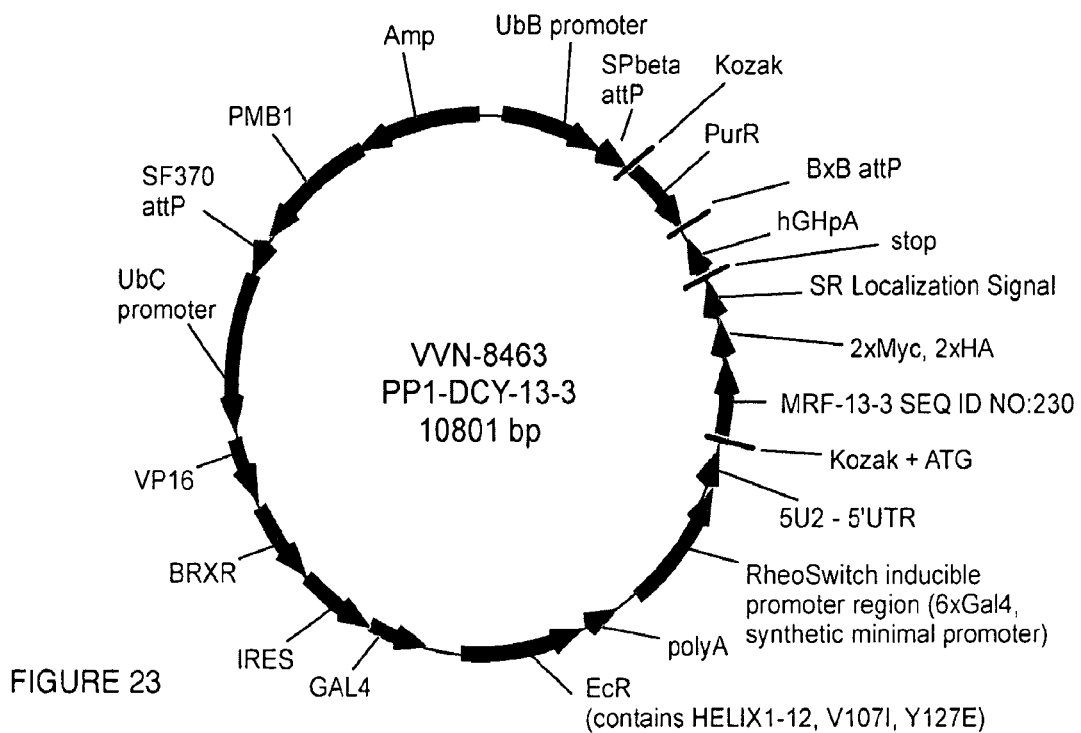
Figure 24:
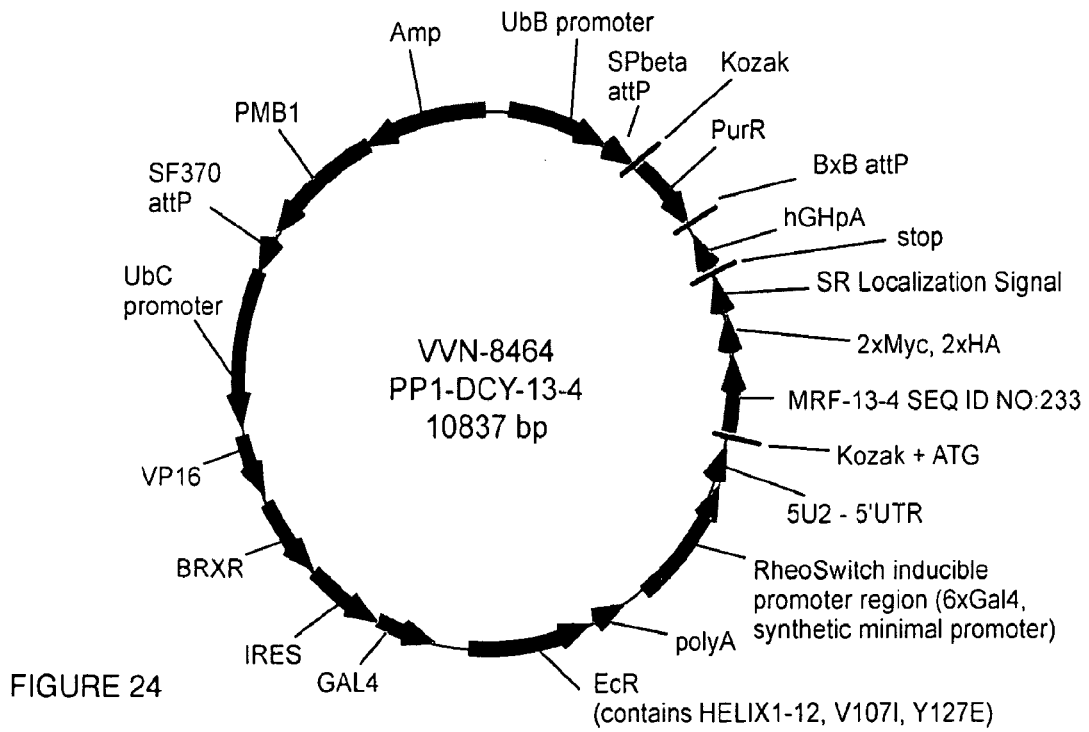
Figure 25:
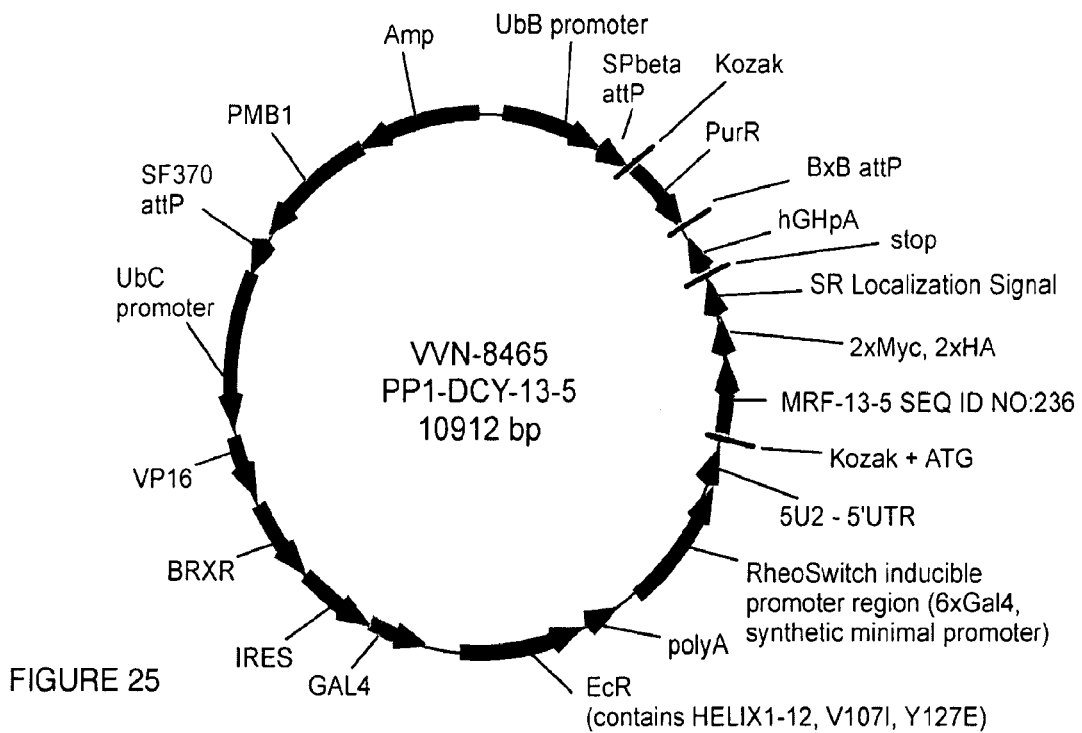

Another way to assemble coding region modules directionally and sequentially employs linear DNA in addition to circular DNA. For example, like the sequential cloning process described above, restriction sites flanking a coding region module are sequences recognized by the restriction enzymes NgoM IV and Cla I; or Xma I and Cla I. A first circular DNA is cut with NgoM IV and Cla I to yield linear DNA with a 5' NgoM IV overhang and a 3' Cla I overhang. A second linear double-stranded DNA is generated by PCR amplification or by synthesizing and annealing complimentary oligonucleotides. The second linear DNA has 5' Cla I overhang and a 3' Xma I overhang, which are compatible cohesive ends with the first DNA linearized. When these first and second DNA fragments are mixed together, annealed, and ligated to form a third circular DNA fragment, the NgoM IV site that was in the first DNA and the Xma I site that was in the second DNA are destroyed in the third circular DNA. Flanking sequences remaining in the third circular DNA still contain intact 5' NgoM IV and 3' Cla I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences. This process is depicted in FIG. 11.

One of ordinary skill in the art recognizes that other restriction site groups can accomplish sequential, directional cloning as described herein. Preferred criteria for restriction endonuclease selection are selecting a pair of endonucleases that generate compatible cohesive ends but whose sites are destroyed upon ligation with each other. Another criteria is to select a third endouclease site that does not generate sticky ends compatible with either of the first two. When such criteria are utilized as a system for sequential, directional cloning, ligands, polyligands and other coding regions or expression components can be combinatorially assembled as desired. The same sequential process can be utilized for epitope, reporter, and/or localization signals.

Polyligands and methods of making polyligands that modulate PP1 activity are disclosed. Therapeutics include delivery of purified ligand or polyligand with or without a localization signal to a cell. Alternatively, ligands and polyligands with or without a localization signals are delivered via viral or retroviral constructs such as those employing adenovirus, lentivirus, adeno-associated virus, or other viral or retroviral constructs that provide for expression of protein product in a cell.

EXAMPLES

Assays, Methods, Results. Ligands of the invention are assayed for PP1 modulating activity using one or more of the following methods.

Method 1. A biochemical assay is performed employing commercially-obtained PP1 enzyme, commercially-obtained PP1 substrate, commercially-obtained PP1 inhibitor (control), and semi-purified inhibitor ligand of the invention (decoy). PP1 enzyme is obtained from Biobol (Plymouth Meeting, Pa.), Sigma-Aldrich (St. Louis, Mo.), New England Biolabs (Ipswich, Mass.) or Promega (Madison, Wisc.). Fluorogenic or chromogenic substrates that become fluorescent or colored upon phosphate removal represent convenient detection systems. An example fluorogenic substrate is fluorescein diphosphate, available from Sigma-Aldrich. An example of a chromogenic substrate is p-nitrophenyl phosphate (PNPP) available from New England Biolabs (Ipswich, Mass.). Ligands are linked to an epitope tag at one end of the polypeptide for immobilzation, for example, on a microtiter plate. The tagged ligand is made using an in vitro transcription/translation system such as a reticulocyte lysate system well known in the art. A vector polynucleotide comprising a promotor, such as T7 and/or T3 and/or SP6 promotor, a ligand coding sequence, and an epitope tag coding sequence is employed to synthesize the tagged ligand in an in vitro transcription/translation system. In vitro transcription/translation protocols are disclosed in reference manuals such as: Current Protocols in Molecular Biology (eds. Ausubel et al., Wiley, 2004 edition.) and Molecular Cloning: A Laboratory Manual (Sambrook and Russell (Cold Spring Harbor Laboratory Press, 2001, third edition). Immunoreagent-containing methods such as western blots, elisas, and immunoprecipitations are performed as described in: Using Antibodies: A Laboratory Manual (Harlow and Lane, Cold Spring Harbor Laboratory Press, 1999).

Specifically, the tagged decoy ligand synthesized using an in vitro transcription/translation system is semi-purified via immunoprecipitation of its epitope tag. The protein content of this material is quantitated and added in duplicate wells to a microtiter plate containing phosphatase enzyme and substrate. The reaction is stopped by the addition of sodium hydroxide. Phosphatase activity is a direct measure of the de-phosphorylation of substrate, p-nitrophenyl phosphate (PNPP), by phosphatase. The catalysis of colorless p-nitrophenyl phosphate by PP1 results in the production of a yellow color with a maximum absorbance at 405 nm. The control experiments include absence of phosphatase enzyme and/or absence of decoy ligand and/or presence/absence of known phosphatase inhibitors. Known PP1 inhibitors useful in the assay include okadaic acid, microstatin, or INH-2 (1-2 peptide).

Method 2. A similar assay is performed employing the same reagents as above using PP1 of rabbit origin.

Method 3. A similar cell-based assay is performed employing same reagents as above, but synthesizing the ligand in a mammalian cell system instead of an in vitro transcription/translation system. Decoy ligands are linked to an epitope tag at one end of the polypeptide for immobilzation and/or for purification and/or for identification in a western blot. Optionally, tagged ligands are also linked to a cellular localization signal for phenotypic comparison of pan-cellular and localized PP1 modulation. A vector polynucleotide comprising a constitutive promotor, such as the CMV promotor, a ligand coding sequence, an epitope tag coding sequence, and optionally a localization signal coding sequence is employed to express the ligand in cells. Transfection and expression protocols are disclosed in reference manuals such as: Current Protocols in Molecular Biology (eds. Ausubel et al., Wiley, 2004 edition.) and Molecular Cloning: A Laboratory Manual (Sambrook and Russell (Cold Spring Harbor Laboratory Press, 2001, third edition). Western Blots and immunoreagent-containing methods are performed as described in: Using Antibodies: A Laboratory Manual (Harlow and Lane, Cold Spring Harbor Laboratory Press, 1999).

Specifically, tagged ligand synthesized in cells is semi-purified and immobilized onto a microtiter plate coated with an anti-tag antibody. Microtiter plates are rinsed to substantially remove non-immobilized components. PP1 enzyme and fluorogenic substrate are then added and appearance of fluorescence is measured. Control experiments include absence of PP1 enzyme, and/or absence of decoy ligand, and/or presence/absence of known PP1 inhibitor. Known PP1 inhibitors useful in the assay include okadaic acid, microstatin or inhibitor-2 (I-2/INH-2).

Method 4. A cell-based assay is performed with an inducible and sarcoplasmic reticulum-localized decoy ligand. Molecular alterations in cells will be identified as appearance of the decoy ligand as visualized with specific antibodies for the epitope tag present on the decoy. Decoy ligands are linked to an epitope tag at one end of the polypeptide for immobilization and/or for purification and/or for identification in immunodetection. Furthermore, the localization of the decoy ligand will be demonstrated by co-localization with phospholamban (PLB), a known marker of the sarcoplasmic reticulum (SR). A vector polynucleotide comprising an inducible promoter, a decoy ligand coding sequence, an SR-localization sequence (Amino Acid Sequence: QARQNLQNAFIAF-CLILICLLLICIIVMLL (SEQ ID NO: 272); Nucleotide Sequence: caggccaggcagaacctccagaat-gctttcattgcttttgtctgattct-catctgcctcctgctgatttgcattatcgtcatgctcctg (SEQ ID NO: 273)), and an epitope coding sequence such as HA is employed to express the decoy ligand in cells. Transfection and expression protocols are disclosed in reference manuals such as: Current Protocols in Molecular Biology (eds. Ausubel et al., Wiley, 2004 edition) and Molecular Cloning: A Laboratory Manual (Sambrook and Russell, Cold Spring Harbor Laboratory Press, 2001, third edition). Immunodetection and immunoreagent-containing methods are performed as described in: Using Antibodies: A Laboratory Manual (Harlow and Lane, Cold Spring Harbor Laboratory Press, 1999). Immunofluorescence was performed according to manufacturers' protocols.

Specifically, the vector polynucleotide construct is stably integrated into P19 mouse embryo carcinoma cells using integrases and antibiotic selection. The stably-transfected P19 cells are then compelled to differentiate into cardiomyocytes via exposure to dimethyl sulfoxide (DMSO). This is necessary because cardiomyocytes contain SR structures whereas P19 cells normally do not. Once cardiomyocytes differentiation is complete, indicated by synchronized beating of cells in culture, these cells are induced to express the SR-localized decoy ligand through the addition of the inducing ligand (RSL1) for 24 hours. Cell are fixed with paraformaldehyde and exposed to antibodies specific to HA (rat anti-HA, Roche Molecular Diagnostics) or PLB (ABR). Secondary antibodies containing either red or green fluorophores (Invitrogen) indicate the location of the respective proteins within the cell. Where both proteins are present, the resulting image has an orange to yellow color.

To perform such assays, the following technologies were utilized: UltraVector™ (US2004/0185556, PCT/US2004/013517, WO2005/040336), RheoSwitch® (U.S. Pat. No. 7,091,038; US 20040033600; US 20060200416;), and AttSite™ Recombination (US 20060172377). UltraVector allows for fast and efficient assembly of novel gene programs in a scalable format. RheoSwitch allows for inducible expression of a chosen gene of interest providing a time-controlled and dose-dependent control. It consists of two engineered receptor proteins, an inducible promoter for the gene of interest (GOI) and a synthetic activator drug (a diacylhydrazine small molecule). AttSite Recombination is based on site-specific enzymes that catalyze DNA integration. In contrast to random integration, AttSite recombination integrates into a limited number of sites in a genome, lowering the risk of interrupting a crucial gene. Integration is achieved by co-transfection of plasmids (represented by FIGS. 21-29) with a plasmid (VVN-3217, pREC027) containing a recombinase enzyme (from *Streptococcus Pyogenes* Strain SF370.1 serotype M1) allowing AttSite Recombination.

P19 cardiomyocyte cells were used to demonstrate SR localization and PP1 inhibitory function. P19 cells are mouse embryonic carcinoma cells that can be differentiated into cardiomyocytes by exposure to dimethylsulfoxide (DMSO) or Oxytocin (see FIGS. 30A-D). In response to those compounds, P19 cells acquire the characteristics of slow twitch cardiac muscles and beat like a heart muscle in a culture dish. During the process of differentiation into muscle cells, the sarco(endo)plasmic reticulum is formed. P19 cells were plated in bacteriological Petri dishes and exposed to DMSO for 48 hours. The subsequent embryoid bodies (large cells masses) were transferred to mammalian tissue culture plates in regular medium. After 5 days, the cells reached confluency in the plate. By eight days, the cells synchronize and beat in the culture dish. Differentiated cells were fixed with 4% paraformaldehyde and incubated with rabbit anti-Troponin I, followed with AlexaFluor 546-conjugated goat anti-rabbit IgG secondary antibody. The cell nuclei were counterstained with DAPI. The cells were imaged on a Zeiss Axioscope fitted with appropriate filters and an Axiovision M2 camera.

The PP1 polyligands disclosed in FIG. 31 were designed and modeled in linear and three-dimensional space and optimized for PP1 interaction in silico. Components and sequences of embodiments of polyligands (decoys) are shown in FIGS. 1A and 1B and the sequence listing. Vectors containing constructs for each embodiment are shown in FIGS. 12-20 for in vitro translation experiments; and FIGS. 21-29 for P19 cell experiments. All vectors shown in FIG. 31 were sequence-validated except VVN-8394 and VVN-8395. Polyligands were tested in biochemical assays described in Method 1 using commercially available PP1 enzyme (FIG. 31). This assay quantitatively measured the PP1 modulatory activity of the ligands. Seven of eight assayed ligands inhibited PP1 activity at mid-nanomolar concentrations (approximately 46 to 97 nM), which was roughly 10-20 times more effective than INH-2 which required 1000 nM to achieve the same degree of inhibition (FIG. 31).

The assay used to generate the data in FIG. 31 is as follows. Polyligands were transcribed in vitro from plasmid DNA (FIGS. 12-20) using Ambion's SP6 Megascript Kit (AM1330; according to manufacturer's protocol). RNA was subsequently translated in vitro using Ambion's Retic Lysate IVT Kit (AM1200; according to manufacturer's protocol) and immunoprecipitated from the reticulocyte lysate employing the Profound HA Tag IP Kit from Pierce (23610; according to manufacturer's protocol). Next, translated products were quantified using Pierce's Coomassie Plus Protein Reagent (1856210; microplate procedure). Following quantification, enzymatic reactions were performed in duplicate wells of a low-binding microtiter plate (TRP 96196) at 30° C. for 30 min as follows:

Controls: 0.5 units of PP1 (Biomol, SE-497), 30 mM p-nitrophenyl phosphate (NEB, P0757S), 2 mM manganese chloride (Fluka, 48795) in 100 mM Tris-HCl, pH 8.2, 40 mM NaCl, 1 mM DTT, 20% glycerol. A corresponding control without enzyme was also performed in duplicate.

INH-2 Inhibitor: 0.5 units of PP1 (Biomol, SE-497), 30 mM p-nitrophenyl phosphate (NEB, P0757S), 2 mM manganese chloride (Fluka, 48795), 1000 nM INH-2 (NEB, P0755S) in 100 mM Tris-HCl, pH 8.2, 40 mM NaCl, 1 mM DTT, 20% glycerol. A corresponding control without enzyme was also performed in duplicate.

Polyligand Reactions: 0.5 units of PP1 (Biomol, SE-497), 30 mM p-nitrophenyl phosphate (NEB, P0757S), 2 mM manganese chloride (Fluka, 48795), 5 μL polyligand in 100 mM Tris-HCl, pH 8.2, 40 mM NaCl, 1 mM DTT, 20% glycerol. A corresponding control without enzyme was also performed in duplicate.

Reactions were stopped with NaOH (JTBaker, 5671-02) and the plate was read at 405 nm using a plate reader (Molecular Devices).

Additional polyligands were tested in a more rudimentary biochemical assay for PP1 inhibition than described above. However, the rudimentary assay did not yield conclusive data.

Additional polyligands were tested in biochemical assays described in Method 2, using PP1 of rabbit origin (FIG. 39). Percent inhibition was calculated by subtracting the value obtained by dividing the OD405 of each decoy by the OD405 of the Positive Control from one; multiplied by 100. I-2, a 204 amino acid heat-stable protein that specifically inhibits type 1 protein phosphatases, was used as a control for PP1 inhibition. FIG. 39 shows that there is no interaction with the PP1 of rabbit origin, which shows that the PP1 decoys do not inhibit the non-human PP1. Vectors containing constructs for each embodiment shown in FIG. 39 are shown in FIGS. 41-48. All vectors shown in FIG. 39 were sequence-validated.

Figure 32:
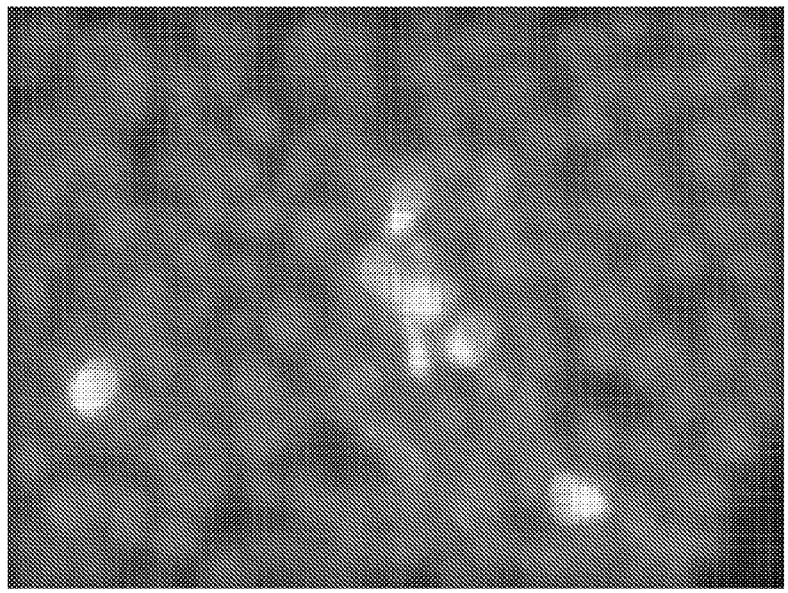
FIG. 32 shows transient expression of the vector shown in FIG. 24 in P19 cells. Expression of SEQ ID NO:233 fused to an SR localization signal was induced by addition of diacylhydrazine activator drug, (N-(2-ethyl-3-methoxybenzoyl)-N'-(3,5-dimethylbenzoyl)-N'-tert-butylhydrazine, for 24 hours. Red color illustrates localization of phospholamban. Green color illustrates localization of polyligand decoy SEQ ID NO:233. Blue color are nuclei. This micrograph is a merged image where red and green overlap (yellow) is an indication of co-localization of phospholamban and PP1 decoy. Phospholamban was imaged using anti-phospholamban antibody and secondary antibody conjugated to AlexaFluor 546 (red); cell nuclei were stained with DAPI (blue); the HA-tagged decoy was imaged using rat anti-HA antibody and secondary antibody conjugated to AlexaFluor 488 (green). Twenty thousand P19 mouse embryocarcinoma cells were plated on 24-well dishes 24 hours before transfection. Cells were transfected with 0.4 μg vector (VVN8464) and 1.2 μg Fugene 6 (Roche Molecular Diagnostics). Cells were returned to the incubator for 48 hours before exposing them to 1 μM activator drug. The induced cells were returned to the incubator for 24 hours. The cells were fixed with 4% paraformaldehyde and stained with rabbit anti-PLB followed by goat anti-rabbit IgG conjugated to AlexaFluor 546. Then cells were stained with rat anti-HA followed by rabbit anti-rat IgG antibody conjugated to AlexaFluor 488. Finally, cells were counterstained with 4',6-diamidino-2-phenylindole (DAPI). The stained cells were imaged with a Zeiss AxioObserver Microscope fitted with an AxioCam MR2 camera and epi-fluorescence filters designed to detect blue fluorescence (DAPI), green fluorescence (Alexa 488) or red fluorescence (Alexa 546).

Experiments were carried out to test the UltraVector backbone-containing inducible RheoSwitch system for inducible expression of polyligands fused to an SR-localization signal in P19 cells before and after differentiation. Short-term (transient) expression of constructs (such as those shown in FIGS. 21-29) in undifferentiated P19 cells confirmed that our polyligands are expressed upon RheoSwitch induction with activator drug and are targeted to the endoplasmic reticulum (FIG. 32).

Figure 26:
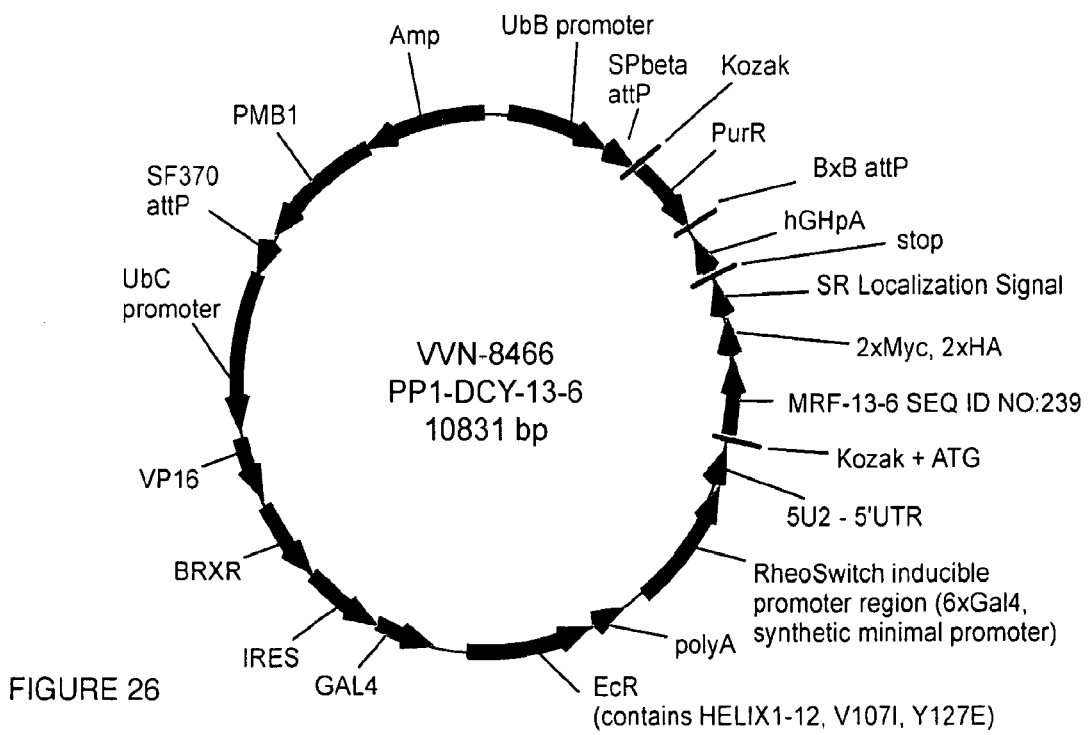
Figure 27:
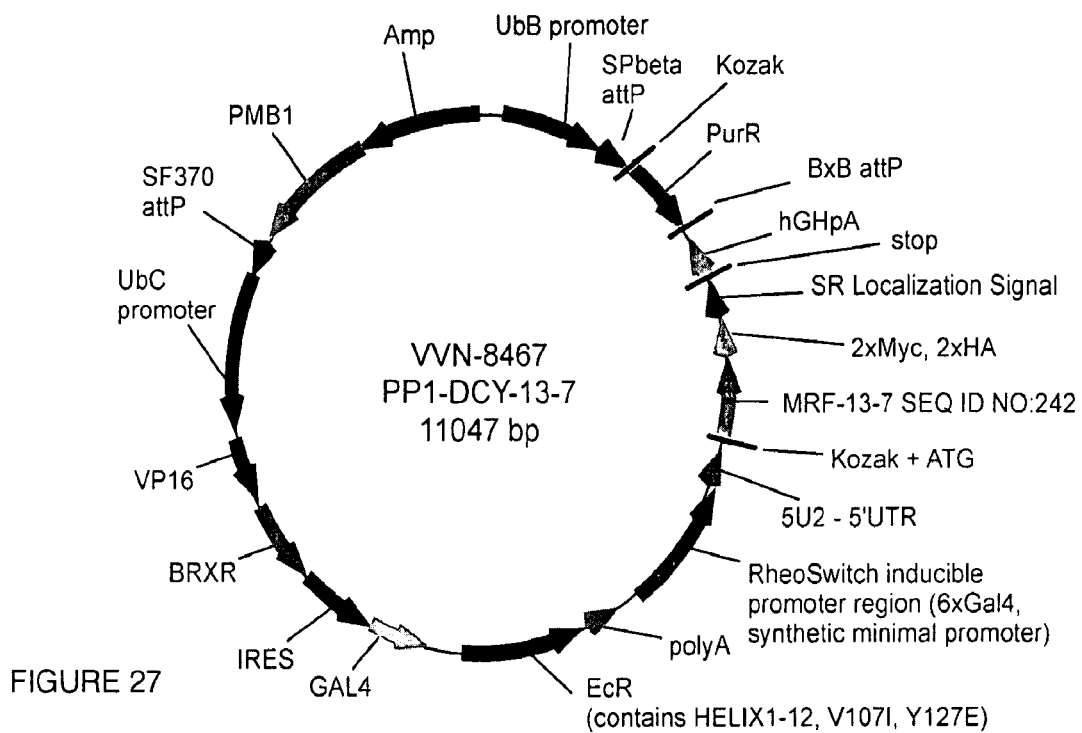
Figure 28:
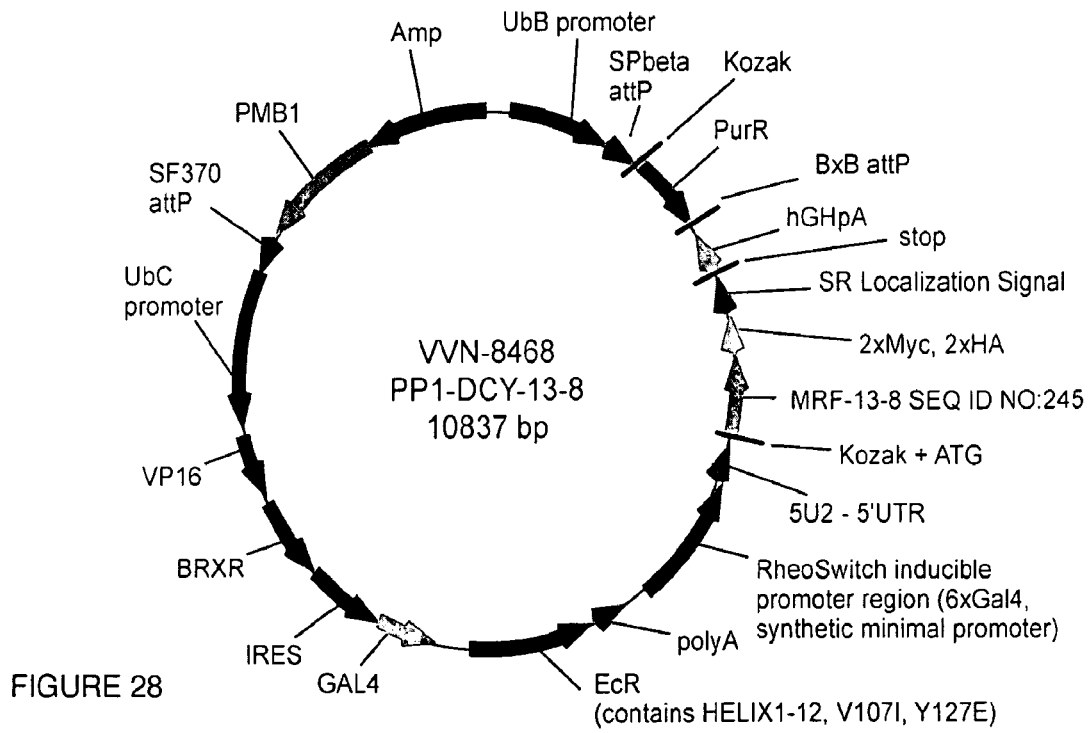
Figure 29:
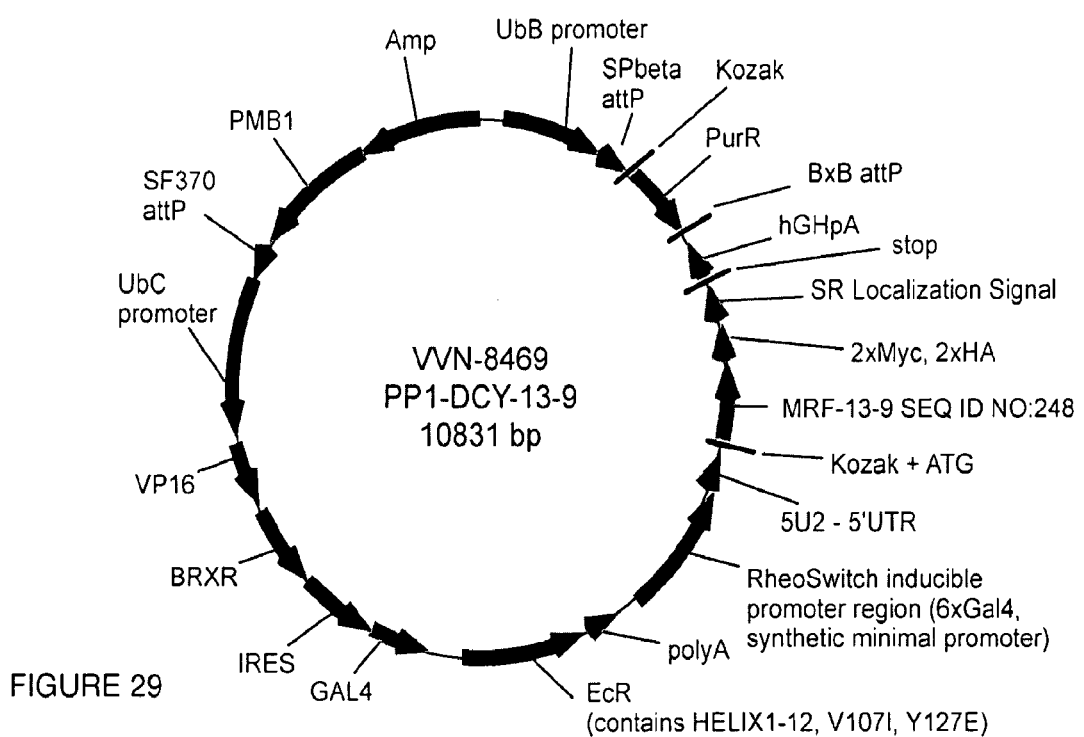
Figure 30:
FIGS. 30A-D show P19 cells.
Figure 30:
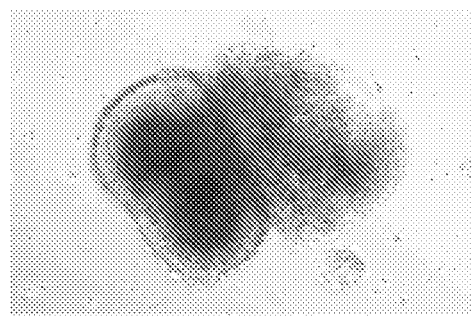
Figure 30:
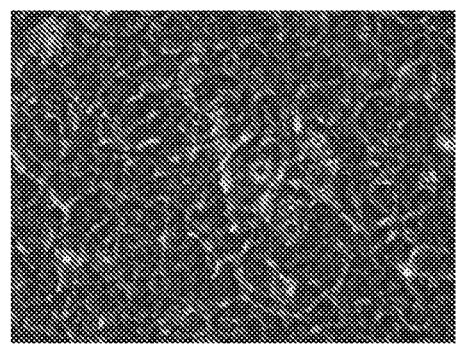
Figure 30:
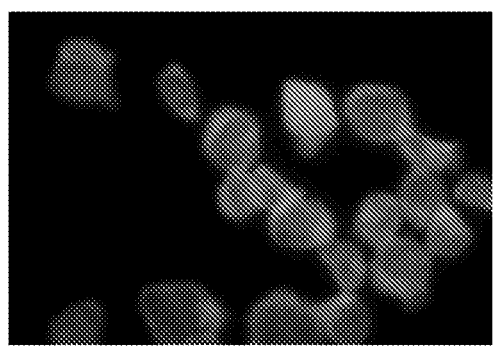
Figure 33:
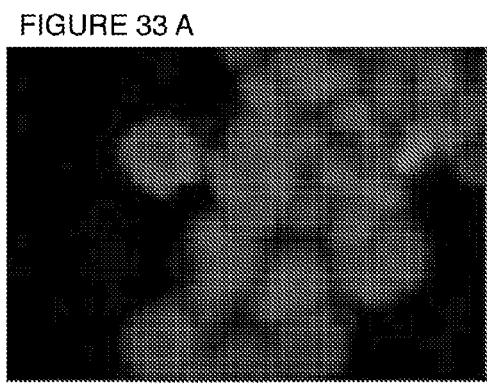
FIGS. 33A and 33B show expression of SR-localized decoy (VVN8464) in the presence and absence of activator drug, after being integrated into the genome of P19 cells using AttSite Recombinase technology (co-transfection with a plasmid carrying Streptococcus Pyogenes SF370.1 recombinase, VVN-3217). The polyligand decoys were expressed from the RheoSwitch-inducible promoter by exposure to 500
Figure 33:
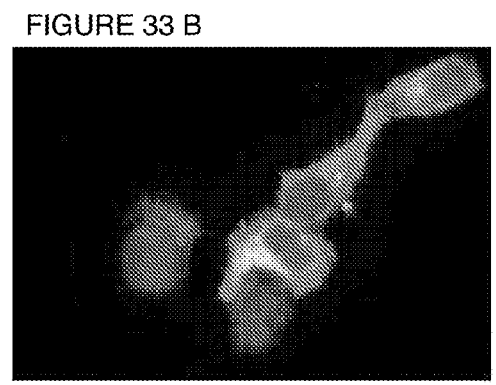
Figure 34:
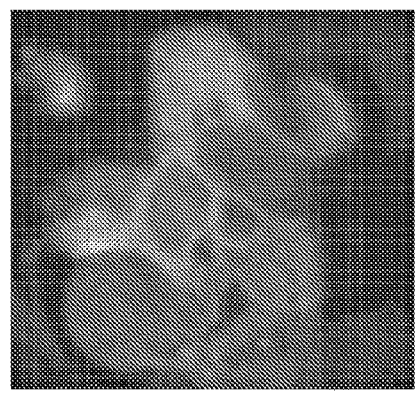
FIG. 34 shows P19 cells with stably integrated inducible polyligand construct differentiated into cardiomycoytes. Shown is a representative merged image of immunostaining for phospholamban phophorylated at serine 16 (red color) and for HA epitope (green color) to detect our polyligand. Cells were also counterstained with DAPI to show the nuclei. Yellow color indicates co-localization of phosphorylated phospholamban and polyligand.
Figure 40:
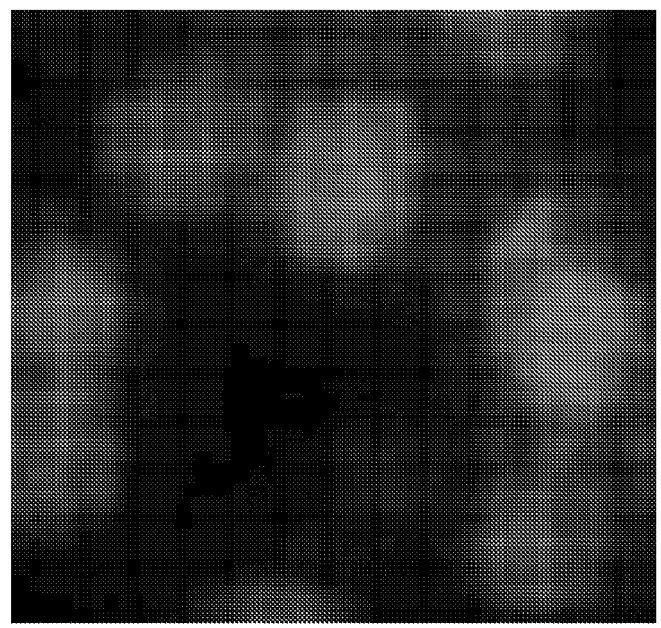
FIG. 40 shows p19 cells without stably integrated polyligand construct, immunostained for phospholamban phosphorylated at serine 16 (red color).
Figure 41:
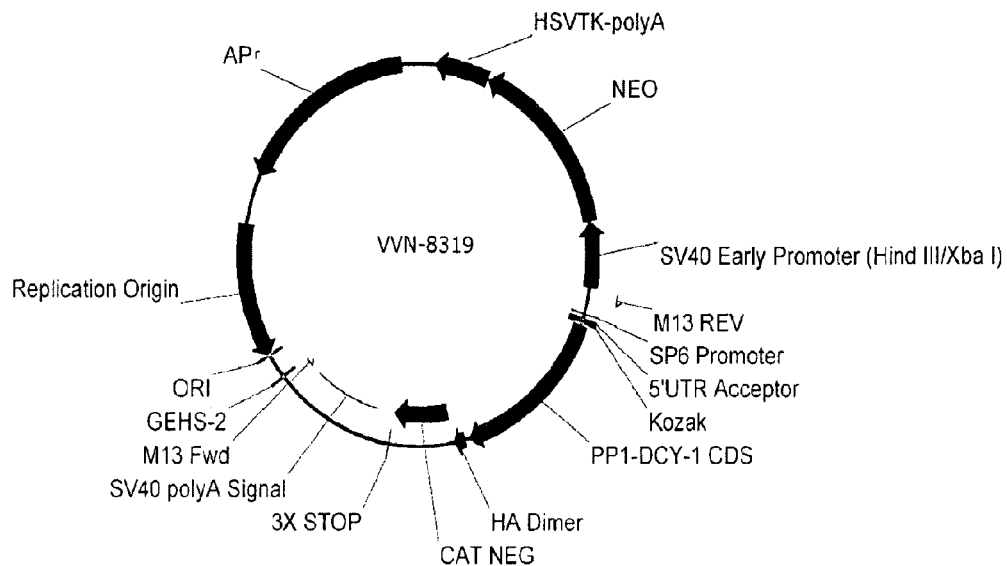
FIGS. 41-48 show vectors for in vitro transcription/translation used to generate the data of FIG. 39.
Figure 42:
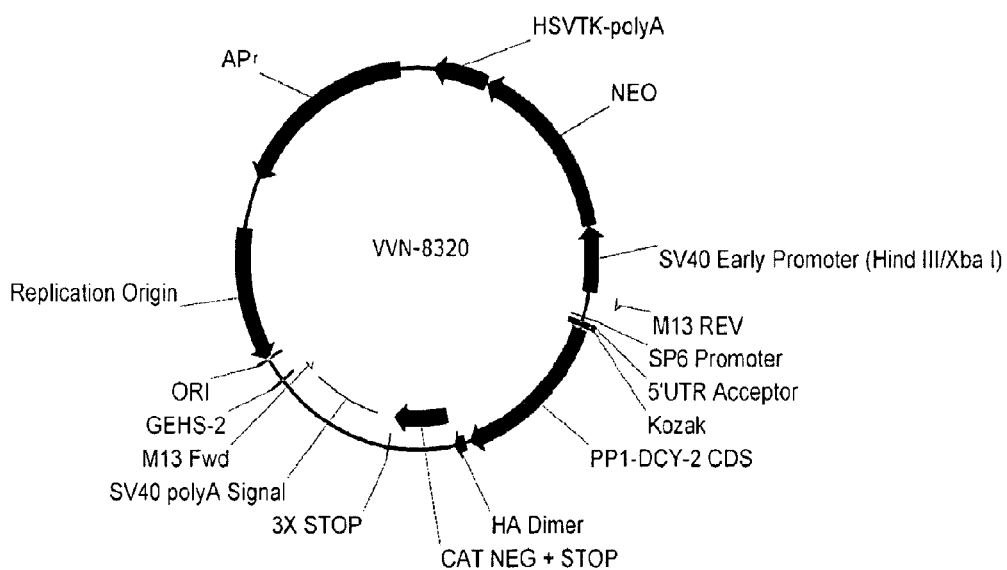
Figure 43:
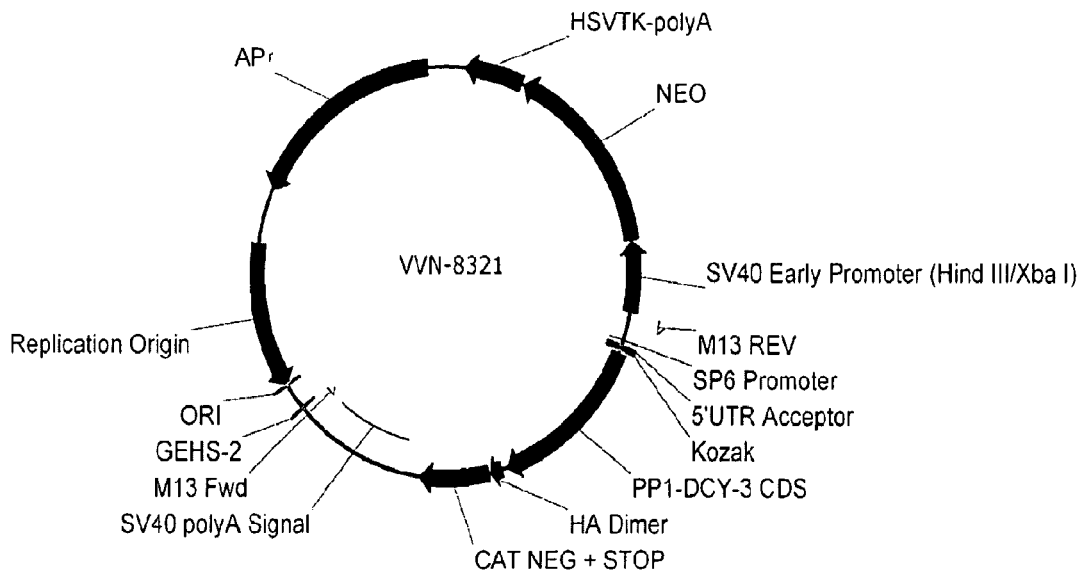
Figure 44:
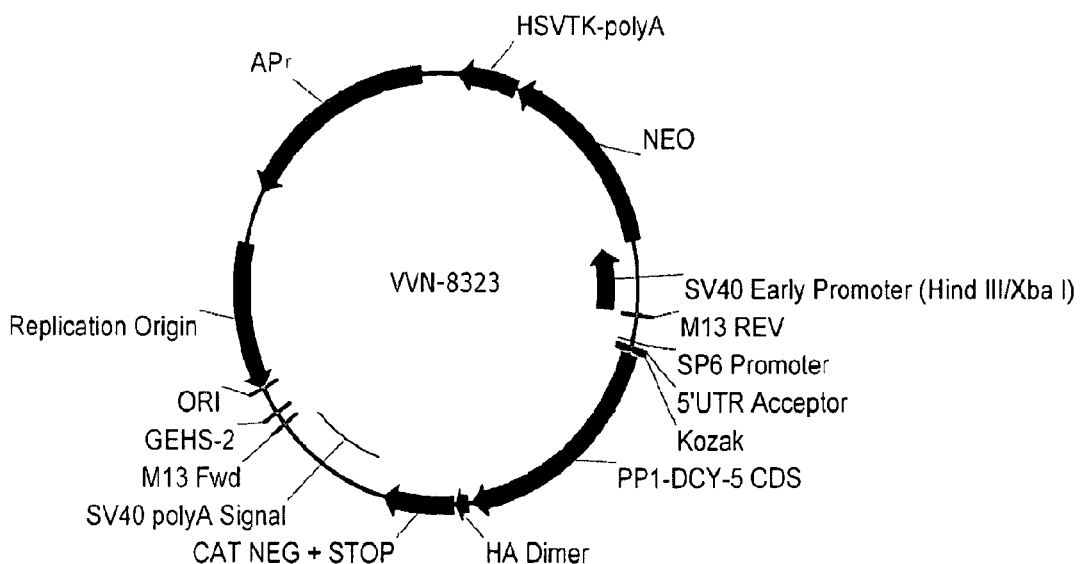
Figure 45:
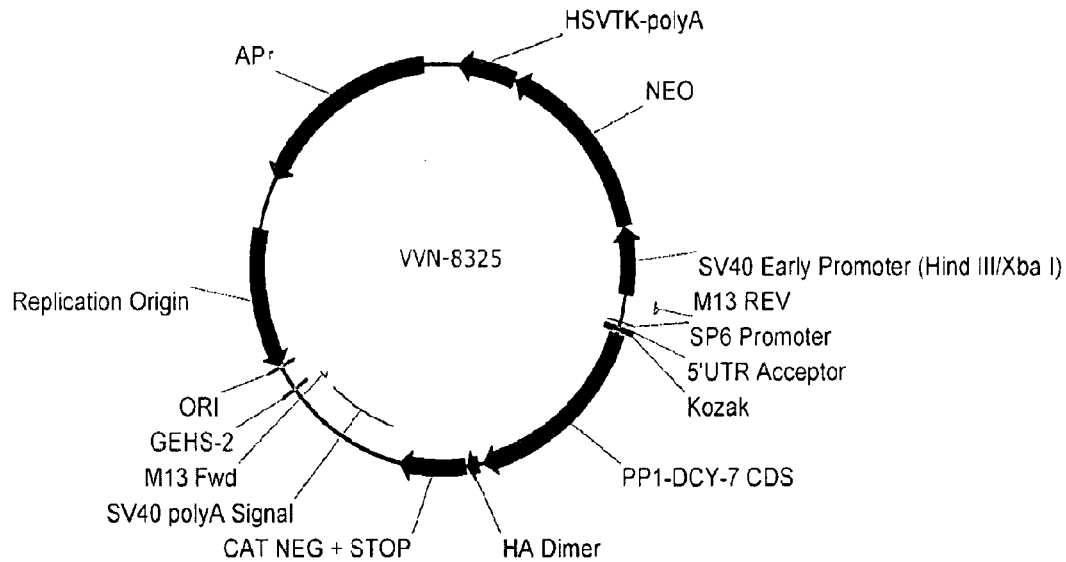
Figure 46:
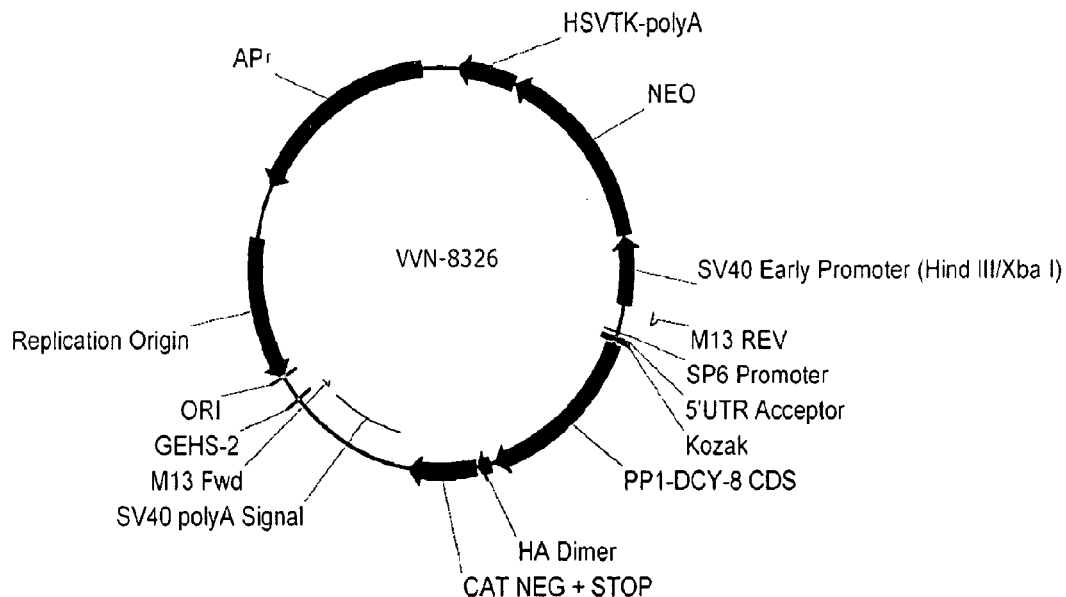
Figure 47:
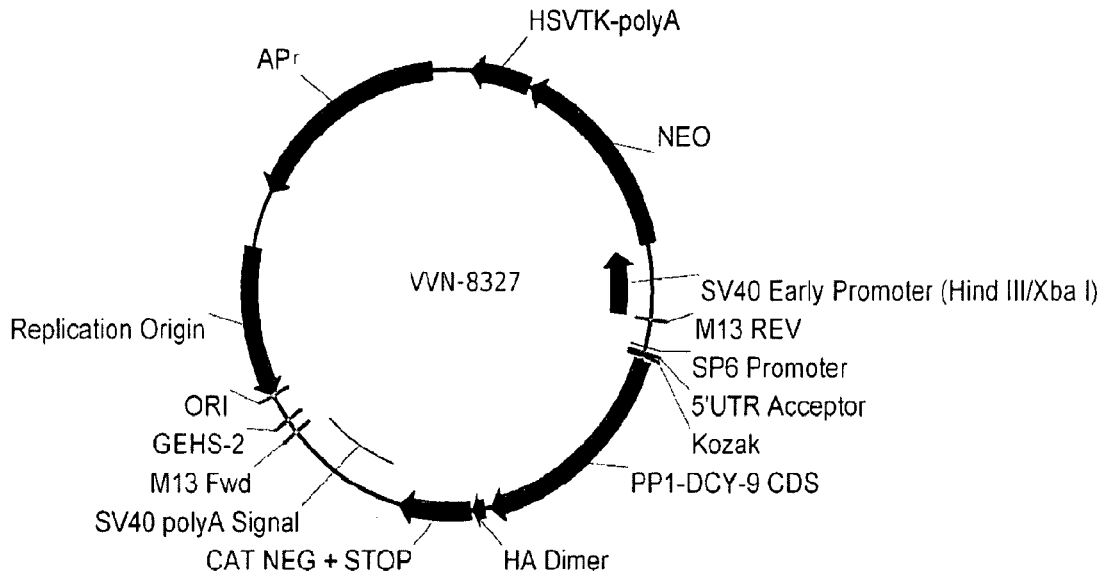
Figure 48:
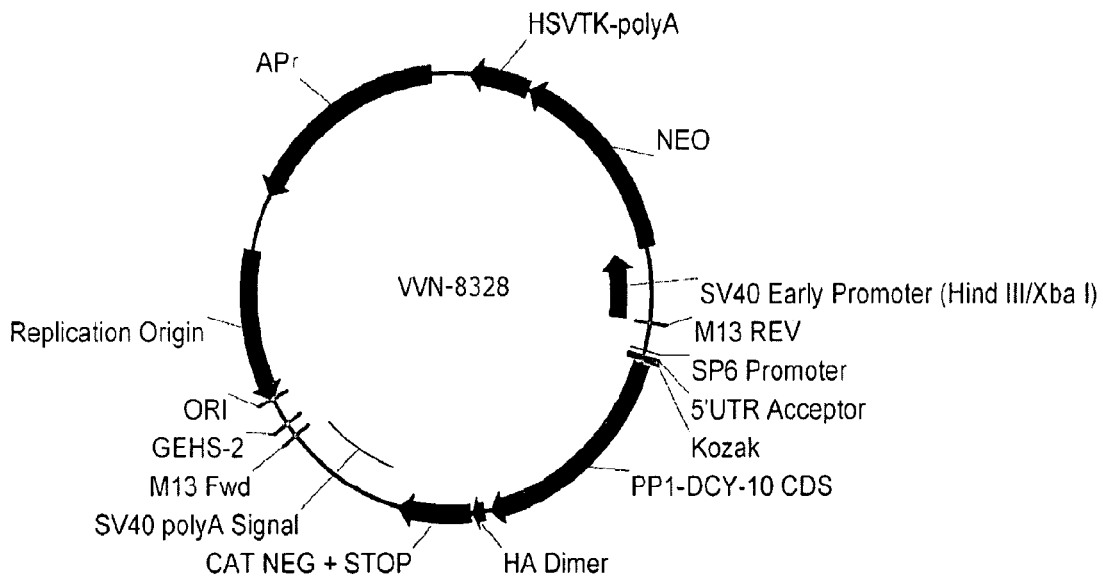

Subsequently, P19 cells with stable genome integration of the Rheoswitch system and polyligand of interest were made in order to reduce the variations that accompany transient expression. The AttSite recombination technology was used to establish long-term cultures of P19-based cardiomyocyte precursor cells with stably-integrated inducible PP1 polyligand construct (FIG. 26). Representative data (FIG. 33A-B) shows that our stable cultures have no detectable SR-localized polyligand expression in the absence of activator drug, but can be induced to express the polyligands when activator drug is added. Furthermore, P19 cells with stable integrations were differentiated into cardiomyocytes and then activator drug was added (FIG. 34), resulting in induced expression of SR-localized polyligand (vector shown in FIG. 24). FIG. 34 shows P19 cells immunostained for phospholamban phosphorylated at serine 16 (red color) and for HA epitope (green color) to detect the SR localized polyligand. Cells were also counterstained with DAPI to show the nuclei. Yellow color indicated co-localization of phospholambin and decoy. FIG. 40 shows the results of a negative control (no polyligand) in P19 cells immunostained for phospholamban phosphorylated at serine 16 (red color).

ADDITIONAL EXAMPLES

Example 1

A polypeptide comprising a heteropolyligand, an endoplasmic reticulum cellular localization signal, and a His6 epitope is synthesized. Examples of such polypeptides are generically represented by FIGS. 8A, 8B, 8D, 8E and 8F. The polypeptide is synthesized on an automated peptide synthesizer or is recombinantly expressed and purified. Purified polypeptide is solubilized in media and added to cells. The polypeptide is endocytosed by the cells, and transported to the endoplasmic reticulum. Verification is performed by immunohistochemical staining using an anti-His6 antibody.

Example 2

A transgene is constructed using a cytomegalovirus (CMV) promoter to direct expression of a fusion protein comprising SEQ ID NO:255, SEQ ID NO:263, and SEQ ID NO:261 (POLYLIGAND), green fluorescent protein (REPORTER), and a plasma membrane localization signal (LOCALIZATION SIGNAL). Such a transgene is generically represented by FIG. 9C. The transgene is transfected into cells for transient expression. Verification of expression and location is performed by visualization of green fluorescent protein by confocal microscopy.

Example 3

A transgene construct is built to produce a protein product with expression driven by a tissue-specific promoter. The transgene comprises a synthetic gene expression unit engineered to encode three domains. Each of these three domains is synthesized as a pair of complimentary polynucleotides that are annealed in solution, ligated and inserted into a vector. Starting at the amino-terminus, the three domains in the expression unit are nucleotide sequences that encode a PP1 ligand, a FLAG epitope, and a nuclear localization signal. The PP1 ligand is a monomeric ligand, homopolymeric ligand or heteropolymeric ligand as described herein. Nucleotide sequences encoding a FLAG epitope are placed downstream of nucleotide sequences encoding the PP1 ligand. Finally, nucleotide sequences encoding the localization signal are placed downstream of those encoding the FLAG epitope. The assembled gene expression unit is subsequently subcloned into an expression vector, such as that shown in FIG. 10A, and used to transiently transfect cells. Verification is performed by immunohistochemical staining using an anti-FLAG antibody.

Example 4

Modulation of PP1 cellular function by subcellularly localized PP1 polyligand is illustrated. A transgene construct containing nucleic acids that encode a polyligand fusion protein (decoy ligand), epitope, and sarco(endo)plasmic reticulum localization signal is made. The expression unit contains nucleotides that encode SEQ ID NO:224 (POLYLIGAND), a c-Myc epitope (EPITOPE), and a sarco(endo)plasmic reticulum localization signal (LOCALIZATION SIGNAL). This expression unit is subsequently subcloned into a vector between a CMV promoter and an SV40 polyadenylation signal (generically depicted in FIG. 10A). The completed transgene-containing expression vector is then used to transfect cells. Inhibition of PP1 activity is demonstrated by phenotypic observation against non-localized and mock transfected controls.

Example 5

Ligand function and localization is demonstrated in vivo by making a transgene construct used to generate mice expressing a ligand fusion protein targeted to the endoplasmic reticulum. The transgene construct is shown generically in FIG. 10B. The expression unit contains nucleotides that encode SEQ ID NO:233, a hemagluttinin epitope, and an sarco(endo)plasmic reticulum localization signal. This expression unit is subsequently subcloned into a vector between nucleotide sequences including an inducible promoter and an SV40 polyadenylation signal. The completed transgene is then injected into pronuclei of fertilized mouse oocytes. The resultant pups are screened for the presence of the transgene by PCR. Transgenic founder mice are bred with wild-type mice. Heterozygous transgenic animals from at least the third generation are used for the following tests, with their non-transgenic littermates serving as controls.

Test 1: Southern blotting analysis is performed to determine the copy number. Southern blots are hybridized with a radio-labeled probe generated from a fragment of the transgene. The probe detects bands containing DNA from transgenic mice, but does not detect bands containing DNA from non-transgenic mice. Intensities of the transgenic mice bands are measured and compared with the transgene plasmid control bands to estimate copy number. This demonstrates that mice in this example harbor the transgene in their genomes.

Test 2: Tissue homogenates are prepared for western blot analysis. This experiment demonstrates the transgene is expressed in tissues of transgenic mice because hemagluttinin epitope is detected in transgenic homogenates but not in non-transgenic homogenates.

Test 3: Function is assessed by phenotypic observation or analysis against controls.

These examples demonstrate synthesis of PP1 ligands and delivery to a localized region of a cell for therapeutic or experimental purposes. The purified polypeptide ligands can be formulated for oral or parenteral administration, topical administration, or in tablet, capsule, or liquid form, intranasal or inhaled aerosol, subcutaneous, intramuscular, intraperitoneal, or other injection; intravenous instillation; or any other routes of administration. Furthermore, the nucleotide sequences encoding the ligands permit incorporation into a vector designed to deliver and express a gene product in a cell. Such vectors include plasmids, cosmids, artificial chromosomes, and modified viruses. Delivery to eukaryotic cells can be accomplished in vivo or ex vivo. Ex vivo delivery methods include isolation of the intended recipient's cells or donor cells and delivery of the vector to those cells, followed by treatment of the recipient with the cells.

Disclosed are ligands and polyligands that modulate PP1 activity and methods of making and using these ligands. The ligands and polyligands are synthesized chemically or recombinantly and are utilized as research tools or as therapeutics. The invention includes linking the ligands and polyligands to cellular localization signals for subcellular therapeutics.

What is claimed is:

1. An isolated polynucleotide encoding a polypeptide polyligand comprising monomeric ligands encoded by a polynucleotide selected from the group consisting of SEQ ID NO: 231, SEQ ID NO: 232, SEQ ID NO: 234, and SEQ ID NO: 235,
wherein said polypeptide polyligand inhibits protein phosphatase 1 activity.

2. A vector comprising the isolated polynucleotide of claim 1.

3. A recombinant host cell comprising the vector of claim 2.

4. A method of inhibiting protein phosphatase 1 in a cell comprising transfecting the vector of claim 2 into a host cell and culturing the transfected host cell under conditions suitable to produce at least one copy of the peptide.

5. The isolated polynucleotide of claim 1, wherein the polynucleotide is flanked on one end by a sequence cleavable by a first restriction endonuclease, and wherein the polynucleotide is flanked on the other end by a sequence cleavable by a second restriction endonuclease, and wherein the first and second restriction endonucleases generate noncompatible cohesive ends.

6. The isolated polynucleotide of claim 5, wherein the polynucleotide is flanked on one end by a sequence cleavable by NgoM IV, and wherein the polynucleotide is flanked on the other end by sequences cleavable by Xma I and Cla I.

7. The isolated polynucleotide of claim 1, wherein at least one of said monomeric ligands does not contain a phosphorylatable amino acid residue.

8. A composition comprising the isolated polynucleotide of claim 1.

9. The isolated polynucleotide of claim 1, wherein said polyligand is a heteropolyligand.

10. The isolated polynucleotide of claim 1, wherein said polyligand is a homopolyligand.

11. The isolated polynucleotide of claim 1, wherein said polypeptide polyligand is at least 85% identical to SEQ ID NO: 230 or SEQ ID NO: 233.

12. The isolated polynucleotide of claim 1, wherein said polypeptide polyligand is at least 90% identical to SEQ ID NO: 230 or SEQ ID NO: 233.

13. The isolated polynucleotide of claim 1, wherein said polypeptide polyligand is at least 95% identical to SEQ ID NO: 230 or SEQ ID NO: 233.

14. The isolated polynucleotide of claim 1, wherein said polypeptide polyligand is at least 96% identical to SEQ ID NO: 230 or SEQ ID NO: 233.

15. The isolated polynucleotide of claim 1, wherein said polypeptide polyligand is at least 97% identical to SEQ ID NO: 230 or SEQ ID NO: 233.

16. The isolated polynucleotide of claim 1, wherein said polypeptide polyligand is at least 98% identical to SEQ ID NO: 230 or SEQ ID NO: 233.

17. The isolated polynucleotide of claim 1, wherein said polypeptide polyligand is at least 99% identical to SEQ ID NO: 230 or SEQ ID NO: 233.

18. The isolated polynucleotide of claim 1, wherein said polypeptide polyligand is SEQ ID NO: 230 or SEQ ID NO: 233.

\* \* \* \* \*

UNITED STATES PATENT AND TRADEMARK OFFICE
CERTIFICATE OF CORRECTION

| | | |
|---|---|---|
| PATENT NO. | : 8,455,628 B2 | Page 1 of 1 |
| APPLICATION NO. | : 12/598137 | |
| DATED | : June 4, 2013 | |
| INVENTOR(S) | : Reed et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 737 days.

Signed and Sealed this
Twenty-fifth Day of March, 2014

Michelle K. Lee
*Deputy Director of the United States Patent and Trademark Office*